US008877731B2

(12) United States Patent
Beigelman et al.

(10) Patent No.: US 8,877,731 B2
(45) Date of Patent: Nov. 4, 2014

(54) AZIDO NUCLEOSIDES AND NUCLEOTIDE ANALOGS

(75) Inventors: Leonid Beigelman, San Mateo, CA (US); Jerome Deval, Pacifica, CA (US); David Bernard Smith, San Mateo, CA (US); Guangyi Wang, Carlsbad, CA (US); Vivek Kumar Rajwanshi, Cupertino, CA (US)

(73) Assignee: Alios Biopharma, Inc., South San Francisco, CA (US)

( * ) Notice: Subject to any disclaimer, the term of this patent is extended or adjusted under 35 U.S.C. 154(b) by 321 days.

(21) Appl. No.: 13/236,486

(22) Filed: Sep. 19, 2011

(65) Prior Publication Data
US 2012/0070415 A1   Mar. 22, 2012

Related U.S. Application Data

(60) Provisional application No. 61/385,441, filed on Sep. 22, 2010.

(51) Int. Cl.
| | | |
|---|---|---|
| A61K 31/70 | (2006.01) | |
| A01N 43/04 | (2006.01) | |
| C07H 19/00 | (2006.01) | |
| C07H 19/04 | (2006.01) | |
| C07H 19/10 | (2006.01) | |
| C07H 19/048 | (2006.01) | |
| C07H 19/20 | (2006.01) | |
| C07H 19/167 | (2006.01) | |
| C07H 19/173 | (2006.01) | |
| A61K 31/7068 | (2006.01) | |
| C07H 19/056 | (2006.01) | |
| C07H 19/09 | (2006.01) | |
| A61K 31/7056 | (2006.01) | |
| A61K 45/06 | (2006.01) | |
| A61K 31/7072 | (2006.01) | |
| A61K 31/708 | (2006.01) | |
| A61K 31/7105 | (2006.01) | |
| C07H 19/11 | (2006.01) | |
| C07H 19/067 | (2006.01) | |
| C07H 19/19 | (2006.01) | |
| A61K 31/7076 | (2006.01) | |
| C07H 19/073 | (2006.01) | |

(52) U.S. Cl.
CPC .......... *C07H 19/056* (2013.01); *A61K 31/7068* (2013.01); *C07H 19/167* (2013.01); *C07H 19/09* (2013.01); *A61K 31/7056* (2013.01); *A61K 45/06* (2013.01); *A61K 31/7072* (2013.01); *C07H 19/20* (2013.01); *A61K 31/708* (2013.01); *A61K 31/7105* (2013.01); *C07H 19/11* (2013.01); *C07H 19/10* (2013.01); *C07H 19/067* (2013.01); *C07H 19/19* (2013.01); *A61K 31/7076* (2013.01); *C07H 19/073* (2013.01)

USPC ............... 514/45; 514/46; 514/47; 514/48; 514/49; 514/50; 514/51; 536/26.12; 536/26.13; 536/26.23; 536/26.26; 536/26.7; 536/26.8; 536/27.6; 536/27.7; 536/27.8; 536/27.81; 536/28.5; 536/28.53

(58) Field of Classification Search
None
See application file for complete search history.

(56) References Cited

U.S. PATENT DOCUMENTS

| 5,449,664 | A | 9/1995 | Verheyden et al. |
|---|---|---|---|
| 5,681,940 | A | 10/1997 | Wang |
| 5,712,378 | A | 1/1998 | Wang |
| 6,787,525 | B1 | 9/2004 | Schott et al. |
| 7,094,768 | B2 * | 8/2006 | Roberts et al. ................. 514/45 |
| 7,151,089 | B2 * | 12/2006 | Roberts et al. ................. 514/43 |
| 7,629,328 | B2 * | 12/2009 | Roberts et al. ................. 514/45 |
| 7,915,232 | B2 | 3/2011 | Martin et al. |
| 2003/0064945 | A1 | 4/2003 | McSwiggen |
| 2003/0124513 | A1 | 7/2003 | McSwiggen |
| 2004/0259934 | A1 | 12/2004 | Olsen et al. |
| 2006/0040890 | A1 | 2/2006 | Martin et al. |
| 2007/0042988 | A1 | 2/2007 | Klumpp et al. |
| 2007/0066815 | A1 | 3/2007 | Sarma |
| 2008/0008682 | A1 | 1/2008 | Chong et al. |
| 2008/0039428 | A1 | 2/2008 | Allaway et al. |
| 2008/0107628 | A1 | 5/2008 | Boojamra et al. |
| 2008/0161254 | A1 | 7/2008 | Dener et al. |
| 2008/0188458 | A1 | 8/2008 | Young et al. |
| 2009/0176732 | A1 | 7/2009 | Beigelman et al. |
| 2009/0318380 | A1 | 12/2009 | Sofia et al. |
| 2010/0151001 | A1 | 6/2010 | Schott et al. |

(Continued)

FOREIGN PATENT DOCUMENTS

| EP | 0371366 | 6/1990 |
|---|---|---|
| EP | 0457326 | 11/1991 |

(Continued)

OTHER PUBLICATIONS

Gwack et al., "DNA Helicase Activity of the Hepatitis C Virus Nonstructural Protein 3," European Journal of Biochemistry, 250 (1), 47-54 (1997).*

(Continued)

*Primary Examiner* — Lawrence E Crane
(74) *Attorney, Agent, or Firm* — Knobbe Martens Olson & Bear LLP

(57) ABSTRACT

Disclosed herein are nucleosides, nucleotides and analogs thereof, pharmaceutical compositions that include one or more of nucleosides, nucleotides and analogs thereof, and methods of synthesizing the same. Also disclosed herein are methods of ameliorating and/or treating a disease and/or a condition, including an infection from a paramyxovirus and/or an orthomyxovirus, with a nucleoside, a nucleotide and an analog thereof. Examples of viral infections include a respiratory syncytial viral (RSV) and influenza infection.

30 Claims, 1 Drawing Sheet

(56) References Cited

U.S. PATENT DOCUMENTS

| | | | |
|---|---|---|---|
| 2010/0234584 A1 | 9/2010 | Chang et al. |
| 2010/0240604 A1 | 9/2010 | Beigelman et al. |
| 2010/0249068 A1 | 9/2010 | Beigelman et al. |
| 2010/0297079 A1 | 11/2010 | Almond et al. |
| 2010/0331397 A1 | 12/2010 | Beigelman et al. |
| 2011/0020272 A1 | 1/2011 | Schubert |
| 2012/0070411 A1 | 3/2012 | Beigelman et al. |
| 2012/0071434 A1 | 3/2012 | Smith et al. |
| 2012/0165286 A1 | 6/2012 | Beigelman et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |

FOREIGN PATENT DOCUMENTS

| | | | |
|---|---|---|---|
| EP | 2177527 A1 | 1/2009 |
| EP | 2166016 | 3/2010 |
| WO | WO 92/21343 | 12/1992 |
| WO | WO 96/14329 | 5/1996 |
| WO | WO 98/16184 | 4/1998 |
| WO | WO 98/16186 | 4/1998 |
| WO | WO 99/14226 | 3/1999 |
| WO | WO 00/34298 | 6/2000 |
| WO | WO 00/66604 | 11/2000 |
| WO | WO 02/100415 | 12/2002 |
| WO | WO 03/026589 | 4/2003 |
| WO | WO 03/026675 | 4/2003 |
| WO | WO 03/039523 | 5/2003 |
| WO | WO 03/070193 | 8/2003 |
| WO | WO 03/070912 | 8/2003 |
| WO | WO 03/073989 | 9/2003 |
| WO | WO 03/102131 | 12/2003 |
| WO | WO 2004/002422 | 1/2004 |
| WO | WO 2004/002999 | 1/2004 |
| WO | WO 2004/003000 | 1/2004 |
| WO | WO 2004/014312 | 2/2004 |
| WO | WO 2004/046159 | 6/2004 |
| WO | WO 2004/052906 | 6/2004 |
| WO | WO 2004/062676 | 7/2004 |
| WO | WO 2004/080466 | 9/2004 |
| WO | WO 2004/106356 | 12/2004 |
| WO | WO 2005/000864 | 1/2005 |
| WO | WO 2005/020884 | 3/2005 |
| WO | WO 2005/021568 | 3/2005 |
| WO | WO 2006/000922 | 1/2006 |
| WO | WO 2006/094347 | 9/2006 |
| WO | WO 2007/005779 | 1/2007 |
| WO | WO 2007/020193 | 2/2007 |
| WO | WO 2007/038859 | 4/2007 |
| WO | WO 2007/038860 | 4/2007 |
| WO | WO 2007/113538 | 10/2007 |
| WO | WO 2008/005542 | 1/2008 |
| WO | WO 2008/043704 | 4/2008 |
| WO | WO 2008/043791 | 4/2008 |
| WO | WO 2008/071571 | 6/2008 |
| WO | WO 2008/083465 | 7/2008 |
| WO | WO 2008/086042 | 7/2008 |
| WO | WO 2008/089105 | 7/2008 |
| WO | WO 2008/095040 | 8/2008 |
| WO | WO 2008/100447 | 8/2008 |
| WO | WO 2008/117047 | 10/2008 |
| WO | WO 2008/121634 | 10/2008 |
| WO | WO 2008/124384 | 10/2008 |
| WO | WO 2008/125583 | 10/2008 |
| WO | WO 2008/125599 | 10/2008 |
| WO | WO 2008/136815 | 11/2008 |
| WO | WO 2009/009951 | 1/2009 |
| WO | WO 2009/025759 | 2/2009 |
| WO | WO 2009/040269 | 4/2009 |
| WO | WO 2009/064848 | 5/2009 |
| WO | WO 2009/067409 | 5/2009 |
| WO | WO 2009/069095 | 6/2009 |
| WO | WO 2009/080836 | 7/2009 |
| WO | WO 2009/085267 | 7/2009 |
| WO | WO 2009/086192 | 7/2009 |
| WO | WO 2009/086201 | 7/2009 |
| WO | WO 2009/102318 | 8/2009 |
| WO | WO 2009/120991 | 10/2009 |
| WO | WO 2009/132123 | 10/2009 |
| WO | WO 2009/149377 | 12/2009 |
| WO | WO 2009/152095 | 12/2009 |
| WO | WO 2010/017178 | 2/2010 |
| WO | WO 2010/018233 | 2/2010 |
| WO | WO 2010/022126 | 2/2010 |
| WO | WO 2010/022128 | 2/2010 |
| WO | WO 2010/026153 | 3/2010 |
| WO | WO 2010/030858 A1 | 3/2010 |
| WO | WO 2010/031829 | 3/2010 |
| WO | WO 2010/036407 | 4/2010 |
| WO | WO 2010/075554 | 7/2010 |
| WO | WO 2010/081082 | 7/2010 |
| WO | WO 2010/084115 | 7/2010 |
| WO | WO 2010/091386 | 8/2010 |
| WO | WO 2010/108135 | 9/2010 |
| WO | WO 2010/108140 | 9/2010 |
| WO | WO 2010/121128 | 10/2010 |
| WO | WO 2010/145778 | 12/2010 |
| WO | WO 2011/004276 | 1/2011 |
| WO | WO 2011/015658 | 2/2011 |
| WO | WO 2012/040124 | 3/2012 |
| WO | WO 2013/096679 | 6/2013 |
| WO | WO 2013/142124 | 9/2013 |
| WO | WO 2013/142159 | 9/2013 |
| WO | WO 2013/142525 | 9/2013 |

OTHER PUBLICATIONS

Porter et al. (eds.), Chapter 150(Respiratory Viruses); Section 11 (Infectious Diseases) in the Merck Manual of Diagnosis and Therapy, 19th Edition, Merck & Co., Inc., Rahway, NJ, 2011, only title page and text pp. 1405-1408 ("Influenza") supplied.*

McGuigan et al., "The application of the phosphoramidate ProTide approach confers micromolar potency against hepatitis C virus on inactive agent 4'-azidoinosine: kinase bypass on a dual base/sugar modified nucleoside", *Bioorg Med Chem Lett.* (2009) 19(11):3122-4.

International Search Report and Written Opinion mailed Nov. 15, 2011 for PCT Application No. PCT/US2011/052217, filed Sep. 19, 2011.

Corrected Version International Search Report and Written Opinion mailed Nov. 15, 2011 for PCT Application No. PCT/US2011/052217, filed Sep. 19, 2011.

Ali, et al., "Selected replicon variants with low-level in vitro resistance to the hepatitis C virus NS5B polymerase inhibitor PSI-6130 lack cross-resistance with R1479" *Antimicrobial Agents and Chemotherapy* (2008) 52(12):4356-4369.

De Clercq, E., "Emerging antiviral drugs" *Expert Opinion on Emerging Drugs* (2008) 13(3):393-416.

De Keczer, et al., "Enzymatic nucleoside isotope exchange an alternate route to a [14C]-labeled HCV polymerase inhibitor" Synthesis and Applications of Isotopically Labelled Compounds, Proceedings of the International Symposium,8th, Boston, MA, United States, Jun. 1-5, 2003 (2004) Meeting Date May 9, 2003.

De Palma, et al., "Potential use of antiviral agents in polio eradication" *Emerging Infectious Disease* (2008) 14(4):545-551.

Delang, et al., "Statins potentiate the in vitro anti-hepatitis C virus activity of selective hepatitis C virus inhibitors and delay or prevent resistance development" *Hepatology* (2009) 50(1):6-16.

Gaudieri, et al., "Hepatitis C virus drug resistance and immune-driven adaptations: relevance to new antiviral therapy" *Hepatology* (2009) 49(4):1069-1082.

Jin, et al., "Synthesis and antiviral activity of fluoro sugar nucleosides. 1: Studies on 4'-azido-2'-deoxy-2'-fluoro-arabinofuranosyl nucleosides" *Archives of Pharmacal Research* (1995) 18(5):364-5.

Klumpp, et al., "2'-Deoxy-4'-azido Nucleoside Analogs Are Highly Potent Inhibitors of Hepatitis C Virus Replication Despite the Lack of 2'-L-Hydroxyl Groups," *Journal of Biological Chemistry* (2008) 283(4):2167-2175.

(56) References Cited

OTHER PUBLICATIONS

Klumpp et al., "The Novel Nucleoside Analog R1479 (4'-Azidocytidine)" *Journal of Biological Chemistry* (2006) 281(7):3793-3799.

Lam, et al., "PSI-7851, a pronucleotide of β-D-2'-deoxy-2'-fluoro-2'-C-methyluridine monophosphate, is a potent and pan-genotype inhibitor of hepatitis C virus replication" *Antimicrobial Agents and Chemotherapy* (2010) 54(8):3187-3196.

Le Pogam et al., "In vitro selected Con1 subgenomic replicons resistant to 2'-C-Methyl-Cytidine or to R1479 show lack of cross resistance" *Virology* (2006) 351(2):349-359.

Li et al., "Chemical stability of 4'-azidocytidine and its prodrug balapiravir" *Drug Development and Industrial Pharmacy* (2010) 36(4):413-420.

Maag et al., "Synthesis and anti-HIV activity of 4'-azido- and 4'-methoxynucleosides" *Journal of Medicinal Chemistry* (1992) 35(8):1440-51.

McCown, et al., "The hepatitis C virus replicon presents a higher barrier to resistance to nucleoside analogs than to nonnucleoside polymerase or protease inhibitors" *Antimicrobial Agents and Chemotherapy* (2008) 52(5):1604-1612.

McGuigan, et al., "The application of phosphoramidate ProTide technology to the potent anti-HCV compound 4'-azidocytidine (R1479)" *Bioorganic & Medicinal Chemistry Letters* (2009) 19(15):4250-4254.

Paeshuyse et al., "Comparative in vitro anti-hepatitis C virus activities of a selected series of polymerase, protease, and helicase inhibitors," *Antimicrobial Agents and Chemotherapy* (2008) 52(9):3433-3437.

Perrone et al., "Application of the Phosphoramidate ProTide Approach to 4'-Azidouridine Confers Sub-micromolar Potency versus Hepatitis C Virus on an Inactive Nucleoside" *Journal of Medicinal Chemistry* (2007) 50(8):1840-1849.

Perrone, et al., "First Example of Phosphoramidate Approach Applied to a 4'-Substituted Purine Nucleoside (4'-Azidoadenosine):Conversion of an Inactive Nucleoside to a Submicromolar Compound versus Hepatitis C Virus" *Journal of Medicinal Chemistry* (2007) 50(22):5463-5470.

Pockros, et al, "R1626 plus peginterferon alfa-2a provides potent suppression of hepatitis C virus RNA and significant antiviral synergy in combination with ribarin," *Hepatology* (2008) 48(2):385-397 & 2093.

Roberts, et al., "Robust antiviral activity of R1626, a novel nucleoside analog: a randomized, placebo-controlled study in patients with chronic hepatitis C" *Hepatology* (2008) 48(2):398-406.

Rondla, et al., "Anti-hepatitis C virus activity of novel β-d-2'-C-methyl-4'-azido pyrimidine nucleoside phosphoramidate prodrugs," *Antiviral Chemistry & Chemotherapy* (2009) 20(2):99-106.

Shim, et al., "Recent patents on nucleoside and nucleotide inhibitors for HCV" *Recent Patents on Anti-infective Drug Discovery* (2006) 1(3):323-331.

Smith et al., "Design, synthesis, and antiviral properties of 4'-substituted ribonucleosides as inhibitors of hepatitis C virus replication: The discovery of R1479" *Bioorganic & Medicinal Chemistry Letters* (2007) 17(9):2570-2576.

Smith et al., "The Design, Synthesis, and Antiviral Activity of 4'-Azidocytidine Analogues against Hepatitis C Virus Replication: The Discovery of 4'-Azidoarabinocytidine." *Journal of Medicinal Chemistry* (2009) 52(1):219-223.

Smith et al., "The Design, Synthesis, and Antiviral Activity of Monofluoro and Difluoro Analogues of 4'-Azidocytidine against Hepatitis C Virus Replication: The Discovery of 4'-Azido-2'-deoxy-2'-fluorocytidine and 4'-Azido-2'-dideoxy-2',2'-difluorocytidine" *Journal of Medicinal Chemistry* (2009) 52(9):2971-2978.

Stankiewicz-Drogon, et al., "New acridone-4-carboxylic acid derivatives as potential inhibitors of Hepatitis C virus infection" *Bioorganic amp; Medicinal Chemistry* (2008) 16(19):8846-8852.

Vliegen, et al., "Substituted imidazopyridines as potent inhibitors of HCV replication," *Journal of Hepatology* (2009) 50(5):999-1009.

Second Written Opinion dated Aug. 14, 2012 for PCT/US2011/052217, filed Sep. 19, 2011.

Third Written Opinion dated Nov. 9, 2012 for PCT/US2011/052217, filed Sep. 19, 2011.

International Preliminary Report on Patentability dated Dec. 12, 2012 for PCT Application No. PCT/US2011/052217,filed Sep. 19, 2011.

CAS Registry No. 1026639-60-0, Entry Date Jun. 8, 2008, (https://stneasy.cas.org), retrieved on May 3, 2013.

CAS Registry No. 1026065-66-6, Entry Date Jun. 6, 2008, (https://stneasy.cas.org), retrieved on May 3, 2013.

CAS Registry No. 1158729-23-7, Entry date Jun. 17, 2009, (https://stneasy.cas.org), retrieved on Mar. 21, 2014.

CAS Registry No. 130108-92-8, Entry date Oct. 26, 1990, (https://stneasy.cas.org), retrieved on Mar. 21, 2014.

CAS Registry No. 130108-93-9, Entry date Oct. 26, 1990, (https://stneasy.cas.org), retrieved on Mar. 21, 2014.

CAS Registry No. 130108-94-0, Entry date Oct. 26, 1990, (https://stneasy.cas.org), retrieved on Mar. 21, 2014.

CAS Registry No. 130108-97-3, Entry date Oct. 26, 1990, (https://stneasy.cas.org), retrieved on Mar. 21, 2014.

CAS Registry No. 139418-97-6, Entry date Mar. 6, 1992, (https://stneasy.cas.org), retrieved on Mar. 21, 2014.

CAS Registry No. 139418-99-8, Entry date Mar. 6, 1992, (https://stneasy.cas.org), retrieved on Mar. 21, 2014.

CAS Registry No. 139419-00-4, Entry date Mar. 6, 1992, (https://stneasy.cas.org), retrieved on Mar. 21, 2014.

CAS Registry No. 139442-01-6, Entry date Mar. 6, 1992, (https://stneasy.cas.org), retrieved on Mar. 21, 2014.

CAS Registry No. 690270-29-2, Entry date Jun. 7, 2004, (https://stneasy.cas.org), retrieved on Mar. 21, 2014.

CAS Registry No. 926309-82-2, Entry date Mar. 14, 2007, (https://stneasy.cas.org), retrieved on Mar. 21, 2014.

Chang, W. et al: "Synthesis and Anti-HCV Activity of 3',4'-Oxetane Nucleosides" *Bioorganic & Medicinal Chemistry Letters* (2010), 20(15): 4539-4543.

Kohgo, S. et al: "Synthesis of 4'-C-Ethynyl-—-D-arabino- and 4'-C-Ethynyl-2'-deoxy-If-Dcribo-pentofuranosyl Pyrimidines, and Their Biological Evaluation" *Bioscience, Biotechnology, and Biochemistry* (1999), 63(6): 1146-1149.

Kozak, J. et al: "Synthesis of 4'-Trifluoromethyl Nucleoside Analogs" *Nucleosides & Nucleotides* (1998),17(12): 2221-2239.

Waga, T. et al: "Synthesis and Biological Evaluation of 4'-C-Methyl Nucleosides", *Nucleosides & Nucleotides* (1996), 15(1-3): 287-304.

Wang, Q. et al: "Synthesis and Anti-HIV Activity of 2'-Deoxy-2'-Fluoro-4'-C-Ethynyl Nucleoside Analogs" *Bioorganic & Medicinal Chemistry Letters* (2010), 20(14): 4053-4056.

\* cited by examiner

| Compound | Structure |
|---|---|
| BMS-433771 | 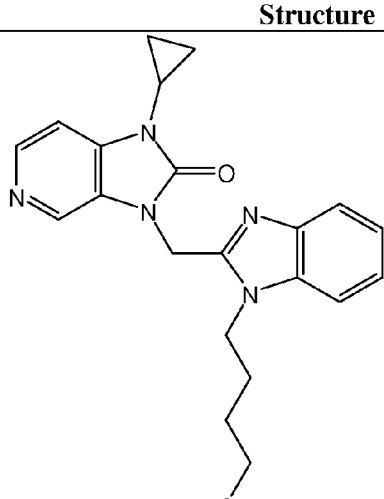 |
| TMC-353121 | 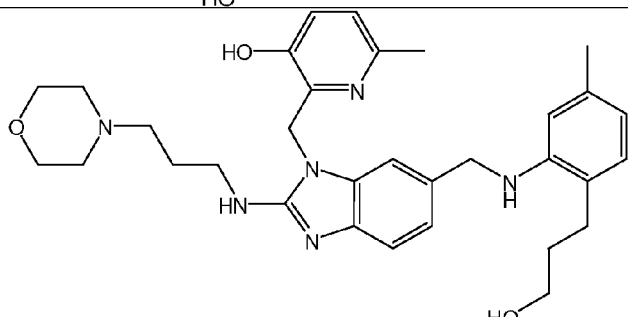 |

US 8,877,731 B2

AZIDO NUCLEOSIDES AND NUCLEOTIDE ANALOGS

CROSS-REFERENCE TO RELATED APPLICATIONS

This application claims priority to U.S. Provisional Patent Application No. 61/385,441, entitled "AZIDO NUCLEOSIDES AND NUCLEOTIDES ANALOGS" filed Sep. 22, 2010; which is incorporated herein by reference in its entirety, including any drawings.

BACKGROUND

1. Field

The present application relates to the fields of chemistry, biochemistry and medicine. More particularly, disclosed herein are nucleoside, nucleotides and analogs thereof, pharmaceutical compositions that include one or more nucleosides, nucleotides and analogs thereof, and methods of synthesizing the same. Also disclosed herein are methods of ameliorating and/or treating a paramyxovirus and/or an orthomyxovirus viral infection with one or more nucleosides, nucleotides and analogs thereof.

2. Description

Respiratory viral infections, including upper and lower respiratory tract viral infections, infects and is the leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

Nucleoside analogs are a class of compounds that have been shown to exert antiviral activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof.

Some embodiments disclosed herein relate to methods of ameliorating and/or treating a paramyxovirus viral infection that can include administering to a subject suffering from the paramyxovirus viral infection a therapeutically effective amount of one or more compounds of Formula (I) and/or Formula (II), or a pharmaceutically acceptable salt thereof, or a pharmaceutical composition that includes one or more compounds of Formula (I) and/or Formula (II), or a pharmaceutically acceptable salt thereof. Other embodiments described herein relate to using one or more compounds of Formula (I) and/or Formula (II), or a pharmaceutically acceptable salt thereof, in the manufacture of a medicament for ameliorating and/or treating a paramyxovirus viral infection. Still other embodiments described herein relate to compounds of Formula (I) and/or Formula (II), or a pharmaceutically acceptable salt thereof, that can be used for ameliorating and/or treating a paramyxovirus viral infection. Yet still other embodiments disclosed herein relate to methods of ameliorating and/or treating a paramyxovirus viral infection that can include contacting a cell infected with the paramyxovirus viral infection with a therapeutically effective amount of one or more compounds of Formula (I) and/or Formula (II), or a pharmaceutically acceptable salt thereof, or a pharmaceutical composition that includes one or more compounds of Formula (I) and/or Formula (II), or a pharmaceutically acceptable salt thereof. Some embodiments disclosed herein relate to methods of inhibiting the replication of a paramyxovirus that can include contacting a cell infection with the paramyxovirus with an effective amount of one or more compounds of Formula (I) and/or Formula (II), or a pharmaceutically acceptable salt thereof, or a pharmaceutical composition that includes one or more compounds of Formula (I) and/or Formula (II), or a pharmaceutically acceptable salt thereof. For example, the paramyxovirus viral infection can be a respiratory syncytial viral infection.

Some embodiments disclosed herein relate to methods of ameliorating and/or treating an orthomyxovirus viral infection that can include administering to a subject suffering from the orthomyxovirus viral infection a therapeutically effective amount of one or more compounds of Formula (I) and/or Formula (II), or a pharmaceutically acceptable salt thereof, or a pharmaceutical composition that includes one or more compounds of Formula (I) and/or Formula (II), or a pharmaceutically acceptable salt thereof. Other embodiments described herein relate to using one or more compounds of Formula (I) and/or Formula (II), or a pharmaceutically acceptable salt thereof, in the manufacture of a medicament for ameliorating and/or treating an orthomyxovirus viral infection. Still other embodiments described herein relate to compounds of Formula (I) and/or Formula (II), or a pharmaceutically acceptable salt thereof, that can be used for ameliorating and/or treating an orthomyxovirus viral infection. Yet still other embodiments disclosed herein relate to methods of ameliorating and/or treating an orthomyxovirus viral infection that can include contacting a cell infected with the orthomyxovirus viral infection with a therapeutically effective amount of one or more compounds of Formula (I) and/or Formula (II), or a pharmaceutically acceptable salt thereof, or a pharmaceutical composition that includes one or more compounds of Formula (I) and/or Formula (II), or a pharmaceutically acceptable salt thereof. Some embodiments disclosed herein relate to methods of inhibiting the replication of an orthomyxovirus that can include contacting a cell infection with the orthomyxovirus with an effective amount of one or more compounds of Formula (I) and/or Formula (II), or a pharmaceutically acceptable salt thereof, or a pharmaceutical composition that includes one or more compounds of Formula (I) and/or Formula (II), or a pharmaceutically acceptable salt thereof. For example, the orthomyxovirus viral infection can be an influenza viral infection (such as influenza A, B and/or C).

Some embodiments disclosed herein relate to methods of ameliorating and/or treating a paramyxovirus viral infection and/or an orthomyxovirus viral infection that can include administering to a subject suffering from the viral infection a therapeutically effective amount of a compound described herein or a pharmaceutically acceptable salt thereof (for example, one or more compounds of Formulae (I) and/or (II), or a pharmaceutically acceptable salt thereof), or a pharmaceutical composition that includes one or more compounds described herein, in combination with one or more agents described herein. Some embodiments disclosed herein relate to methods of ameliorating and/or treating a paramyxovirus viral infection and/or an orthomyxovirus viral infection that can include contacting a cell infected with the viral infection with a therapeutically effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein.

BRIEF DESCRIPTION OF THE DRAWINGS

FIG. 1 shows example RSV agents.

DETAILED DESCRIPTION

Human Respiratory Syncytial Virus (RSV) is a member of the Parayxoviridae family. RSV is a single stranded RNA virus. RSV can cause respiratory infections, and can be associated with bronchiolitis and pneumonia.

RSV is transmitted person to person via direct or close contact with contaminated respiratory droplets or fomites. Symptoms of an RSV infection include coughing, sneezing, runny nose, fever, decrease in appetite, and wheezing. RSV is the most common cause of bronchiolitis and pneumonia in children under one year of age in the world, and can be the cause of tracheobronchitis in older children and adults. In the United States, between 75,000 and 125,000 infants are hospitalized each year with RSV. Among adults older than 65 years of age, an estimated 14,000 deaths and 177,000 hospitalizations have been attributed to RSV.

Treatment options for people infected with RSV are currently limited. Antibiotics, usually prescribed to treat bacterial infections, and over-the-counter medication are not effective in treating RSV and may help only to relieve some of the symptoms. In severe cases, a nebulized bronchodilator, such as albuterol, may be prescribed to relieve some of the symptoms, such as wheezing. RespiGram® (RSV-IGIV, MedImmune, approved for high risk children younger than 24 months of age), Synagis® (palivizumab, MedImmune, approved for high risk children younger than 24 months of age), and Virzole® (ribavirin by aerosol, ICN pharmaceuticals) have been approved for treatment of RSV.

Influenza is a single stranded RNA virus and a member of the Orthomyxoviridae family. There are currently three species of influenza; influenza A, influenza B and influenza C. Influenza A has been further classified based on the viral surface proteins into hemagglutinin (H or HA) and neuramidase (N). There are approximately 16 H antigens (H1 to H16) and 9 N antigens (N1 to N9). Influenza A includes several subtype, including H1N1, H1N2, H2N2, H3N1, H3N2, H3N8, H5N1, H5N2, H5N3, H5N8, H5N9, H7N1, H7N2, H7N3, H7N4, H7N7, H9N2, H10N7. As with RSV, influenza viruses can be transmitted from person to person via direct contact with infected secretions and/or contaminated surfaces or objections. Complications from an influenza viral infection include pneumonia, bronchitis, dehydration, and sinus and ear infections. Medications currently approved by the FDA against an influenza infection include amantadine, rimantadine, Relenza® (zanamivir, GlaxoSmithKline) and Tamiflu® (oseltamivir, Genentech).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, R*, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}, R^{27}, R^{28}, R^{29}, R^{30}, R^{31}, R^{1a}, R^{2a}, R^{3a}, R^{4a}, R^{5a}, R^{6a}, R^{7a}, R^{8a}, R^{9a}, R^{10a}, R^{11a}, R^{12a}, R^{13a}, R^{14a}, R^{15a}, R^{16a}, R^{17a}, R^{18a}, R^{19a}, R^{20a}, R^{21a}, R^{22a}, R^{23a}, R^{24a}, R^{25a}, R^{26a}, R^{27a}, R^{28a}, R^{29a}, R^{30a}, R^{31a}, R^a, R^b, R^A, R^B$ and $R^C$ represent substituents that can be attached to the indicated atom. An R group may be substituted or unsubstituted. If two "R" groups are described as being "taken together" the R groups and the atoms they are attached to can form a cycloalkyl, aryl, heteroaryl or heterocycle. For example, without limitation, if $R^{1a}$ and $R^{1b}$ of an $NR^{1a}R^{1b}$ group are indicated to be "taken together," it means that they are covalently bonded to one another to form a ring:

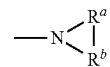

Whenever a group is described as being "optionally substituted" that group may be unsubstituted or substituted with one or more of the indicated substituents Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, such as but not limited to phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein X is a halogen.

A "trihalomethanesulfonamido" group refers to an "X$_3$CS(O)$_2$N(R$_A$)—" group wherein X is a halogen and R$_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include, methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-β—C(=O)—, cyclobutyl-O—C(=O)—, cyclopentyl-O—C(=O)—, cyclohexyl-O—C(=O)—, phenyl-O—C(=O)—, and benzyl-O—C(=O)—. N-linked amino acid ester derivatives can be substituted or unsubstituted.

The terms "phosphorothioate" and "phosphothioate" refer to a compound of the general formula

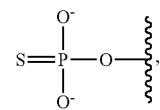

its protonated forms (for example,

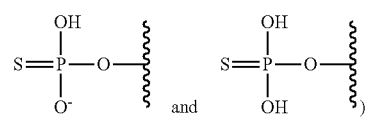

and its tautomers (such as

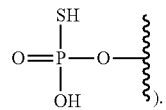

As used herein, the term "phosphate" is used in its ordinary sense as understood by those skilled in the art, and includes its protonated forms (for example,

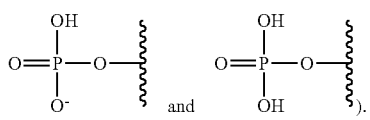

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

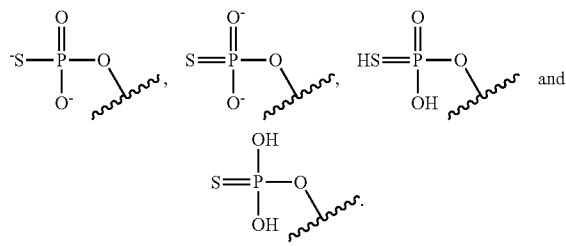
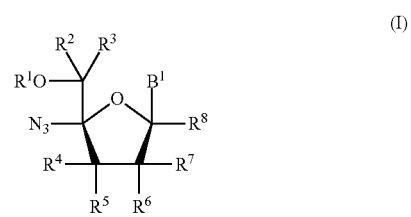

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof, wherein:

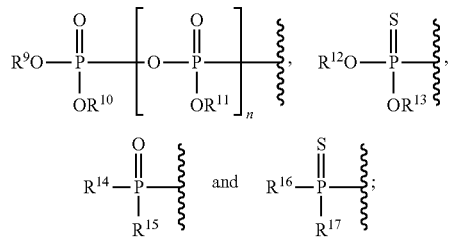

wherein $B^1$ can be selected from an optionally substituted heterocyclic base and an optionally substituted heterocyclic base with a protected amino group; $R^1$ can be selected from hydrogen, an optionally substituted acyl,

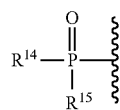

n can be 0, 1 or 2; $R^2$ and $R^3$ can be independently selected from hydrogen, an optionally substituted $C_{1-6}$ alkyl and an optionally substituted $C_{1-6}$ haloalkyl; $R^4$ can be selected from hydrogen, halogen, optionally substituted $C_{1-6}$ alkyl, —$OR^{18}$ and —$OC(\!=\!O)R^{19}$; $R^5$ can be selected from hydrogen, halogen, optionally substituted $C_{1-6}$ alkyl, —$OR^{20}$ and —$OC(\!=\!O)R^{21}$, or when $R^1$ is

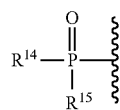

and $R^{14}$ is $O^-$, hydroxy or an —O-optionally substituted $C_{1-6}$ alkyl, then $R^{15}$ and $R^5$ together can be O, or when $R^1$ is

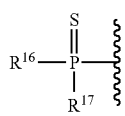

and $R^{16}$ is $O^-$, hydroxy or an —O-optionally substituted $C_{1-6}$ alkyl, then $R^{17}$ and $R^5$ together can be O; $R^6$ can be selected from hydrogen, halogen, optionally substituted $C_{1-6}$ alkyl, —$OR^{22}$ and —$OC(\!=\!O)R^{23}$; or $R^5$ and $R^6$ can be both oxygen atoms and linked together by a carbonyl group; $R^7$ can be selected from hydrogen, halogen, optionally substituted $C_{1-6}$ alkyl, —$OR^{24}$ and —$OC(\!=\!O)R^{25}$; $R^8$ can be selected from hydrogen, an optionally substituted $C_{1-6}$ alkyl and an optionally substituted $C_{1-6}$ haloalkyl; $R^9$, $R^{10}$, each $R^{11}$, $R^{12}$ and $R^{13}$ can be independently absent or hydrogen; $R^{14}$ can be selected from an —O-optionally substituted aryl, an —O-optionally substituted heteroaryl and an —O-optionally substituted heterocyclyl, and $R^{15}$ can be

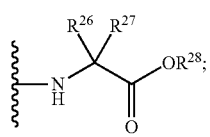

or $R^{14}$ can be an optionally substituted N-linked amino acid or an optionally substituted N-linked amino acid ester derivative, and $R^{15}$ can be an optionally substituted N-linked amino acid or an optionally substituted N-linked amino acid ester derivative; or $R^{14}$ can be O⁻, hydroxy or an —O-optionally substituted $C_{1-6}$ alkyl, and $R^{15}$ and $R^5$ together can be O; $R^{16}$ can be selected from the group consisting of an —O-optionally substituted aryl, an —O-optionally substituted heteroaryl and an —O-optionally substituted heterocyclyl, and $R^{17}$ can be an optionally substituted N-linked amino acid or an optionally substituted N-linked amino acid ester derivative; or $R^{16}$ can be an optionally substituted N-linked amino acid or an optionally substituted N-linked amino acid ester derivative, and $R^{17}$ can be an optionally substituted N-linked amino acid or an optionally substituted N-linked amino acid ester derivative; or $R^{16}$ can be O⁻, hydroxy or an —O-optionally substituted $C_{1-6}$ alkyl, and $R^{17}$ and $R^5$ together can be O; $R^{18}$, $R^{20}$, $R^{22}$ and $R^{24}$ can be independently selected from hydrogen and an optionally substituted $C_{1-6}$ alkyl; $R^{19}$, $R^{21}$, $R^{23}$ and $R^{25}$ can be independently selected from an optionally substituted $C_{1-6}$ alkyl and an optionally substituted $C_{3-6}$ cycloalkyl; $R^{26}$ can be hydrogen or an optionally substituted $C_{1-4}$-alkyl; $R^{27}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl, and an optionally substituted aryl($C_{1-6}$ alkyl); and $R^{28}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl), and an optionally substituted haloalkyl, or $R^{26}$ and $R^{27}$ can be taken together to form an optionally substituted $C_{3-6}$ cycloalkyl.

$R^1$ can be various substituents. In some embodiments, $R^1$ can be hydrogen when at least one of $R^2$ and $R^3$ is an optionally substituted $C_{1-6}$ alkyl or an optionally substituted $C_{1-6}$ haloalkyl. In some embodiments, $R^1$, $R^2$, $R^3$, $R^4$, and $R^8$ are all hydrogen, and $B^1$ is an optionally substituted

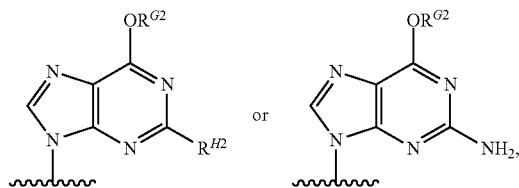

as described herein.

In some embodiments, $R^1$ can be an acyl. For example, $R^1$ can be —C(=O)H, —C(=O)-an optionally substituted alkyl, —C(=O)-an optionally substituted alkenyl, —C(=O)-an optionally substituted alkynyl, or —C(=O)-an optionally substituted aryl. In some embodiments, —C(=O)-an optionally substituted alkyl can be an —C(=O)-an optionally substituted $C_{1-6}$ alkyl. In other embodiments, —C(=O)-an optionally substituted alkenyl can be an —C(=O)-an optionally substituted $C_{2-6}$ alkenyl. In still other embodiments, —C(=O)-an optionally substituted alkynyl can be an —C(=O)-an optionally substituted $C_{2-6}$ alkynyl. In yet still other embodiments, —C(=O)-an optionally substituted aryl can be an —C(=O)-an optionally substituted $C_{6-10}$ aryl.

In some embodiments, $R^1$ can be

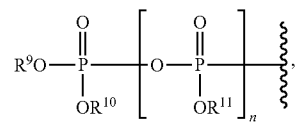

wherein n can be 0, 1 or 2. Those skilled in the art understand that when n is 0, $R^1$ can be a mono-phosphate Likewise, when n is 1 or 2, those skilled in the art understand $R^1$ can be a di-phosphate or a tri-phosphate, respectively. In some embodiments, at least one of $R^9$, $R^{10}$ and $R^{11}$ can be absent. Those skilled in the art understand that when $R^9$, $R^{10}$ and/or $R^{11}$ is absent, the oxygen associated with $R^9$, $R^{10}$ and/or $R^{11}$ can have a negative charge, which can be denoted as O⁻. In some embodiments, at least one of $R^9$, $R^{10}$ and $R^{11}$ can be hydrogen. In some embodiments, n can be 0, and $R^9$ and $R^{10}$ can be both absent. In other embodiments, n can be 0, and $R^9$ and $R^{10}$ can be both hydrogen. In some embodiments, n can be 1, and $R^9$, $R^{10}$ and $R^{11}$ can be absent. In other embodiments, n can be 1, and $R^9$, $R^{10}$ and $R^{11}$ can be hydrogen. In some embodiments, n can be 2, and $R^9$, $R^{10}$ and each $R^{11}$ can be absent. In other embodiments, n can be 2, and $R^9$, $R^{10}$ and each $R^{11}$ can be hydrogen. In some embodiments, $R^1$ can be

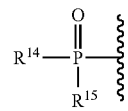

when $B^1$ is selected from a substituted adenine, substituted guanine, substituted 5-methyuracil, substituted uracil and

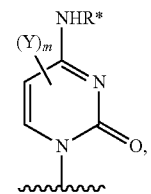

wherein R* can be selected from an acyl, —O-amide, an optionally substituted $C_{1-6}$ alkyl and an optionally substituted $C_{3-7}$ cycloalkyl; and Y can be selected from any of the substituents included in the definition of "substituted;" and m can be an integer in the range of 1 to 2. In some embodiments, $R^1$ can be

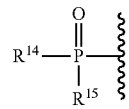

when $B^1$ is a substituted adenine or substituted guanine.

In some embodiments, $R^1$ can be

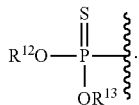

In some embodiments, at least one of $R^{12}$ and $R^{13}$ can be absent. For example, $R^{12}$ can be absent, $R^{13}$ can be absent or $R^{12}$ and $R^{13}$ can be absent. Those skilled in the art understand that when $R^{12}$ and/or $R^{13}$ are absent, the oxygen associated with $R^{12}$ and/or $R^{13}$ can have a negative charge, respectively, which can be denoted as $O^-$. In some embodiments, at least one of $R^{12}$ and $R^{13}$ can be hydrogen. Examples of at least one of $R^{12}$ and $R^{13}$ being hydrogen include the following:

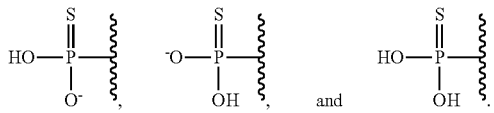

In some embodiments, both $R^{12}$ and $R^{13}$ can be hydrogen.

In some embodiments, $R^1$ can be

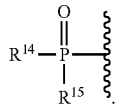

In some embodiment, $R^{14}$ can be selected from an —O-optionally substituted aryl, an —O-optionally substituted heteroaryl and an —O-optionally substituted heterocyclyl, and $R^{15}$ can be

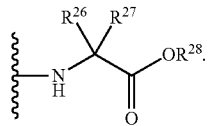

In some embodiments, $R^{14}$ can be an —O-optionally substituted heteroaryl. In other embodiments, $R^{14}$ can be an —O-optionally substituted heterocyclyl. In some embodiments, $R^{14}$ can be an —O-optionally substituted aryl. For example, the —O-optionally substituted aryl can be an —O-optionally substituted phenyl or an —O-optionally substituted naphthyl. If $R^{14}$ is an —O-substituted phenyl, the phenyl ring can be substituted one or more times Likewise, if $R^{14}$ is an —O-substituted naphthyl, the naphthyl ring can be substituted one or more times. Suitable substituents that can be present on an —O-optionally substituted phenyl and an —O-optionally substituted naphthyl include electron-donating groups and electron-withdrawing groups. In some embodiments, $R^{14}$ can be an —O-para-substituted phenyl. In other embodiment, $R^{14}$ can be an —O-unsubstituted phenyl or an —O-unsubstituted naphthyl.

In some embodiments, when $R^{15}$ has the structure

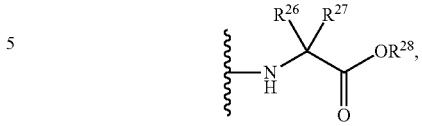

then $R^{26}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); $R^{27}$ can be hydrogen or an optionally substituted $C_{1-4}$-alkyl; and $R^{28}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted $C_{1-6}$ haloalkyl, or $R^{26}$ and $R^{27}$ can be taken together to form an optionally substituted $C_{3-6}$ cycloalkyl.

In some embodiments, $R^{26}$ can be hydrogen. In other embodiments, $R^{26}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{26}$ is substituted, $R^{26}$ can be substituted with one or more substituents selected from N-amido, mercapto, alkylthio, an optionally substituted aryl, hydroxy, an optionally substituted heteroaryl, O-carboxy, and amino. In some embodiment, $R^{26}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, $R^{26}$ can be methyl.

In some embodiments, $R^{27}$ can be hydrogen. In other embodiments, $R^{27}$ can be an optionally substituted $C_{1-4}$-alkyl, such as methyl, ethyl, n-propyl, isopropyl, n-butyl, isobutyl and tert-butyl. In an embodiment, $R^{27}$ can be methyl. In some embodiments, $R^{26}$ and $R^{27}$ can be taken together to form an optionally substituted $C_{3-6}$ cycloalkyl. Depending on the groups that are selected for $R^{26}$ and $R^{27}$, the carbon to which $R^{26}$ and $R^{27}$ are attached may be a chiral center. In some embodiment, the carbon to which $R^{26}$ and $R^{27}$ are attached may be a (R)-chiral center. In other embodiments, the carbon to which $R^{26}$ and $R^{27}$ are attached may be a (S)-chiral center.

As to $R^{28}$, in some embodiments, $R^{28}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments, $R^{28}$ can be an optionally substituted $C_{3-6}$ cycloalkyl. For example, $R^{28}$ can be an optionally substituted cyclopropyl, an optionally substituted cyclobutyl, an optionally substituted cyclopentyl or an optionally substituted cyclohexyl. In some embodiments, $R^{28}$ can be an optionally substituted cyclohexyl. In still other embodiments, $R^{28}$ can be an optionally substituted aryl, such as optionally substituted phenyl and optionally substituted naphthyl. In yet still other embodiments, $R^{28}$ can be an optionally substituted aryl($C_{1-6}$ alkyl). In some embodiments, $R^{28}$ can be an optionally substituted benzyl. In some embodiments, $R^{28}$ can be an optionally substituted $C_{1-6}$ haloalkyl, for example, $CF_3$. In some embodiments, $R^{28}$ can be hydrogen.

In some embodiments, $R^{14}$ can be an optionally substituted N-linked amino acid or an optionally substituted N-linked amino acid ester derivative, and $R^{15}$ can be an optionally substituted N-linked amino acid or an optionally substituted N-linked amino acid ester derivative. Various amino acids and amino acid ester derivatives can be used, including those described herein. In some embodiments, one or both of $R^{14}$ and $R^{15}$ can be an optionally substituted N-linked α-amino acid. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In other embodiments, one or both of $R^{14}$ and $R^{15}$ can be an optionally substituted N-linked α-amino acid ester derivative. For example, $R^{14}$ and/or $R^{15}$ can be an ester derivative of any of the following an amino acids described herein: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In some embodiment, one or both of $R^{14}$ and $R^{15}$ can be an ester derivative of alanine. In some embodiments, one or both of $R^{14}$ and $R^{15}$ can be an optionally substituted N-linked amino acid $C_{1-6}$ alkyl ester. In some embodiments, one or both of $R^{14}$ and $R^{15}$ can be an optionally substituted N-linked amino acid $C_{3-6}$ cycloalkyl ester. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, $R^{14}$ and $R^{15}$ can each have the structure

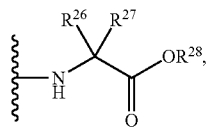

wherein each $R^{26}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); each $R^{27}$ can be hydrogen or an optionally substituted $C_{1-4}$-alkyl; and each $R^{28}$ can be selected from hydrogen, an optionally substituted $C_{1-6}$-alkyl, an optionally substituted $C_{3-6}$ cycloalkyl, an optionally substituted aryl, an optionally substituted aryl ($C_{1-6}$ alkyl) and an optionally substituted $C_{1-6}$ haloalkyl, or the $R^{26}$ and the $R^{27}$ attached to the same carbon can be taken together to form an optionally substituted $C_{3-6}$ cycloalkyl.

In some embodiments, one or both of $R^{26}$ can be hydrogen. In other embodiments, one or both of $R^{26}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{26}$ is substituted, $R^{26}$ can be substituted with one or more substituents selected from N-amido, mercapto, alkylthio, an optionally substituted aryl, hydroxy, an optionally substituted heteroaryl, O-carboxy, and amino. In some embodiment, one or both of $R^{26}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, one or both of $R^{26}$ can be methyl.

In some embodiments, one or both of $R^{27}$ can be hydrogen. In other embodiments, one or both of $R^{27}$ can be an optionally substituted $C_{1-4}$ alkyl, such as methyl, ethyl, n-propyl, isopropyl, n-butyl, isobutyl and tert-butyl. In an embodiment, one or both of $R^{27}$ can be methyl. In some embodiments, one or both of $R^{26}$ and $R^{27}$ attached to the same carbon can be taken together to form an optionally substituted $C_{3-6}$ cycloalkyl (for example, an optionally substituted cyclopropyl, an optionally substituted cyclobutyl, an optionally substituted cyclopentyl or optionally substituted cyclohexyl). Depending on the groups that are selected for $R^{26}$ and $R^{27}$, the carbon to which $R^{26}$ and $R^{27}$ are attached may be a chiral center. In some embodiment, the carbon to which $R^{26}$ and $R^{27}$ are attached may be a (R)-chiral center. In other embodiments, the carbon to which $R^{26}$ and $R^{27}$ are attached may be a (S)-chiral center.

In some embodiments, one or both of $R^{28}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments, one or both of $R^{28}$ can be an optionally substituted $C_{3-6}$ cycloalkyl. For example, $R^{28}$ can be an optionally substituted cyclopropyl, an optionally substituted cyclobutyl, an optionally substituted cyclopentyl or an optionally substituted cyclohexyl. In still other embodiments, one or both of $R^{28}$ can be an optionally substituted aryl, such as optionally substituted phenyl and optionally substituted naphthyl. In yet still other embodiments, one or both of $R^{28}$ can be an optionally substituted aryl($C_{1-6}$ alkyl). In some embodiments, one or both of $R^{28}$ can be an optionally substituted benzyl. In some embodiments, one or both of $R^{28}$ can be an optionally substituted $C_{1-6}$haloalkyl, for example, $CF_3$. In some embodiments, one or both of $R^{28}$ can be hydrogen. In some embodiments, $R^{14}$ and $R^{15}$ can be the same. In other embodiments, $R^{14}$ and $R^{15}$ can be different.

In some embodiments, $R^{14}$ can be $O^-$, hydroxy or an —O-optionally substituted $C_{1-6}$ alkyl, and $R^{15}$ and $R^5$ together can be O, such that a compound of Formula (I), or a pharmaceutically acceptable salt thereof, has the structure:

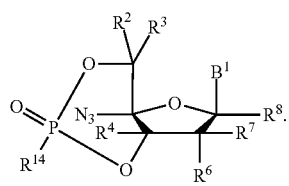

In some embodiments, $R^{14}$ can be $O^-$. In some embodiments, $R^{14}$ can be hydroxy. In some embodiments, $R^{14}$ can be an —O-optionally substituted $C_{1-6}$ alkyl, for example an optionally substituted version of methoxy, ethoxy, n-propoxy, isopropoxy, n-butoxy, isobutoxy, tert-butoxy, pentoxy (branched and straight-chained), and hexoxy (branched and straight-chained). In some embodiments, $R^{14}$ can be an —O-unsubstituted $C_{1-6}$ alkyl.

In some embodiments, $R^1$ can be

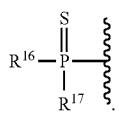

In some embodiment, $R^{16}$ can be selected from an —O-optionally substituted aryl, an —O-optionally substituted heteroaryl and an —O-optionally substituted heterocyclyl, and $R^{17}$ can be an optionally substituted N-linked amino acid or an optionally substituted N-linked amino acid ester derivative. In some embodiments, $R^{16}$ can be an —O-optionally substituted heteroaryl. In other embodiments, $R^{16}$ can be an —O-optionally substituted heterocyclyl. In some embodiments, $R^{16}$ can be an —O-optionally substituted aryl. For example, the optionally substituted aryl can be an optionally substituted phenyl or an optionally substituted naphthyl. If $R^{16}$ is an —O-substituted phenyl or —O-substituted naphthyl, the phenyl and naphthyl ring can be substituted one or more times. Suitable substituents that can be present on optionally substituted phenyl and an optionally substituted naphthyl include electron-donating groups and electron-withdrawing groups. In some embodiments, $R^{16}$ can be an —O-para-substituted phenyl. In other embodiment, $R^{16}$ can be an —O-unsubstituted phenyl or an —O-unsubstituted naphthyl. In some embodiments, $R^{17}$ can be an optionally substituted N-linked amino acid or an optionally substituted N-linked amino acid ester derivative of any one of the following amino acids alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Suitable ester derivatives include those described herein, such as an optionally substituted $C_{1-6}$ alkyl ester, an optionally substituted $C_{3-6}$ cycloalkyl ester, an optionally substituted $C_{6-10}$ aryl ester, and an optionally substituted aryl($C_{1-6}$ alkyl) ester.

In some embodiments, $R^{16}$ and $R^{17}$ can each have the structure

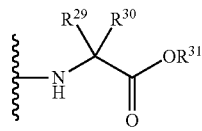

wherein each $R^{29}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); each $R^{30}$ can be hydrogen or an optionally substituted $C_{1-4}$-alkyl; and each $R^{31}$ can be selected from hydrogen, an optionally substituted $C_{1-6}$-alkyl, an optionally substituted $C_{3-6}$ cycloalkyl, an optionally substituted aryl, an optionally substituted aryl ($C_{1-6}$ alkyl) and an optionally substituted $C_{1-6}$ haloalkyl, or the $R^{29}$ and the $R^{30}$ attached to the same carbon can be taken together to form an optionally substituted $C_{3-6}$ cycloalkyl.

In some embodiments, one or both of $R^{29}$ can be hydrogen. In other embodiments, one or both of $R^{29}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl and tert-butyl. When $R^{29}$ is substituted, $R^{29}$ can be substituted with one or more substituents selected from N-amido, mercapto, alkylthio, an optionally substituted aryl, hydroxy, an optionally substituted heteroaryl, O-carboxy, and amino. In some embodiment, one or both of $R^{29}$ can be an unsubstituted $C_{1-6}$-alkyl, such as methyl, ethyl, n-propyl, iso-propyl, n-butyl, isobutyl, tert-butyl, pentyl (branched and straight-chained), and hexyl (branched and straight-chained). In an embodiment, one or both of $R^{29}$ can be methyl.

In some embodiments, one or both of $R^{30}$ can be hydrogen. In other embodiments, one or both of $R^{30}$ can be an optionally substituted $C_{1-4}$-alkyl, such as methyl, ethyl, n-propyl, iso-propyl, n-butyl, isobutyl and tert-butyl. In an embodiment, one or both of $R^{30}$ can be methyl. In some embodiments, one or both of $R^{29}$ and $R^{30}$ attached to the same carbon can be taken together to form an optionally substituted $C_{3-6}$ cycloalkyl. Depending on the groups that are selected for $R^{29}$ and $R^{30}$, the carbon to which $R^{29}$ and $R^{30}$ are attached may be a chiral center. In some embodiment, the carbon to which $R^{29}$ and $R^{30}$ are attached may be a (R)-chiral center. In other embodiments, the carbon to which $R^{29}$ and $R^{30}$ are attached may be a (S)-chiral center.

In some embodiments, one or both of $R^{31}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments, one or both of $R^{31}$ can be an optionally substituted $C_{3-6}$ cycloalkyl. For example, $R^{31}$ can be an optionally substituted cyclopropyl, an optionally substituted cyclobutyl, an optionally substituted cyclopentyl or an optionally substituted cyclohexyl. In some embodiments, $R^{31}$ can be an optionally substituted cyclohexyl. In still other embodiments, one or both of $R^{31}$ can be an optionally substituted aryl, such as optionally substituted phenyl and optionally substituted naphthyl. In yet still other embodiments, one or both of $R^{31}$ can be an optionally substituted aryl($C_{1-6}$ alkyl). In some embodiments, one or both of $R^{31}$ can be an optionally substituted benzyl. In some embodiments, one or both of $R^{31}$ can be an optionally substituted $C_{1-6}$ haloalkyl, for example, $CF_3$. In some embodiments, one or both of $R^{31}$ can be hydrogen. In some embodiments, $R^{16}$ and $R^{17}$ can be the same. In other embodiments, $R^{16}$ and $R^{17}$ can be different.

In some embodiments, $R^{16}$ can be $O^-$, hydroxy or an —O-optionally substituted $C_{1-6}$ alkyl, and $R^{17}$ and $R^5$ together can be O, such that a compound of Formula (I), or a pharmaceutically acceptable salt thereof, has the structure:

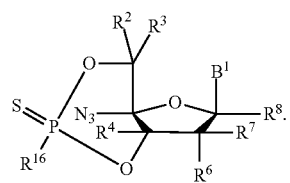

In some embodiments, $R^{16}$ can be $O^-$. In some embodiments, $R^{16}$ can be hydroxy. In some embodiments, $R^{16}$ can be an —O-optionally substituted $C_{1-6}$ alkyl, for example an optionally substituted version of methoxy, ethoxy, n-propoxy, iso-propoxy, n-butoxy, isobutoxy, tert-butoxy, pentoxy (branched and straight-chained), and hexoxy (branched and straight-chained). In some embodiments, $R^{16}$ can be an —O-unsubstituted $C_{1-6}$ alkyl.

Examples of suitable

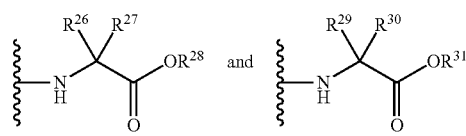

groups include the following:

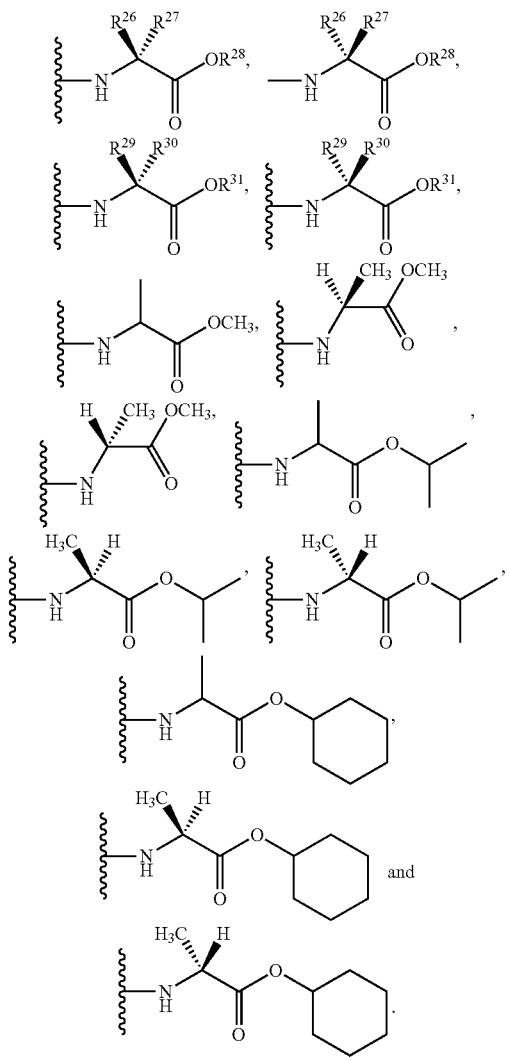

The substituents attached to the 5'-position of a compound of Formula (I) can vary. In some embodiments, $R^2$ and $R^3$ can be the same. In other embodiments, $R^2$ and $R^3$ can be different. In some embodiments, $R^2$ and $R^3$ can be both hydrogen. In some embodiments, at least of $R^2$ and $R^3$ can be an optionally substituted $C_{1-6}$-alkyl; and the other of $R^2$ and $R^3$ can be hydrogen. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, at least one of $R^2$ and $R^3$ can be methyl, and the other of $R^2$ and $R^3$ can be hydrogen. In other embodiments, at least of $R^2$ and $R^3$ can be an optionally substituted $C_{1-6}$-haloalkyl, and the other of $R^2$ and $R^3$ can be hydrogen. One example of a suitable optionally substituted $C_{1-6}$-haloalkyl is $CF_3$. In some embodiments, at least one of $R^2$ and $R^3$ can be hydrogen; and the other of $R^2$ and $R^3$ can be an optionally substituted $C_{1-6}$ alkyl or an optionally substituted $C_{1-6}$ haloalkyl; and $R^1$ can be hydrogen. When the substituents attached to the 5'-carbon make the 5'-carbon chiral, in some embodiments, the 5'-carbon can be a (R)-stereocenter. In other embodiments, the 5'-carbon can be an (S)-stereocenter.

The substituents attached to the 2'-carbon and the 3'-carbon can also vary. In some embodiments, $R^4$ can be hydrogen. In other embodiments, $R^4$ can be a halogen. Example of halogens include F, Cl, Br and I. In still other embodiments, $R^4$ can be an optionally substituted $C_{1-6}$ alkyl. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments $R^4$ can be —$OR^{18}$. When $R^{18}$ is hydrogen, $R^4$ can be hydroxy. Alternatively, when $R^{18}$ is an optionally substituted $C_{1-6}$ alkyl, $R^4$ can be an optionally substituted $C_{1-6}$ alkoxy. Suitable alkoxy groups include methoxy, ethoxy, n-propoxy, isopropoxy, n-butoxy, isobutoxy, tert-butoxy, pentoxy (branched and straight-chained), and hexoxy (branched and straight-chained). In some embodiments, $R^4$ can be —$OC(=O)R^{19}$, in which $R^{19}$ can be an optionally substituted $C_{1-6}$ alkyl. Examples of suitable $C_{1-6}$ alkyl groups are described herein.

In some embodiments, $R^5$ can be hydrogen. In other embodiments, $R^5$ can be a halogen, including those described herein. In still other embodiments, $R^5$ can be an optionally substituted $C_{1-6}$ alkyl. In yet still other embodiments $R^5$ can be —$OR^{20}$. In some embodiments, $R^5$ can be —OH. In other embodiments, $R^{20}$ can be —$OR^{20}$, wherein $R^{20}$ can be an optionally substituted $C_{1-6}$ alkyl. In still other embodiments, $R^5$ can be —$OC(=O)R^{21}$, in which $R^{21}$ can be an optionally substituted $C_{1-6}$ alkyl. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained).

In some embodiments, $R^6$ can be hydrogen. In other embodiments, $R^6$ can be a halogen. In still other embodiments, $R^6$ can be an optionally substituted $C_{1-6}$ alkyl. In yet still other embodiments $R^6$ can be —$OR^{22}$, wherein $R^{22}$ can be hydrogen. In some embodiments, $R^6$ can be —$OR^{22}$, wherein $R^{22}$ can be an optionally substituted $C_{1-6}$ alkyl. Examples of substituents that can be $R^6$ include, but are not limited to, methoxy, ethoxy, n-propoxy, isopropoxy, n-butoxy, isobutoxy, tert-butoxy, pentoxy (branched or straight-chained) and hexoxy (branched or straight-chained). In some embodiments, $R^6$ can be —$OC(=O)R^{23}$, wherein $R^{23}$ can be an optionally substituted $C_{1-6}$ alkyl. Examples of suitable $C_{1-6}$ alkyl groups are described herein. In some embodiments, $R^6$ can be hydrogen, halogen or —$OR^{22}$.

In some embodiments, $R^7$ can be hydrogen. In other embodiments, $R^7$ can be a halogen. In still other embodiments, $R^7$ can be an optionally substituted $C_{1-6}$ alkyl. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In yet still other embodiments $R^7$ can be —$OR^{24}$, wherein $R^{24}$ can be hydrogen or an optionally substituted $C_{1-6}$ alkyl. A non-limiting list of $R^7$ groups include hydroxy, methoxy, ethoxy, n-propoxy, isopropoxy, n-butoxy, isobutoxy, tert-butoxy, pentoxy (branched and straight-chained), and hexoxy (branched and straight-chained). In some embodiments, $R^7$ can be —OC(=O)$R^{25}$, wherein $R^{25}$ can be an optionally substituted $C_{1-6}$ alkyl, such as those described herein. In some embodiments, $R^7$ is hydrogen or halogen. In some embodiments, $R^7$ is —O$R^{24}$ or an optionally substituted $C_{1-6}$ alkyl.

In some embodiments, $R^5$ and $R^6$ can both be hydroxy. In still other embodiments, $R^5$ and $R^6$ can both be both oxygen atoms and linked together by a carbonyl group, for example, —O—C(=O)—O—. In some embodiments, at least one of $R^6$ and $R^7$ can be a halogen. In some embodiments, $R^6$ and $R^7$ can both be a halogen. In some embodiments, $R^6$ can be hydroxy and $R^7$ can be a halogen. In other embodiments, $R^5$ and $R^6$ can be both hydroxy groups, and $R^7$ can be a halogen. In still other embodiments, $R^6$ can be hydrogen and $R^7$ can be an optionally substituted $C_{1-6}$ alkyl. In yet still other embodiments, at least one of $R^5$ and $R^6$ can be a hydroxy and $R^7$ can be an optionally substituted $C_{1-6}$ alkyl. In some embodiments, at least one of $R^5$ and $R^6$ can be a hydroxy and $R^7$ can be a halogen. For example, $R^5$ can be hydroxy, $R^6$ can be a hydrogen and $R^7$ can be a halogen; or $R^5$ can be hydrogen, $R^6$ can be hydroxy, and $R^7$ can be a halogen; $R^5$ can be hydroxy, $R^6$ can be hydroxy and $R^7$ can be a halogen. In other embodiments, at least one of $R^5$ and $R^6$ can be an optionally substituted $C_{1-6}$ alkoxy. In some embodiments, $R^5$ and $R^7$ can be hydroxy, and $R^6$ can be hydrogen. In some embodiments, $R^5$ can be a hydroxy, and both $R^6$ and $R^7$ can be halogen. In some embodiments, $R^5$ can be a hydroxy and $R^6$ can be halogen.

In some embodiments, $R^8$ can be hydrogen. In other embodiments, $R^8$ can be an optionally substituted $C_{1-6}$ alkyl. Examples of $R^8$ groups include optionally substituted variants of the following: methyl, ethyl, n-propyl, isopropyl, n-butyl, isobutyl, tert-butyl, pentyl (branched and straight-chained), and hexyl (branched and straight-chained). In still other embodiments, can be an optionally substituted $C_{1-6}$ haloalkyl. In some embodiments, $R^8$ can be $CF_3$.

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

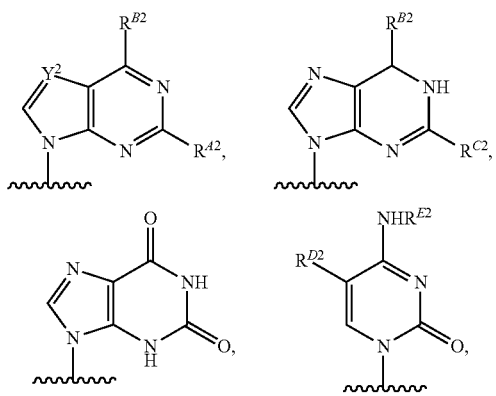

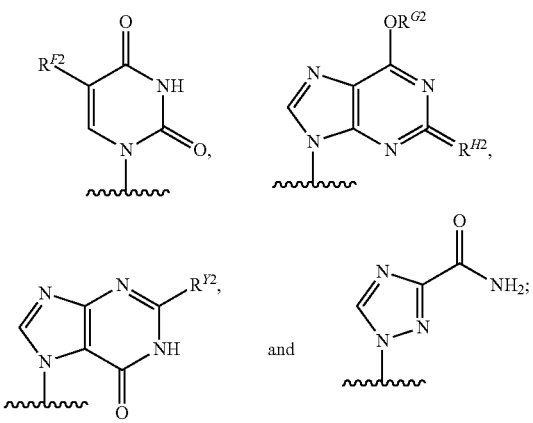

wherein: $R^{A2}$ can be selected from hydrogen, halogen and NHR$^{J2}$, wherein $R^{J2}$ can be selected from hydrogen, —C(=O)$R^{K2}$ and —C(=O)O$R^{L2}$; $R^{B2}$ can be halogen or NHR$^{W2}$, wherein $R^{W2}$ can be selected from hydrogen, an optionally substituted $C_{1-6}$ alkyl, an optionally substituted $C_{2-6}$ alkenyl, an optionally substituted $C_{3-8}$ cycloalkyl, —C(=O)$R^{M2}$ and —C(=O)O$R^{N2}$; $R^{C2}$ can be hydrogen or NHR$^{O2}$, wherein $R^{O2}$ can be selected from hydrogen, —C(=O)$R^{P2}$ and —C(=O)O$R^{Q2}$; $R^{D2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{E2}$ can be selected from hydrogen, an optionally substituted $C_{1-6}$ alkyl, an optionally substituted $C_{3-8}$ cycloalkyl, —C(=O)$R^{R2}$ and —C(=O)O$R^{S2}$; $R^{F2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^2$ can be N (nitrogen) or CR$^{J2}$, wherein $R^{J2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2}$ can be an optionally substituted $C_{1-6}$ alkyl; $R^{H2}$ can be hydrogen or NHR$^{T2}$, wherein $R^{T2}$ can be independently selected from hydrogen, —C(=O)$R^{U2}$ and —C(=O)O$R^{V2}$, $R^{Y2}$ can be hydrogen or NHR$^{Z2}$, wherein $R^{Z2}$ can be selected from hydrogen, —C(=O)$R^{AA2}$ and —C(=O)O$R^{BB2}$; and $R^{K2}$, $R^{L2}$, $R^{M2}$, $R^{N2}$, $R^{P2}$, $R^{Q2}$, $R^{R2}$, $R^{S2}$, $R^{U2}$, $R^{V2}$, $R^{AA2}$ and $R^{BB2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloalkynyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted."

In some embodiments, $B^1$ can be

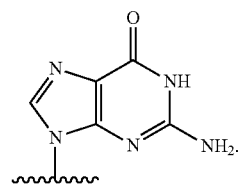 [SMILES: *n1cnc2c(=O)[nH]c(N)nc21]

In other embodiments, $B^1$ can be

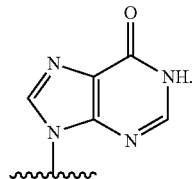 [SMILES: *n1cnc2c(=O)[nH]cnc21]

In still other embodiments, $B^1$ can be

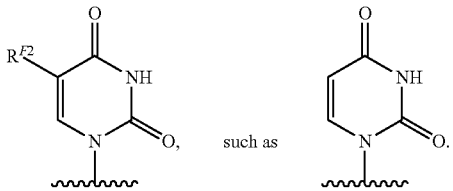 such as

In yet still other embodiments, $B^1$ can be

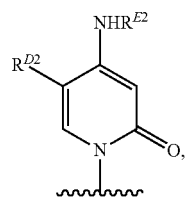

for example,

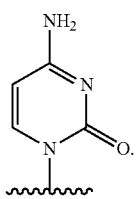 [SMILES: *n1ccc(N)nc1=O]

In some embodiments, $R^{D2}$ can be hydrogen. In other embodiments, $R^{B1}$ can be

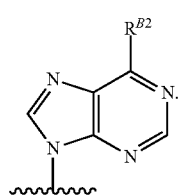

In some embodiments, $R^{B2}$ can be $NH_2$. In other embodiments, $R^{B2}$ can be $NHR^{W2}$, wherein $R^{W2}$ can be —C(=O)$R^{M2}$ or —C(=O)OR$^{N2}$. In still other embodiments, $B^1$ can be

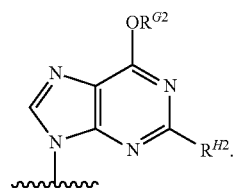

In some embodiments, $B^1$ can be

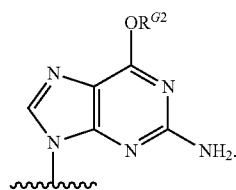

In other embodiments, when $R^2$, $R^3$, $R^4$, and $R^8$ are all hydrogen, then $R^1$ cannot be hydrogen. In still other embodiments, when $R^2$ and $R^3$ are hydrogen, then $R^1$ cannot be hydrogen. In yet still other embodiments, $R^1$ cannot be hydrogen. In some embodiments, $R^1$ cannot be hydrogen when $B^1$ is adenine, guanine, 5-methyluracil, uracil or cytosine. In other embodiments, when $R^2$ and $R^3$ are hydrogen and at least one of $R^5$ and $R^6$ is hydroxy, alkoxy or aryloxy, then $R^1$ cannot be hydrogen.

In some embodiments, when $R^2$ and $R^3$ are both hydrogen, $R^5$ is hydroxy, $R^4$ and $R^6$ are both hydrogen, $R^7$ is halogen, $R^8$ is hydrogen, and $B^1$ is

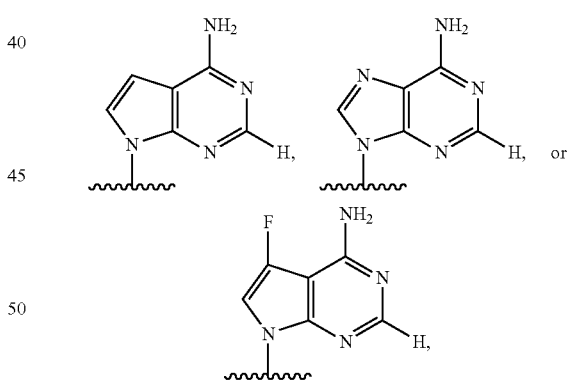

then $R^1$ cannot be

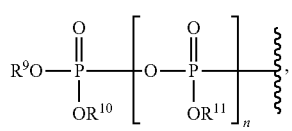

wherein, n is 0 or 2; and $R^9$, $R^{10}$, and each $R^{11}$ are absent or hydrogen. In other embodiments, when $R^2$ and $R^3$ are both hydrogen, at least one of $R^5$ and $R^6$ are hydroxy, and $B^1$ is

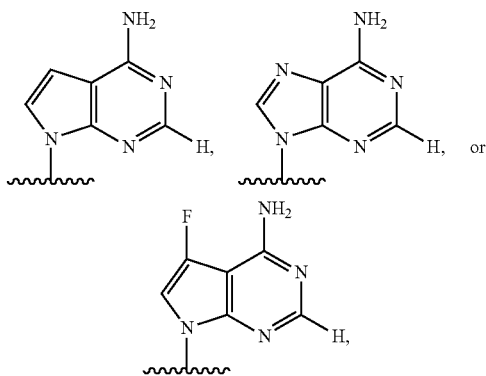

then R¹ cannot be

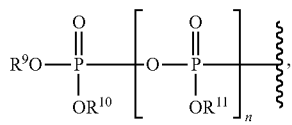

wherein, n is 0, 1 or 2; and $R^9$, $R^{10}$, and each $R^{11}$ are independently absent or hydrogen. In still other embodiments, when $R^2$ and $R^3$ are both hydrogen, at least one of $R^5$ and $R^6$ are hydroxy, then $R^1$ cannot be

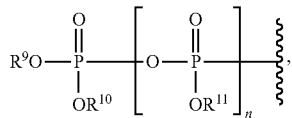

wherein, n is 0, 1 or 2; and $R^9$, $R^{10}$, and each $R^{11}$ are independently absent or hydrogen. In yet still other embodiments, when at least one of $R^5$ and $R^6$ are hydroxy, then $R^1$ cannot be

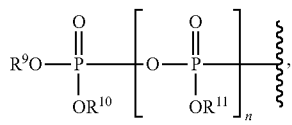

wherein, n is 0, 1 or 2; and $R^9$, $R^{10}$, and each $R^{11}$ are independently absent or hydrogen. In some embodiments, $R^1$ cannot be

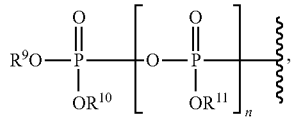

wherein, n is 0; and $R^9$ and $R^{10}$ are independently absent or hydrogen. In other embodiments, $R^1$ cannot be

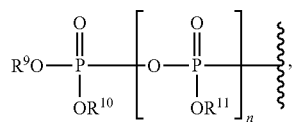

wherein, n is 1; and $R^9$, $R^{10}$, and $R^{11}$ are independently absent or hydrogen. In still other embodiments, $R^1$ cannot be

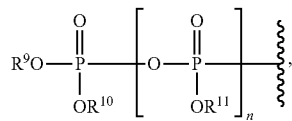

wherein, n is 2; and $R^9$, $R^{10}$, and each $R^{11}$ are independently absent or hydrogen. In still other embodiments, when at least one of $R^2$ and $R^3$ is an optionally substituted $C_{1-6}$ alkyl, at least one of $R^5$ and $R^6$ are hydroxy, then $R^1$ cannot be

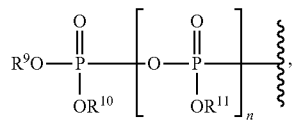

wherein, n is 0, 1 or 2; and $R^9$, $R^{10}$, and each $R^{11}$ are independently absent or hydrogen. In yet still other embodiments, $B^1$ cannot be adenine or an optionally substituted adenine when at least one of $R^2$ and $R^3$ is not hydrogen. In some embodiments, when at least one of $R^2$ and $R^3$ is an optionally substituted $C_{1-6}$ alkyl, then $B^1$ cannot be an optionally substituted adenine or an optionally substituted adenine with one or more protected amino groups.

In some embodiments, when $R^1$ is

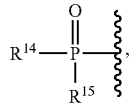

$R^2$ and $R^3$ are both hydrogen, $R^4$ is hydrogen, $R^5$ is OH, $R^6$ is selected from halogen, hydrogen, and hydroxy, $R^7$ is selected from halogen, hydrogen, methyl, and hydroxy, $R^8$ is hydrogen, $B^1$ is selected from

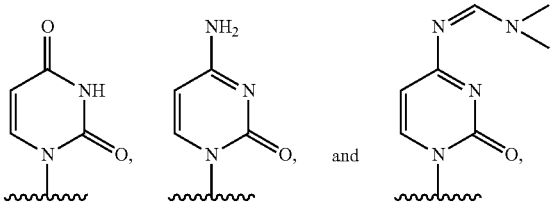

$R^{14}$ is an —O-optionally substituted aryl, then $R^{15}$ cannot be

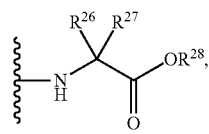

wherein $R^{26}$ is selected from hydrogen and $C_{1-4}$ alkyl; $R^{27}$ is selected from hydrogen, —CH$_3$, —CH$_2$CH$_3$, —CH(CH$_3$)$_2$, —CH$_2$CH(CH$_3$)$_2$, —CH$_2$CH$_2$SCH$_3$, —CH$_2$CH$_2$C(=O)OCH$_2$CH$_3$, —CH$_2$C(=O)OCH$_2$CH$_3$, —CH$_2$-indol-3-yl, —CH$_2$-phenyl, unsubstituted cyclopentyl and —CH(CH$_2$CH$_3$)CH$_3$; and $R^{28}$ is selected from unsubstituted $C_{1-4}$-alkyl, and unsubstituted benzyl and CH$_2$CF$_3$; In some embodiments, when $B^1$ is selected from

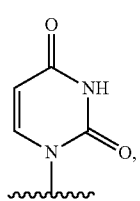 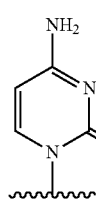 and 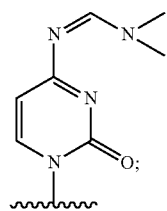

and $R^{14}$ is an —O-optionally substituted aryl, then $R^{15}$ cannot be

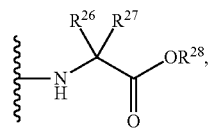

wherein $R^{26}$ is selected from hydrogen and an optionally substituted $C_{1-4}$ alkyl; $R^{27}$ is selected from hydrogen, —CH$_3$, —CH$_2$CH$_3$, —CH(CH$_3$)$_2$, —CH$_2$CH(CH$_3$)$_2$, —CH$_2$CH$_2$SCH$_3$, —CH$_2$CH$_2$C(=O)OCH$_2$CH$_3$, —CH$_2$C(=O)OCH$_2$CH$_3$, —CH$_2$C(=O)OCH(CH$_3$)$_2$, —CH$_2$-indol-3-yl, —CH$_2$-phenyl, cyclopentyl and —CH(CH$_2$CH$_3$)CH$_3$; and $R^{28}$ is selected from an optionally substituted $C_{1-4}$-alkyl and an optionally substituted benzyl. In other embodiments, when $R^1$ is

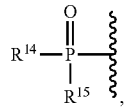

$R^2$, $R^3$, $R^4$, $R^7$, and $R^8$ are all hydrogen, $R^5$ is hydroxy, $R^6$ is hydroxy, $R^{14}$ is —O-naphthyl, $R^{15}$ is

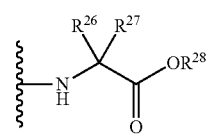

wherein $R^{26}$ is hydrogen, $R^{27}$ is methyl and $R^{28}$ is benzyl, then $B^1$ cannot be

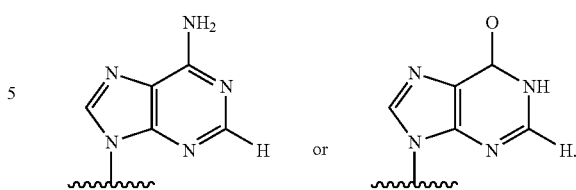

In still other embodiments, when $R^1$ is

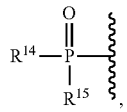

$R^2$, $R^3$, $R^7$ and $R^8$ are all hydrogen, $R^5$ is hydroxy, $R^6$ is hydroxy, $R^{14}$ is —O-phenyl, $R^{15}$ is

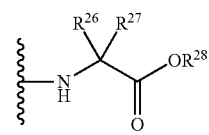

wherein $R^{26}$ and $R^{27}$ are taken together to form an substituted cyclopentyl ring and $R^{28}$ is a $C_{1-4}$ alkyl or benzyl, then $B^1$ cannot be

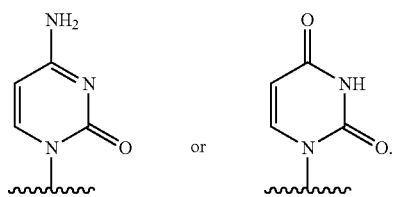 [SMILES: *n1ccc(N)nc1=O ; "or" ; *n1ccc(=O)[nH]c1=O]

In yet still other embodiments, when $R^2$ and $R^3$ are hydrogen, then $R^1$ cannot be

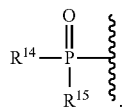

In some embodiments, $R^1$ can be

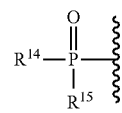

when at least one of $R^2$ and $R^3$ is an optionally substituted $C_{1-6}$ alkyl or an optionally substituted $C_{1-6}$ haloalkyl. In other embodiments, $R^1$ cannot be

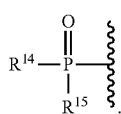

In still other embodiments, when $R^2$ and $R^3$ are hydrogen, and at least one of $R^5$ and $R^6$ are hydroxy, then $R^1$ cannot be

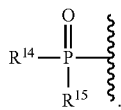

In yet still other embodiments, when $R^5$ is hydroxy, $R^1$ cannot be

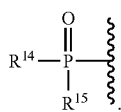

In some embodiments, at least one of $R^2$ and $R^3$ cannot be hydrogen. In some embodiments, at least of one of $R^5$ and $R^6$ cannot hydroxy. For example, $R^5$ cannot be hydroxy, $R^6$ cannot be hydroxy, or both of $R^5$ and $R^6$ cannot be hydroxy.

Methods of Use:

Some embodiments described herein relate to a method of ameliorating, treating and/or preventing a viral infection selected from a paramyxovirus viral infection and an orthomyxovirus viral infection, which can include administering a therapeutically effective amount of a compound of Formula (II), or a pharmaceutically acceptable salt thereof:

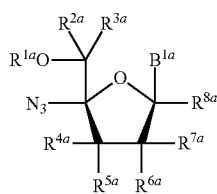

(II)

wherein $B^{1a}$ can be selected from an optionally substituted heterocyclic base and an optionally substituted heterocyclic base with a protected amino group; $R^{1a}$ can be selected from hydrogen, an optionally substituted acyl

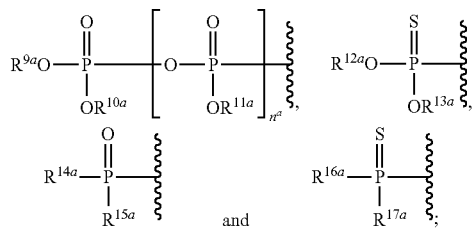

$n^a$ can be 0, 1 or 2; $R^{2a}$ and $R^{3a}$ can be independently selected hydrogen, an optionally substituted $C_{1-6}$ alkyl and an optionally substituted $C_{1-6}$ haloalkyl; $R^{4a}$ can be selected hydrogen, halogen, optionally substituted $C_{1-6}$ alkyl, —$OR^{18a}$ and —OC(=O)$R^{19a}$; $R^{5a}$ can be selected from hydrogen, halogen, optionally substituted $C_{1-6}$ alkyl, —$OR^{20a}$ and —OC(=O)$R^{21a}$, or when $R^{1a}$ is

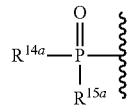

and $R^{14a}$ is O⁻, hydroxy or an —O-optionally substituted $C_{1-6}$ alkyl, then $R^{15a}$ and $R^{5a}$ together can be O, or when $R^{1a}$ is

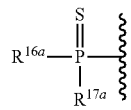

and $R^{16a}$ is O⁻, hydroxy or an —O-optionally substituted $C_{1-6}$ alkyl, then $R^{17a}$ and $R^{5a}$ together can be O; $R^{6a}$ can be selected from hydrogen, halogen, optionally substituted $C_{1-6}$ alkyl, —$OR^{22a}$ and —OC(=O)$R^{23a}$; or $R^{5a}$ and $R^{6a}$ can be both oxygen atoms and linked together by a carbonyl group; $R^{7a}$ can be selected from hydrogen, halogen, optionally substituted $C_{1-6}$ alkyl, —$OR^{24a}$ and —OC(=O)$R^{25a}$; $R^{8a}$ can be selected from hydrogen, an optionally substituted $C_{1-6}$ alkyl and an optionally substituted $C_{1-6}$ haloalkyl; $R^{9a}$, $R^{10a}$, each $R^{11a}$, $R^{12a}$ and $R^{13a}$ can be independently absent or hydrogen; $R^{14a}$ can be selected from an —O-optionally substituted aryl, an —O-optionally substituted heteroaryl and an —O-optionally substituted heterocyclyl, and $R^{15a}$ can be an optionally substituted N-linked amino acid or an optionally substituted N-linked amino acid ester derivative; or $R^{14a}$ can be an optionally substituted N-linked amino acid or an optionally substituted N-linked amino acid ester derivative, and $R^{15a}$ can be an optionally substituted N-linked amino acid or an optionally substituted N-linked amino acid ester derivative; or $R^{14a}$ can be O⁻, hydroxy or an —O-optionally substituted $C_{1-6}$ alkyl, and $R^{15a}$ and $R^{5a}$ together can be O; $R^{16a}$ can be selected from an —O-optionally substituted aryl, an —O-optionally substituted heteroaryl and an —O-optionally substituted heterocyclyl, and $R^{17a}$ can be an optionally substituted N-linked amino acid or an optionally substituted N-linked amino acid ester derivative; or $R^{16a}$ can be an optionally substituted N-linked amino acid or an optionally substituted N-linked amino acid ester derivative, and $R^{17a}$ can be an optionally substituted N-linked amino acid or an optionally substituted N-linked amino acid ester derivative; or $R^{16a}$ can be O⁻, hydroxy or an —O-optionally substituted $C_{1-6}$ alkyl, and $R^{17a}$ and $R^{5a}$ together can be O; $R^{18a}$, $R^{20a}$, $R^{22a}$ and $R^{24a}$ can be independently hydrogen or an optionally substituted $C_{1-6}$ alkyl; and $R^{19a}$, $R^{21a}$, $R^{23a}$ and $R^{25a}$ can be independently an optionally substituted $C_{1-6}$ alkyl.

Other embodiments described herein relate to a method of inhibiting viral replication of a virus selected from a paramyxovirus and an orthomyxovirus, which can include contacting a cell infected with the virus with an effective amount of a compound of Formula (II) (including a compound of Formula (IIa), or a pharmaceutically acceptable salt thereof.

In some embodiments, the paramyxovirus viral infection can be a respiratory syncytial viral infection. In some embodiments, a therapeutically effective amount of one or more compounds of Formula (II), or a pharmaceutically acceptable salt thereof, (including a compound of Formula (IIa), or a pharmaceutically acceptable salt thereof) can be used to treat and/or ameliorate a respiratory syncytial viral infection. For example, the respiratory syncytial viral infection can be from an infection by a type RSV A strain and/or a type RSV B strain. In some embodiments, a therapeutically effective amount of one or more compounds of Formula (II), or a pharmaceutically acceptable salt thereof, (including a compound of Formula (IIa), or a pharmaceutically acceptable salt thereof) can be used to prevent a respiratory syncytial viral infection. In some embodiments, an effective amount of one or more compounds of Formula (II), or a pharmaceutically acceptable salt thereof, (including a compound of Formula (IIa), or a pharmaceutically acceptable salt thereof) can be used to inhibit the replication a respiratory syncytial virus. In some embodiments, a therapeutically effective amount of one or more compounds of Formula (II), or a pharmaceutically acceptable salt thereof, (including a compound of Formula (IIa), or a pharmaceutically acceptable salt thereof) can be used to inhibit the RSV polymerase complex. In some embodiments, a therapeutically effective amount of one or more compounds of Formula (II), or a pharmaceutically acceptable salt thereof, (including a compound of Formula (IIa), or a pharmaceutically acceptable salt thereof) can be used treat and/or ameliorate an upper respiratory viral infection caused by a RSV virus infection. In some embodiments, a therapeutically effective amount of one or more compounds of Formula (II), or a pharmaceutically acceptable salt thereof, (including a compound of Formula (IIa), or a pharmaceutically acceptable salt thereof) can be used treat and/or ameliorate a lower respiratory viral infection caused by a RSV virus infection. In some embodiments, a therapeutically effective amount of one or more compounds of Formula (II), or a pharmaceutically acceptable salt thereof, (including a compound of Formula (IIa), or a pharmaceutically acceptable salt thereof) can be used treat and/or ameliorate one or more symptoms of a RSV virus infection (such as those described herein). In some embodiments, a therapeutically effective amount of one or more compounds of Formula (II), or a pharmaceutically acceptable salt thereof, (including a compound of Formula (IIa), or a pharmaceutically acceptable salt thereof) can be used treat and/or ameliorate bronchiolitis and/or tracheobronchitis due to a RSV virus infection. In some embodiments, a therapeutically effective amount of one or more compounds of Formula (II), or a pharmaceutically acceptable salt thereof, (including a compound of Formula (IIa), or a pharmaceutically acceptable salt thereof) can be used treat and/or ameliorate pneumonia due to a RSV infection. In some embodiments, a therapeutically effective amount of one or more compounds of Formula (II), or a pharmaceutically acceptable salt thereof, (including a compound of Formula (IIa), or a pharmaceutically acceptable salt thereof) can be used treat and/or ameliorate coup due to a RSV virus infection.

In some embodiments, the orthomyxovirus viral infection can be an influenza viral infection. In some embodiments, a therapeutically effective amount of one or more compounds of Formula (II), or a pharmaceutically acceptable salt thereof, (including a compound of Formula (IIa), or a pharmaceutically acceptable salt thereof) can be used to prevent an influenza viral infection. In some embodiments, an effective amount of one or more compounds of Formula (II), or a pharmaceutically acceptable salt thereof, (including a compound of Formula (IIa), or a pharmaceutically acceptable salt thereof) can be used to inhibit the replication an influenza virus. In some embodiments, a therapeutically effective amount of one or more compounds of Formula (II), or a pharmaceutically acceptable salt thereof, (including a compound of Formula (IIa), or a pharmaceutically acceptable salt thereof) can be used to inhibit the influenza polymerase complex. In some embodiments, the influenza viral infection can be an influenza A viral infection. In other embodiments, the influenza viral infection can be an influenza B viral infection. In some embodiments, a compound of Formula (II), or a pharmaceutically acceptable salt thereof, (including a compound of Formula (IIa), or a pharmaceutically acceptable salt thereof) can be used to treat and/or ameliorate one or more subtypes of influenza. For example, a compound of Formula (II), or a pharmaceutically acceptable salt thereof, (including a compound of Formula (IIa), or a pharmaceutically acceptable salt thereof), can be used to treat H1N1 and/or H3N2.

In some embodiments, a therapeutically effective amount of one or more compounds of Formula (I), or a pharmaceutically acceptable salt thereof, can be used to treat and/or ameliorate a respiratory syncytial viral infection. In other embodiments, a therapeutically effective amount of one or more compounds of Formula (I), or a pharmaceutically acceptable salt thereof, can be used to treat and/or ameliorate an influenza viral infection. In some embodiments, a therapeutically effective amount of one or more compounds of Formula (I), or a pharmaceutically acceptable salt thereof, can be used to prevent a respiratory syncytial viral infection. In other embodiments, a therapeutically effective amount of one or more compounds of Formula (I), or a pharmaceutically acceptable salt thereof, can be used to prevent an influenza viral infection. In some embodiments, a therapeutically effective amount of one or more compounds of Formula (I), or a pharmaceutically acceptable salt thereof, can be used to inhibit the replication a respiratory syncytial virus. In some embodiments, a therapeutically effective amount of one or more compounds of Formula (I), or a pharmaceutically acceptable salt thereof, can be used to inhibit the replication an influenza virus. In some embodiments, a therapeutically effective amount of one or more compounds of Formula (I), or a pharmaceutically acceptable salt thereof, can be used to inhibit the RSV polymerase complex. In some embodiments, a therapeutically effective amount of one or more compounds of Formula (I), or a pharmaceutically acceptable salt thereof, can be used to inhibit the influenza polymerase complex. In some embodiments, a therapeutically effective amount of one or more compounds of Formula (I), or a pharmaceutically acceptable salt thereof, can be used treat and/or ameliorate an upper respiratory viral infection caused by a RSV virus infection. In some embodiments, a therapeutically effective amount of one or more compounds of Formula (I), or a pharmaceutically acceptable salt thereof, can be used treat and/or ameliorate a lower respiratory viral infection caused by a RSV virus infection. In some embodiments, a therapeutically effective amount of one or more compounds of Formula (I), or a pharmaceutically acceptable salt thereof, can be used treat and/or ameliorate one or more symptoms of a RSV virus infection (such as those described herein). In some embodiments, a therapeutically effective amount of one or more compounds of Formula (I), or a pharmaceutically acceptable salt thereof, can be used treat and/or ameliorate bronchiolitis and/or tracheobronchitis due to a RSV virus infection. In some embodiments, a therapeutically effective amount of one or more compounds of Formula (I), or a pharmaceutically acceptable salt thereof, can be used treat and/or ameliorate pneumonia due to a RSV virus infection. In some embodiments, a therapeutically effective amount of one or more compounds of Formula (I), or a pharmaceutically acceptable salt thereof, can be used treat and/or ameliorate coup due to a RSV virus infection.

In some embodiments, a therapeutically effective amount of one or more compounds of Formula (I), or a pharmaceutically acceptable salt thereof, can be used to prevent an influenza viral infection. In some embodiments, the influenza viral infection can be an influenza A viral infection. In other embodiments, the influenza viral infection can be an influenza B viral infection. In some embodiments, a compound of Formula (I), or a pharmaceutically acceptable salt thereof, can be used to treat and/or ameliorate one or more subtypes of influenza. For example, a compound of Formula (I), or a pharmaceutically acceptable salt thereof, can be used to treat H1N1 and/or H3N2. The one or more compounds of Formula (I) or a pharmaceutically acceptable salt thereof, that can be used to treat, ameliorate and/or prevent a paramyxovirus and/or or an orthomyxovirus viral infection can be a compound of Formula (I), or pharmaceutically acceptable salt thereof, provided in any of the embodiments described in paragraphs [0082]-[0117].

In some embodiments, $R^{1a}$ can be hydrogen. In some embodiments, $R^{1a}$ can be an optionally substituted acyl. For example, $R^{1a}$ can be —C(=O)H, —C(=O)-an optionally substituted alkyl, —C(=O)-an optionally substituted alkenyl, —C(=O)-an optionally substituted alkynyl, or —C(=O)-an optionally substituted aryl. In some embodiments, —C(=O)-an optionally substituted alkyl can be an —C(=O)-an optionally substituted $C_{1-6}$ alkyl. In other embodiments, —C(=O)-an optionally substituted alkenyl can be an —C(=O)-an optionally substituted $C_{2-6}$ alkenyl. In still other embodiments, —C(=O)-an optionally substituted alkynyl can be an —C(=O)-an optionally substituted $C_{2-6}$ alkynyl. In yet still other embodiments, —C(=O)-an optionally substituted aryl can be an —C(=O)-an optionally substituted $C_{6-10}$ aryl.

In some embodiments, $R^{1a}$ can be

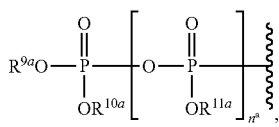

wherein $n^a$ can be 0, 1 or 2. Those skilled in the art understand that when n is 0, $R^{1a}$ can be a mono-phosphate Likewise, when $n^a$ is 1 or 2, those skilled in the art understand $R^{1a}$ can be a di-phosphate or a tri-phosphate, respectively. In some embodiments, at least one of $R^{9a}$, $R^{10a}$ and each $R^{11a}$ can be absent. Those skilled in the art understand that when $R^{9a}$, $R^{10a}$ and/or each $R^{11a}$ is absent, the oxygen associated with $R^{9a}$, $R^{10a}$ and/or each $R^{11a}$ can have a negative charge, which can be denoted as O⁻. In some embodiments, at least one of $R^{9a}$, $R^{10a}$ and each $R^{11a}$ can be hydrogen. In some embodiments, $n^a$ can be 0, and $R^{9a}$ and $R^{10a}$ can be both absent. In other embodiments, $n^a$ can be 0, and $R^{9a}$ and $R^{10a}$ can be both hydrogen. In some embodiments, $n^a$ can be 1, and $R^{9a}$, $R^{10a}$ and $R^{11a}$ can be absent. In other embodiments, $n^a$ can be 1, and $R^{9a}$, $R^{10a}$ and $R^{11a}$ can be hydrogen. In some embodiments, $n^a$ can be 2, and $R^{9a}$, $R^{10a}$ and each $R^{11a}$ can be absent. In other embodiments, $n^a$ can be 2, and $R^{9a}$, $R^{10a}$ and each $R^{11a}$ can be both hydrogen.

In some embodiments, $R^{1a}$ can be

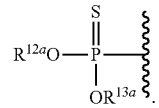

In some embodiments, at least one of $R^{12a}$ and $R^{13a}$ can be both absent. For example, $R^{12a}$ can be absent, $R^{13a}$ can be absent or $R^{12a}$ and $R^{13a}$ can be absent. Those skilled in the art understand that when $R^{12a}/R^{13a}$ are absent, the oxygen associated with $R^{12a}/R^{13a}$ can have a negative charge. In some embodiments, at least one of $R^{12a}$ and $R^{13a}$ can be hydrogen. Examples of at least one of $R^{12a}$ and $R^{13a}$ being hydrogen include the following:

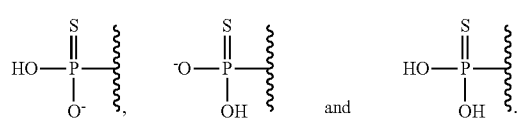

In some embodiments, $R^{12a}$ and $R^{13a}$ can be hydrogen.

In some embodiments, $R^{1a}$ can be

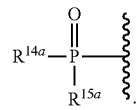

In some embodiment, $R^{14a}$ can be selected from an —O-optionally substituted aryl, an —O-optionally substituted heteroaryl and an —O-optionally substituted heterocyclyl, and $R^{15a}$ can be an optionally substituted N-linked amino acid or an optionally substituted N-linked amino acid ester derivative. Various amino acids and amino acid ester derivatives can be used, including those described herein. In some embodiments, $R^{15a}$ can be an optionally substituted N-linked α-amino acid. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In other embodiments, $R^{15a}$ can be an optionally substituted N-linked α-amino acid ester derivative. For example, $R^{15a}$ can be an ester derivative of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In some embodiment, $R^{15a}$ can be an ester derivative of alanine. In some embodiments, the ester of the optionally substituted N-linked amino acid ester derivative can be a $C_{1-6}$ alkyl ester. In other embodiments, the ester of the optionally substituted N-linked amino acid ester derivative can be a $C_{3-6}$ cycloalkyl ester. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, $R^{15a}$ can have the structure:

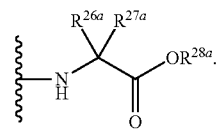

wherein $R^{26a}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); $R^{27a}$ can be hydrogen or an optionally substituted $C_{1-4}$-alkyl; and $R^{28a}$ can be selected from hydrogen, an optionally substituted $C_{1-6}$-alkyl, an optionally substituted $C_{3-6}$ cycloalkyl, an optionally substituted aryl, an optionally substituted aryl ($C_{1-6}$ alkyl) and an optionally substituted $C_{1-6}$ haloalkyl, or $R^{26a}$ and $R^{27a}$ can be taken together to form an optionally substituted $C_{3-6}$ cycloalkyl.

In some embodiments, $R^{26a}$ can be hydrogen. In other embodiments, $R^{26a}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{26a}$ is substituted, $R^{26a}$ can be substituted with one or more substituents selected from N-amido, mercapto, alkylthio, an optionally substituted aryl, hydroxy, an optionally substituted heteroaryl, O-carboxy, and amino. In some embodiment, $R^{26a}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, $R^{26a}$ can be methyl.

In some embodiments, $R^{27a}$ can be hydrogen. In other embodiments, $R^{27a}$ can be an optionally substituted $C_{1-4}$-alkyl, such as methyl, ethyl, n-propyl, isopropyl, n-butyl, isobutyl and tert-butyl. In an embodiment, $R^{27a}$ can be methyl. In some embodiments, $R^{26a}$ and $R^{27a}$ can be taken together to form an optionally substituted $C_{3-6}$ cycloalkyl. Depending on the groups that are selected for $R^{26a}$ and $R^{27a}$, the carbon to which $R^{26a}$ and $R^{27a}$ are attached may be a chiral center. In some embodiment, the carbon to which $R^{26a}$ and $R^{27a}$ are attached may be a (R)-chiral center. In other embodiments, the carbon to which $R^{26a}$ and $R^{27a}$ are attached may be a (S)-chiral center.

As to $R^{28a}$, in some embodiments, $R^{28a}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments, $R^{28a}$ can be an optionally substituted $C_{3-6}$ cycloalkyl. For example, $R^{28a}$ can be an optionally substituted cyclopropyl, an optionally substituted cyclobutyl, an optionally substituted cyclopentyl or an optionally substituted cyclohexyl. In some embodiments, $R^{28a}$ can be an optionally substituted cyclohexyl. In still other embodiments, $R^{28a}$ can be an optionally substituted aryl, such as optionally substituted phenyl and optionally substituted naphthyl. In yet still other embodiments, $R^{28a}$ can be an optionally substituted aryl($C_{1-6}$ alkyl). In some embodiments, $R^{28a}$ can be an optionally substituted benzyl. In some embodiments, $R^{28a}$ can be an optionally substituted $C_{1-6}$ haloalkyl, for example, $CF_3$. In some embodiments, $R^{28a}$ can be hydrogen.

In some embodiments, $R^{14a}$ can be an optionally substituted N-linked amino acid or an optionally substituted N-linked amino acid ester derivative, and $R^{15a}$ can be an optionally substituted N-linked amino acid or an optionally substituted N-linked amino acid ester derivative. Various amino acids and amino acid ester derivatives can be used, including those described herein. In some embodiments, one or both of $R^{14a}$ and $R^{15a}$ can be an optionally substituted N-linked α-amino acid. Suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In other embodiments, one or both of $R^{14a}$ and $R^{15a}$ can be an optionally substituted N-linked α-amino acid ester derivative. For example, $R^{14a}$ and/or $R^{15a}$ can be an ester derivative of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In some embodiment, one or both of $R^{14a}$ and $R^{15a}$ can be an ester derivative of alanine. In some embodiments, one or both of $R^{14a}$ and $R^{15a}$ can be an optionally substituted N-linked amino acid $C_{1-6}$ alkyl ester derivative. In other embodiments, one or both of $R^{14a}$ and $R^{15a}$ can be an optionally substituted N-linked amino acid $C_{3-6}$ cycloalkyl ester derivative. In some embodiments, the optionally substituted N-linked amino acid or the optionally substituted N-linked amino acid ester derivative can be in the L-configuration. In other embodiments, the optionally substituted N-linked amino acid or the optionally substituted N-linked amino acid ester derivative can be in the D-configuration.

In some embodiments, $R^{14a}$ and $R^{15a}$ can each have the structure

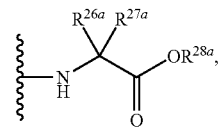

wherein each $R^{26a}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); each $R^{27a}$ can be hydrogen or an optionally substituted $C_{1-4}$-alkyl; and each $R^{28a}$ can be selected from hydrogen, an optionally substituted $C_{1-6}$-alkyl, an optionally substituted $C_{3-6}$ cycloalkyl, an optionally substituted aryl, an optionally substituted aryl ($C_{1-6}$ alkyl) and an optionally substituted $C_{1-6}$ haloalkyl, or the $R^{26a}$ and the $R^{27a}$ attached to the same carbon can be taken together to form an optionally substituted $C_{3-6}$ cycloalkyl.

In some embodiments, one or both of $R^{26a}$ can be hydrogen. In other embodiments, one or both of $R^{26a}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, and tert-butyl, pentyl (branched and straight-chained), and hexyl (branched and straight-chained). When $R^{26a}$ is substituted, $R^{26a}$ can be substituted with one or more substituents selected from N-amido, mercapto, alkylthio, an optionally substituted aryl, hydroxy, an optionally substituted heteroaryl, O-carboxy, and amino. In some embodiment, one or both of $R^{26a}$ can be an unsubstituted $C_{1-6}$-alkyl, such as methyl, ethyl, n-propyl, isopropyl, n-butyl, isobutyl, and tert-butyl, pentyl (branched and straight-chained), and hexyl (branched and straight-chained). In an embodiment, one or both of $R^{26a}$ can be methyl.

In some embodiments, one or both of $R^{27a}$ can be hydrogen. In other embodiments, one or both of $R^{27a}$ can be an optionally substituted $C_{1-4}$-alkyl, such as methyl, ethyl, n-propyl, isopropyl, n-butyl, isobutyl and tert-butyl. In an embodiment, one or both of $R^{27a}$ can be methyl. In some embodiments, one or both of $R^{26a}$ and $R^{27a}$ attached to the same carbon can be taken together to form an optionally substituted $C_{3-6}$ cycloalkyl. Depending on the groups that are selected for $R^{26a}$ and $R^{27a}$, the carbon to which $R^{26a}$ and $R^{27a}$ are attached may be a chiral center. In some embodiment, the carbon to which $R^{26a}$ and $R^{27a}$ are attached may be a (R)-chiral center. In other embodiments, the carbon to which $R^{26a}$ and $R^{27a}$ are attached may be a (S)-chiral center.

In some embodiments, one or both of $R^{28a}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments, one or both of $R^{28a}$ can be an optionally substituted $C_{3-6}$ cycloalkyl. For example, $R^{28a}$ can be an optionally substituted cyclopropyl, an optionally substituted cyclobutyl, an optionally substituted cyclopentyl or an optionally substituted cyclohexyl. In some embodiments, $R^{28a}$ can be an optionally substituted cyclohexyl. In still other embodiments, one or both of $R^{28a}$ can be an optionally substituted aryl, such as optionally substituted phenyl and optionally substituted naphthyl. In yet still other embodiments, one or both of $R^{28a}$ can be an optionally substituted aryl($C_{1-6}$ alkyl). In some embodiments, one or both of $R^{28a}$ can be an optionally substituted benzyl. In some embodiments, one or both of $R^{28a}$ can be an optionally substituted $C_{1-6}$ haloalkyl, for example, $CF_3$. In some embodiments, one or both of $R^{28a}$ can be hydrogen. In some embodiments, $R^{14a}$ and $R^{15a}$ can be the same. In other embodiments, $R^{14a}$ and $R^{15a}$ can be different.

In some embodiments, $R^{14a}$ can be $O^-$, hydroxy or an —O-optionally substituted $C_{1-6}$ alkyl, and $R^{15a}$ and $R^{5a}$ together can be O, such that a compound of Formula (II), or a pharmaceutically acceptable salt thereof, has the structure:

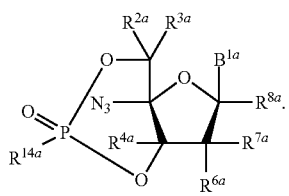

In some embodiments, $R^{14a}$ can be $O^-$. In some embodiments, $R^{14a}$ can be hydroxy. In some embodiments, $R^{14a}$ can be an —O-optionally substituted $C_{1-6}$ alkyl, for example, an optionally substituted version of methoxy, ethoxy, n-propoxy, isopropoxy, n-butoxy, isobutoxy, tert-butoxy, pentoxy (branched and straight-chained), and hexoxy (branched and straight-chained). In some embodiments, $R^{14a}$ can be an —O-unsubstituted $C_{1-6}$ alkyl.

In some embodiments, $R^{1a}$ can be

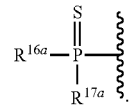

In some embodiment, $R^{16a}$ can be selected from an —O-optionally substituted aryl, an —O-optionally substituted heteroaryl and an —O-optionally substituted heterocyclyl, and $R^{17a}$ can be an optionally substituted N-linked amino acid or an optionally substituted N-linked amino acid ester derivative. In some embodiments, $R^{16a}$ can be an —O-optionally substituted heteroaryl. In other embodiments, $R^{16a}$ can be an —O-optionally substituted heterocyclyl. In some embodiments, $R^{16a}$ can be an —O-optionally substituted aryl. For example, the —O-optionally substituted aryl can be an —O-optionally substituted phenyl or an —O-optionally substituted naphthyl. If $R^{16a}$ is an —O-substituted phenyl or an —O-optionally substituted naphthyl, the phenyl and naphthyl ring can be substituted one or more times. Suitable substituents that can be present on an —O-optionally substituted phenyl and an —O-optionally substituted naphthyl include electron-donating groups and electron-withdrawing groups. In some embodiments, $R^{16a}$ can be an —O-para-substituted phenyl. In other embodiment, $R^{16a}$ can be an —O-unsubstituted phenyl or an —O-unsubstituted naphthyl. In some embodiments, $R^{17a}$ can be an optionally substituted N-linked amino acid or an optionally substituted N-linked amino acid ester derivative of any one of the following amino acids alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Suitable ester derivatives include those described herein, such as an optionally substituted $C_{1-6}$ alkyl ester, an optionally substituted $C_{3-6}$ cycloalkyl ester, an optionally substituted $C_{6-10}$ aryl ester, and an optionally substituted aryl($C_{1-6}$ alkyl) ester.

In some embodiments, $R^{16a}$ and $R^{17a}$ can each have the structure

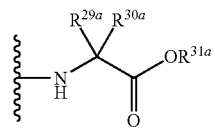

wherein each $R^{29a}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); each $R^{30a}$ can be hydrogen or an optionally substituted $C_{1-4}$-alkyl; and each $R^{31a}$ can be selected from hydrogen, an optionally substituted $C_{1-6}$-alkyl, an optionally substituted $C_{3-6}$ cycloalkyl, an optionally substituted aryl, an optionally substituted aryl ($C_{1-6}$ alkyl) and an optionally substituted $C_{1-6}$ haloalkyl, or the $R^{29a}$ and the $R^{30a}$ attached to the same carbon can be taken together to form an optionally substituted $C_{3-6}$ cycloalkyl.

In some embodiments, one or both of $R^{29a}$ can be hydrogen. In other embodiments, one or both of $R^{29a}$ can be an optionally substituted $C_{1-6}$-alkyl. Examples of suitable optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). When $R^{29a}$ is substituted, $R^{29a}$ can be substituted with one or more substituents selected from N-amido, mercapto, alkylthio, an optionally substituted aryl, hydroxy, an optionally substituted heteroaryl, O-carboxy, and amino. In some embodiment, one or both of $R^{29a}$ can be an unsubstituted $C_{1-6}$-alkyl, such as methyl, ethyl, n-propyl, isopropyl, n-butyl, isobutyl, tert-butyl, pentyl (branched and straight-chained), and hexyl (branched and straight-chained). In an embodiment, one or both of $R^{29a}$ can be methyl.

In some embodiments, one or both of $R^{30a}$ can be hydrogen. In other embodiments, one or both of $R^{30a}$ can be an optionally substituted $C_{1-4}$-alkyl, such as methyl, ethyl, n-propyl, isopropyl, n-butyl, isobutyl and tert-butyl. In an embodiment, one or both of $R^{30a}$ can be methyl. In some embodiments, one or both of $R^{29a}$ and $R^{30a}$ attached to the same carbon can be taken together to form an optionally substituted $C_{3-6}$ cycloalkyl. Depending on the groups that are selected for $R^{29a}$ and $R^{30a}$, the carbon to which $R^{29a}$ and $R^{30a}$ are attached may be a chiral center. In some embodiment, the carbon to which $R^{29a}$ and $R^{30a}$ are attached may be a (R)-chiral center. In other embodiments, the carbon to which $R^{29a}$ and $R^{30a}$ are attached may be a (S)-chiral center.

In some embodiments, one or both of $R^{31a}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments, one or both of $R^{31a}$ can be an optionally substituted $C_{3-6}$ cycloalkyl. For example, $R^{31a}$ can be an optionally substituted cyclopropyl, an optionally substituted cyclobutyl, an optionally substituted cyclopentyl or an optionally substituted cyclohexyl. In some embodiments, $R^{31a}$ can be an optionally substituted cyclohexyl. In still other embodiments, one or both of $R^{31a}$ can be an optionally substituted aryl, such as optionally substituted phenyl and optionally substituted naphthyl. In yet still other embodiments, one or both of $R^{31a}$ can be an optionally substituted aryl($C_{1-6}$ alkyl). In some embodiments, one or both of $R^{31a}$ can be an optionally substituted benzyl. In some embodiments, one or both of $R^{31a}$ can be an optionally substituted $C_{1-6}$ haloalkyl, for example, $CF_3$. In some embodiments, one or both of $R^{31a}$ can be hydrogen. In some embodiments, $R^{16a}$ and $R^{17a}$ can be the same. In other embodiments, $R^{16a}$ and $R^{17a}$ can be different.

In some embodiments, $R^{16a}$ can be $O^-$, hydroxy or an —O-optionally substituted $C_{1-6}$ alkyl, and $R^{17a}$ and $R^{5a}$ together can be O, such that a compound of Formula (II), or a pharmaceutically acceptable salt thereof, has the structure:

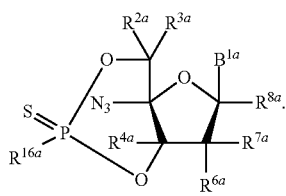

In some embodiments, $R^{16a}$ can be $O^-$. In some embodiments, $R^{16a}$ can be hydroxy. In some embodiments, $R^{16a}$ can be an —O-optionally substituted $C_{1-6}$ alkyl, for example an optionally substituted version of methoxy, ethoxy, n-propoxy, isopropoxy, n-butoxy, isobutoxy, tert-butoxy, pentoxy (branched and straight-chained), and hexoxy (branched and straight-chained). In some embodiments, $R^{16a}$ can be an —O-unsubstituted $C_{1-6}$ alkyl.

Examples of suitable

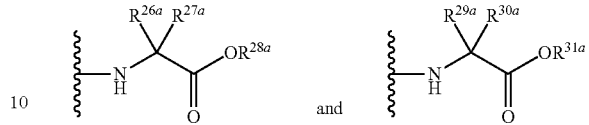

groups include the following:

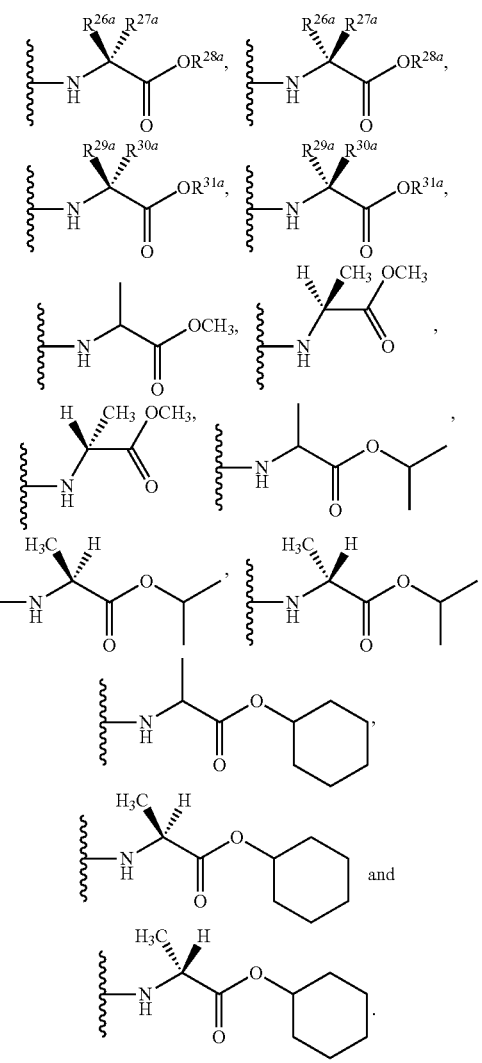

The substituents attached to the 5'-position of a compound of Formula (II) can vary. In some embodiments, $R^{2a}$ and $R^{3a}$ can be the same. In other embodiments, $R^{2a}$ and $R^{3a}$ can be different. In some embodiments, $R^{2a}$ and $R^{3a}$ can be both hydrogen. In other embodiments, at least one of $R^{2a}$ and $R^{3a}$ cannot be hydrogen. In some embodiments, at least of $R^{2a}$ and $R^{3a}$ can be an optionally substituted $C_{1-6}$-alkyl; and the other of $R^{2a}$ and $R^{3a}$ can be hydrogen. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, at least one of $R^{2a}$ and $R^{3a}$ can be methyl, and the other of $R^{2a}$ and $R^{3a}$ can be hydrogen. In other embodiments, at least one of $R^{2a}$ and $R^{3a}$ can be an optionally substituted $C_{1-6}$-haloalkyl, and the other of $R^{2a}$ and $R^{3a}$ can be hydrogen. One example of a suitable optionally substituted $C_{1-6}$-haloalkyl is $CF_3$. In some embodiments, at least one of $R^{2a}$ and $R^{3a}$ can be hydrogen; and the other of $R^{2a}$ and $R^{3a}$ can be an optionally substituted $C_{1-6}$ alkyl or an optionally substituted $C_{1-6}$ haloalkyl; and $R^{1a}$ can be hydrogen. When the substituents attached to the 5'-carbon make the 5'-carbon chiral, in some embodiments, the 5'-carbon can be a (R)-stereocenter. In other embodiments, the 5'-carbon can be an (S)-stereocenter.

The substituents attached to the 2'-carbon and the 3'-carbon can also vary. In some embodiments, $R^{4a}$ can be hydrogen. In other embodiments, $R^{4a}$ can be a halogen. Example of halogens include F, Cl, Br and I. In still other embodiments, $R^{4a}$ can be an optionally substituted $C_{1-6}$ alkyl. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In other embodiments $R^{4a}$ can be $-OR^{18a}$. When $R^{18a}$ is hydrogen, $R^{4a}$ can be hydroxy. Alternatively, when $R^{18a}$ is an optionally substituted $C_{1-6}$ alkyl, $R^{4a}$ can be an optionally substituted $C_{1-6}$ alkoxy. Suitable alkoxy groups include methoxy, ethoxy, n-propoxy, isopropoxy, n-butoxy, isobutoxy, tert-butoxy, pentoxy (branched and straight-chained), and hexoxy (branched and straight-chained). In some embodiments, $R^{4a}$ can be $-OC(=O)R^{19a}$, in which $R^{19a}$ can be an optionally substituted $C_{1-6}$ alkyl. Examples of suitable $C_{1-6}$ alkyl groups are described herein.

In some embodiments, $R^{5a}$ can be hydrogen. In other embodiments, $R^{5a}$ can be a halogen, including those described herein. In still other embodiments, $R^{5a}$ can be an optionally substituted $C_{1-6}$ alkyl. In yet still other embodiments $R^{5a}$ can be $-OR^{20a}$. In some embodiments, $R^{5a}$ can be $-OH$. In other embodiments, $R^{20a}$ can be $-OR^{20a}$, wherein $R^{20a}$ can be an optionally substituted $C_{1-6}$ alkyl. In still other embodiments, $R^{5a}$ can be $-OC(=O)R^{21a}$, in which $R^{21a}$ can be an optionally substituted $C_{1-6}$ alkyl. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained).

In some embodiments, $R^{6a}$ can be hydrogen. In other embodiments, $R^{6a}$ can be a halogen. In still other embodiments, $R^{6a}$ can be an optionally substituted $C_{1-6}$ alkyl. In yet still other embodiments $R^{6a}$ can be $-OR^{22a}$, wherein $R^{22a}$ can be hydrogen. In some embodiments, $R^{6a}$ can be $-OR^{22a}$, wherein $R^{22a}$ can be an optionally substituted $C_{1-6}$ alkyl. Examples of substituents that can be $R^{6a}$ include, but are not limited to, methoxy, ethoxy, n-propoxy, isopropoxy, n-butoxy, isobutoxy, tert-butoxy, pentoxy (branched and straight-chained), and hexoxy (branched and straight-chained). In some embodiments, $R^{6a}$ can be $-OC(=O)R^{23a}$, wherein $R^{23a}$ can be an optionally substituted $C_{1-6}$ alkyl. Examples of suitable $C_{1-6}$ alkyl groups are described herein. In some embodiments, $R^{6a}$ can be hydrogen, halogen or $-OR^{22a}$.

In some embodiments, $R^{7a}$ can be hydrogen. In other embodiments, $R^{7a}$ can be a halogen. In still other embodiments, $R^{7a}$ can be an optionally substituted $C_{1-6}$ alkyl. Examples of suitable optionally substituted $C_{1-6}$ alkyls include optionally substituted variants of the following: methyl, ethyl, n-propyl, isopropyl, n-butyl, isobutyl, tert-butyl, pentyl (branched and straight-chained), and hexyl (branched and straight-chained). In yet still other embodiments $R^{7a}$ can be $-OR^{24a}$, wherein $R^{24a}$ can be hydrogen or a an optionally substituted $C_{1-6}$ alkyl. A non-limiting list of $R^{7a}$ groups include hydroxy, methoxy, ethoxy, n-propoxy, isopropoxy, n-butoxy, isobutoxy and tert-butoxy. In some embodiments, $R^{7a}$ can be $-OC(=O)R^{25a}$, wherein $R^{25a}$ can be an optionally substituted $C_{1-6}$ alkyl, such as those described herein. In some embodiments, $R^{7a}$ is hydrogen or halogen. In some embodiments, $R^{7a}$ is $-OR^{24a}$ or an optionally substituted $C_{1-6}$ alkyl.

In some embodiments, $R^{5a}$ and $R^{6a}$ can both be hydroxy. In other embodiments, at least of one of $R^{5a}$ and $R^{6a}$ cannot hydroxy. For example, $R^{5a}$ cannot be hydroxy, $R^{6a}$ cannot be hydroxy, or both of $R^{5a}$ and $R^{6a}$ cannot be hydroxy. In still other embodiments, $R^{5a}$ and $R^{6a}$ can both be both oxygen atoms and linked together by a carbonyl group, for example, $-O-C(=O)-O-$. In some embodiments, at least one of $R^{6a}$ and $R^{7a}$ can be a halogen. In some embodiments, $R^{6a}$ and $R^{7a}$ can both be a halogen. In some embodiments, $R^{6a}$ can be hydroxy and $R^{7a}$ can be a halogen. In other embodiments, $R^{5a}$ and $R^{6a}$ can be both hydroxy groups and $R^{7a}$ can be a halogen. In still other embodiments, $R^{6a}$ can be hydrogen and $R^{7a}$ can be an optionally substituted $C_{1-6}$ alkyl. In yet still other embodiments, at least one of $R^{5a}$ and $R^{6a}$ can be a hydroxy and $R^{7a}$ can be an optionally substituted $C_{1-6}$ alkyl. In some embodiments, at least one of $R^{5a}$ and $R^{6a}$ can be a hydroxy and $R^{7a}$ can be a halogen. For example, $R^{5a}$ can be hydroxy, $R^{6a}$ can be a hydrogen and $R^{7a}$ can be a halogen; or $R^{5a}$ can be hydrogen, $R^{6a}$ can be hydroxy and $R^{7a}$ can be a halogen; $R^{5a}$ can be hydroxy, $R^{6a}$ can be hydroxy and $R^{7a}$ can be a halogen. In other embodiments, at least one of $R^{5a}$ and $R^{6a}$ can be an optionally substituted $C_{1-6}$ alkoxy. In some embodiments, $R^{5a}$ and $R^{7a}$ can be hydroxy, and $R^{6a}$ can be hydrogen. In some embodiments, $R^{5a}$ can be a hydroxy, and both $R^{6a}$ and $R^{7a}$ can be halogen. In some embodiments, $R^{5a}$ can be a hydroxy and $R^{6a}$ can be halogen.

In some embodiments, $R^{8a}$ can be hydrogen. In other embodiments, $R^{8a}$ can be an optionally substituted $C_{1-6}$ alkyl. Examples of $R^{8a}$ groups include optionally substituted variants of the following: methyl, ethyl, n-propyl, isopropyl, n-butyl, isobutyl, tert-butyl, pentyl (branched and straight-chained), and hexyl (branched and straight-chained). In still other embodiments, can be an optionally substituted $C_{1-6}$ haloalkyl. In some embodiments, $R^{8a}$ can be $CF_3$.

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

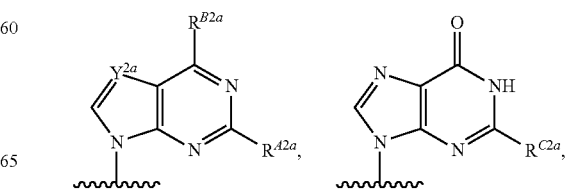

-continued

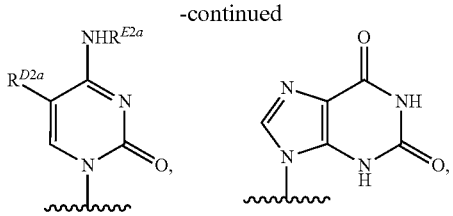

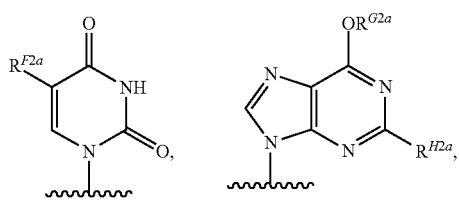

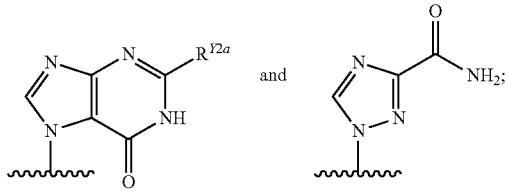

wherein: $R^{A2a}$ can be selected from hydrogen, halogen and $NHR^{J2a}$, wherein $R^{J2a}$ can be selected from hydrogen, —C(=O)$R^{K2a}$ and —C(=O)O$R^{L2a}$; $R^{B2a}$ can be halogen or $NHR^{W2a}$, wherein $R^{W2a}$ can be selected from hydrogen, an optionally substituted $C_{1-6}$ alkyl, an optionally substituted $C_{2-6}$ alkenyl, an optionally substituted $C_{3-8}$ cycloalkyl, —C(=O)$R^{M2a}$ and —C(=O)O$R^{N2a}$; $R^{C2a}$ can be hydrogen or $NHR^{O2a}$, wherein $R^{O2a}$ can be selected from hydrogen, —C(=O)$R^{P2a}$ and —C(=O)O$R^{Q2a}$; $R^{D2a}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{E2a}$ can be selected from hydrogen, an optionally substituted $C_{1-6}$ alkyl, an optionally substituted $C_{3-8}$ cycloalkyl, —C(=O)$R^{R2a}$ and —C(=O)O$R^{S2a}$; $R^{F2a}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^{2a}$ can be N (nitrogen) or $CR^{I2a}$, wherein $R^{I2a}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{G2a}$ can be an optionally substituted $C_{1-6}$ alkyl; $R^{H2a}$ can be hydrogen or $NHR^{T2a}$, wherein $R^{T2a}$ can be independently selected from hydrogen, —C(=O)$R^{U2a}$ and —C(=O)O$R^{V2a}$, $R^{Y2a}$ can be hydrogen or $NHR^{Z2a}$, wherein $R^{Z2a}$ can be selected from hydrogen, —C(=O)$R^{AA2a}$ and —C(=O)O$R^{BB2a}$; and $R^{K2a}$, $R^{L2a}$, $R^{M2a}$, $R^{N2a}$, $R^{P2a}$, $R^{Q2a}$, $R^{R2a}$, $R^{S2a}$, $R^{U2a}$, $R^{V2a}$, $R^{AA2a}$ and $R^{BB2a}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloalkynyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted."

In some embodiments, $B^{1a}$ can be

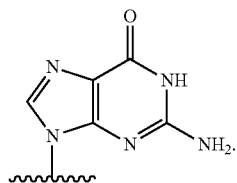 [SMILES: *n1cnc2c(=O)[nH]c(N)nc21]

In other embodiments, $B^{1a}$ can be

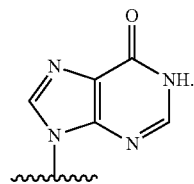 [SMILES: *n1cnc2c(=O)[nH]cnc21]

In still other embodiments, $B^{1a}$ can be

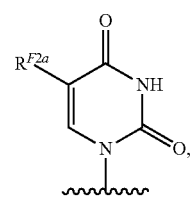

such as

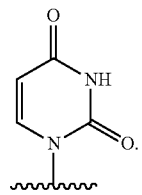

In yet still other embodiments, $B^{1a}$ can be

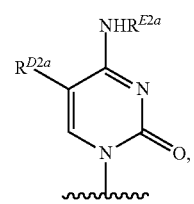

for example,

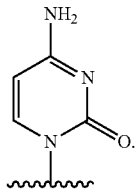

In some embodiments, $R^{D2a}$ can be hydrogen. In other embodiments, $B^{1a}$ can be

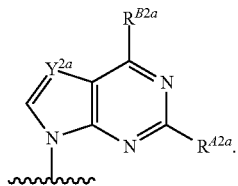

In some embodiments, $R^{B2a}$ can be $NH_2$. In other embodiments, $R^{B2a}$ can be $NHR^{W2a}$, wherein $R^{W2a}$ can be —C(=O)$R^{M2a}$ or —C(=O)OR$^{N2a}$. In still other embodiments, $B^{1a}$ can be

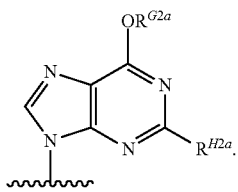

In some embodiments, $B^{1a}$ can be

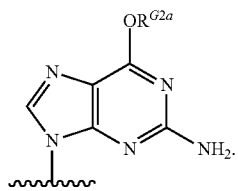

In some embodiments, when $R^{14a}$ is an —O-optionally substituted aryl, an —O-optionally substituted heteroaryl or an —O-optionally substituted heterocyclyl; and $R^{15a}$ has the structure:

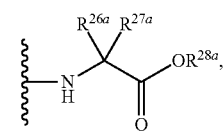

then $R^{26a}$ and $R^{27a}$ cannot be taken together to form an optionally substituted $C_{3-6}$ cycloalkyl. In some embodiments, when $R^{14a}$ and $R^{15a}$ each have the structure

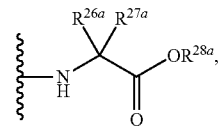

then one or both of $R^{26a}$ and $R^{27a}$ cannot be taken together to form an optionally substituted $C_{3-6}$ cycloalkyl. In some embodiments, when $R^{16a}$ is an —O-optionally substituted aryl, an —O-optionally substituted heteroaryl or an —O-optionally substituted heterocyclyl; and $R^{17a}$ has the structure:

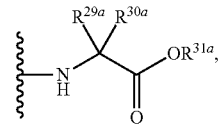

then $R^{29a}$ and $R^{30a}$ cannot be taken together to form an optionally substituted $C_{3-6}$ cycloalkyl. In some embodiments, when $R^{16a}$ and $R^{17a}$ each have the structure

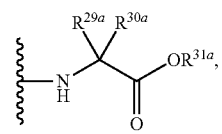

then one or both of $R^{29a}$ and $R^{30a}$ cannot be taken together to form an optionally substituted $C_{3-6}$ cycloalkyl. In other embodiments, $R^{1a}$ cannot be hydrogen.

Some embodiments described herein relate to a compound of Formula (II), or a pharmaceutically acceptable salt thereof, wherein $B^{1a}$ can be selected from an optionally substituted heterocyclic base and an optionally substituted heterocyclic base with a protected amino group; $R^{1a}$ can be selected from hydrogen,

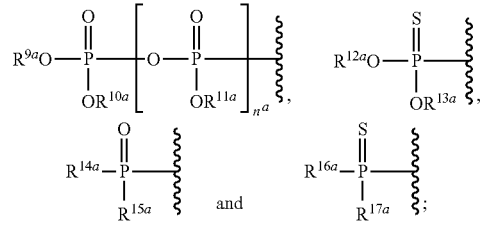

$n^a$ can be 0, 1 or 2; $R^{2a}$ and $R^{3a}$ can be independently selected from hydrogen, an optionally substituted $C_{1-6}$ alkyl and an optionally substituted $C_{1-6}$ haloalkyl; $R^{4a}$ can be selected from hydrogen, halogen, optionally substituted $C_{1-6}$ alkyl, —OR$^{18a}$ and —OC(=O)R$^{19a}$; $R^{5a}$ can be selected from hydrogen, halogen, optionally substituted $C_{1-6}$ alkyl, —OR$^{20a}$ and —OC(=O)R$^{21a}$; $R^{6a}$ can be selected from hydrogen, halogen, optionally substituted $C_{1-6}$ alkyl, —OR$^{22a}$ and —OC(=O)R$^{23a}$; or $R^{5a}$ and $R^{6a}$ can be both oxygen atoms and linked together by a carbonyl group; $R^{7a}$ can be selected from hydrogen, halogen, optionally substituted $C_{1-6}$ alkyl, —OR$^{24a}$ and —OC(=O)R$^{25a}$; $R^{8a}$ can be selected from hydrogen, an optionally substituted $C_{1-6}$ alkyl and an optionally substituted $C_{1-6}$ haloalkyl; $R^{9a}$, $R^{10a}$, each $R^{11a}$, $R^{12a}$ and $R^{13a}$ can be independently absent or hydrogen; $R^{14a}$ and $R^{16a}$ can be independently selected from an —O-optionally substituted aryl, an —O-optionally substituted heteroaryl and an —O-optionally substituted heterocyclyl; $R^{15a}$ can be

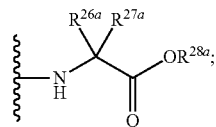

$R^{17a}$ can be an optionally substituted N-linked amino acid or an optionally substituted N-linked amino acid ester derivative; $R^{18a}$, $R^{20a}$, $R^{22a}$ and $R^{24a}$ can be independently selected from hydrogen and an optionally substituted $C_{1-6}$ alkyl; $R^{19a}$, $R^{21a}$, $R^{23a}$ and $R^{25a}$ can be independently selected from an optionally substituted $C_{1-6}$ alkyl and an optionally substituted $C_{3-6}$ cycloalkyl; $R^{26a}$ can be hydrogen or an optionally substituted $C_{1-4}$-alkyl; $R^{27a}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl, and an optionally substituted aryl($C_{1-6}$ alkyl); and $R^{28a}$ can be selected from hydrogen, an optionally substituted $C_{1-6}$-alkyl, an optionally substituted $C_{3-6}$ cycloalkyl, an optionally substituted $C_{10}$ aryl, an optionally substituted aryl ($C_{1-6}$ alkyl), and an optionally substituted haloalkyl, or $R^{26a}$ and $R^{27a}$ can be taken together to form an optionally substituted $C_{3-6}$ cycloalkyl. Some embodiments described herein related to a compound of Formula (II), or a pharmaceutically acceptable salt thereof, wherein $B^{1a}$ can be selected from an optionally substituted heterocyclic base and an optionally substituted heterocyclic base with a protected amino group; $R^{1a}$ can be selected from hydrogen,

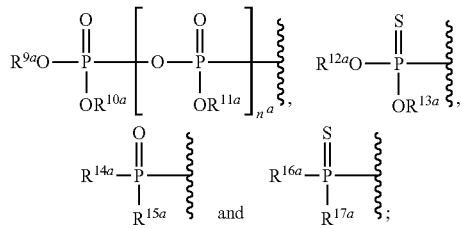

$n^a$ can be 0, 1 or 2; $R^{2a}$ and $R^{3a}$ can be independently selected hydrogen, an optionally substituted $C_{1-6}$ alkyl and an optionally substituted $C_{1-6}$ haloalkyl; $R^{4a}$ can be selected hydrogen, halogen, optionally substituted $C_{1-6}$ alkyl, —$OR^{18a}$ and —$OC(=O)R^{19a}$; $R^{5a}$ can be selected from hydrogen, halogen, optionally substituted $C_{1-6}$ alkyl, —$OR^{20a}$ and —$OC(=O)R^{21a}$; $R^{6a}$ can be selected from hydrogen, halogen, optionally substituted $C_{1-6}$ alkyl, —$OR^{22a}$ and —$OC(=O)R^{23a}$; or $R^{5a}$ and $R^{6a}$ can be both oxygen atoms and linked together by a carbonyl group; $R^{7a}$ can be selected from hydrogen, halogen, optionally substituted $C_{1-6}$ alkyl, —$OR^{24a}$ and —$OC(=O)R^{25a}$; $R^{8a}$ can be selected from hydrogen, an optionally substituted $C_{1-6}$ alkyl and an optionally substituted $C_{1-6}$ haloalkyl; $R^{9a}$, $R^{10a}$ each $R^{11a}$, $R^{12a}$ and $R^{13a}$ can be independently absent or hydrogen; $R^{14a}$ and $R^{16a}$ can be independently selected from an —O-optionally substituted aryl, an —O-optionally substituted heteroaryl and an —O-optionally substituted heterocyclyl; $R^{15a}$ and $R^{17a}$ can be independently an optionally substituted N-linked amino acid or an optionally substituted N-linked amino acid ester derivative; $R^{18a}$, $R^{20a}$, $R^{22a}$ and $R^{24a}$ can be independently hydrogen or an optionally substituted $C_{1-6}$ alkyl; and $R^{19a}$, $R^{21a}$, $R^{23a}$ and $R^{25a}$ can be independently an optionally substituted $C_{1-6}$ alkyl.

In some embodiments, the compound of Formula (II) can have the structure of Formula (IIa), or a pharmaceutically acceptable salt thereof:

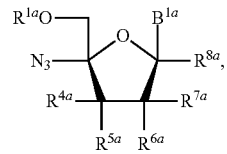

wherein $R^{1a}$ and $B^{1a}$ can be the same as $R^{1a}$ and $B^{1a}$ of a compound of Formula (II), including embodiments described herein; $R^{4a}$ can be hydrogen or hydroxy; $R^{5a}$ can be hydrogen, halogen or hydroxy; $R^{6a}$ can be hydrogen, halogen, hydroxy or —O—$C_{1-6}$ alkyl, $R^{7A}$ can be hydrogen, halogen, hydroxy or an optionally substituted $C_{1-6}$ alkyl; and $R^{8a}$ can be hydrogen or methyl. In some embodiments for Formula (IIa), $B^{1a}$ can be a substituted or unsubstituted uracil, a substituted or unsubstituted adenine, a substituted or unsubstituted guanine or a substituted or unsubstituted cytosine.

Examples of compounds of Formulae (I) and/or (II) include, but are not limited to, the following (for Formula (I), $R^{1a}$ is $R^1$ in the compounds of this paragraph).

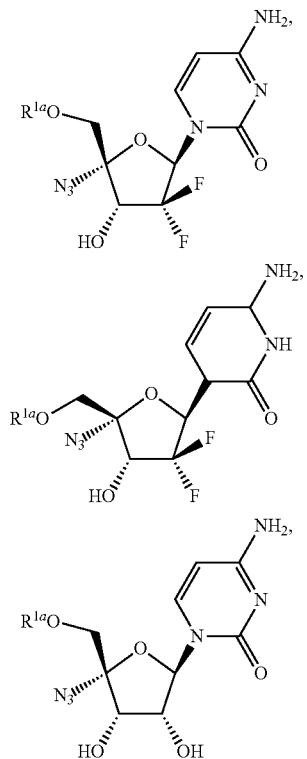

53
-continued
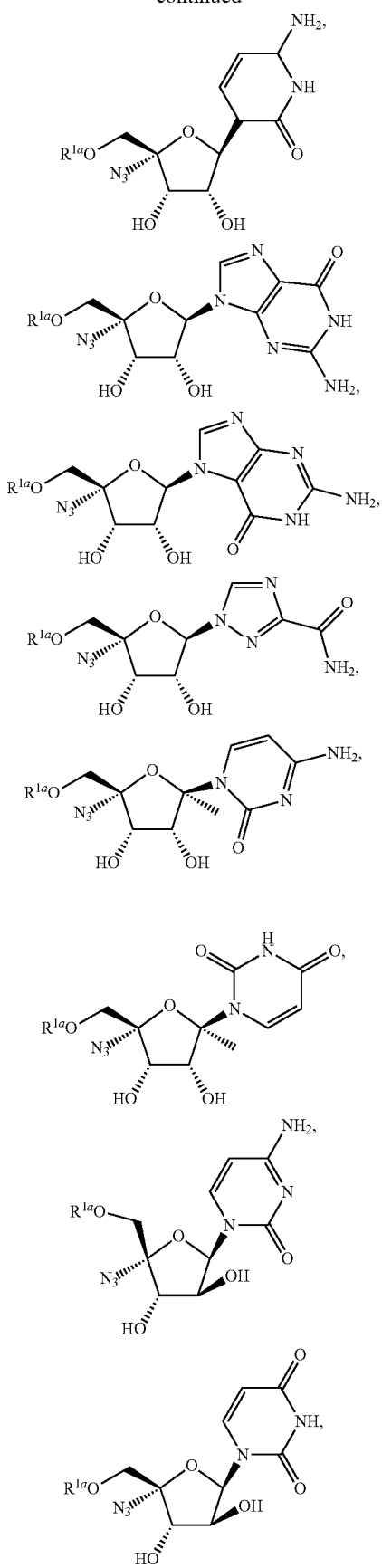
54
-continued
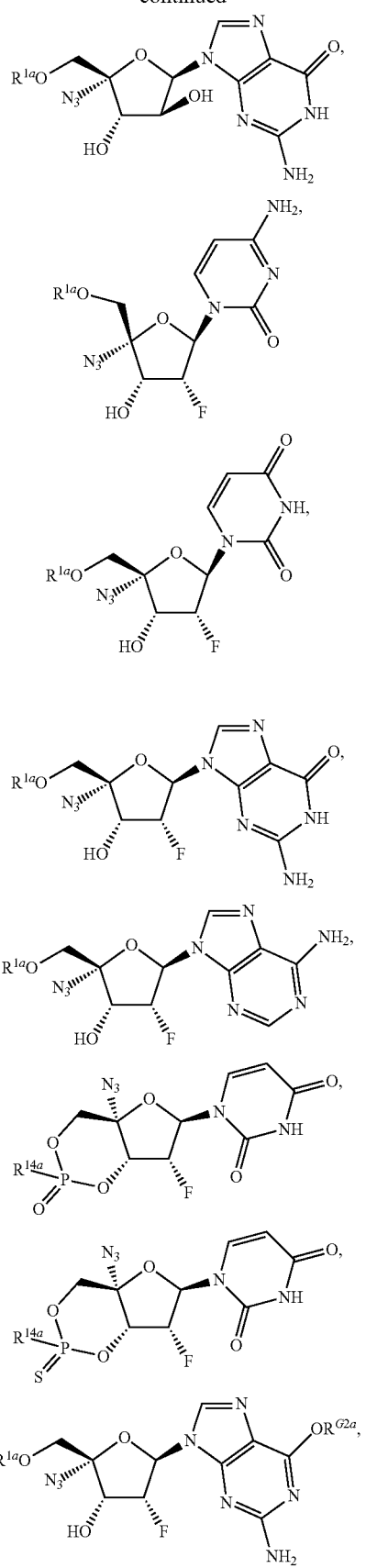

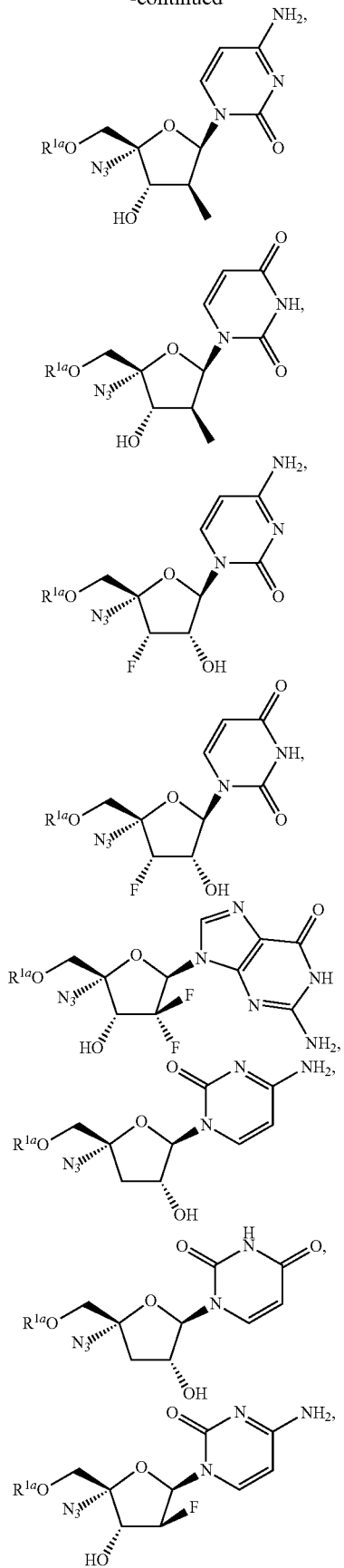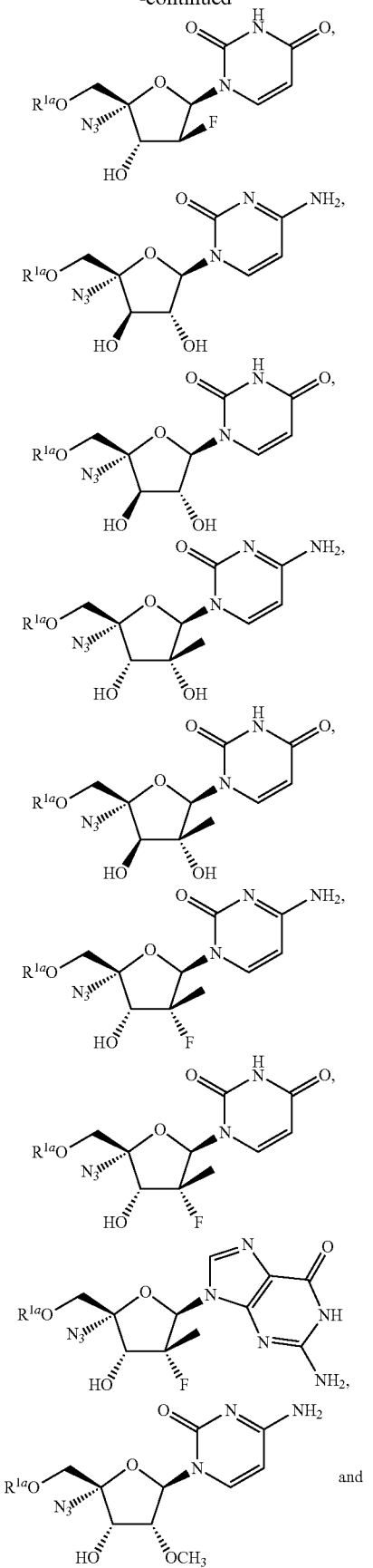

-continued
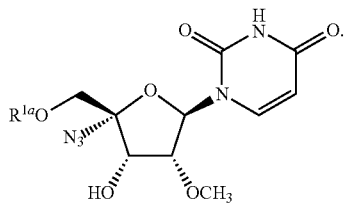
Additional examples of compounds of Formulae (I) and/or (II) include, but are not limited to, the following:
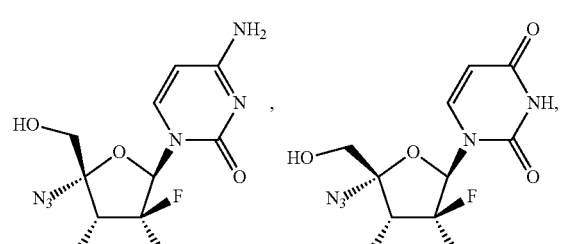
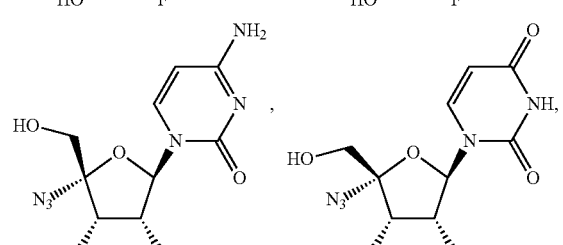
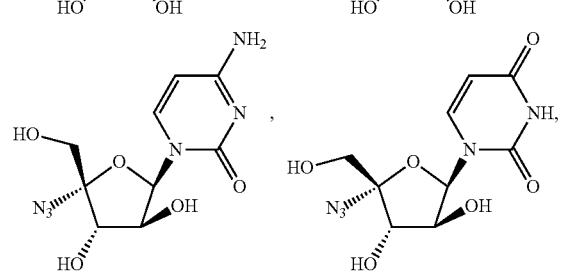
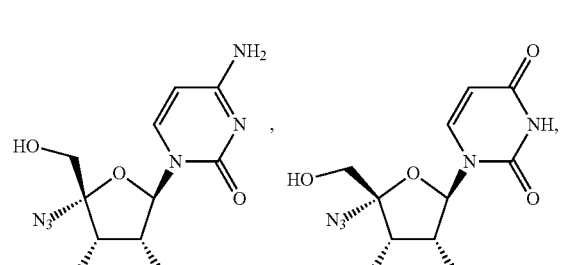
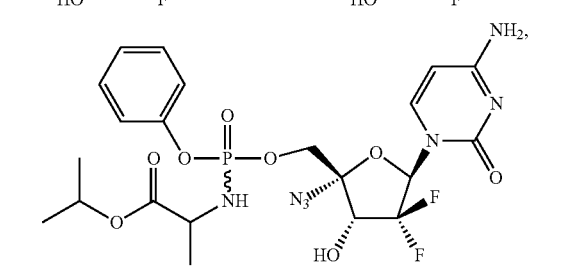
-continued
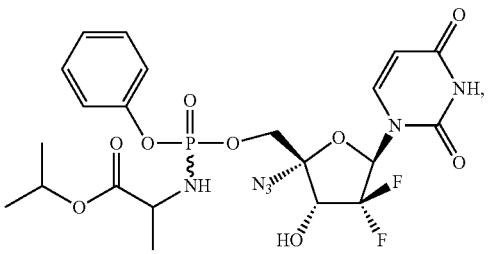
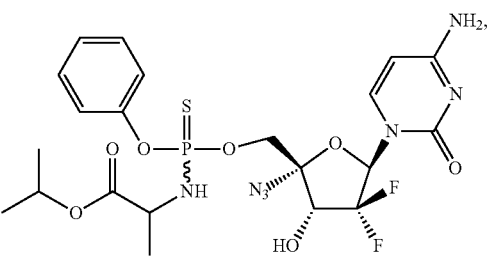
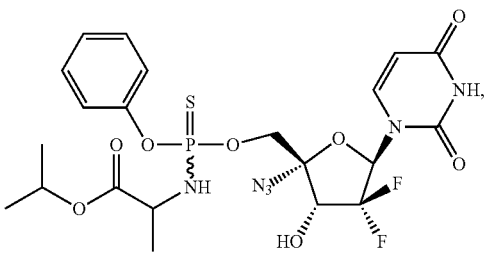
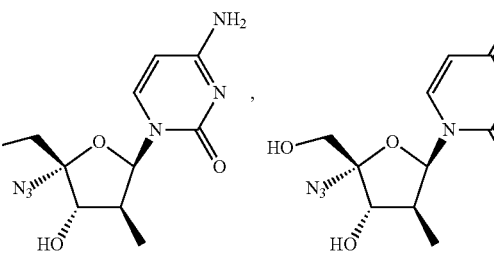
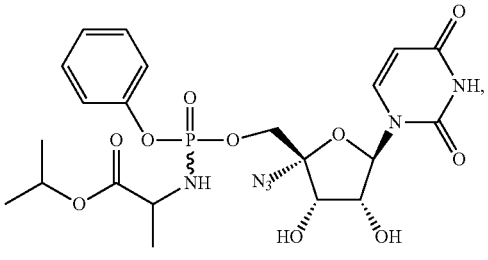

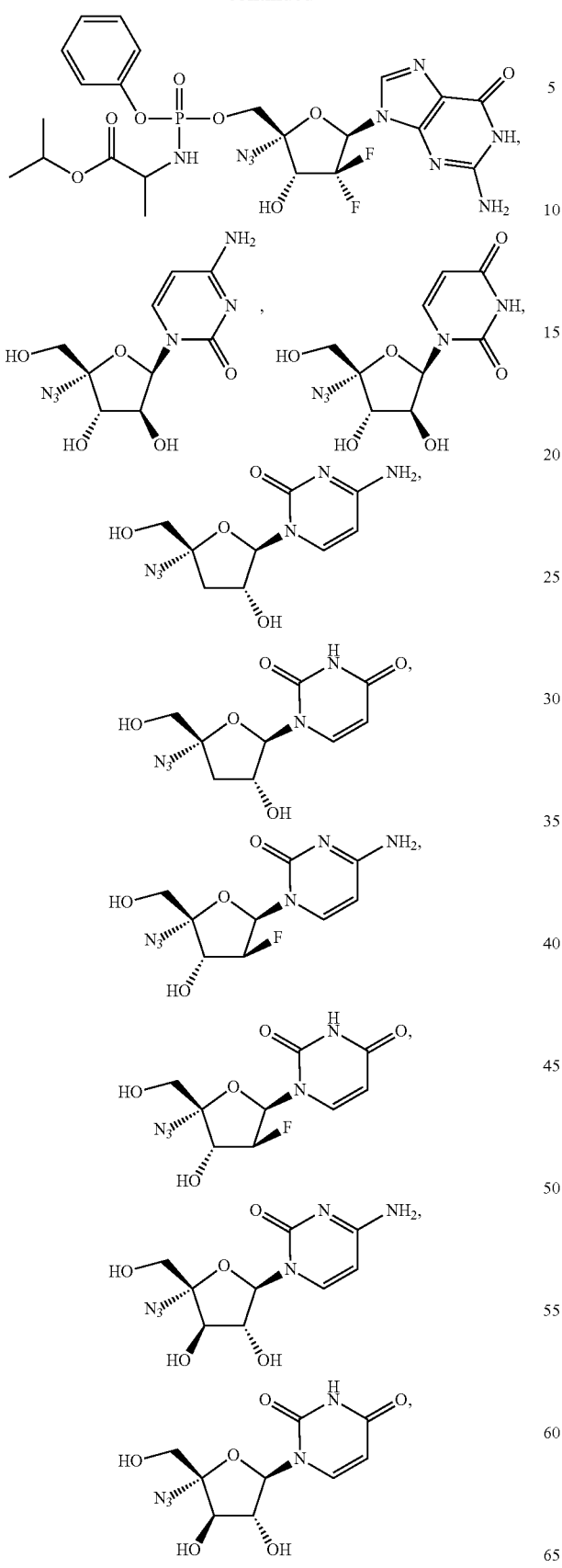
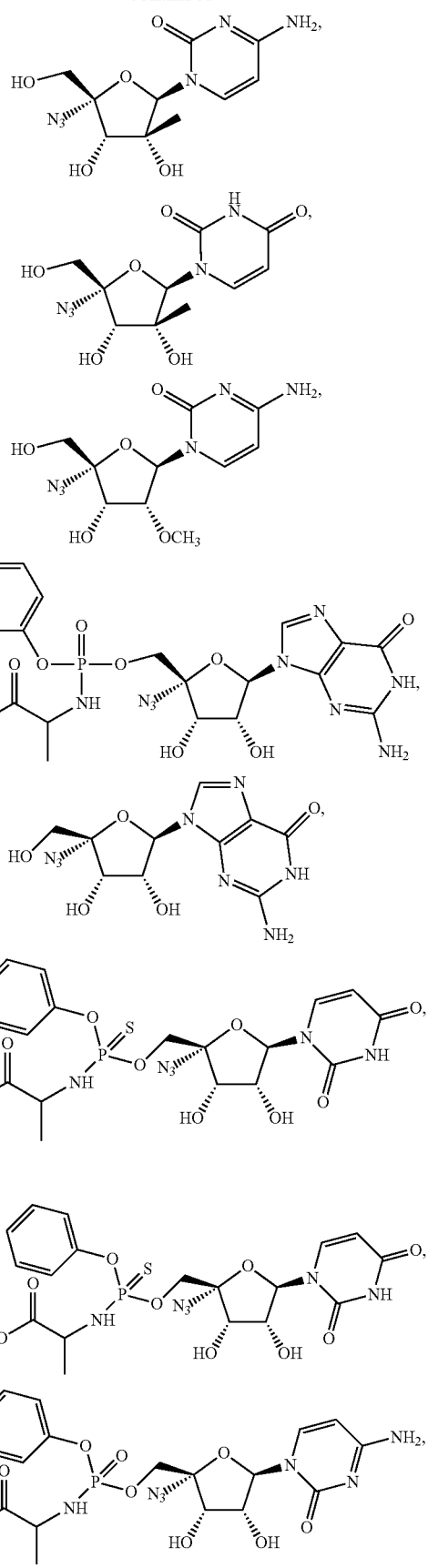

61
-continued
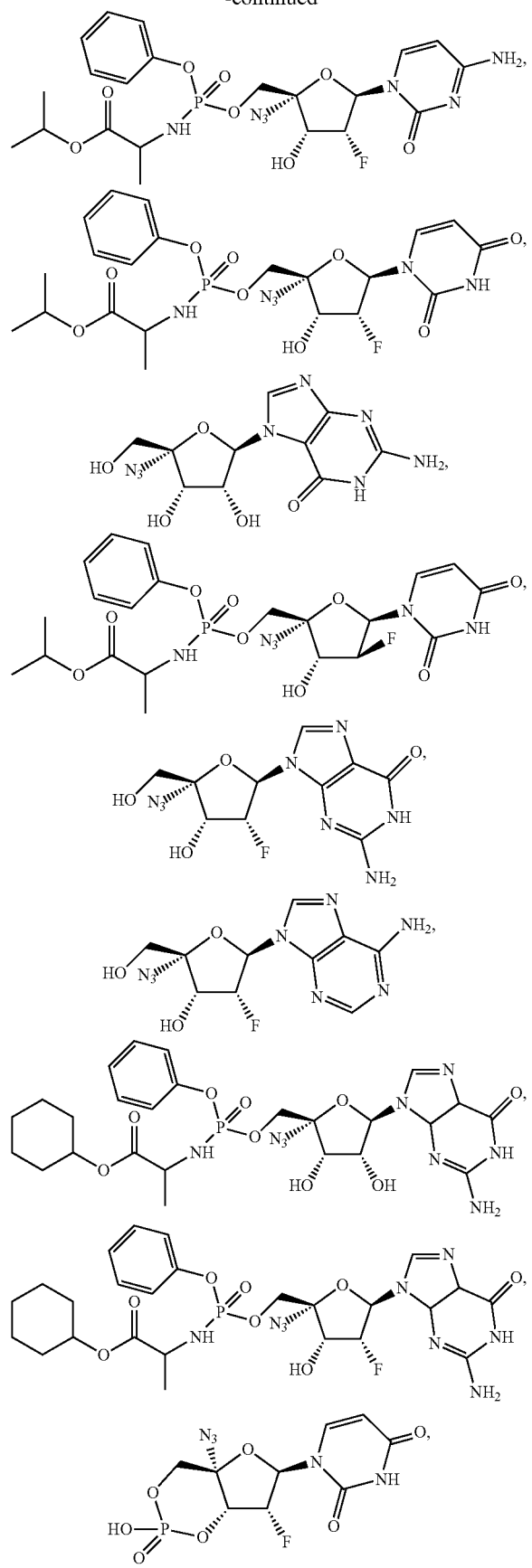
62
-continued
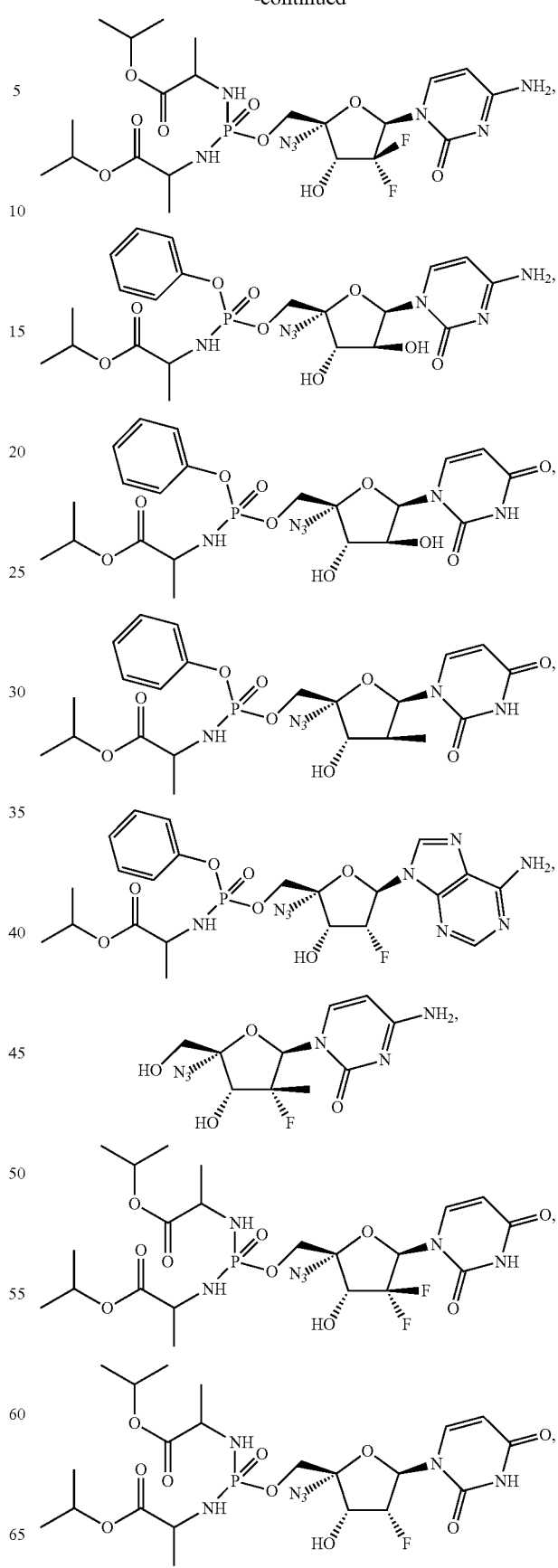

-continued

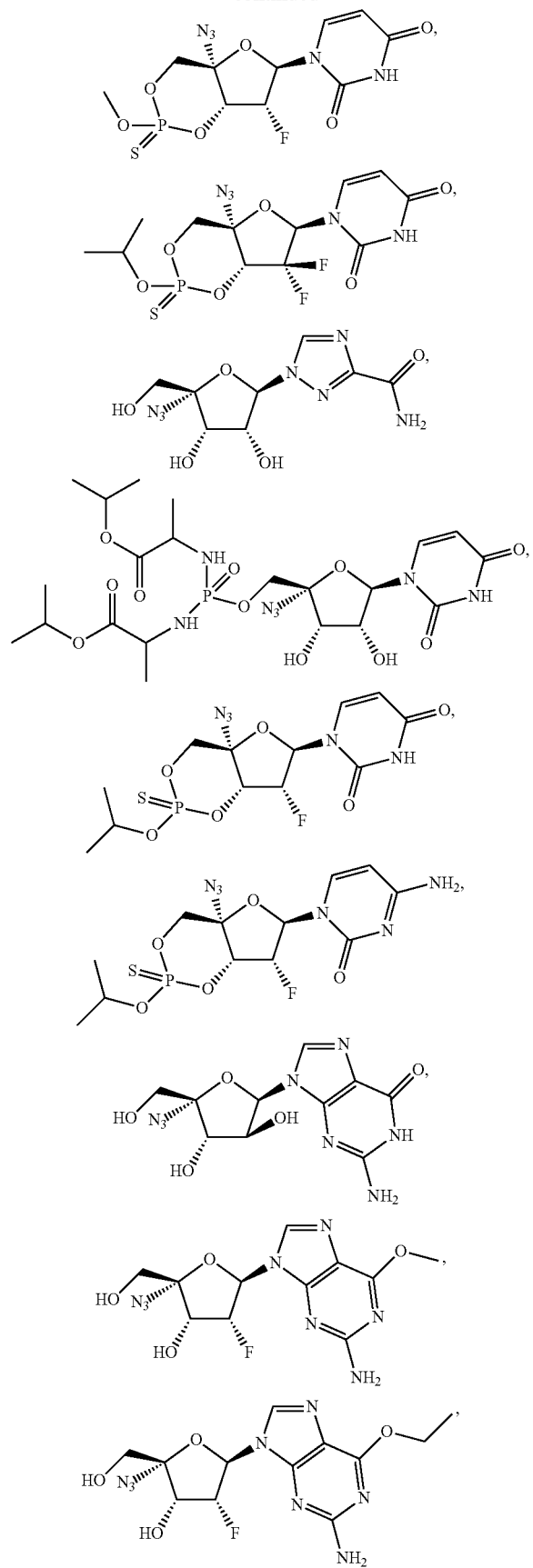

-continued

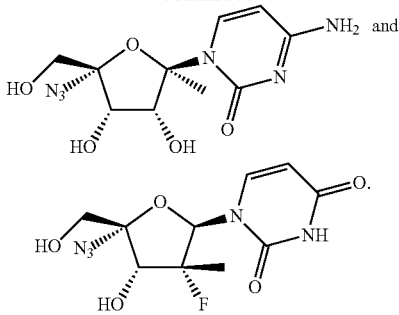

As used herein, the terms "prevent" and "preventing," mean a subject does not develop an infection because the subject has an immunity against the infection, or if a subject becomes infected, the severity of the disease is less compared to the severity of the disease if the subject has not been administered/received the compound. Examples of forms of prevention include prophylactic administration to a subject who has been or may be exposed to an infectious agent, such as a paramyxovirus (e.g., RSV) and/or an orthomyxovirus (e.g., influenza).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "therapeutically effective amount" is used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a paramyxovirus viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, an effective amount of a compound of Formulae (II) and/or (IIa), or a pharmaceutically acceptable salt thereof, is an amount that is effective to reduce viral titers to undetectable levels, for example, to about 1000 to about 5000, to about 500 to about 1000, or to about 100 to about 500 genome copies/mL serum. In some embodiments, an effective amount of a compound of Formula (II) and/or (IIa), or a pharmaceutically acceptable salt thereof, is an amount that is effective to reduce viral load compared to the viral load before administration of the compound of Formula (II) and/or (IIa), or a pharmaceutically acceptable salt thereof. For example, wherein the viral load is measure before administration of the compound of Formula (II) and/or (IIa), or a pharmaceutically acceptable salt thereof, and again after completion of the treatment regime with the compound of Formula (II) and/or (IIa), or a pharmaceutically acceptable salt thereof (for example, 1 week after completion). In some embodiments, an effective amount of a compound of Formula (II) and/or (IIa), or a pharmaceutically acceptable salt thereof, can be an amount that is effective to reduce viral load to lower than about 100 genome copies/mL serum. In some embodiments, an effective amount of a compound of Formula (II) and/or (IIa), or a pharmaceutically acceptable salt thereof, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formula (II) and/or (IIa), or a pharmaceutically acceptable salt thereof. For example, wherein the viral load is measure before administration of the compound of Formula (II) and/or (IIa), or a pharmaceutically acceptable salt thereof, and again after completion of the treatment regime with the compound of Formula (II) and/or (IIa), or a pharmaceutically acceptable salt thereof (for example, 1 week after completion).

In some embodiments, a compound of Formula (II) and/or (IIa), or a pharmaceutically acceptable salt thereof, can result in at least a 1, 2, 3, 4, 5, 10, 15, 20, 25, 50, 75, 100-fold or more reduction in the replication of a paramyxovirus and/or an orthomyxovirus relative to pre-treatment levels in a subject, as determined after completion of the treatment regime (for example, 1 week after completion). In some embodiments, a compound of Formula (II) and/or (IIa), or a pharmaceutically acceptable salt thereof, can result in a reduction of the replication of paramyxovirus and/or an orthomyxovirus relative to pre-treatment levels in the range of about 2 to about 5 fold, about 10 to about 20 fold, about 15 to about 40 fold, or about 50 to about 100 fold. In some embodiments, a compound of Formula (II) and/or (IIa), or a pharmaceutically acceptable salt thereof, can result in a reduction of paramyxovirus replication in the range of 1 to 1.5 log, 1.5 log to 2 log, 2 log to 2.5 log, 2.5 to 3 log, 3 log to 3.5 log or 3.5 to 4 log more reduction of paramyxovirus replication compared to the reduction of paramyxovirus reduction achieved by ribavirin (Virazole®), or may achieve the same reduction as that of ribavirin (Virazole®) therapy in a shorter period of time, for example, in one week, two weeks, one month, two months, or three months, as compared to the reduction achieved after six months of ribavirin (Virazole®) therapy. In some embodiments, a compound of Formula (II) and/or (IIa), or a pharmaceutically acceptable salt thereof, can result in a reduction of orthomyxovirus replication in the range of 1 to 1.5 log, 1.5 log to 2 log, 2 log to 2.5 log, 2.5 to 3 log, 3 log to 3.5 log or 3.5 to 4 log more reduction of orthomyxovirus replication compared to the reduction of orthomyxovirus reduction achieved by oseltamivir (Tamiflu®), or may achieve the same reduction as that of oseltamivir (Tamiflu®) therapy in a shorter period of time, for example, in one week, two weeks, one month, two months, or three months, as compared to the reduction achieved after six months of oseltamivir (Tamiflu®) therapy.

In some embodiments, an effective amount of a compound of Formula (II) and/or a compound of Formula (II), or a pharmaceutically acceptable salt thereof, is an amount that is effective to achieve a sustained viral response, for example, non-detectable or substantially non-detectable paramyxovirus and/or an orthomyxovirus RNA (e.g., less than about 500, less than about 400, less than about 200, or less than about 100 genome copies per milliliter serum) is found in the subject's serum for a period of at least about one week, two weeks, one month, at least about two months, at least about three months, at least about four months, at least about five months, or at least about six months following cessation of therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), and/or a compound of Formula (II), or a pharmaceutically acceptable salt thereof, can be administered to a subject infected with RSV that is resistant to one or more different anti-RSV agents (for example, ribavirin). In some embodiments, development of resistant RSV strains is delayed when patients are treated with a compound of Formula (I), and/or a compound of Formula (II), or a pharmaceutically acceptable salt thereof, compared to the development of RSV strains resistant to other RSV drugs. In some embodiments, a compound of Formula (I), and/or a compound of Formula (II), or a pharmaceutically acceptable salt thereof, can be administered to a subject infected with an influenza virus that is resistant to one or more different anti-influenza agents (for example, amantadine and rimantadine). In some embodiments, development of resistant influenza strains is delayed when patients are treated with a compound of Formula (I), and/or a compound of Formula (II), or a pharmaceutically acceptable salt thereof, compared to the development of influenza strains resistant to other influenza drugs.

In some embodiments, a compound of Formula (I), and/or a compound of Formula (II), or a pharmaceutically acceptable salt thereof, can decrease the percentage of subjects that experience complications from a RSV viral infection compared to the percentage of subjects that experience complication being treated with ribavirin. In some embodiments, a compound of Formula (I), and/or a compound of Formula (II), or a pharmaceutically acceptable salt thereof, can decrease the percentage of subjects that experience complications from an influenza viral infection compared to the percentage of subjects that experience complication being treated with oseltamivir. For example, the percentage of subjects being treated with a compound of Formula (I), and/or a compound of Formula (II), or a pharmaceutically acceptable salt thereof, that experience complications can be 10%, 25%, 40%, 50%, 60%, 70%, 80% and 90% less compared to subjects being treated with ribavirin or oseltamivir.

In some embodiments, a compound of Formula (I), and/or a compound of Formula (II), or a pharmaceutically acceptable salt thereof, or a pharmaceutical composition that includes a compound described herein, can be used in combination with one or more additional agent(s). In some embodiments, a compound of Formula (I), and/or a compound of Formula (II), or a pharmaceutically acceptable salt thereof, can be used in combination with one or more agents currently used in a conventional standard of care for treating RSV. For example, the additional agent can be ribavirin, palivizumab and RSV-IGIV. For the treatment of RSV, additional agents include but are not limited to ALN-RSV01 (Alnylam Pharmaceuticals), BMS-433771 (1-cyclopropyl-3-[[1-(4-hydroxybutyl)benzimidazol-2-yl]methyl]imidazo

[4,5-c]pyridin-2-one), RFI-641 ((4,4"-bis-{4,6-bis-[3-(bis-carbamoylmethyl-sulfamoyl)-phenylamino]-(1,3,5)triazin-2-ylamino }-biphenyl-2,2"-disulfonic-acid)), RSV604 ((S)-1-(2-fluorophenyl)-3-(2-oxo-5-phenyl-2,3-dihydro-1H-benzo[e][1,4]di-azepin-3-yl)-urea), MDT-637, BTA9881, TMC-353121 (Tibotec), MBX-300, YM-53403 (N-cyclopropyl-6-[4-[(2-phenylbenzoyl)amino]benzoyl]-4,5-dihydrothieno [3,2-d][1]benzazepine-2-carboxamide), motavizumab (Medi-524, MedImmune), Medi-559, Medi-534 and Medi-557. In some embodiments, a compound of Formula (I), and/or a compound of Formula (II), or a pharmaceutically acceptable salt thereof, can be used in combination with one or more agents currently used in a conventional standard of care for treating influenza. For example, the additional agent can be amantadine, rimantadine, zanamivir and oseltamivir. For the treatment of influenza, additional agents include but are not limited to peramivir ((1S,2S,3S,4R)-3- [(1S)-1-acetamido-2-ethylbutyl]-4-(diaminomethylideneamino)-2-hydroxycyclopentane-1-carboxylic acid), laninamivir ((4S, 5R, 6R)-5-acetamido-4-carbamimidamido-6-[(1R,2R)-3-hydroxy -2-methoxypropyl]-5,6-dihydro-4H-pyran-2-carboxylic acid), favipirvir (T-705, 6-fluoro-3-hydroxy-2-pyrazinecarboxamide), fludase (DAS181, NexBio), ADS-8902 (Adamas Pharmaceuticals), IFN-b (Synairgen), beraprost N-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid) and Neugene®.

In some embodiments, a compound of Formula (I), and/or a compound of Formula (II), or a pharmaceutically acceptable salt thereof, can be administered with one or more additional agent(s) together in a single pharmaceutical composition. In some embodiments, a compound of Formula (I), and/or a compound of Formula (II), or a pharmaceutically acceptable salt thereof, can be administered with one or more additional agent(s) as two or more separate pharmaceutical compositions. For example, a compound of Formula (I), and/or a compound of Formula (II), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), and/or a compound of Formula (II), or a pharmaceutically acceptable salt thereof, and at least one of the other additional agent(s) can be in a second pharmaceutical composition.

The order of administration of a compound of Formula (I), and/or a compound of Formula (II), or a pharmaceutically acceptable salt thereof, with one or more additional agent(s) can vary. In some embodiments, a compound of Formula (I), and/or a compound of Formula (II), or a pharmaceutically acceptable salt thereof, can be administered prior to all additional agents. In other embodiments, a compound of Formula (I), and/or a compound of Formula (II), or a pharmaceutically acceptable salt thereof, can be administered prior to at least one additional agent. In still other embodiments, a compound of Formula (I), and/or a compound of Formula (II), or a pharmaceutically acceptable salt thereof, can be administered concomitantly with one or more additional agent(s). In yet still other embodiments, a compound of Formula (I), and/or a compound of Formula (II), or a pharmaceutically acceptable salt thereof, can be administered subsequent to the administration of at least one additional agent. In some embodiments, a compound of Formula (I), and/or a compound of Formula (II), or a pharmaceutically acceptable salt thereof, can be administered subsequent to the administration of all additional agents.

A potential advantage of utilizing a compound of Formula (I), and/or a compound of Formula (II), or a pharmaceutically acceptable salt of the foregoing, in combination with one or more additional agent(s) described (including pharmaceutically acceptable salts and prodrugs thereof) may be a reduction in the required amount(s) of one or more compounds (including pharmaceutically acceptable salts and prodrugs thereof) that is effective in treating a disease condition disclosed herein (for example, RSV and/or influenza), as compared to the amount required to achieve same therapeutic result when one or more compounds described (including pharmaceutically acceptable salts and prodrugs thereof) are administered without a compound of Formula (I), and/or a compound of Formula (II), or a pharmaceutically acceptable salt the foregoing. For example, the amount of a compound described (including a pharmaceutically acceptable salt and prodrug thereof), can be less compared to the amount of the compound described (including a pharmaceutically acceptable salt and prodrug thereof), needed to achieve the same viral load reduction when administered as a monotherapy. Another potential advantage of utilizing a compound of Formula (I), and/or a compound of Formula (II), or a pharmaceutically acceptable salt of the foregoing, in combination with one or more additional agent(s) described (including pharmaceutically acceptable salts and prodrugs thereof) is that the use of two or more compounds having different mechanism of actions can create a higher barrier to the development of resistant viral strains compared to the barrier when a compound is administered as monotherapy.

Additional advantages of utilizing a compound of Formula (I), and/or a compound of Formula (II), or a pharmaceutically acceptable salt the foregoing, in combination with one or more additional agent(s) described (including pharmaceutically acceptable salts and prodrugs thereof) may include little to no cross resistance between a compound of Formula (I), and/or a compound of Formula (II), or a pharmaceutically acceptable salt the foregoing, and one or more additional agent(s) described (including pharmaceutically acceptable salts and prodrugs thereof) thereof; different routes for elimination of a compound of Formula (I), and/or a compound of Formula (II), or a pharmaceutically acceptable salt the foregoing, and one or more additional agent(s) described (including pharmaceutically acceptable salts and prodrugs thereof); little to no overlapping toxicities between a compound of Formula (I), and/or a compound of Formula (II), or a pharmaceutically acceptable salt the foregoing, and one or more additional agent(s) described (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) described (including pharmaceutically acceptable salts and prodrugs thereof).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Synthesis

Compounds of Formula (I) and Formula (II), and those described herein may be prepared in various ways. Some compounds of Formulae (I) and (II) can be obtained commercially and/or prepared utilizing known synthetic procedures. General synthetic routes to the compounds of Formulae (I) and (II), and some examples of starting materials used to synthesize the compounds of Formulae (I) and (II) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

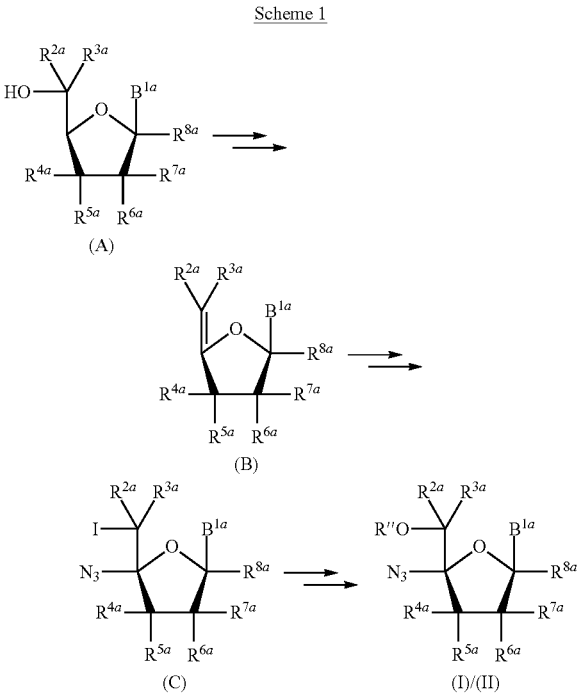

Scheme 1

As shown in Scheme 1, compounds of Formulae (I) and (II) can be prepared from a nucleoside, for example, a nucleoside of Formula (A). In Scheme 1, $R^{2a}$, $R^{3a}$, $R^{4a}$, $R^{5a}$, $R^{6a}$, $R^{7a}$, $R^{8a}$ and $B^{1a}$ can be the same as $R^{2a}$, $R^{3a}$, $R^{4a}$, $R^{5a}$, $R^{6a}$, $R^{7a}$, $R^{8a}$ and $B^{1a}$ as described herein for Formula (II) for preparing a compound of Formula (II). For preparing a compound of Formula (I), $R^{2a}$, $R^{3a}$, $R^{4a}$, $R^{5a}$, $R^{6a}$, $R^{7a}$, $R^{8a}$ and $B^{1a}$ can be the same as $R^2$, $R^3$, $R^4$, $R^5$, $R^6$, $R^7$, $R^8$ and $B^{1a}$ as described herein for Formula (I). The nucleoside can undergo elimination and form an olefin having the general formula of Formula (B). A compound of Formula (B) can be treated with an iodinating reagent in the presence of an azide source to form a compound of Formula (C). A compound of Formula (C) can then be transformed to a compound of Formula (I) and/or a compound of Formula (II) through displacement of the iodide with an oxygen nucleophile. The displacement can occur directly or following an in situ oxidation of the iodide of a compound of Formula (C).

Scheme 2

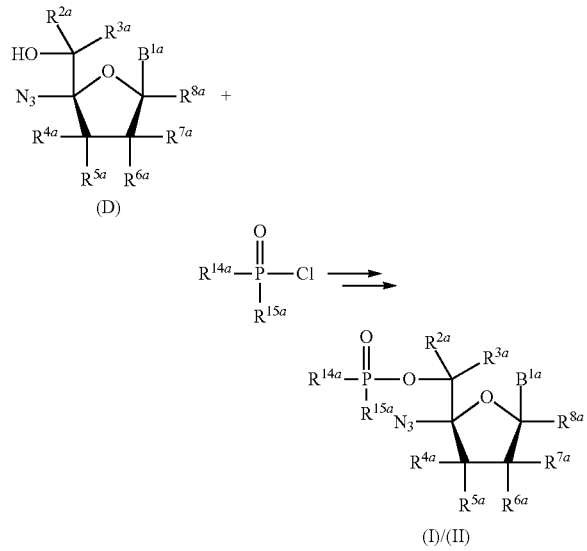

Phosphoramidate can be prepared using various methods known to those skilled in the art. One method is shown in Scheme 2. In Scheme 2, $R^{2a}$, $R^{3a}$, $R^{4a}$, $R^{5a}$, $R^{6a}$, $R^{7a}$, $R^{8a}$, $R^{14a}$, $R^{15a}$ and $B^{1a}$ can be the same as $R^{2a}$, $R^{3a}$, $R^{4a}$, $R^{5a}$, $R^{6a}$, $R^{7a}$, $R^{8a}$, $R^{14a}$, $R^{15a}$ and $B^{1a}$ as described herein for Formula (II) for preparing a compound of Formula (II). For preparing a compound of Formula (I), $R^{2a}$, $R^{3a}$, $R^{4a}$, $R^{5a}$, $R^{6a}$, $R^{7a}$, $R^{8a}$, $R^{14a}$, $R^{15a}$ and $B^{1a}$ can be the same as $R^2$, $R^3$, $R^4$, $R^5$, $R^6$, $R^7$, $R^8$, $R^{14}$, $R^{15}$ and $B^{1a}$ as described herein for Formula (I).

Scheme 3

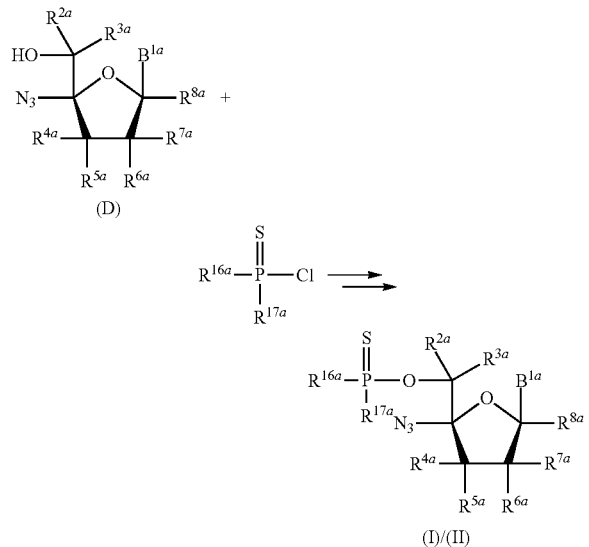

Various methods for preparing a compound of Formula (I) and/or a compound of Formula (II), wherein $R^1$ is a thiophosphoramidates, are known by those skilled in the art. For example, a compound of Formula (I) and/or a compound of Formula (II) can be prepared as shown in Scheme 3. In Scheme 3, $R^{2a}$, $R^{3a}$, $R^{4a}$, $R^{5a}$, $R^{6a}$, $R^{7a}$, $R^{8a}$, $R^{16a}$, $R^{17a}$ and $B^{1a}$ can be the same as $R^{2a}$, $R^{3a}$, $R^{4a}$, $R^{5a}$, $R^{6a}$, $R^{7a}$, $R^{8a}$, $R^{16a}$, $R^{17a}$ and $B^{1a}$ as described herein for Formula (II) for preparing a compound of Formula (II). For preparing a compound of Formula (I), $R^{2a}$, $R^{3a}$, $R^{4a}$, $R^{5a}$, $R^{6a}$, $R^{7a}$, $R^{8a}$, $R^{16a}$, $R^{17a}$ and $B^{1a}$ can be the same as $R^2$, $R^3$, $R^4$, $R^5$, $R^6$, $R^7$, $R^8$, $R^{16}$, $R^{17}$ and $B^{1a}$, as described herein for Formula (I).

Suitable phosphorochloridates and thiophosphorochloridates can be commercially obtained or prepared by synthetic methods known to those skilled in the art. An example of a general structure of a phosphorochloridates and thiophosphorochloridates are shown in Schemes 2 and 3, respectively. In some embodiments, the phosphorochloridate or the thiophosphorochloridate can be coupled to a compound of Formula (D). In some embodiments, to facilitate the coupling, a Grignard reagent can be used. Suitable Grignard reagents are known to those skilled in the art and include, but are not limited to, alkylmagnesium chlorides and alkylmagnesium bromides. In other embodiments, the phosphorochloridate or the thiophosphorochloridate can be added to a compound of Formula (D) using a base. Suitable bases are known to those skilled in the art. Examples of bases include, but are not limited to, an amine base, such as an alkylamine (including mono-, di- and tri-alkylamines (e.g., triethylamine)), optionally substituted pyridines (e.g. collidine) and optionally substituted imidzoles (e.g., N-methylimidazole)).

Scheme 4:

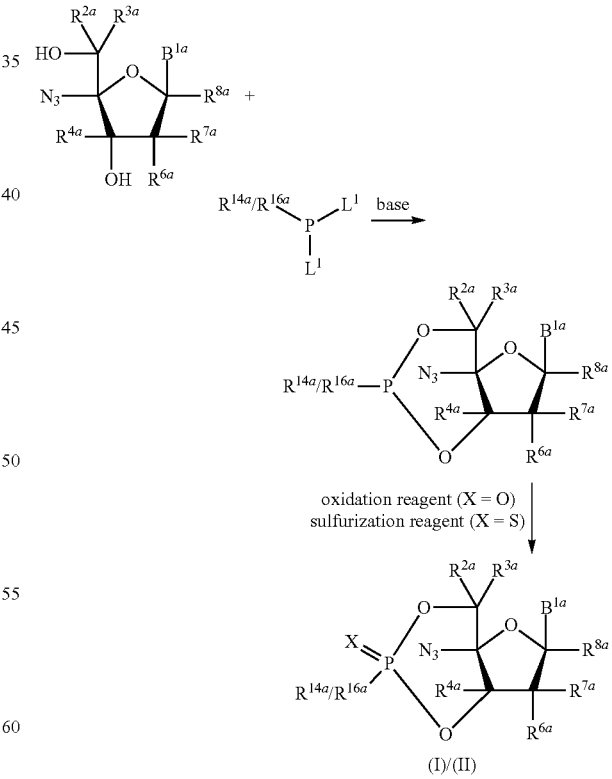

A method for forming a compound of Formula (I) and/or a compound of Formula (II), wherein the 5'-carbon is joined to the 3'-carbon is shown in Scheme 4. In Scheme 4, $R^{2a}$, $R^{3a}$, $R^{4a}$, $R^{6a}$, $R^{7a}$, $R^{8a}$, $R^{14a}$, $R^{16a}$ and $B^{1a}$ can be the same as $R^{2a}$, $R^{3a}$, $R^{4a}$, $R^{6a}$, $R^{7a}$, $R^{8a}$, $R^{14a}$, $R^{16a}$ and $B^{1a}$ as described herein for Formula (II) for preparing a compound of Formula (II), each $L^1$ can be a halogen, a sulfonate ester or an amine (mono- or di-substituted), and X can be oxygen or sulfur. For preparing a compound of Formula (I), $R^{2a}$, $R^{3a}$, $R^{4a}$, $R^{6a}$, $R^{7a}$, $R^{8a}$, $R^{14a}$, $R^{16a}$ and $B^{1a}$ can be the same as $R^2$, $R^3$, $R^4$, $R^6$, $R^7$, $R^8$, $R^{14}$, $R^{16}$ and $B^{1a}$ as described herein for Formula (I). As illustrated in Scheme 4, a compound having a hydroxy group attached to the 3'-carbon and a hydroxy group attached to the 5'-carbon can be reacted with a compound having the formula, $(R^{14}/R^{16a})P(L^1)_2$, in the presence of a base, to produce a phosphite compound. Suitable bases are known to those skilled in the art and described herein. The phosphorus can then be oxidized to phosphorus (V) using a suitable oxidizing agent, to produce a compound where X is O (oxygen). Alternatively, the phosphite compound can be reacted with a sulfurization reagent to produce a compound where X is S (sulfur). Suitable oxidizing and sulfurization agents are known to those skilled in the art. For example, the oxidation can be carried out using iodine as the oxidizing agent and water as the oxygen donor. Suitable sulfurization agents include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

During the synthesis of any of the compounds described herein, if desired, any hydroxy groups attached to the pentose ring, and any —NH and/or $NH_2$ groups present on the $B^{1A}$ can be protected with one or more suitable protecting groups. Suitable protecting groups are described herein. For example, when $R^{5a}$ and $R^{6a}$ are both hydroxy groups, $R^{5a}$ and $R^{6a}$ can be protected with one or more triarylmethyl groups, one or more silyl groups or a single achiral or chiral protecting group (for example, by forming an orthoester, cyclic acetal or cyclic ketal). Likewise, any —NH and/or $NH_2$ groups present on the $B^{1A}$ can be protected, such as with a triarylmethyl and a silyl group(s). Examples of triarylmethyl groups include but are not limited to, trityl, monomethoxytrityl (MMTr), 4,4'-dimethoxytrityl (DMTr), 4,4',4''-trimethoxytrityl (TMTr), 4,4',4''-tris-(benzoyloxy)trityl (TBTr), 4,4',4''-tris(4,5-dichlorophthalimido)trityl (CPTr), 4,4',4''-tris(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4''-tris-(tert-butylphenyl)methyl (TTTr) and 4,4'-di-3,5-hexadienoxytrityl. Examples of silyl groups include, but are not limited to, trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy)propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal. Those skilled in the art will appreciate that groups attached to the pentose ring and any —NH and/or $NH_2$ groups present on the $B^{1A}$ can be protected with various protecting groups, and any protecting groups present can be exchanged for other protecting groups. The selection and exchange of the protecting groups is within the skill of those of ordinary skill in the art. Any protecting group(s) can be removed by methods known in the art, for example, with an acid (e.g., a mineral or an organic acid), a base or a fluoride source.

Pharmaceutical Compositions

Some embodiments described herein relates to a pharmaceutical composition, that can include a therapeutically effective amount of one or more compounds described herein (e.g., a compound of Formula (I) and/or a compound of Formula (II), or a pharmaceutically acceptable salt thereof) and a pharmaceutically acceptable carrier, diluent, excipient or combination thereof.

The term "pharmaceutical composition" refers to a mixture of a compound disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

EXAMPLES

Additional embodiments are disclosed in further detail in the following examples, which are not in any way intended to limit the scope of the claims.

Example 1

Preparation of 4'-azido-2'-deoxy-2',2'-difluorocytidine (1)

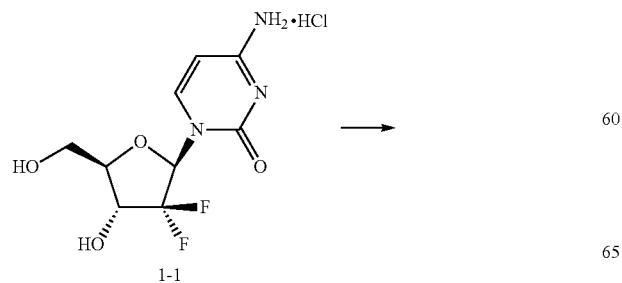

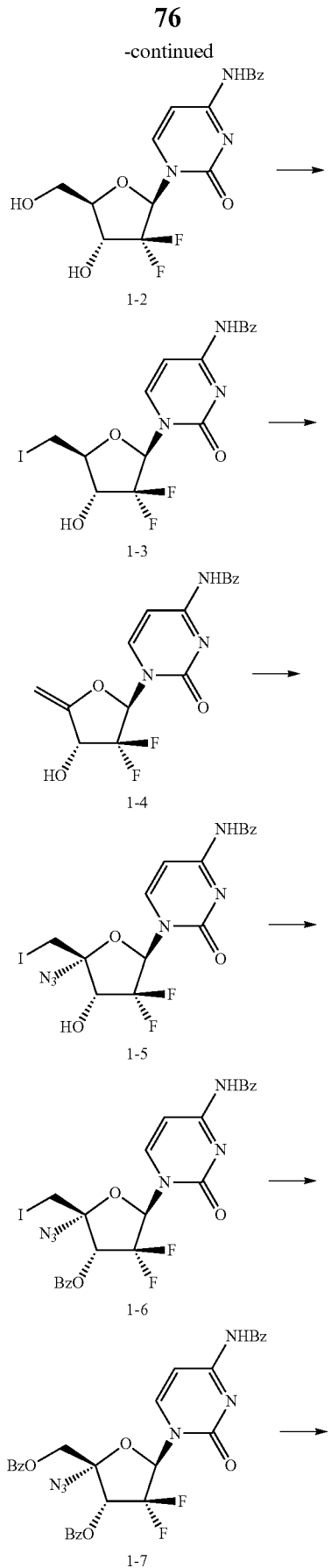

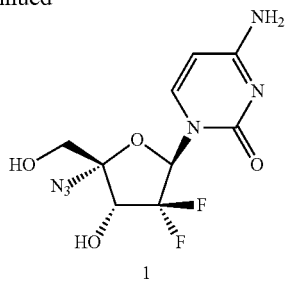

Step 1. Compound 1-2—Compound 1-1 (30.0 g, 0.1 mol) was suspended in anhydrous pyridine (300 mL) and stirred at room temperature (R.T.) for 1 hour. The suspension was cooled to 0° C. and TMSCl (27.3 g, 0.25 mmol) was added dropwise. After addition was complete, the mixture was warmed to R.T. and stirred for 30 min. The mixture was then re-cooled to 0° C. and BzCl (15.5 g, 0.11 mol) was added dropwise. The mixture was warmed to R.T. and stirred overnight. The reaction was cooled to 0° C. and quenched with $H_2O$. Aqueous ammonia was added, and the reaction was stirred at R.T. for 2 hours. The solution was concentrated and the residue was taken up into ethyl acetate (EA) and $H_2O$. The aqueous phase was extracted with EA several times, and the combined organic layers were dried over $Na_2SO_4$ and concentrated. The residue was purified on a silica gel column to give compound 1-2 as a white solid (28.2 g, 76%). ESI-LCMS: m/z=368 [M+Na]$^+$.

Step 2. Compound 1-3—To a stirred suspension of compound 1-2 (18.4 g, 50 mmol), PPh$_3$ (22.3 g, 85 mmol) and pyridine (25 mL) in anhydrous THF (300 mL) was added a solution of $I_2$ (19.05 g, 75 mmol) in THF (80 mL) dropwise at 0° C. After addition, the mixture was warmed to R.T. and stirred for 60 hours. The precipitate was removed by filtration, and the filtrate was concentrated. The residue was dissolved in dichloromethane (DCM) and washed with saturated $Na_2S_2O_3$ aqueous solution and then brine. The organic layer was dried over $Na_2SO_4$ and concentrated. The residue was purified on a silica gel column to afford compound 1-3 (16.4 g, 69%). ESI-LCMS: m/z=478 [M+H]$^+$.

Step 3. Compound 1-4—To a stirred solution of compound 1-3 (17.0 g, 35.6 mmol) in anhydrous dimethylformamide (DMF) (300 mL) was added dropwise a solution of t-BuOK (10.0 g, 89.1 mmol) in DMF (120 mL) at 0° C. over 20 min. Stirring was continued at 0° C. for 45 min, and then concentrated hydrochloric acid (4.5 mL) was added. A pH value of 8-9 was achieved by adding a saturated $NaHCO_3$ solution. The precipitate was removed by filtration, and the filtrate was diluted with ethyl acetate. The solution was washed with brine and dried over $Na_2SO_4$. The solvent was removed, and the residue was purified on a silica gel column to afford compound 1-4 as a white solid (8.6 g, 69%). ESI-LCMS: m/z=350 [M+H]$^+$.

Step 4. Compound 1-5—To a stirred solution of Bn Et$_3$NCl (37.4 g, 0.16 mol) in MeCN (600 mL) was added NaN$_3$ (10.8 g, 0.16 mol). The mixture was sonicated for 20 min, and then stirred at R.T. for 16 hours. The solution was filtrated into a solution of compound 1-4 (11.5 g, 32.9 mmol) and N-methylmorpholine (3.5 g) in anhydrous THF (200 mL). The mixture was cooled to 0° C. and a solution of $I_2$ (33.6 g, 0.14 mol) in THF (100 mL) was added dropwise. Stirring was continued at 0-10° C. for 20 hours. N-Acetyl cystein was added until no gas evolved. Saturated $Na_2S_2O_3$ aq. was added until a light yellow solution was achieved. The solution was concentrated and then diluted with EA. The organic phase was washed with brine and dried over $Na_2SO_4$. The solvent was removed, and the residue was purified on a silica gel column to give compound 1-5 (14.7 g, 84%). ESI-LCMS: m/z=519 [M+H]$^+$.

Step 5. Compound 1-6—To a stirred solution of compound 1-5 (12.5 g, 24.8 mmol) in anhydrous pyridine (200 mL) was added BzCl (4.3 g, 30 mmol) dropwise at 0° C. The mixture was then stirred at R.T. for 10 hours. The reaction was quenched with $H_2O$, and the solution was concentrated. The residue was dissolved in EA and washed with saturated $NaHCO_3$. The organic layer was dried over $Na_2SO_4$ and concentrated. The residue was purified on a silica gel column to give compound 1-6 as a white foam (11.2 g). ESI-LCMS: m/z=623 [M+H]$^+$.

Step 6. Compound 1-7—Compound 1-6 (9.43 g, 15.2 mmol), BzONa (21.9 g, 152 mmol) and 15-crown-5 (33.4 g, 152 mmol) were suspended in 200 mL DMF. The mixture was stirred at 60-70° C. for 3 days. The precipitate was removed by filtration, and the filtrate was diluted with EA. The solvent was washed with brine and dried over $Na_2SO_4$. The solvent was removed, and the residue was purified on a silica gel column to afford compound 1-7 as a white foam (4.4 g, 46%). ESI-LCMS: m/z=617 [M+H]$^+$.

Step 7. Compound (1)—Compound 1-7 (4.4 g, 7.13 mmol) was dissolved in 100 mL of saturated methanolic ammonia, and the resulting solution was stirred at R.T. for 14 hours. The solvent was removed, and the residue was purified on a silica gel column (DCM/MeOH=30:1 to 10:1) to give (1) as a white solid (1.9 g, 88%). $^1$H NMR (CD$_3$OD, 400 M Hz) δ 7.70 (d, J=7.6 Hz, 1H), 6.40 (t, J=7.2 Hz, 1H), 5.93 (d, J=7.6 Hz, 1H), 4.50 (t, J=13.2 Hz, 1H), 3.88 (dd, J$_1$=12.0 Hz, J$_2$=26.8 Hz, 2H); ESI-MS: m/z=305 [M+H]$^+$, 609 [2M+H]$^+$.

Example 2

Preparation of 4'-azido-2'-deoxy-2'-fluorocytidine (2)

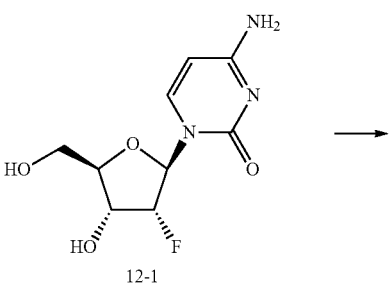

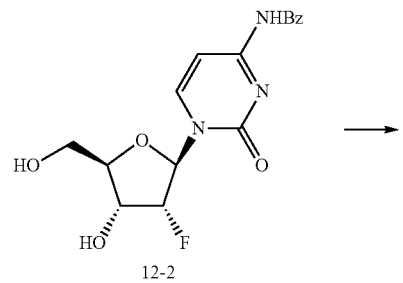

-continued

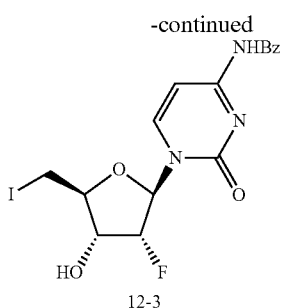
12-3

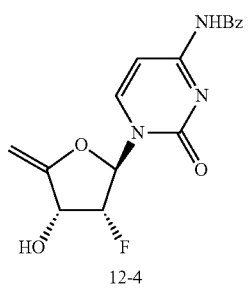
12-4

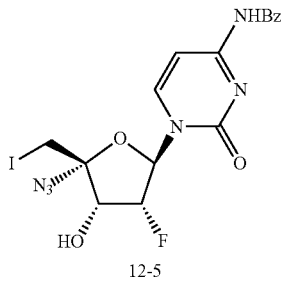
12-5

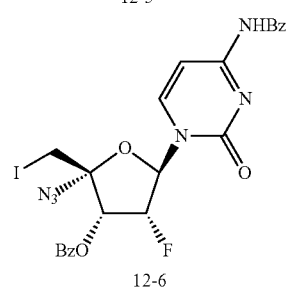
12-6

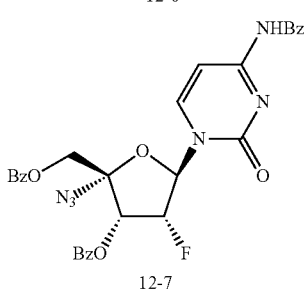
12-7

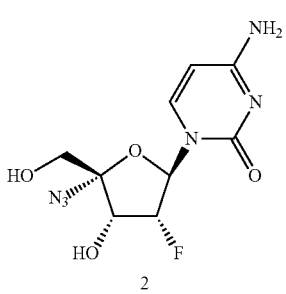
2

Step 1. Compound 12-2—To a stirred solution of compound 12-1 (21.0 g, 85.7 mmol) in DMF (100 mL) was added benzoyl anhydride (9.66 g, 87 mmol) in portions. The mixture was stirred at R.T. overnight. The solvent was removed under reduced pressure, and the residue was triturated with $CH_2Cl_2$ to give compound 12-2 as a white solid (29.90 g, 100%).

Step 2. Compound 12-3—To a stirred suspension of compound 12-2 (10.0 g, 28.65 mmol), $PPh_3$ (15.01 g, 57.30 mmol) and pyridine (20 mL) in anhydrous THF (100 mL) was added dropwise a solution of $I_2$ (14.55 g, 57.30 mmol) in THF (50 mL) at 0° C. After addition. the mixture was warmed to R.T. and stirred for 14 hours. The reaction was quenched with saturated aqueous $Na_2S_2O_3$ (150 mL) and extracted with EA (100 mL, 3 times). The organic layer was dried over $Na_2SO_4$ and concentrated. The residue was purified on a silica gel column (DCM/MeOH=100:1 to 50:1) to afford compound 12-3 (4.61 g, 35.1%) as a white solid.

Step 3. Compound 12-4—To a stirred solution of compound 12-3 (4.6 g, 10.02 mmol) in anhydrous DMF (100 mL) was added dropwise a suspension of t-BuOK (3.36 g, 30.06 mmol) in DMF (20 mL) at 0° C. over 10 min. The mixture was stirred at R.T. for 2 hours. The mixtures was then quenched with saturated aqueous $NH_4Cl$ (50 mL), and extracted with THF and EA. The organic layer was washed with brine and dried over $Na_2SO_4$. The solvent was removed, and the residue was purified on a silica gel column (MeOH/DCM=1/100 to 1/30) to afford compound 12-4 as white solid (3.30 g, 99.6%).

Step 4. Compound 12-5—To a stirred solution of $BnEt_3NCl$ (11.69 g, 50.2 mmol) in MeCN (50 mL) was added $NaN_3$ (3.26 g, 50.2 mmol). The mixture was sonicated for 20 min and then stirred at R.T. for 16 hours. The solution was filtrated into a solution of compound 12-4 (3.31 g, 10.02 mmol) and NMM (5.02 g, 50.2 mmol) in anhydrous THF (80 mL). The mixture was cooled to 0° C., and a solution of $I_2$ (12.5 g, 50.2 mmol) in THF (40 mL) was added dropwise. Stirring was continued at 0-10° C. for 20 hours. N-Acetyl cystein was added until no gas evolved. Saturated aqueous $Na_2S_2O_3$ was added until a light yellow solution achieved. The solution was concentrated and then diluted with EA. The organic phase was washed with brine and dried over $Na_2SO_4$. The solvent was removed, and the residue was purified on a silica gel column (PE:EA:DCM=1:1:1) to give compound 12-5 (14.7 g, 84%) as a white foam. $^1H$ NMR ($CD_3OD$, 400 MHz) δ 11.41 (s, 1H), 8.19 (d, J=7.2 Hz, 1H), 8.00 (d, J=7.2 Hz, 1H), 7.62-7.66 (m, 1H), 7.50-7.54 (m, 2H), 7.39 (d, J=7.2 Hz, 1H), 6.44 (d, J=6.8 Hz, 1H), 6.13 (d, J=20.4 Hz, 1H), 5.36-5.41 (m, 1H), 4.70-4.76 (m, 1H), 3.72 (dd, $J_1$=17.6 Hz, $J_2$=11.6 Hz, 2H).

Step 5. Compound 12-6—To a stirred solution of compound 12-5 (3.6 g, 7.20 mmol) in anhydrous pyridine (80 mL) was added BzCl (1.31 g, 9.36 mmol) dropwise at 0° C. The mixture was stirred at R.T. for 10 hours. The reaction was quenched with $H_2O$, and the solution was concentrated. The residue was dissolved in EA and washed with saturated aqueous $NaHCO_3$. The organic layer was dried over $Na_2SO_4$ and concentrated. The residue was purified on a silica gel column (PE/EA=10/1 to 1/1) to give compound 12-6 (3.2 g, 73.7%) as a pale yellow foam.

Step 6. Compound 12-7—Compound 12-6 (2.0 g, 3.31 mmol), BzONa (4.76 g, 33.1 mmol) and 15-crown-5 (7.28 g, 33.1 mmol) were suspended in DMF (100 mL). The mixture was stirred at 60-70° C. for 3 days. The precipitate removed by filtration, and the filtrate was diluted with EA. The solution was washed with brine and dried over $Na_2SO_4$. The solvent was removed, and the residue was purified on a silica gel column (PE/EA=4/1 to 2/1) to afford compound 12-7 as a light yellow foam (1.0 g, 50.7%).

Step 7. Compound (2)—Compound 12-7 (0.5 g, 0.84 mmol) was dissolved in methanolic ammonia (30 mL), and the mixture was stirred at R.T. for 14 hours. The solvent was removed, and the residue was purified on a silica gel column (DCM/MeOH=30:1 to 10:1) to give (2) as white solids (0.11 g, 41.8%). $^1$H NMR (CD$_3$OD, 400 MHz) δ 7.83 (d, J=7.6 Hz, 1H), 6.10 (dd, J$_1$=19.6 Hz, J$_2$=1.6 Hz, 1H), 5.94 (d, J=7.6 Hz, 1H), 5.10 (ddd, J$_1$=53.6 Hz, J$_2$=5.2 Hz, J$_3$=1.2 Hz, 1H), 4.57 (t, J=5.2 Hz, 1H), 3.82 (dd, J$_1$=38.0 Hz, J$_2$=12.4 Hz, 2H); ESI-MS: m/z=287 [M+H]$^+$, 573 [2M+H]$^+$.

Example 3

Preparation of 3'-deoxy-3'-alpha-fluoro-4'-azidocytidine (3)

Compound (3) was prepared using the procedure set forth in the *Journal of Medicinal Chemistry* (2009) 52:2971-2978, which are hereby incorporated by reference for the limited purpose of disclosing the procedure of preparing (3).

Example 4

Preparation of 4'-azido-3'-deoxycytidine (4)

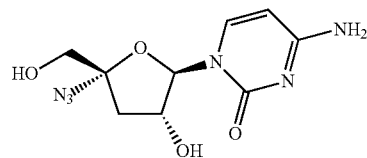 [SMILES: [N-]=[N+]=N[C@@]1(CO)C[C@@H](O)[C@H](n2ccc(N)nc2=O)O1]

Compound (4) was prepared using the procedure set forth in the *Journal of Medicinal Chemistry* (2009) 52:2971-2978, which are hereby incorporated by reference for the limited purpose of disclosing the procedure of preparing (4).

Example 5

Preparation of 4'-azido-2'-deoxy-2',2'-difluorouridine (5)

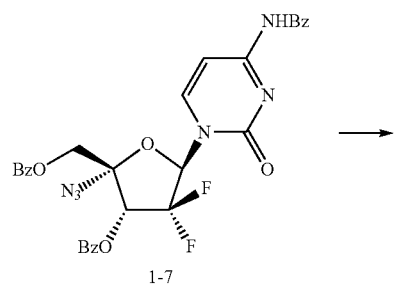
1-7

-continued

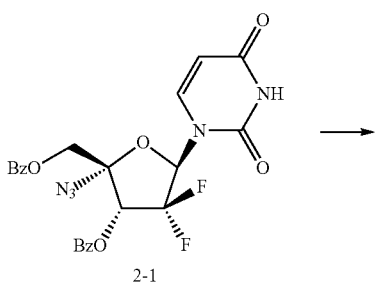
2-1

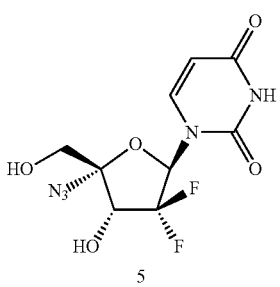
5

Step 1. Compound 2-1—Compound 1-7 (860 mg, 1.40 mmol) was dissolved in 80% acetic acid (AcOH) aqueous solution, and the mixture was refluxed for 14 hours. The solvent was removed under reduced pressure. The residue was co-evaporated with toluene and absorbed on silica gel. The residue was loaded on a silica gel column and eluted with PE/EA=4:1 to 2:1 to give compound 2-1 as a white foam (520 mg, 72%).

Step 2. Compound (5)—Compound 2-1 (520 mg, 1.01 mmol) was dissolved in saturated methanolic ammonia, and the resulting solution was stirred at R.T. for 12 hours. The solvent was removed, and the residue was purified on a silica gel column (DCM/MeOH=30:1 to 10:1) to give (5) as a white solid (290 mg, 95%). $^1$H NMR (CD$_3$OD, 400 MHz) δ7.69 (d, J=8.4 Hz, 1H), 6.30 (t, J=7.2 Hz, 1H), 5.74 (d, J=8.4 Hz, 1H), 5.17 (t, J=12.8 Hz, 1H), 3.87 (dd, J$_1$=12.8 Hz, J$_2$=26.8 Hz, 2H). ESI-TOF-MS: m/z=306 [M+H]$^+$.

Example 6

Preparation of 4'-azido-2'-deoxy-2'-methylarabinouridine (6)

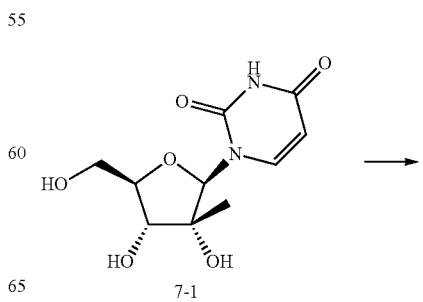
7-1

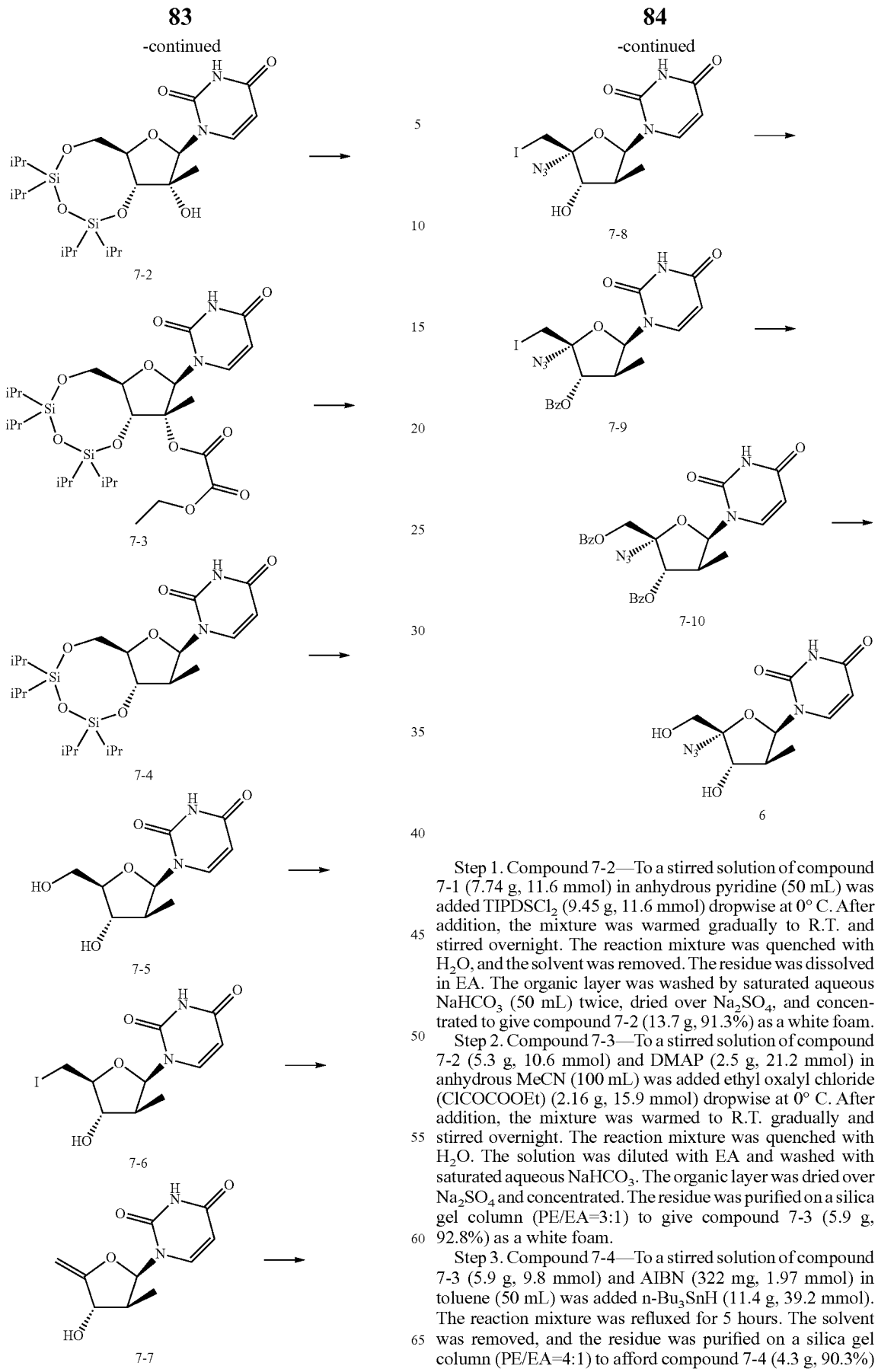

Step 1. Compound 7-2—To a stirred solution of compound 7-1 (7.74 g, 11.6 mmol) in anhydrous pyridine (50 mL) was added TIPDSCl₂ (9.45 g, 11.6 mmol) dropwise at 0° C. After addition, the mixture was warmed gradually to R.T. and stirred overnight. The reaction mixture was quenched with H₂O, and the solvent was removed. The residue was dissolved in EA. The organic layer was washed by saturated aqueous NaHCO₃ (50 mL) twice, dried over Na₂SO₄, and concentrated to give compound 7-2 (13.7 g, 91.3%) as a white foam.

Step 2. Compound 7-3—To a stirred solution of compound 7-2 (5.3 g, 10.6 mmol) and DMAP (2.5 g, 21.2 mmol) in anhydrous MeCN (100 mL) was added ethyl oxalyl chloride (ClCOCOOEt) (2.16 g, 15.9 mmol) dropwise at 0° C. After addition, the mixture was warmed to R.T. gradually and stirred overnight. The reaction mixture was quenched with H₂O. The solution was diluted with EA and washed with saturated aqueous NaHCO₃. The organic layer was dried over Na₂SO₄ and concentrated. The residue was purified on a silica gel column (PE/EA=3:1) to give compound 7-3 (5.9 g, 92.8%) as a white foam.

Step 3. Compound 7-4—To a stirred solution of compound 7-3 (5.9 g, 9.8 mmol) and AIBN (322 mg, 1.97 mmol) in toluene (50 mL) was added n-Bu₃SnH (11.4 g, 39.2 mmol). The reaction mixture was refluxed for 5 hours. The solvent was removed, and the residue was purified on a silica gel column (PE/EA=4:1) to afford compound 7-4 (4.3 g, 90.3%) as a mixture of 2'-epimers.

Step 4. Compound 7-5—A mixture of compound 7-4 (4.3 g, 8.87 mmol) and NH$_4$F (1.85 g, 50 mmol) in anhydrous MeOH (50 mL) was refluxed for 10 hours. The solvent was removed under reduced pressure. The residue was purified by column chromatography (DCM/MeOH=10:1 to 8:1) to give compound 7-5 (1.96 g, 91.2%) as a mixture of 2'-epimers with a ratio of 10:1. $^1$H NMR for the major one (CD$_3$OD, 400 MHz) δ 8.06 (d, J=10.4 Hz, 1H), 6.20 (d, J=19.2 Hz, 1H), 6.65 (d, J=10.4 Hz, 1H), 3.83-3.93 (m, 2H), 3.69-3.77 (m, 2H), 2.46-2.55 (m, 1H), 0.94 (d, J=8.4 Hz, 3H).

Step 5. Compound 7-6—To a stirred solution of compound 7-5 (1.96 g, 8.09 mmol), PPh$_3$ (4.24 g, 16.18 mmol) and imidazole (1.10 g, 16.2 mmol) in anhydrous THF (30 mL) was added dropwise a solution of I$_2$ (3.287 g, 12.94 mmol) in anhydrous THF (5 ml) at 0° C. After addition, the mixture was warmed to R.T. gradually and stirred overnight. The reaction was quenched with saturated Na$_2$S$_2$O$_3$, extracted with EA and washed with brine. The organic layer was dried over Na$_2$SO$_4$, concentrated and purified on a silica gel column to give compound 7-6 (2.14 g, 75.1%).

Step 6. Compound 7-7—To a stirred solution of compound 7-6 (2.14 g, 6.07 mmol) in anhydrous MeOH (100 mL) was added NaOMe (6.56 g, 121.4 mmol) dropwise at 0° C. After addition, the reaction was refluxed for 16 hours. The reaction was quenched with AcOH (10 ml) and concentrated. The residue was purified on a silica gel column (DCM/MeOH=100:1 to 50:1) to afford compound 7-7 (1.21 g, 89.0%) as a white solid.

Step 7. Compound 7-8—To a stirred solution of BnEt$_3$NCl (7.44 g, 31.35 mmol) in anhydrous MeCN (30 mL) was added NaN$_3$ (2.08 g, 32 mmol). The mixture was sonicated for 20 min and then stirred at R.T. for 16 hours. The solution was filtered into a solution of compound 7-7 (1.21 g, 5.4 mmol) and NMM (6 mL) in anhydrous THF (70 mL). The mixture was cooled to 0° C. and a solution of I$_2$ (7.96 g, 31.3 mmol) in THF (20 mL) was added dropwise. The reaction was stirred at R.T. for 20 hours. N-acetyl cystein was added until no gas evolved. Saturated aqueous Na$_2$S$_2$O$_3$ was added until a light yellow solution achieved. The solution was concentrated and diluted with EA (100 mL). The organic layer was washed with brine and dried over Na$_2$SO$_4$. The solvent was removed, and the residue was purified on silica gel to give compound 7-8 (2.01 g, 94.3%) as a pale yellow foam.

Step 8. Compound 7-9—To a stirred solution of compound 7-8 (2.01 g, 5.12 mmol) in anhydrous pyridine (50 mL) was added BzCl (1.306 g, 10.01 mmol) dropwise at 0° C. The reaction was stirred at R.T. for 12 hours. The reaction was quenched by saturated NaHCO$_3$ and extracted with EA. The organic layer was washed with brine and dried over Na$_2$SO$_4$. The organic layer was concentrated and purified on a silica column (PE/EA=3:1) to give compound 7-9 (1.73 g, 68.1%).

Step 9. Compound 7-10—Compound 7-9 (1.73 g, 3.6 mmol), BzONa (5.183 g, 36 mmol) and 15-crown-5 (7.92 g, 36 mmol) were suspended in 100 mL DMF. The mixture was stirred at 90-100° C. for 3 days. The precipitate was removed by filtration, and the filtrate was diluted with EA. The solvent was washed with brine and dried over Na$_2$SO$_4$. The solvent was evaporated, and the residue was purified on a silica gel column (PE/EA=10:1 to 1:1) to afford compound 7-10 (1.1 g, crude).

Step 10. Compound (6)—Compound 7-10 (1.1 g, 2.2 mmol) was dissolved in 100 mL of methanolic ammonia, and the mixture was stirred at R.T. for 14 hours. The solvent was removed, and the residue was purified on a silica gel column (DCM/MeOH=30:1 to 10:1) to give (6) as white solids (400 mg, 63%). $^1$H NMR (CD$_3$OD, 400 MHz) δ 7.95 (d, J=8.8 Hz, 1H), 6.37 (d, J=6.0 Hz, 1H), 5.70 (d, J=7.6 Hz, 1H), 4.04 (d, J=10.0 Hz, 1H), 3.83-3.92 (m, 2H), 2.66-2.76 (m, 1H), 0.98 (d, J=6.8 Hz, 3H); ESI-MS: m/z=282.09 [M−H]$^-$.

Example 7

Preparation of 4'-azidocytidine (7)

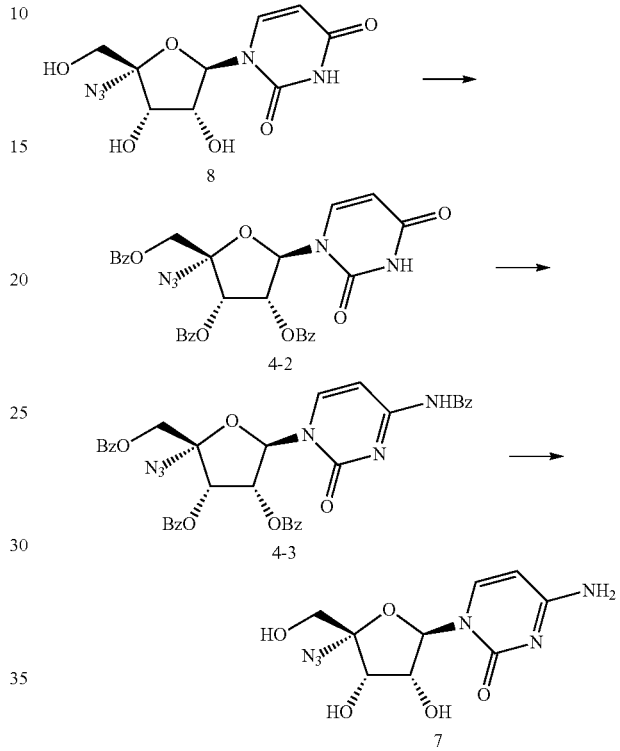

Step 1. Compound 4-2—To a stirred solution of compound (8) (9.8 g, 34.4 mmol) in anhydrous pyridine (150 mL) was added BzCl (15.47 g, 110.08 mmol) dropwise at 0° C. The mixture was then stirred at R.T. for 14 hours. The reaction was quenched with H$_2$O, and the solution was concentrated. The residue was dissolved in EA and washed with saturated NaHCO$_3$. The organic layer was dried over Na$_2$SO$_4$ and concentrated. The residue was purified on a silica gel column (PE/EA=3:1) to give compound 4-2 (19.1 g, 93%).

Step 2. Compound 4-3—Compound 4-2 (6.12 g, 10 mmol), 4-dimethylaminopyridine (DMAP) (1.22 g, 10 mmol), TPSCl (6.04 g, 20 mmol) and Et$_3$N (5.05 g, 50 mmol) were suspended in 100 mL of MeCN. The mixture was stirred at R.T. for 14 hours. To the mixture was added NH$_3$ in THF (100 ml). The mixture stirred at R.T. for 2 hours. The solvent was removed, and the residue was purified by column (DCM/MeOH=100:1 to 50:1) to give crude product (8.1 g). The crude produce was dissolved in pyridine and BzCl (2.05 g, 14.6 mmol) was added. The mixture was stirred at R.T for 16 hours and quenched with water. The solvent was removed, and the residue was purified on a silica gel column to give compound 4-3 as a white foam (4.3 g, 61%).

Step 3. Compound (7)—Compound 4-3 (4.3 g, 7.2 mmol) was dissolved in 100 mL of saturated methanolic ammonia, and the mixture was stirred at R.T. for 14 hours. The solvent was removed, and the residue was dissolved in H$_2$O and washed with DCM. The aqueous phase was lyophilized and further purified by prep. HPLC (formic acid in water/methanol) to give (7) as a white solid (1.31 g, 64%). $^1$H NMR (CD$_3$OD, 400 MHz) δ 7.95 (d, J=8 Hz, 1H), 6.13 (d, J=4.8 Hz, 1H), 5.92 (d, J=7.2 Hz, 1H), 4.29-4.35 (m, 2H), 3.66 (dd, J$_1$=35.2 Hz, J$_2$=12 Hz, 2H); ESI-MS: m/z=307.07 [M+Na]$^+$.

Example 8

Preparation of 4'-azidouridine (8)

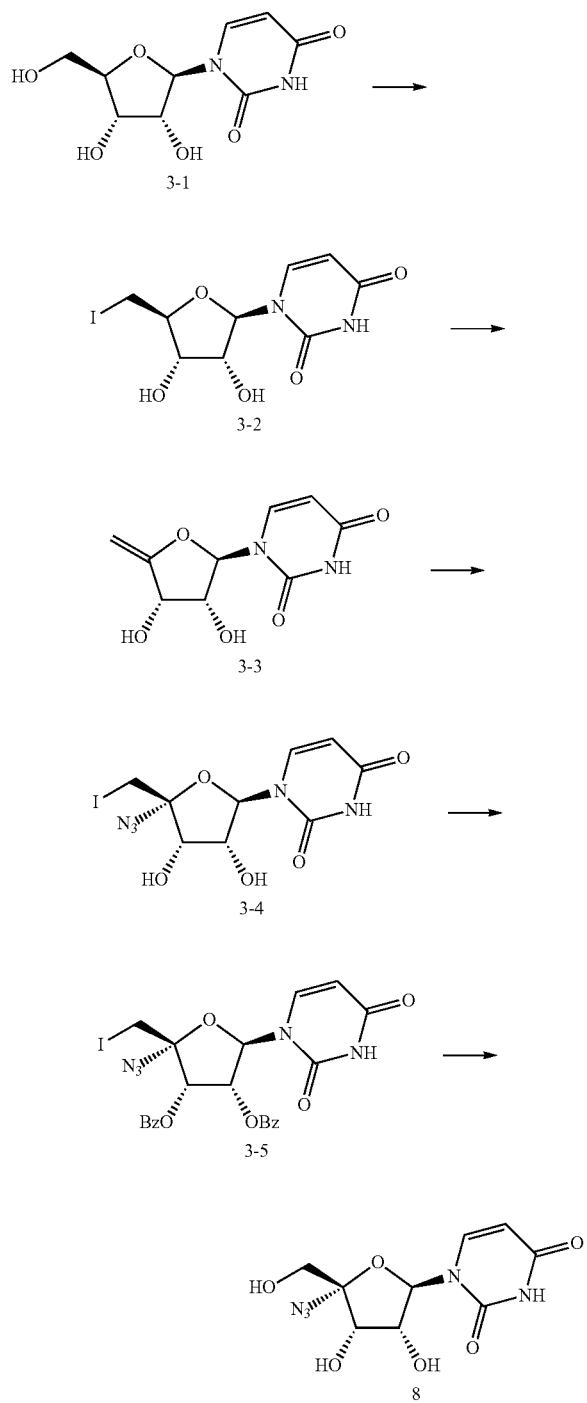

Step 1. Compound 3-2—To a stirred suspension of compound 3-1 (30.5 g, 125 mmol), PPh$_3$ (39.3 g, 150 mmol) and pyridine (100 mL) in anhydrous THF (200 mL) was added dropwise a solution of I$_2$ (38.1 g, 150 mmol) in THF (100 mL) at 0° C. The mixture was warmed to R.T. and stirred for 14 hours. The precipitate was removed by filtration, and the filtrate was concentrated. The residue was dissolved in EA and washed with saturated Na$_2$S$_2$O$_3$ aqueous solution and then brine. The organic layer was dried over Na$_2$SO$_4$ and concentrated. The residue was purified on a silica gel column (DCM/MeOH=100:1 to 20:1) to afford compound 3-2 as a white solid (36.5 g, 83%).

Step 2. Compound 3-3—To a stirred solution of compound 3-2 (36.5 g, 103 mmol) in anhydrous MeOH (400 mL) was added NaOMe. The resulting solution was refluxed for 16 hours at 80° C. The reaction was quenched with CO$_2$ (gas). The precipitate was removed by filtration, and the filtrate was concentrated. The residue was dissolved in THF and washed with brine and dried over Na$_2$SO$_4$. The solvent was removed, and the residue was purified on a silica gel column (MeOH/DCM=1/100 to 1/10) to afford compound 3-3 as a white solid (21.4 g, 93%).

Step 3. Compound 3-4—To a stirred solution of BnEt$_3$NCl (88.3 g, 379 mol) in MeCN (180 mL) was added NaN$_3$ (24.6 g, 379 mmol). The mixture was sonicated for 20 min and then stirred at R.T. for 16 hours. The solution was filtrated into a solution of compound 3-3 (21.4 g, 94.7 mmol) and N-methylmorpholine (NMM) (7.8 g) in anhydrous THF (150 mL). The mixture was cooled to 0° C., and a solution of I$_2$ (96.3 g, 379 mmol) in THF (150 mL) was added dropwise. Stirring was continued at R.T. for 14 hours. N-acetyl cystein was added until no gas evolved. Saturated Na$_2$S$_2$O$_3$ aqueous was added until a light yellow solution achieved. The solution was concentrated and then diluted with EA. The organic phase was washed with brine and dried over Na$_2$SO$_4$. The solvent was removed, and the residue was purified on a silica gel column (DCM/MeOH=100/1 to 20/1) to give compound 3-4 as a white solid (31.8 g, 85%).

Step 4. Compound 3-5—To a stirred solution of compound 3-4 (31.8 g, 80.5 mmol) in anhydrous pyridine (150 mL) was added BzCl (24.8 g, 177 mmol) dropwise at 0° C. The mixture was then stirred at R.T. for 14 hours. The reaction was quenched with water, and the solution was concentrated. The residue was dissolved in EA and washed with saturated NaHCO$_3$. The organic layer was dried over Na$_2$SO$_4$ and concentrated. The residue was purified on a silica gel column (PE/EA=10/1 to 1/1) to give compound 3-5 as a white foam (40.8 g, 84%).

Step 5. Compound (8)—Compound 3-5 (40.8 g, 67.6 mmol), BzONa (97.3 g, 676 mmol) and 15-crown-5 (148.7 g, 676 mmol) were suspended in 1000 mL of DMF. The mixture was stirred at 90-100° C. for 5 days. The precipitate was removed by filtration, and the filtrate was diluted with EA. The solvent was washed with brine and dried over Na$_2$SO$_4$. The solvent was removed, and the residue was purified on a silica gel column (PE/EA=10/1 to 1/1) to afford crude compound (23.8. g), which was further treated with methanolic ammonia and purified on a silica gel column to give (8) as a white solid (8.6 g, 45% for 2 steps). $^1$H NMR (CD$_3$OD, 400 MHz) δ7.90 (d, J=8.0 Hz, 1H), 6.15 (d, J=5.6 Hz, 1H), 5.70 (t, J$_1$=7.6 Hz, J$_2$=0.4 Hz, 1H), 4.36 (t, J=5.6 Hz, 1H), 4.27 (d, J=5.6 Hz, 1H), 3.63 (d, J=11.6 Hz, 1H), 3.55 (d, J=12 Hz, 1H). ESI-TOF-MS: m/z=286 [M+H]⁺.

Example 9

Preparation of 4'-azido-2'-deoxy-2'-methylarabinocytidine (9)

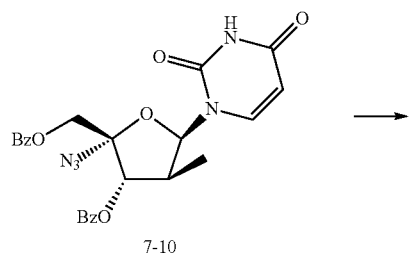

7-10

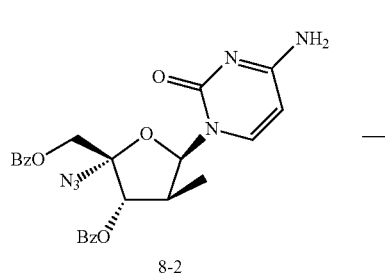

8-2

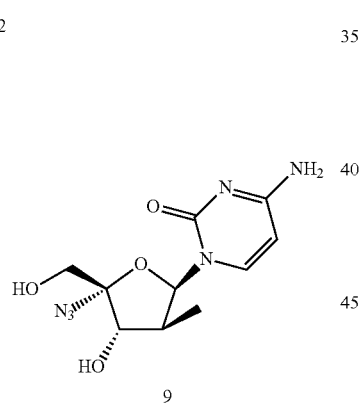

9

Step 1. Compound 8-2—Compound 8-2 (210 mg, 0.43 mmol), DMAP (52.5 mg, 0.43 mmol), TPSCl (259.72 mg, 0.86 mmol) and Et₃N (219 mg, 2.15 mmol) were suspended in MeCN (20 mL). The mixture was stirred at R.T. for 14 hours. To the mixture was added THF.NH₃ (30 mL), and mixture was then stirred at R.T. for 2 hours. The solvent was removed and the residue was purified on a silica gel column (DCM/MeOH=100:1 to 50:1) to give compound 8-2 (100 mg, 47.6%).

Step 2. Compound (9)—Compound 8-2 (100 mg, 0.20 mmol) was dissolved in 50 mL of methanolic ammonia, and the mixture was stirred at R.T. for 14 hours. The solvent was removed, and the residue was purified on a silica gel column (DCM/MeOH=20:1 to 10:1) to give (9) as a white solid (21.6 mg, 37.5%). ¹H NMR (CD₃OD, 400 MHz) δ 8.01 (d, J=6.8 Hz, 1H), 6.42 (br s, 1H), 5.92 (d, J=7.2 Hz, 1H), 3.99 (d, J=10.8 Hz, 1H), 3.87 (dd, J₁=12.0 Hz, J₂=26.8 Hz, 2H), 2.65-2.73 (m, 1H), 0.93 (d, J=6.8 Hz, 3H); ESI-TOF-MS: m/z=565.2 [2M+H]⁺.

Example 10

Preparation of 4'-azidoguanosine (10)

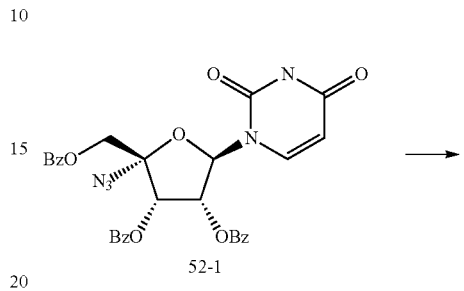

52-1

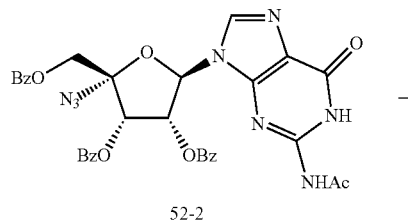

52-2

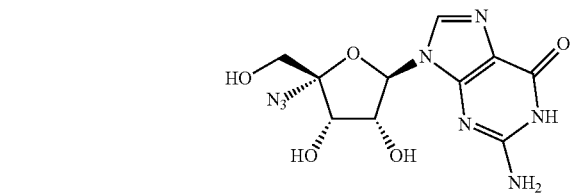

10

Step 1. Compound 52-2—A solution of compound 52-1 (300 mg, 0.5 mmol), N²-acetylguanine (193 mg, 1.0 mmol) and bis(trimethylsilyl)acetamide (BSA) (0.49 mL, 2.0 mmol) in 1,2-dichloroethane (5 mL) was stirred under reflux for 1.5 hours and cooled to R.T. TMSOTf (0.27 mL, 1.5 mmol) was added dropwise, and the resulting mixture was refluxed overnight. Additional N²-acetylguanine (193 mg), BSA (0.49 mL) and TMSOTf (0.27 mL) were added, and the resulting mixture was refluxed for 5 more days. After cooling to R.T., the mixture was poured into NaHCO₃ solution in ice-water, passed through a celite pad, and washed with MeOH/DCM. The filtrate was passed another celite pad. Chromatography on silica gel with 2-10% MeOH in DCM gave 90 mg of compound 52-2 and 39 mg of 53-1, both as solids.

Step 2. Compound (10)—A solution of compound 52-2 (230 mg) in 7 M ammonia in methanol (30 mL) stood at R.T. overnight. The solvent was evaporated, and the residue was triturated with MeOH, filtered, washed thoroughly with methanol to (10) (90 mg) as an off-white solid; ¹H NMR (DMSO-d₆) δ 3.49 (ABX, J=6.0 Hz, 2H), 4.31 (m, 1H), 4.62 (m, 1H), 5.55 (t, J=6.0 Hz, 1H), 5.66 (d, J=6.0 Hz, 1H), 5.75

(d, J=4.8 Hz, 1H), 5.97 (d, J=6.4 Hz, 1H), 6.53 (s, 2H), 7.94 (s, 1H), 9.9 (br, 1H); MS: m/z=298.7 [M+H]$^+$.

Example 11

Preparation of 4'-azidoarabinocytidine (11)

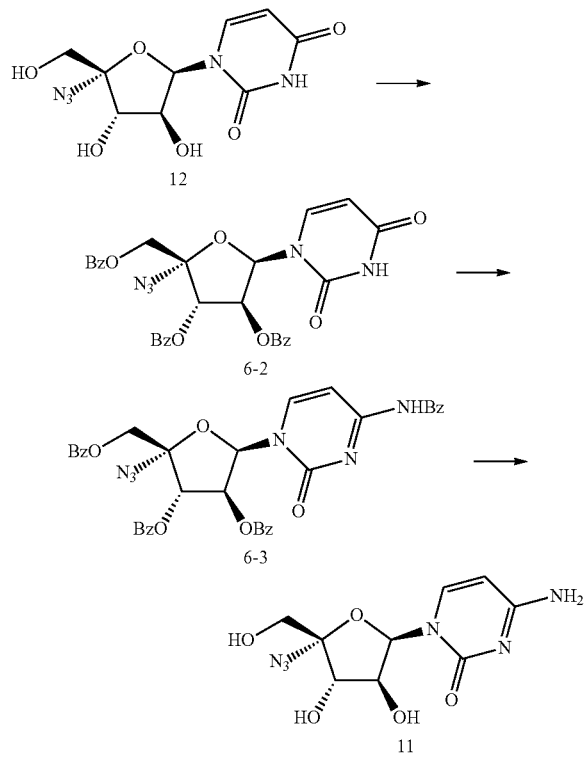

Step 1. Compound 6-2—To a stirred solution of compound 12 (4.6 g, 16.2 mmol) in anhydrous pyridine (40 mL) was added BzCl (7.3 g, 51.8 mmol) dropwise at 0° C. The mixture was stirred at R.T. for 14 hours. The reaction was quenched with H$_2$O and the solution was concentrated. The residue was dissolved in EA and washed with saturated NaHCO$_3$. The organic layer was dried over Na$_2$SO$_4$ and concentrated. The residue was purified on a silica gel column (PE/EA=10/1 to 1/1) to give compound 6-2 (7.4 g, 84.1%).

Step 2. Compound 6-3—Compound 6-2 (7.4 g, 12.4 mmol), DMAP (3.1 g, 24.8 mmol), TPSCl (7.5 g, 24.8 mol) and Et$_3$N (2.5 g, 24.8 mmol) were suspended in MeCN (50 mL). The mixture was stirred at R.T. for 14 hours. The solvent was removed, and the residue was dissolved in NH$_3$ (200 mL) in THF. The mixture was stirred at R.T. for 2 hours. The solvent was removed, and the residue was purified on a silica gel column (DCM/MeOH=100:1 to 50:1) to give the crude product. The crude product was dissolved in anhydrous pyridine (50 mL), and BzCl (1.7 g, 12.2 mmol) was added dropwise at 0° C. The mixture was stirred at R.T. for 14 hours. The reaction was quenched with H$_2$O, and the solution was concentrated. The residue was dissolved in EA and washed with saturated NaHCO$_3$. The organic layer was dried over Na$_2$SO$_4$ and concentrated. The residue was purified on a silica gel column (PE/EA=10/1 to 1/1) to give compound 6-3 as a white foam (4.2 g, 48.4%).

Step 3. Compound (11)—Compound 6-3 (4.2 g, 6.0 mmol) was dissolved in 200 mL of saturated methanolic ammonia, and the mixture was stirred at R.T. for 14 hours. The solvent was removed and then water added. The aqueous mixture was washed with DCM several times and lyophilized to give (11) as a white solid (1.5 g, 88%). $^1$H NMR (CD$_3$OD, 400 MHz) δ 7.74 (d, J=7.2 Hz, 1H), 6.43 (d, J=5.6 Hz, 1H), 5.87 (d, J=7.6 Hz, 1H), 4.39 (dd, J$_1$=2.4 Hz, J$_2$=5.6 Hz, 1H), 4.15 (d, J=5.6 Hz, 1H), 3.80 (s, 1H). ESI-MS: m/z=285 [M+H]$^+$.

Example 12

Preparation of 4'-azidoarabinouridine (12)

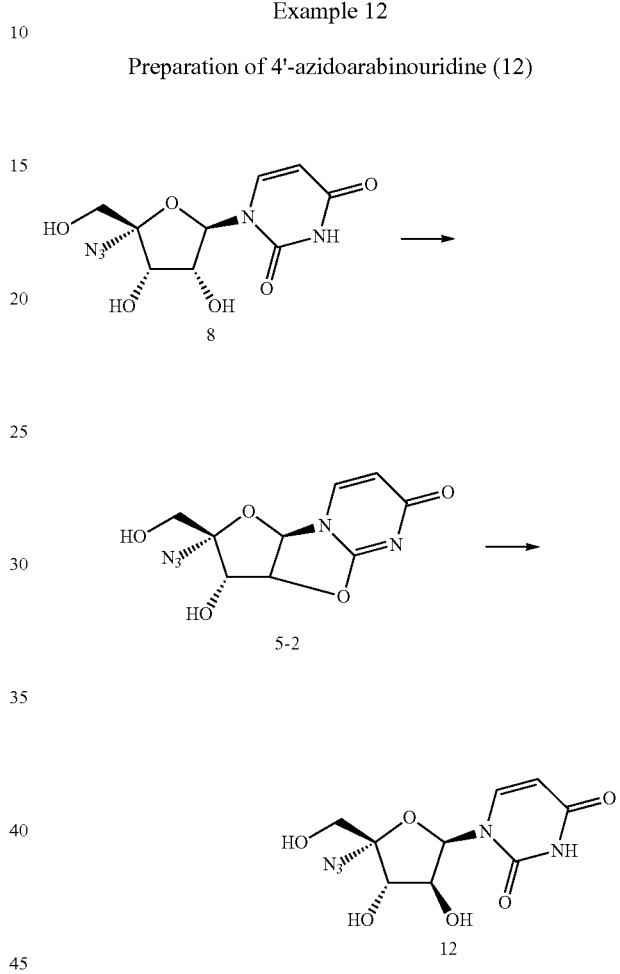

Step 1. Compound 5-2—A mixture of compound (8) (8.4 g, 29.6 mmol), diphenyl carbonate (7.7 g, 35.5 mmol), sodium hydrogen carbonate (0.25 g, 2.96 mmol) in DMF (10 mL) was heated at 100° C. under N$_2$. After 14 h, the reaction mixture was cooled to R.T., and the solvent was removed under reduced pressure. The residue was suspended in MeOH, and the resulting precipitate was collected by filtration to give compound 5-2 as a white solid (6.8 g, 86%). $^1$H NMR (DMSO-d6, 400 MHz) δ 7.91 (d, J=7.6 Hz, 1H), 6.58 (d, J=5.6 Hz, 1H), 6.42 (d, J=6.4 Hz, 1H), 5.83 (dd, J$_1$=3.6 Hz, J$_2$=7.6 Hz, 1H), 5.51 (t, J$_1$=6.0 Hz, J$_2$=5.6 Hz, 1H), 5.32 (dd, J$_1$=2.8 Hz, J$_2$=2.4 Hz, 1H), 5.51 (dd, J$_1$=2.4 Hz, J$_2$=2.4 Hz, 1H), 3.38-3.49 (m, 2H).

Step 2. Compound (12)—A solution of 5-2 (4.8 g, 18.0 mmol) and KOH (0.5 g, 9 mmol) in 9:1 mixture of EtOH/H$_2$O (10 mL) was stirred at R.T. overnight. The solution was quenched with HCl. The solvent was removed, and the residue was purified on a silica gel column (DCM/MeOH=50:1 to 10:1) to give (12) (4.6 g, 90.0%) as a white solid. $^1$H NMR (CD$_3$OD, 400 MHz) δ7.74 (d, J=8.0 Hz, 1H), 6.36 (d, J=6.0

Hz, 1H), 5.67 (d, J=8.0 Hz, 1H), 4.39 (t, J=6.0 Hz, 1H), 4.18 (d, J=6.0 Hz, 1H), 3.82 (s, 2H); ESI-TOF-MS: m/z=286 [M+H]$^+$.

Example 13

Preparation of 4'-azido-2'-C-methylcytidine (13)

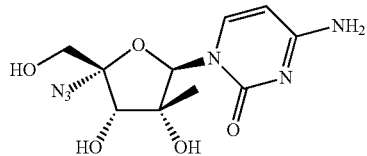 [SMILES: C[C@]1(O)[C@H](n2ccc(N)nc2=O)O[C@@](CO)(N=[N+]=[N-])[C@H]1O]

Compound (13) was prepared using the procedure set forth in the *Journal of Medicinal Chemistry* (2009) 52:219-224, which are hereby incorporated by reference for the limited purpose of disclosing the procedure of preparing (13).

Example 14

Preparation of 4'-azido-2'-deoxy-2'-beta-fluorocytidine (14)

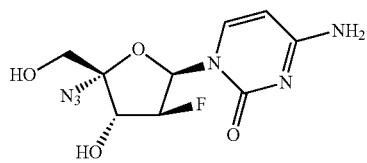 [SMILES: [N-]=[N+]=N[C@]1(CO)O[C@@H](n2ccc(N)nc2=O)[C@@H](F)[C@@H]1O]

4'-azido-2'-deoxy-2'-beta-fluorocytidine was synthesized according to a procedure set forth in *The Journal Of Biological Chemistry* (2008) 283:2167-2175 and the *Journal of Medicinal Chemistry* (2009) 52:2971-2978, which are hereby incorporated by reference for the limited purpose of disclosing the procedure of preparing (14).

Example 15

Preparation of 4'-azidouridine 5'-(O-phenyl-N—(S)-1-(isopropoxycarbonyl)eth-1-yl)thiophosphoramidate (15)

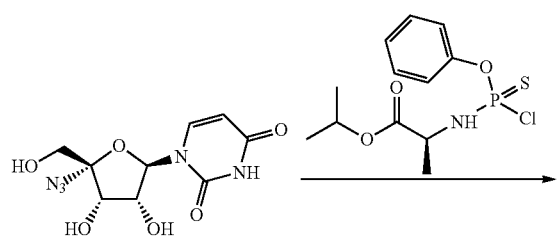

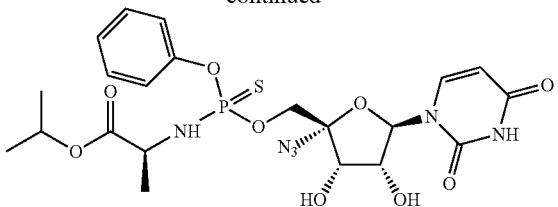

A solution of 4'-azidouridine (76 mg) and (O-phenyl-N—(S)-1-(isopropoxycarbonyl)eth-1-yl)thiophosphoramidic chloride (220 mg) in 2 mL of acetonitrile was treated with N-methylimidazole (0.2 mL), and the mixture was stirred at ambient temperature under an argon atmosphere for 1 day. The mixture was diluted with ethyl acetate and washed successively with saturated aqueous ammonium chloride, water, and brine. After drying the organic layer using sodium sulfate, the solution was filtered and solvent removed under reduced pressure. Following column chromatography using a gradient of 2-12% methanol in dichloromethane, it was noted that there was significant N-methylimidazole present in the crude product. The crude product was dissolved in ethyl acetate and washed several times with 10% aqueous citric acid. The organic layer was dried and filtered as described previously, the solvent was removed and another chromatography was performed. The product (15) (12 mg) was obtained as an off-white powder ($^{31}$P NMR (CDCl$_3$) δ 66.9, 67.8. LCMS: m/z=599.4 [M−H]$^+$).

Example 16

Preparation of 4'-azidouridine 5'-(O-phenyl-N—(S)-neopentoxycarbonyleth-1-yl)thiophosphoramidate (16)

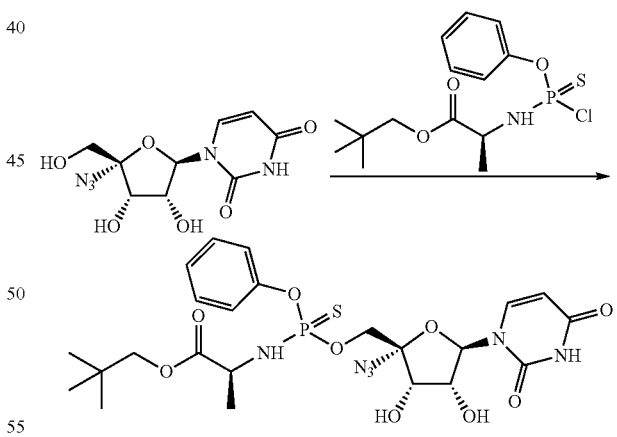

A solution of 4'-azidouridine (140 mg) and (O-phenyl-N—(S)-1-(neopentylcarbonyl)eth-1-yl)thiophosphoramidic chloride (410 mg) in 5 mL of acetonitrile was treated with N-methylimidazole (0.5 mL), and the mixture was stirred at ambient temperature under an argon atmosphere for 2 days. The mixture was diluted with ethyl acetate and washed successively with saturated aqueous ammonium chloride, water, 10% aqueous citric acid and brine. After drying the organic layer using sodium sulfate, the solution was filtered, and solvent removed under reduced pressure. Following two column chromatographies using a gradient of 3-12% methanol in dichloromethane and 2-12% methanol in dichloromethane, the resultant crude product was subjected to a final purification using HPLC. The product (16) (13.5 mg) was obtained as an off-white powder ($^{31}$P NMR (CDCl$_3$) δ67.1, 68.1. LCMS: m/z=597.5 [M−H]$^+$).

Example 17

Preparation of 4′-azido-2′-deoxy-2′-fluorouridine (17)

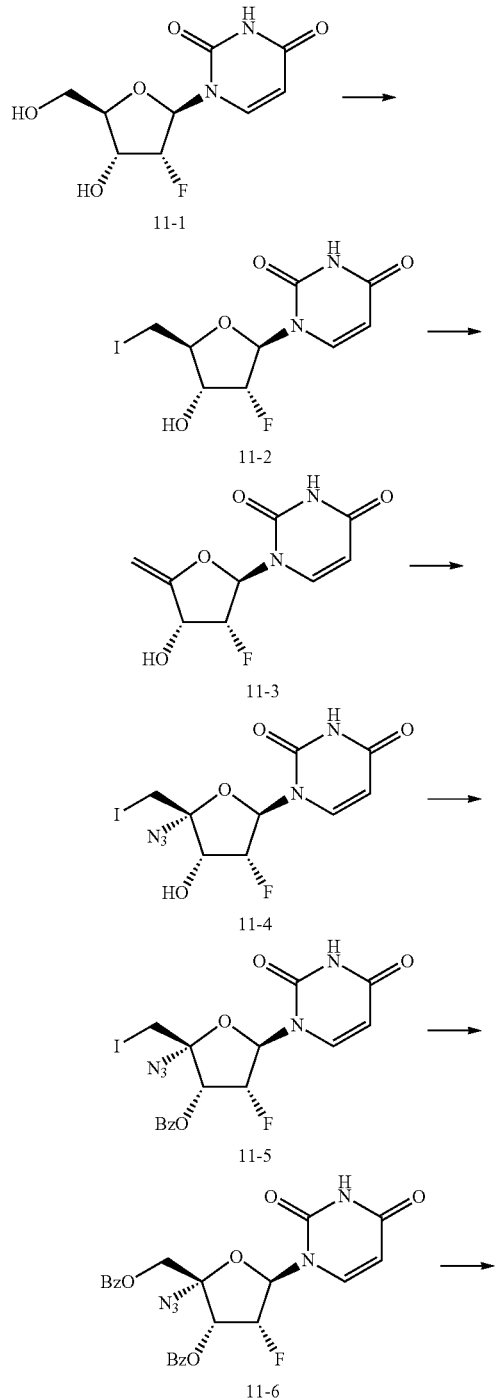

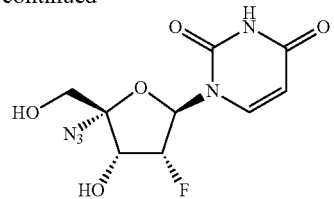

Step 1. Compound 11-2—To a stirred suspension of compound 11-1 (10.0 g, 40.6 mmol), PPh$_3$ (20.3 g, 76.4 mmol) and pyridine (40 mL) in anhydrous THF (50 mL) was added dropwise a solution of I$_2$ (24.0 g, 94.8 mmol) in THF (50 mL) at 0° C. After addition, the mixture was warmed to R.T. and stirred for 16 hours. The precipitate was removed by filtration, and the filtrate was concentrated. The residue was dissolved in EA and washed with saturated aqueous Na$_2$S$_2$O$_3$ and then brine. The organic layer was dried over Na$_2$SO$_4$ and concentrated. The residue was purified on a silica gel column (DCM/MeOH=100:1 to 50:1) to afford compound 11-2 (8.6 g, 59.3%) as a white solid. $^1$H NMR (CD3OD, 400 M Hz) δ 7.70 (d, J=8.0 Hz, 1H), 5.88 (dd, J$_1$=1.6 Hz, J$_2$=20.8, 1H), 5.71 (d, J=8.4 Hz, 1H), 5.24 (dd, J$_1$=2.0 Hz, J$_2$=5.2 Hz, 1H), 5.10 (dd, J$_1$=2.0 Hz, J$_2$=5.2 Hz 1H), 3.78-3.83 (m, 1H), 3.61-3.65 (m, 1H), 3.44 (dd, J$_1$=J$_2$=6.0 Hz, 1H).

Step 2. Compound 11-3—To a stirred solution of compound 11-2 (8.6 g, 24.2 mmol) in anhydrous DMF (40 mL) was added dropwise a solution of t-BuOK (6.3 g, 55.7 mmol) in DMF (40 mL) at 0° C. over 20 min. Stirring was continued for 20 min at 0° C. The mixture was quenched with aqueous NH$_4$Cl, diluted with EA, washed with brine and dried over Na$_2$SO$_4$. The solvent was removed, and the residue was purified on a silica gel column (MeOH/DCM=1/100 to 1/50) to compound 11-3 as a white solid (4.2 g, 76.4%). $^1$H NMR (CD3OD, 400 M Hz) δ 7.51 (d, J=8.0 Hz, 1H), 6.05 (dd, J$_1$=1.2 Hz, J$_2$=17.2 Hz, 1H), 5.73 (d, J=8.0 Hz, 1H), 5.26 (dd, J$_1$=1.2 Hz, J$_2$=4.8 Hz, 1H), 5.13 (dd, J$_1$=1.2 Hz, J$_2$=4.8 Hz, 1H), 4.63 (dd, J$_1$=2.0 Hz, J$_2$=3.2 Hz, 1H), 4.41 (t, J$_1$=2.0 Hz, J$_2$=2.0 Hz, 1H).

Step 3. Compound 11-4—To a stirred solution of BnEt$_3$NCl (20.2 g, 86.3 mol) in MeCN (200 mL) was added NaN$_3$ (5.8 g, 69.2 mol). The mixture was sonicated for 20 min and then stirred at R.T. for 16 hours. The solution was filtrated into a solution of compound 11-3 (4.6 g, 27.2 mmol) and NMM (1.2 g) in anhydrous THF (60 mL). The mixture was cooled to 0° C., and a solution of I$_2$ (24.0 g, 94.5 mol) in THF (40 mL) was added dropwise. Stirring was continued for 16 hours. N-Acetyl cystein was added until no gas evolved. The saturated aqueous Na$_2$S$_2$O$_3$ was added until a light yellow solution achieved. The solution was concentrated and then diluted with EA. The organic phase was washed with brine and dried over Na$_2$SO$_4$. The solvent was removed, and the residue was purified on a silica gel column (DCM/MeOH=200/1 to 50/1) to give compound 11-4 (6.8 g, 85%).

Step 4. Compound 11-5—To a stirred solution of compound 11-4 (6.8 g, 17.2 mmol) in anhydrous pyridine (50 mL) was added dropwise BzCl (2.9 g, 20.6 mmol) at 0° C. The mixture was then stirred at R.T. for 4 hours. The reaction was quenched with H$_2$O, and the solution was concentrated. The residue was dissolved in EA and washed with saturated aqueous NaHCO$_3$. The organic layer was dried over Na$_2$SO$_4$ and concentrated. The residue was purified on a silica gel column (PE/EA=10/1 to 1/1) to give compound 11-5 (7.4 g, 86%) as a white foam.

Step 5. Compound 11-6—Compound 11-5 (7.4 g, 14.9 mmol), BzONa (21.5 g, 149 mmol) and 15-crown-5 (32.8 g, 149 mmol) were suspended in DMF (400 mL). The mixture was stirred at 70-80° C. for 5 days. The precipitate was removed by filtration, and the filtrate was diluted with EA. The solvent was washed with brine and dried over Na$_2$SO$_4$. The solvent was removed, and the residue was purified on a silica gel column (PE/EA=10/1 to 1/1) to afford compound 11-6 (2.4 g, crude).

Step 6. Compound (17)—Compound 11-6 (2.4 g, 4.8 mmol) was dissolved in methanolic ammonia (40 mL), and the mixture was stirred at R.T. for 14 hours. The solvent was removed, and the residue was purified on a silica gel column (DCM/MeOH=30:1 to 10:1) to give (17) as a white solid (150 mg). $^1$H NMR (CD$_3$OD, 400 M Hz) δ 7.83 (d, J=8.4 Hz, 1H), 6.15 (dd, J$_1$=2.0 Hz, J$_2$=15.2 Hz, 1H), 5.70 (d, J=8.0 Hz, 1H), 5.27 (dd, J$_1$=1.2 Hz, J$_2$=5.2 Hz, 1H), 514 (dd, J$_1$=1.2 Hz, J$_2$=5.2 Hz, 1H), 4.57 (dd, J$_1$=5.6 Hz, J$_2$=10.8 Hz, 1H), 3.81 (d, J=12.0 Hz, 1H), 3.71 (d, J=12.0 Hz, 1H); ESI-MS: m/z=287 [M+H]$^+$.

Example 18

Preparation of 4'-azido-2'-deoxy-2',2'-difluorocytidine 5'-(O-phenyl-N—(S)-1-(isopropoxycarbonyl)ethyl)phosphoramidate (18)

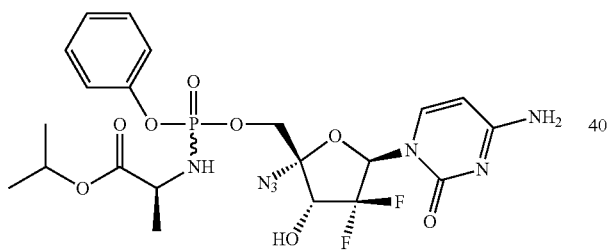

To a stirred mixture of compound (1) (61 mg, 0.2 mmol) in anhydrous THF (5 mL) was added a solution of t-BuMgCl (0.44 mL, 1M in THF) dropwise at −78° C. The mixture was then stirred at 0° C. for 30 min and re-cooled to −78° C. A solution of O-phenyl-N—(S)-1-(isopropoxycarbonyl)ethylphosphoramidic chloride (122 mg, 0.4 mmol) in THF (1 mL) was added dropwise. After addition, the mixture was stirred at 25° C. for 16 hours. The reaction was quenched with HCOOH (80% aq.) at 0° C. The solvent was removed, and the residue was purified on a silica gel column (DCM:MeOH=50:1 to 10:1) to give (18) as a white solid (25 mg, 22%). $^1$H NMR (DMSO-d$_6$, 400 MHz) δ7.52-7.56 (m, 3H), 7.34-7.40 (m, 2H), 7.18-7.24 (m, 3H), 6.94 (br s, 1H), 6.31 (br s, 1H), 6.19 (dd, J$_1$=10 Hz, J$_2$=10.8 Hz, 1H), 5.77 (d, J=7.6 Hz, 1H), 4.81-4.87 (m, 1H), 4.66 (br s, 1H), 4.36-4.46 (m, 2H), 3.77-3.84 (m, 1H), 1.21 (d, J=7.2 Hz, 3H), 1.13 (d, J=2.4 Hz, 3H), 1.21 (d, J=2.8 Hz, 3H). $^{31}$P NMR (DMSO-d$_6$, 162 MHz) δ3.49. ESI-LCMS: m/z=574.1 [M+H]$^+$.

Example 19

Preparation of 4'-azido-2'-deoxy-2',2'-difluorouridine 5'-(O-phenyl-N—(S)-1-(isopropoxycarbonyl)ethyl)phosphoramidate (19)

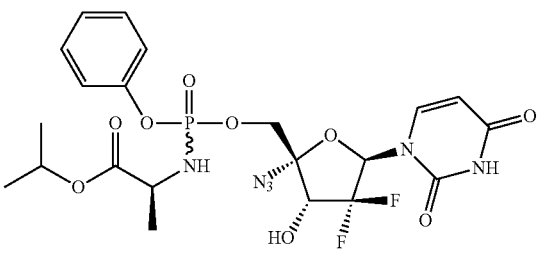

Compound 19 (white solid, 29 mg, 25%) was prepared using the procedure for preparing compound 18 with (compound (2), 61 mg, 0.2 mmol) in place of compound (1). $^1$H NMR (CD$_3$OD, 400 MHz) δ7.43 (d, J=8.0 Hz, 1H), 7.27-7.31 (m, 2H), 7.10-7.19 (m, 3H), 6.22 (t, J=7.2 Hz, 1H), 6.10 (d, J=8.0 Hz, 1H), 4.86-4.90 (m, 1H), 4.31-4.47 (m, 3H), 4.80-4.86 (m, 1H), 1.25 (d, J=7.2 Hz, 3H), 1.14-1.14 (m, 6H). $^{31}$P NMR (CD$_3$OD, 162 MHz) δ1.97, 1.86. ESI-LCMS: m/z=575 [M+H]$^+$.

Example 20

Preparation of 4'-azido-2'-deoxy-2'-fluoroarabinouridine (20)

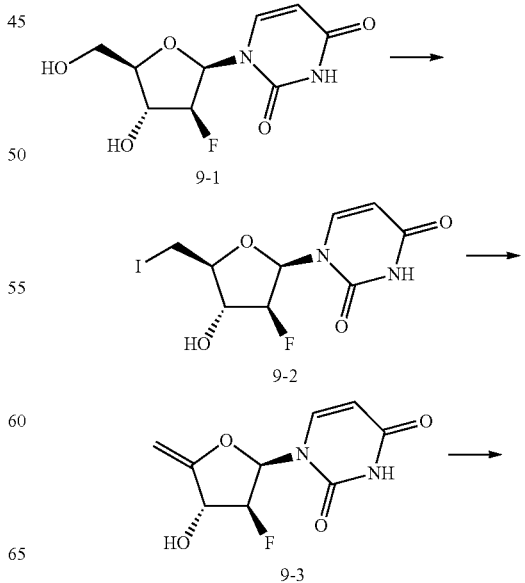

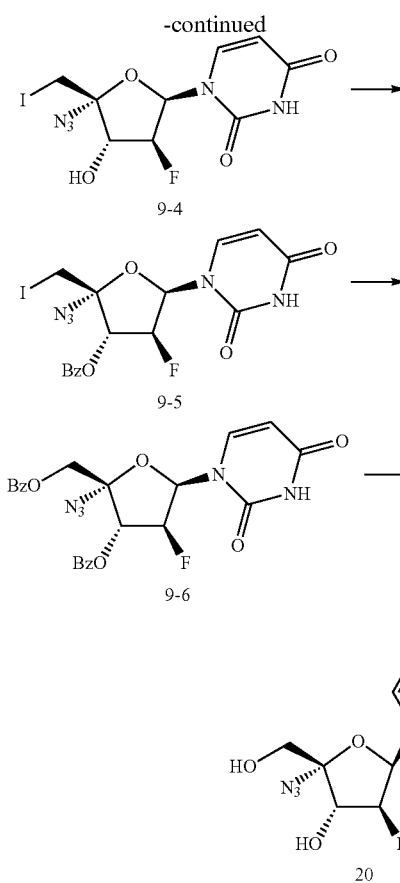

Step 1. Compound 9-2—To a stirred suspension of compound 9-1 (9.0 g, 36.6 mmol), imidazole (15.9 g, 234.0 mmol), PPh₃ (17.96 g, 68.58 mmol) and pyridine (90 mL) in anhydrous THF (360 mL) was added dropwise a solution of I₂ (21.67 g, 85.32 mmol) in THF (350 mL) at 0° C. After addition, the mixture was warmed to R.T. and stirred for 14 hours. The solution was quenched with saturated aqueous Na₂S₂O₃ (150 mL) and extracted with EA (100 mL, 3 times). The organic layer was dried over Na₂SO₄ and concentrated. The residue was purified on a silica gel column (DCM/MeOH=100:1 to 10:1) to afford compound 9-2 (7.1 g, 54%) as a white solid.

Step 2. Compound 9-3—To a stirred solution of compound 9-2 (0.7 g, 1.966 mmol) in anhydrous DMF (20 mL) was added dropwise a suspension of t-BuOK (0.660 g, 5.898 mmol) in DMF (10 mL) at 0° C. over 10 min. The mixture was stirred at R.T. for 2 hrs. The mixture was then quenched with saturated aqueous NH₄Cl (10 mL), and extracted with THF and EA. The organic layer was washed with brine and dried over Na₂SO₄. The solvent was removed, and the residue was purified on a silica gel column (MeOH/DCM=1/100 to 1/30) to afford compound 9-3 as a white solid (0.4 g, 89.2%).

Step 3. Compound 9-4—To a stirred solution of BnEt₃NCl (17.0 g, 73 mmol) in MeCN (73 mL) was added NaN₃ (4.74 g, 73 mmol). The mixture was sonicated for 20 min and then stirred at R.T. for 16 hours. The solution was filtrated into a solution of compound 9-3 (3.33 g, 14.6 mmol) and NMM (7.37 g, 73 mmol) in anhydrous THF (100 mL). The mixture was cooled to 0° C. A solution of I₂ (18.54 g, 73 mmol) in THF (50 mL) was added dropwise. Stirring was continued at 0-10° C. for 20 hours. N-acetyl cystein was added until no gas evolved. Saturated aqueous Na₂S₂O₃ was added until a light yellow solution achieved. The solution was concentrated and then diluted with EA. The organic phase was washed with brine and dried over Na₂SO₄. The solvent was removed, and the residue was purified by column (PE:EA:DCM=1:1:1) to give compound 9-4 (3.9 g, 67.2%) as a white solid. ¹H NMR (CD₃OD, 400 MHz) δ11.59 (br s, 1H), 7.60 (dd, J₁=8.4 Hz, J₂=2.0 Hz, 1H), 6.90 (d, J=5.6 Hz, 1H), 6.35 (dd, J₁=14 Hz, J₂=5.2 Hz, 1H), 5.71 (dd, J₁=8.4 Hz, J₂=2.0 Hz, 1H), 5.32 (dt, J₁=53.6 Hz, J₂=4.8 Hz, 1H), 4.65 (dt, J₁=21.6 Hz, J₂=4.2 Hz, 1H), 3.73 (dd, J₁=19.2 Hz, J₂=11.6 Hz, 2H).

Step 4. Compound 9-5—To a stirred solution of compound 9-4 (1.0 g, 2.51 mmol) in anhydrous pyridine (20 mL) was added BzCl (0.528 g, 3.77 mmol) dropwise at 0° C. The mixture was stirred at R.T. for 10 hours. The reaction was quenched with H₂O, and the solution was concentrated. The residue was dissolved in EA and washed with saturated NaHCO₃. The organic layer was dried over Na₂SO₄ and concentrated. The residue was purified on a silica gel column (PE/EA=10/1 to 1/1) to give compound 9-5 (0.9 g, 72.1%) as a white foam.

Step 5. Compound 9-6—Compound 9-5 (0.85 g, 1.69 mmol), BzONa (2.44 g, 16.9 mmol) and 15-crown-5 (3.71 g, 16.9 mmol) were suspended in DMF (80 mL). The mixture was stirred at 60-70° C. for 3 days. The precipitate was removed by filtration, and the filtrate was diluted with EA. The solution was washed with brine and dried over Na₂SO₄. The solvent was removed, and the residue was purified on a silica gel column (PE/EA=4/1 to 2/1) to afford compound 9-6 (0.6 g, 59.4%) as a light yellow foam.

Step 6. Compound (20)—Compound 9-6 (0.6 g, 1.02 mmol) was dissolved in saturated methanolic ammonia (30 mL), and the mixture was stirred at R.T. for 14 hours. The solvent was removed, and the residue was purified by column (DCM/MeOH=30:1 to 10:1) to give (20) as a white solid (0.1 g, 34.8%). ¹H NMR (CD₃OD, 400 MHz) 7.75 (dd, J₁=8.0 Hz, J₂=1.2 Hz, 1H), 6.46 (dd, J₁=11.2 Hz, J₂=5.2 Hz, 1H,), 5.72 (d, J=8.4 Hz, 1H), 5.21 (dt, J₁=13.6 Hz, J₂=5.2 Hz, 1H), 4.51 (dd, J₁=22 Hz, J₂=4.8 Hz, 1H); ESI-MS: m/z=288 [M+H]⁺.

Example 21

Preparation of 4'-azidouridine 5'-(O-phenyl-N—(S)-1-(isopropoxycarbonyl)eth-1-yl)phosphoramidate (21)

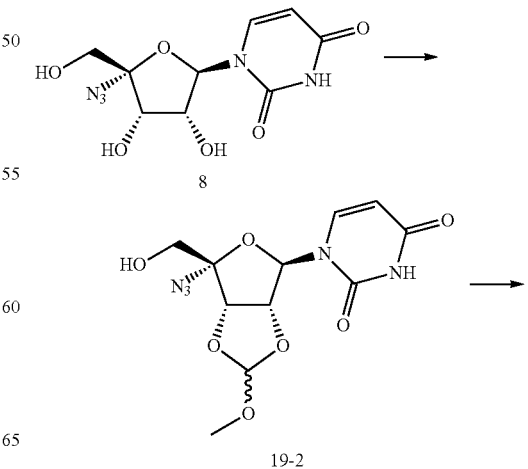

-continued

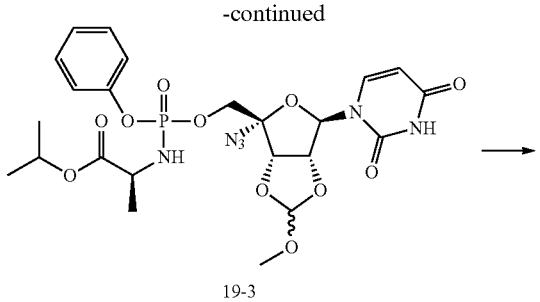

19-3

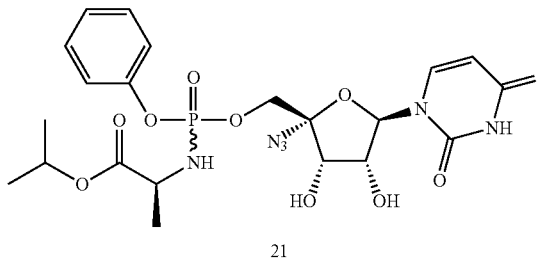

21

Step 1. Compound of 19-2—A mixture of compound (8) (650 mg, 2.3 mmol), trimethyl orthoformate (5.0 mL) and p-toluenesulfonic acid monohydrate (0.73 g, 6.9 mmol) in 1,4-dioxane (10 mL) was stirred at R.T. for 24 hours, cooled with ice, quenched by triethylamine (2 mL) and concentrated. The residue was purified by HPLC to give compound 19-2 as a white foam (168 mg, 22.7%).

Step 2. Compound of 19-3—To a solution of compound 19-2 (186 mg, 0.6 mmol) in THF (10 mL) under argon was added 1.0 M t-BuMgBr in THF (3.0 mL, 3.0 mmol) at 0° C. The resulting solution was stirred at R.T. for 30 min and O-phenyl-N—(S)-1-(isopropoxycarbonyl)ethylphosphoramidic chloride (3 mL, 1M in THF) was added at 0° C. The reaction mixture was stirred at R.T. for 20 hours and quenched with water at 0° C. The solution was diluted with EA, washed with brine, and dried over MgSO$_4$. After concentration, the residue was purified on silica gel (PE:EA=2:1 to 1:1) to give compound 19-3 (192 mg, 58%) as a white foam.

Step 3. Compound (21)—Compound 19-3 (192 mg, 0.35 mmol) was dissolved in 80% formic acid (20 mL) and stirred at R.T. overnight. The solvent was then evaporated at R.T. The residue was purified by chromatography on silica gel with 10-15% MeOH in DCM, followed by reverse-phase HPLC with MeCN/water to give (21) as a white solid (a mixture of 2 P-isomers, 92 mg, 52%). $^1$H NMR (CD$_3$OD, 400 MHz) δ 7.64 (d, J=8.0 Hz, 1H), 7.33-7.38 (m, 2H), 7.17-7.25 (3H), 6.14 (d, J=5.6 Hz, 1H), 5.69 (d, J=8.0 Hz, 1H), 4.93-4.98 (m, 1H), 4.951 (m, 1H), 4.29-4.36 (m, 2H), 4.09-4.21 (m, 1H), 3.88-3.92 (m, 1H), 1.28-1.31 (m, 3H), 1.19-1.23 (m, 6H); $^{31}$P NMR (CD$_3$OD, 162 MHz) δ 3.32, 3.26; ESI-MS: m/z=555 [M+H]$^+$.

Example 22

Preparation of 4'-azidocytidine 5'-(O-phenyl-N—(S)-1-(isopropoxycarbonyl)ethyl)phosphoramidate (22)

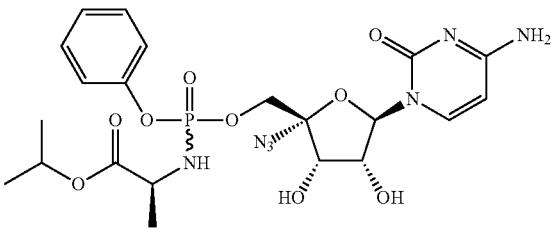 [SMILES: CC(C)OC(=O)[C@H](C)NP(=O)(OC[C@@]1(N=[N+]=[N-])O[C@@H](n2ccc(N)nc2=O)[C@H](O)[C@@H]1O)Oc1ccccc1]

To a stirred solution of compound (7) (150 mg, 0.53 mmol) in dry THF (15 mL) was added t-BuMgCl (1M in THF, 1.33 mmol) dropwise at −78° C. The solution was then warmed to R.T., and the mixture was stirred for 20 min. The mixture was cooled to −78° C. and (O-phenyl-N—(S)-1-(isopropoxycarbonyl)ethyl)phosphoramidic chloride (1M in THF, 1.06 mmol) was added. The mixture was warmed to R.T. gradually and stirred for 3 hours. The reaction was quenched by HCOOH and concentrated. The residue was purified by prep. HPLC to give (22) as a white solid (22.7 mg, 7.9%). $^1$H NMR (DMSO-d$_6$, 400 MHz) δ 7.58-7.60 (m, 1H), 7.53 (br s, 1H), 7.44 (br s, 1H), 7.33-7.38 (m, 2H), 7.15-7.22 (m, 3H), 6.07-6.16 (m, 2H), 5.88-5.90 (m, 1H), 5.71-5.75 (m, 1H), 5.59-5.61 (m, 1H), 4.80-4.89 (m, 1H), 4.17-4.26 (m, 2H), 4.07-4.12 (m, 1H), 3.92-4.05 (m, 1H), 3.72-3.82 (m, 1H), 1.18-1.21 (m, 3H), 1.12-1.15 (m, 6H); $^{31}$P NMR (DMSO-d$_6$, 162 MHz) δ 3.46, 3.41; ESI-MS: m/z=553 [M+H]$^+$.

Example 23

Preparation of 4'-azido-2'-deoxy-2'-fluorocytidine 5'-(O-phenyl-N—(S)-1-(isopropoxycarbonyl)ethyl) phosphoramidate (23)

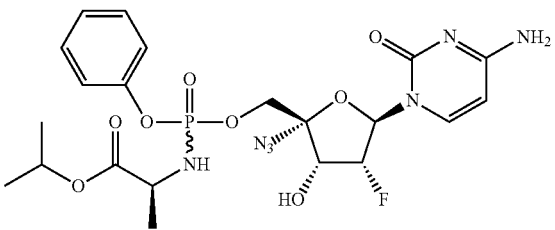 [SMILES: CC(C)OC(=O)[C@H](C)NP(=O)(OC[C@@]1(N=[N+]=[N-])O[C@@H](n2ccc(N)nc2=O)[C@H](F)[C@@H]1O)Oc1ccccc1]

Compound 23 (white solid, 16.2 mg, 5.8%) was prepared using the procedure for preparing compound 22 with (compound (2), 150 mg, 0.52 mmol) in place of compound (7). $^1$H NMR (DMSO-d6, 400 MHz) δ 7.65-7.67 (m, 1H), 7.57 (br s, 1H), 7.48 (br s, 1H), 7.32-7.37 (m, 2H), 7.16-7.22 (m, 3H), 6.00-6.19 (m, 3H), 5.72-5.76 (m, 1H), 5.29-5.30 (m, 1H), 5.16-5.18 (m, 1H), 4.77-4.86 (m, 1H), 4.56-4.66 (m, 2H), 4.11-4.31 (m, 2H), 3.71-4.83 (m, 1H), 1.19-1.21 (m, 3H), 1.12-1.15 (m, 6H); $^{31}$P NMR (DMSO-d6, 162 MHz) δ 3.44; ESI-MS: m/z 555 [M+H]$^{+}$.

Example 24

Preparation of 4'-azido-2'-deoxy-2'-fluorouridine 5'-(O-phenyl-N—(S)-1-(isopropoxycarbonyl)ethyl)phosphoramidate (24)

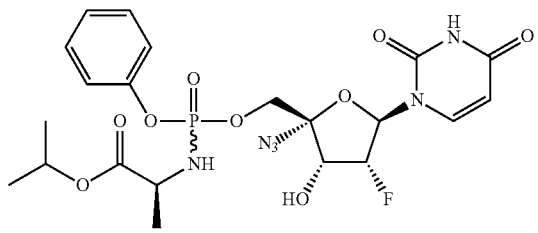 [SMILES: CC(C)OC(=O)[C@H](C)NP(=O)(OC[C@@]1(N=[N+]=[N-])O[C@@H](n2ccc(=O)[nH]c2=O)[C@H](F)[C@@H]1O)Oc1ccccc1]

To a stirred solution of compound (17) (50 mg, 0.17 mmol) in anhydrous THF (20 mL) was added a solution of t-BuMgCl (0.35 mL, 1M in THF) dropwise at −78° C. The mixture was then stirred at R.T. for 40 min and cooled to −78° C. A solution of O-phenyl-N—(S)-1-(isopropoxycarbonyl)ethylphosphoramidic chloride (106 mg, 0.35 mmol) was added dropwise. After addition, the mixture was stirred at R.T. for 18 hours. The reaction was quenched with HCOOH. After concentration, the residue was purified by prep. HPLC to give (24) (11.96 mg, 12.3%) as a white solid. $^{1}$H NMR (CD$_{3}$OD, 400 MHz) δ7.62 (d, J=7.2 Hz, 1H), 7.15-7.62 (m, 5H), 6.03 (d, J=16.4 Hz, 1H), 5.63 (d, J=8.0 Hz, 1H), 5.28 (dd, J$_{1}$=5.6 Hz, J$_{2}$=54 Hz, 1H), 4.91-4.95 (m, 1H), 4.66 (dd, J$_{1}$=5.2 Hz, J$_{2}$=60 Hz, 1H), 4.21-4.35 (m, 2H), 3.88-3.92 (m, 1H), 1.31 (d, J=7.2 Hz, 3H), 1.18-1.21 (m, 6H); $^{31}$P NMR (CD$_{3}$OD, 162 MHz) δ1.77; ESI-MS: m/z=557 [M+H]$^{+}$.

Example 25

Preparation of 2-amino-7-(4-azido-β-D-ribofuranos-1-yl)-1H-purin-6(7H)-one (25)

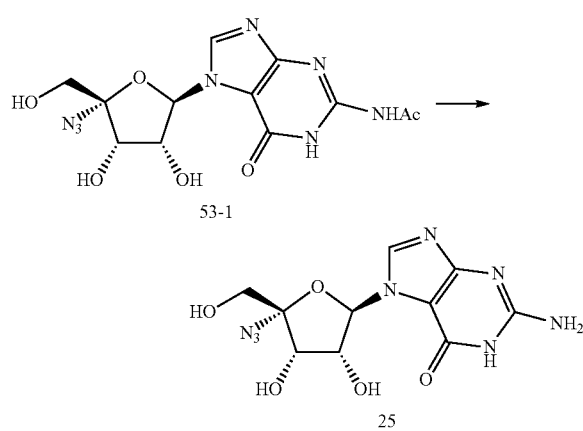

A solution of 53-1 (80 mg) in 7 M ammonia in methanol (15 mL) stood at R.T. overnight. The solvent was evaporated, and the residue was triturated with MeOH, filtered, washed thoroughly with methanol to give (25) (41 mg) as an off-white solid; $^{1}$H NMR (DMSO-d$_{6}$) δ 3.43 (q, J=6.0 Hz, 1H), 3.60 (q, J=6.0 Hz, 1H), 4.30 (t, J=6.0 Hz, 1H), 4.60 (dd, J=6.4, 8.0 Hz, 1H), 5.48 (t, J=6.4 Hz, 1H), 5.59 (d, J=6.8 Hz, 1H), 6.21 (s, 2H), 6.25 (d, J=6.4 Hz, 1H), 8.31 (s, 1H), 10.9 (br, 1H); MS: m/z 298.7 (M+H)$^{+}$.

Example 26

Preparation of 4'-azido-2'-deoxy-2'-fluorouarabinoridine 5'-(O-phenyl-N—(S)-1-(isopropoxycarbonyl)ethyl)phosphoramidate (26)

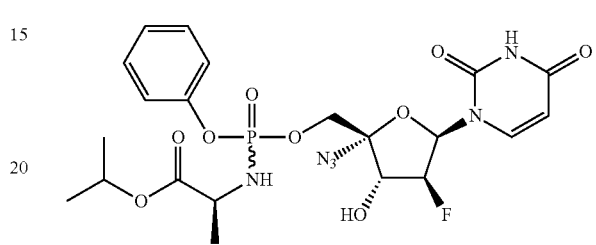

To a stirred solution of 4'-azido-2'-deoxy-2'-fluorouarabinoridine (60 mg, 0.21 mmol) in anhydrous THF (20 mL) was added a solution of t-BuMgCl (0.42 mL, 1M in THF) dropwise at −78° C. The mixture was then stirred at R.T. for 40 min and re-cooled to −78° C. A solution of O-phenyl-N—(S)-1-isopropoxycarbonyl)ethyl)phosphoramidic chloride (127 mg, 0.42 mmol) in THF was added dropwise. After addition, the mixture was stirred at R.T. for 18 hours as checked with LCMS. Then the reaction was quenched with HCOOH. After concentration, the residue was purified by prep. HPLC to give (23) (3.26 mg, 2.7%) as white solid. $^{1}$H NMR (CD$_{3}$OD, 400 MHz) δ7.63 (d, J=7.2 Hz, 1H), 7.21-7.42 (m, 5H), 6.51 (dd, J$_{1}$=4.8 Hz, J$_{2}$=14.8 Hz, 1H), 5.68 (d, J=8.0 Hz, 1H), 5.15-5.30 (m, 1H), 4.98-5.02 (m, 1H), 4.54 (dd, J$_{1}$=3.6 Hz, J$_{2}$=20 Hz, 1H), 4.31-4.43 (m, 2H), 3.93-3.97 (m, 1H), 1.35-1.38 (m, 3H), 1.23-1.26 (m, 6H); $^{31}$P NMR (CD$_{3}$OD, 162 MHz) δ 3.50; ESI-LCMS: m/z 557 [M+H]$^{+}$.

Example 27

Preparation of 4'-azido-2'-deoxy-2'-fluoroguanosine (27)

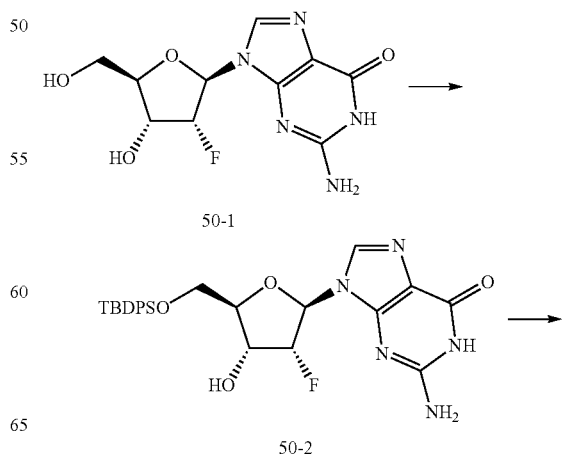

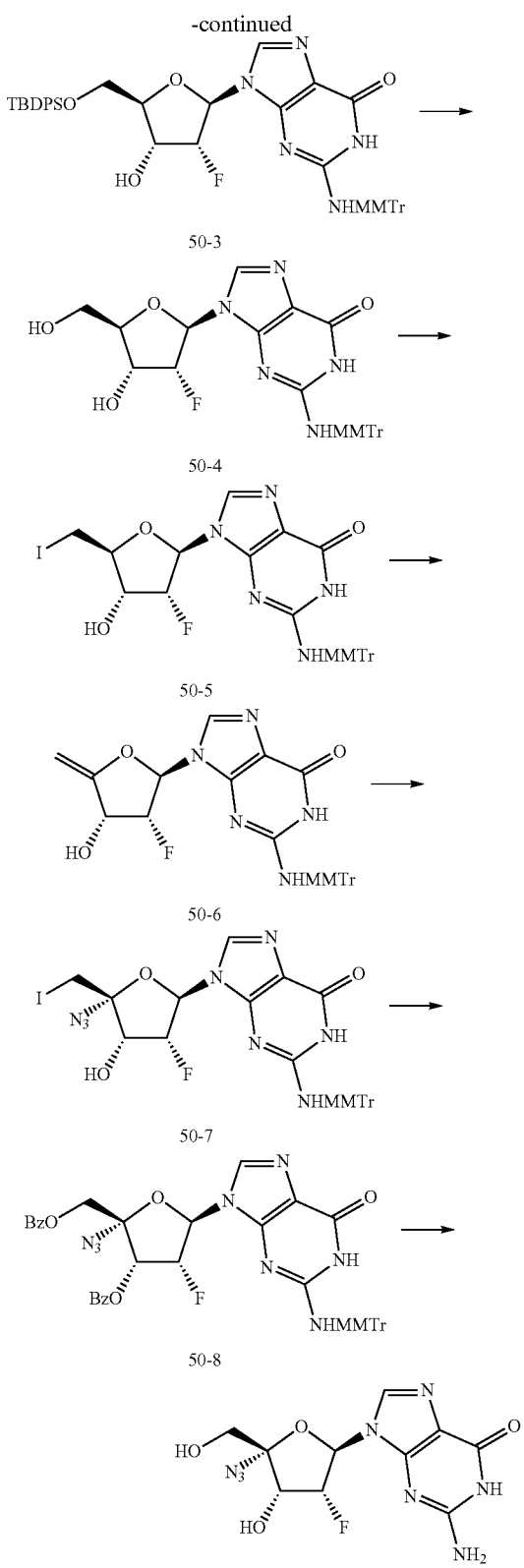

Step 1. Compound 50-2—To an ice-cooled solution of commercial 2'-fluoro-2'-deoxyguanosine (50-1) (5.0 g, 17.54 mmol) in anhydrous DMF (150 mL) was added imidazole (3.0 g, 43.85 mmol) followed by TBDPSCl (5.8 ml, 21.05 mmol) under $N_2$. The reaction mixture was stirred at R.T. overnight. Resulting reaction mixture residue was diluted with EA (300 mL), washed with water and brine. The organic layer was separated, dried over anhydrous $Na_2SO_4$ and filtered. The filtrate was concentrated in vacuum to a white solid, which was purified on silica gel column ($CH_3OH$:DCM; 9:1) to give compound 50-2 (4.1 g, 45%).

Step 2. Compound 50-3—MMTrCl (4.6 g, 15.06 mmol) was added into a solution of compound 50-2 (3.94 g, 7.53 mmol) in anhydrous DMF (40 mL), DMAP (55.0 mg, 0.45 mmol). TEA (2.2 ml, 15.06 mmol) was added. The reaction mixture was stirred at R.T. overnight under $N_2$, until TLC showed the reaction was completed. The reaction mixture was diluted with EA (300 mL), washed with water and brine. The organic layer was separated, dried over anhydrous $Na_2SO_4$ and filtered. The filtrate was concentrated in vacuum to give as residue, which was purified on silica gel column using DCM/MeOH (90:10) to give compound 50-3 (5.2 g, 87%).

Step 3. Compound 50-4—TEA.3HF (4.2 ml, 26.12 mmol), TEA (2.83 ml, 19.6 mmol), was added dropwise into a solution compound 36-3 (5.2 g, 6.53 mmol) in anhydrous THF (25 mL) and stirred at R.T. overnight until TLC showed the reaction was complete. The reaction mixture was diluted with EA (200 mL), washed with water and brine. The organic layer was separated, dried over anhydrous $Na_2SO_4$ and filtered. The filtrate was concentrated in vacuum to give as residue, which was purified on silica gel column using DCM/MeOH (9:1) to give compound 50-4 (3.1 g, 85%).

Step 4. Compound 50-5—To a mixture of compound 50-4 (3.5 g, 6.3 mmol), triphenylphosphine (3.3 g, 12.6 mmol), and imidazole (855 mg, 12.6 mmol), was added anhydrous THF (20 mL). The resulted clear solution was stirred for 5 min. To the solution was slowly added $I_2$ (2.44 g, 9.45 mmol) in THF (4 ml). The reaction mixture was stirred at R.T. for overnight. The reaction mixture was cooled on an ice-water bath, diluted with EA (200 mL), washed with 0.5 M aqueous $Na_2S_2O_3$ and brine. The organic layer was separated, dried over anhydrous $Na_2SO_4$ and filtered. The filtrate was concentrated in vacuum to give as residue, which was purified on silica gel column using DCM/MeOH (93:7 to 90:10) to give compound 50-5 (2.14 g, 51%).

Step 5. Compound 50-6—To a solution of compound 50-5 (5.0 g, 17.54 mmol) in anhydrous THF (30 mL) was added DBU (0.45 ml, 43.85 mmol), and reaction mixture was stirred at 60° C. for overnight. The reaction mixture residue was diluted with EA (150 mL), and washed with water and brine. The organic layer was separated, dried over anhydrous $Na_2SO_4$ and filtered. The filtrate was concentrated in vacuum to give as a white solid, which was purified on silica gel column using DCM/MeOH (95:5) to compound 50-6 (1.09 g, 82%).

Step 6. Compound 50-7—Benzyltriethylammonium chloride (3.73 mmol, 850 mg) and sodium azide (3.85 mmol, 250 mg) were suspended in anhydrous $CH_3CN$ (15 mL). The suspension was sonicated for 5 min and stirred vigorously for 3 hours. The mixture was filtered, and the filtrate containing quaternary ammonium azide was added to a solution of compound 50-6 (1.0 g, 1.86 mmol,) and 4-methylmorpholine (0.64 mmol, 70 uL) in anhydrous THF (15 mL). A solution of $I_2$ (3.12 mmol, 790 mg) in anhydrous THF (5 mL) was added dropwise over 1 hour under stiffing at 0° C. The reaction mixture was stirred at 0° C. for 30 min, and then 20 hours at R.T. to give a 4'-azido intermediate. 4-methylmorpholine (8.5 mmol, 0.94 ml) and DMAP (0.26 g, 2.10 mmol) were added, followed by BzCl (5.55 mmol, 0.65 ml). The reaction mixture was stirred at 0 to 5° C. (ice/water bath) for 2 hours at R.T. A solution of 0.1 M Na$_2$SO$_3$ in saturated aqueous NaHCO$_3$ (50 mL) was added, and the mixture was shaken. The mixture was diluted with EA (250 mL), and washed with saturated aqueous NaHCO$_3$ and water. The organic layer was separated and the aqueous layer washed with saturated aqueous NaCl solution, dried (Na$_2$SO$_4$), filtered, and evaporated in-vacuo, and purified by silica gel (DCM/MeOH; 95:5) to give compound 50-7 (1.27 g).

Step 7. Compound 50-8—Compound 50-7 (894 mg, 1.1 mmol) was dissolved in DMF (20 mL), together with 15-crown-5 (0.88 mL, 4.4 mmol) and sodium benzoate (635 mg, 4.44 mmol). The resulting suspension was stirred for 16 hours at 110° C. Additional sodium benzoate (160 mg, 1.1 mmol) and 15-crown-5 (0.22 mL, 1.1 mmol) were added, and the mixture was stirred for 1 day at 110° C. The resulted light brown suspension was filtered through celite, and the filtrate evaporated to dryness under reduced pressure. The residue was treated with EtOAc, and the mixture was washed with aqueous NaHCO$_3$, brine. The organic layer was separated, washed with water, dried (Na$_2$SO$_4$), and evaporated to dryness under reduced pressure. Purification by silica gel column chromatography provided compound 50-8 as an off-white solid (580 mg, 65%).

Step 8. Compound (27)—A solution of compound 50-8 (580 mg, 0.72 mmol) in 7N NH$_3$ in CH$_3$OH (30 mL) was stirred at R.T. overnight. The solvent was evaporated in vacuo, and the residue was purified on silica gel column using DCM/MeOH (95:5 to 90:10) to give 4'-azido-2'-fluoro-N$^2$-(4-methoxytrityl)-2'-deoxyguanosine (332 mg, 77%). 4'-Azido-2'-fluoro-N$^2$-(4-methoxytrityl)-2'-deoxyguanosine (80 mg, 0.13 mmol) was dissolved in 80% HCOOH (3 mL), stirred at R.T. for 3 hours. The solvent was evaporated at R.T. and co-evaporated with MeOH/toluene (3 times). Purification using RP-HPLC (water:acetonitrile) gave (27) (26.0 mg, 61%) as a white foam after lyophilization. $^1$H NMR (DMSO-d$_6$) δ 3.55-3.67 (m, 2H), 4.69-4.77 (m, 1H), 5.37 (dd, J=2.4, 4.8 Hz, 1H), 5.51 (t, J=2.8 Hz, 1H), 5.65 (t, J=6.0 Hz, 1H), 6.13 (d, J=7.6 Hz, 1H), 6.30 (dd, J=2.4, 18.4 Hz, 1H), 6.60 (br s, 1H), 7.91 (s, 1H), 10.74 (br s, 1H); $^{19}$F NMR δ (−199.0 to −199.25, m); ESI-LCMS m/z=325.3 [M+H]$^+$.

Example 28

Preparation of 4'-azido-2'-deoxy-2'-fluoroadenosine (28)

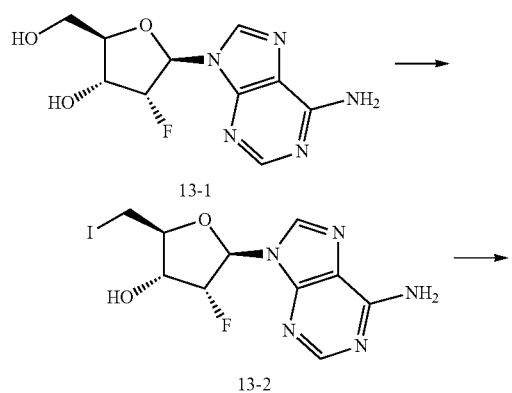

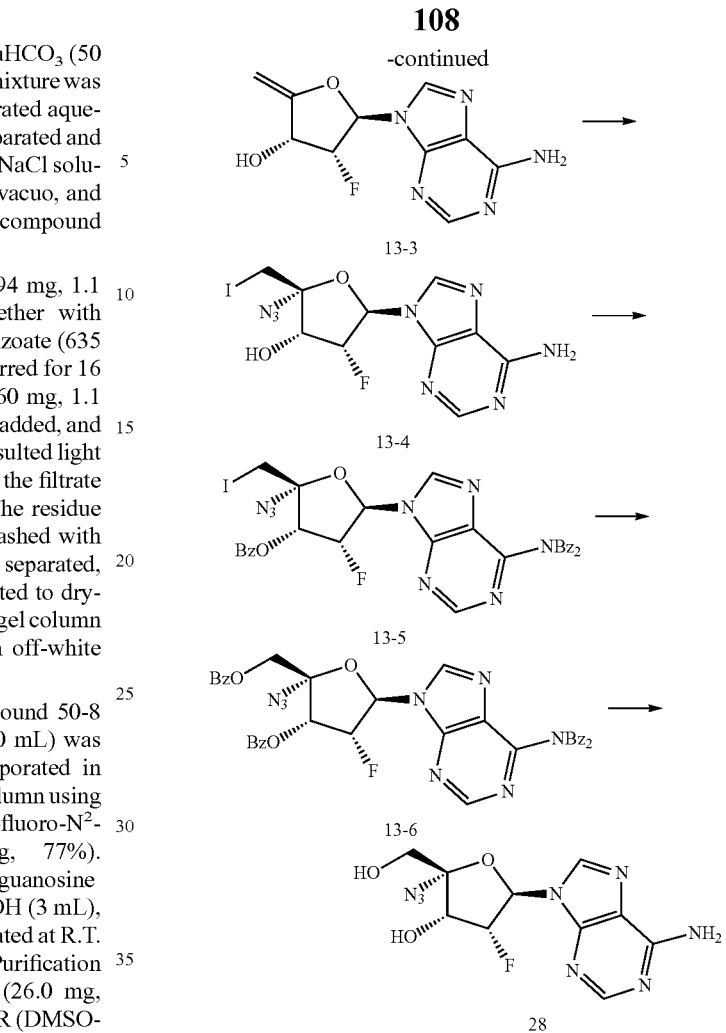

Step 1. Compound 13-2—To a stirred suspension of compound 13-1 (2.5 g, 9.3 mmol), PPh$_3$ (7.8 g, 29.8 mmol) and pyridine (2 mL) in anhydrous THF (50 mL) was added dropwise a solution of I$_2$ (7.6 g, 29.9 mmol) in THF (5 mL) at 0° C. After addition, the mixture was warmed to R.T. and stirred for 48 hours. The solution was quenched with MeOH (50 mL) and concentrated, and the residue was purified on a silica gel column (DCM/MeOH=100:1 to 10:1) to afford compound 13-2 as a white solid (3.1 g, 87.9%). $^1$H NMR (DMSO-d6, 400 MHz) δ8.31 (s, 1H), 8.14 (s, 1H), 7.36 (br s, 2H), 6.23-6.22 (d, J=19.6 Hz, 1H), 5.93-5.95 (m, 1H), 5.57-5.69 (m, 1H), 4.48-4.54 (m, 1H), 3.89-3.90 (m, 1H), 3.59-3.62 (m, 1H), 3.40-3.44 (m, 1H).

Step 2. Compound 13-3—To a stirred solution of compound 13-2 (3.1 g, 8.2 mmol) in anhydrous THF (50 mL) was added DBU (3.7 g, 24.0 mmol). The mixture was stirred at 60° C. for 2 hours. The reaction mixture was concentrated, and the residue was triturated with DCM to afford compound 13-3 as a white solid (1.6 g, 77.7%). $^1$H NMR (DMSO-d6, 400 MHz) δ8.32 (s, 1H), 8.16 (s, 1H), 7.42 (bs, 2H), 6.54 (d, J=18.0 Hz, 1H), 6.04-6.06 (m, 1H), 5.56-5.71 (m, 1H), 4.42-4.51 (m, 1H), 4.44 (s, 1H), 4.26 (s, 1H).

Step 3. Compound 13-4—To a stirred solution of BnEt$_3$NCl (17.0 g, 73 mmol) in MeCN (73 mL) was added NaN$_3$ (4.74 g, 73 mmol). The mixture was sonicated for 20 min and then stirred at R.T. for 16 hours. The solution (56 mL) was filtrated into a solution of compound 13-3 (1.8 g, 7.2 mmol) and NMM (4.5 g, 56.3 mmol) in anhydrous THF (50 mL). The mixture was cooled to 0° C., and a solution of I₂ (14.2 g, 55.9 mmol) in THF (10 mL) was added dropwise. Stirring was continued at R.T. for 20 hours. N-Acetyl cystein was added until no gas evolved. Saturated aqueous Na₂S₂O₃ was added until a light yellow solution achieved. The solution was separated, and the water layer was extracted by EA (50 mL, 2 times). The combined organic layer was dried and concentrated, and the residue was purified on a silica gel column to give compound 13-4 (crude 3.9 g, >100%).

Step 4. Compound 13-5—To a stirred solution of compound 13-4 (crude 3.9 g, 7.2 mmol) in anhydrous pyridine (30 mL) was added BzCl (5.88 g, 42 mmol) dropwise at 0° C. The mixture was stirred at R.T. for 16 hours. The reaction was quenched with H₂O, and the solution was concentrated. The residue was dissolved in EA and washed with saturated aqueous NaHCO₃. The organic layer was dried over Na₂SO₄ and concentrated. The residue was purified on a silica gel column (PE/EA=10/1 to 1/1) to give compound 13-5 (2.1 g, 39.8% for two step). ¹H NMR (CDCl₃, 400 MHz) δ8.73 (s, 1H), 8.25 (s, 1H), 8.15-8.17 (m, 2H), 7.85-7.87 (m, 4H), 7.64-7.70 (m, 1H), 7.48-7.54 (m, 4H), 7.36-7.40 (m, 4H), 6.44-6.49 (m, 1H), 6.29-6.36 (m, 1H), 6.00-6.16 (m, 1H), 3.69-3.78 (m, 2H).

Step 5. Compound 13-6—Compound 13-5 (1.5 g, 2.05 mmol), BzONa (2.9 g, 20.1 mmol) and 15-crown-5 (4.4 g, 20.0 mmol) were suspended in DMF (80 mL). The mixture was stirred at 105° C. for 16 hours. The precipitate was removed by filtration, and the filtrate was diluted with EA. The solvent was washed with brine and dried over Na₂SO₄. The solvent was removed, and the residue was purified on a silica gel column (PE/EA=4/1 to 2/1) to afford compound 13-6 (crude 1.3 g, 73%).

Step 6. Compound (28)—Compound 13-6 (1.3 g, 2.1 mmol) was dissolved in methanolic ammonia (30 mL), and the mixture was stirred at R.T. for 16 hours. The solvent was removed, and the residue was purified on a silica gel column (DCM/MeOH=30:1 to 10:1) to (28) as a white solid (450 mg, 69.1%). ¹H NMR (CD₃OD, 400 MHz) δ 8.36 (s, 1H), 8.22 (s, 1H), 6.67 (dd, $J_1$=16.8 Hz, $J_2$=2.8 Hz, 1H), 5.56-5.71 (m, 1H), 4.96 (dd, $J_1$=20.8 Hz, $J_2$=5.4 Hz, 1H), 3.85-3.79 (m, 2H); ESI-MS: m/z=310.9 [M+H]⁺.

Example 29

Preparation of 4'-azidoguanosine 5'-[O-phenyl-N—((S)-cyclohexoxycarbonyleth-1-yl))phosphoramidate (29)

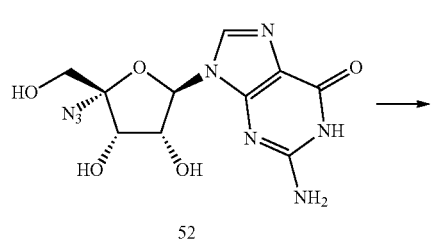

52

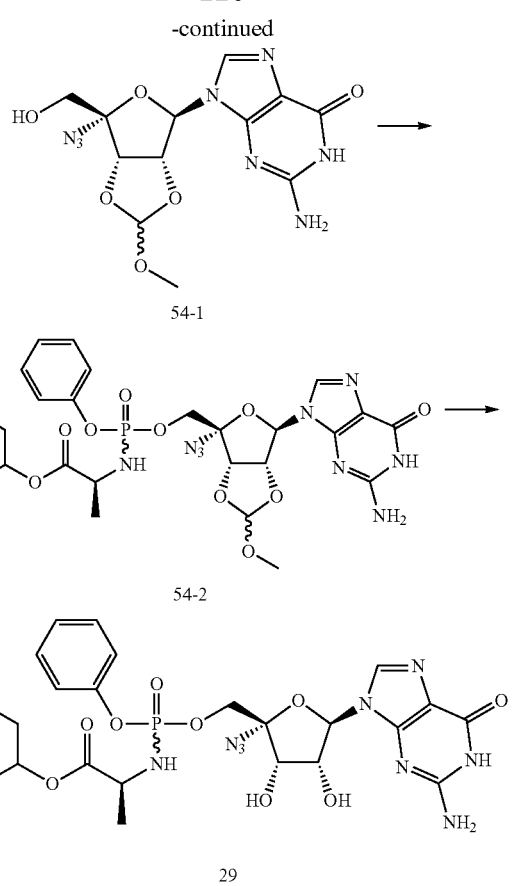

Step 1. Compound 54-1—A mixture of compound 52 (293 mg, 0.9 mmol) and p-TSOH (257 mg, 1.35 mmol), and trimethylorthoformate (5.4 mL) in 1,4-dioxane was stirred at R.T. overnight. Dowex MWA-1 basic resin was added and stirred for 3 hours. The resin was filtered out and washed thoroughly with MeOH/DCM. Chromatography on silica gel with 7-12% MeOH in DCM gave compound 53-1 (245 mg).

Step 2. Compound 54-2—Tert-butylmagnesium bromide in THF (1.0 M, 0.29 mL) was added dropwise to a stirred solution of compound 54-1 in anhydrous THF (0.8 mL). The resulting solution was stirred at R.T. for 15 min. O-Phenyl-N—(S)-1-(cyclohexoxycarbonyl)ethylphosphoramidic chloride (0.29 mL) was added dropwise during 5 min, and the resulting mixture was stirred at R.T. overnight. The mixture was cooled with ice, quenched with TEA (0.1 mL) and aqueous NH₄Cl, diluted with ethyl acetate, washed with aqueous NH₄Cl four times, washed with 5% NaHCO₃ two times, dried over Na₂SO₄, and concentrated. Chromatography on silica gel with 3-7% MeOH in DCM gave the crude compound 53-2 as an off-white solid.

Step 3. Compound (29)—Compound 54-2 was dissolved in 4 mL of 80% formic acid and 20% water, and the resulting solution stood at R.T. for 5 hours. The solvent was evaporated at 30° C. Chromatography on silica gel with 10-15% MeOH in DCM gave crude 53 (63 mg), which was further purified on RP HPLC with acetonitrile and water to give (29) (36 mg) as a white solid; ¹H NMR (CD₃OD, two P-isomers) δ 1.20-1.56 (m, 9H), 1.65-1.83 (m, 4H), 3.83-3.92 (m, 1H), 4.29 (ABX, J=5.6 Hz, 1.6H), 4.30 (ABX, J=5.6 Hz, 0.4H), 4.59 (d, J=5.6 Hz, 0.8H), 4.66-4.74 (m, 1H), 4.85 (t, J=5.6 Hz, 0.8H), 4.91

(t, J=5.6 Hz, 0.2H), 6.07 (d, J=5.6 Hz, 0.2H), 6.10 (d, J=5.6 Hz, 0.8H), 7.10-7.36 (m, 5H), 7.85 (s, 0.2H), 7.86 (s, 0.8H); MS: m/z=763.3 [M+H]$^+$.

Example 30

Preparation of 4'-azido-2'-deoxy-2',2'-difluoroguanosine (30)

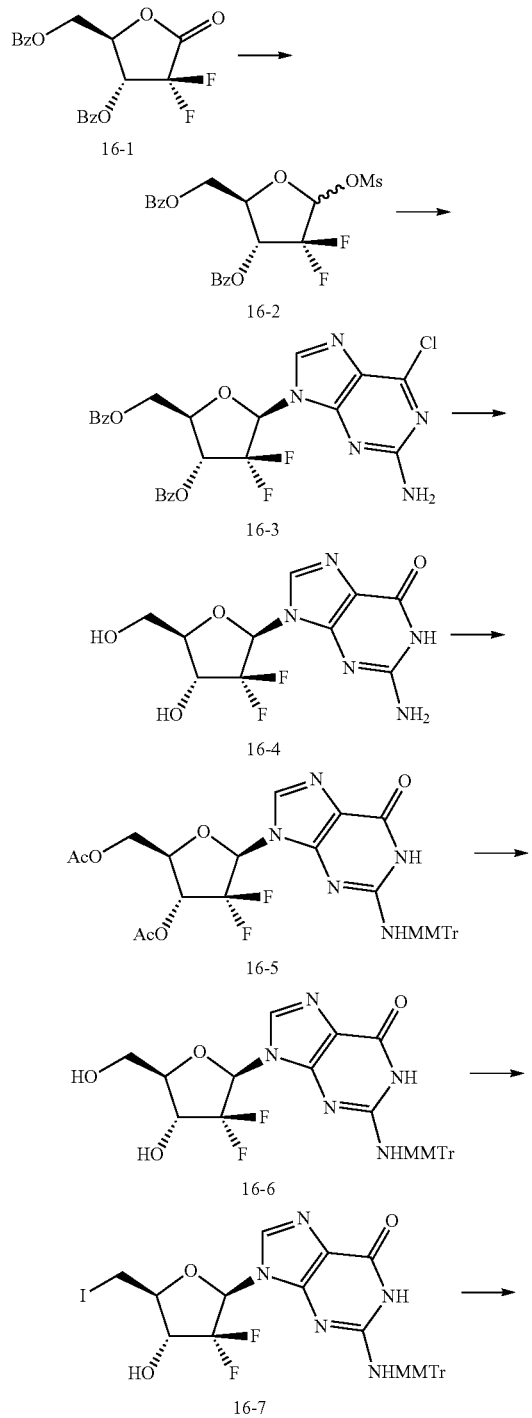

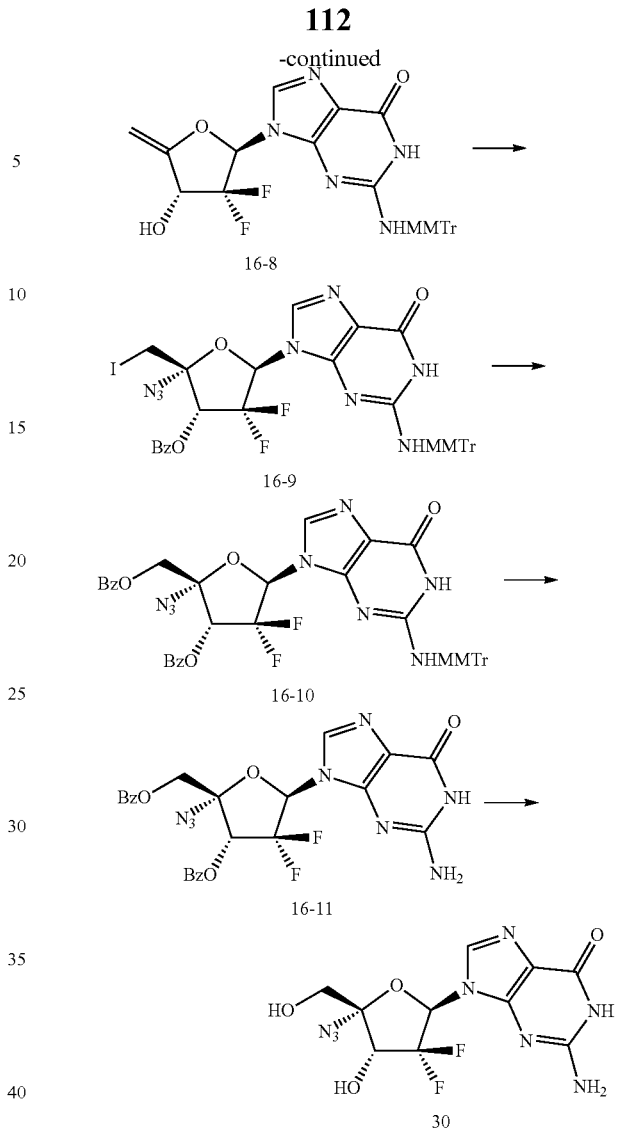

Step 1. Compound 16-2—To a stirred solution of compound 16-1 (100.0 g, 265.9 mmol) in dry THF (1000 mL) was added Li(O-t-Bu)$_3$AlH (318.9 mL, 318.9 mmol) at −78° C. under N$_2$. The mixture was stirred at −78° C. for 1 hour and then at R.T. for an additional 1 hour. The reaction mixture was cooled to −50° C. and quenched with ice and a saturated NH$_4$Cl solution. The resulting mixture was extracted with EtOAc. The organic layer was dried over Na$_2$SO$_4$ and concentrated to afford the crude product (100.5 g) as a white solid, which was dissolved in dry DCM (600 mL). To the mixture was added dropwise NEt$_3$ (110 mL) and MsCl (45.5 g, 298.0 mmol) at 0° C., and the reaction mixture was stirred at R.T. for 2 hour, quenched with ice water at 0° C., and extracted with DCM. The organic layer was dried over Na$_2$SO$_4$, concentrated and purified on silica gel column to afford compound 16-2 (113.4 g, yield 93.9%) as a white solid.

Step 2. Compound 16-3—To a suspension of compound 6-chloro-9H-purin-2-amine (70.1 g, 414.7 mmol), HMDS (480 mL) and (NH$_4$)$_2$SO$_4$ (0.8 g) was added dry DCE (400 mL). The mixture was refluxed under N$_2$ for 18 hours and then cooled to R.T. To the silylated 2-amino-6-chloropurine solution was added compound 16-2 (78.0 g, 171.1 mmol) and TMSOTf (60 mL, 331.9 mmol). The reaction mixture was refluxed overnight and concentrated and neutralized with a NaHCO$_3$ solution. The resulting precipitate was filtered off, and the filtrate was extracted with EtOAc. The organic layer was dried over Na$_2$SO$_4$ and concentrated. Purification on a silica gel column to give compound 16-3 (10.8 g, yield 11.9%) as a light yellow solid. $^1$H NMR (CDCl$_3$, 400 MHz) δ 8.36 (s, 1H), 8.36-8.05 (m, 4H), 7.68-7.44 (m, 6H), 6.75 (dd, J$_1$=5.6 Hz, J$_2$=10.8 Hz, 1H), 5.77-5.72 (m, 1H), 4.86-4.67 (m, 3H); ESI-MS: m/z=530 [M+H]$^+$.

Step 3. Compound of 16-4—To a stirred solution of compound 16-3 (10.8 g, 20.4 mmol) in dry MeOH (100 mL) was added NaOMe (5.2 g, 96.3 mmol) and 2-mercapto-ethanol (6.7 mL). The reaction mixture was stirred at refluxing overnight. The pH value was then adjusted to 9-10 with AcOH (conc.). The residue was washed by MeOH to give compound 16-4 (pure, 5.1 g, yield 82.7%) as white solids. $^1$H NMR (DMSO-d6, 400 MHz) δ 8.28 (s, 1H), 6.78 (s, 2H), 6.54 (t, J=6.8 Hz, 1H), 4.43-4.35 (m, 1H), 3.89-3.64 (m, 3H); ESI-MS: m/z=304 [M+H]$^+$.

Step 4. Compound 16-5—To a stirred suspension of compound 16-4 (5.1 g, 16.8 mmol) in anhydrous pyridine (100 mL) was added Ac$_2$O (6.9 g, 67.3 mmol) at 0° C. The mixture was stirred at R.T. for 18 hours. The reaction was then concentrated, and the residue was co-evaporated with pyridine. The residue was suspended in anhydrous pyridine (100 mL). MMTrCl (10.4 g, 33.6 mmol) and AgNO$_3$ (5.7 g, 33.6 mmol) were added at R.T. The reaction mixture was stirred for 18 hours, then quenched with water and extracted with EtOAc. The organic layer was dried over Na$_2$SO$_4$ and purified by silica gel column to give compound 16-5 as white solids (7.2 g, 65%).

Step 5. Compound 16-6—Compound 16-5 was dissolved in MeOH/NH3 at −70° C. The mixture was stirred at R.T. for 18 hours. The solvent was concentrated, and the residue was purified by silica gel column to give compound 16-6 (5.8 g, yield 59.9%) as a white solid. $^1$H NMR (CD$_3$OD, 400 MHz) δ 8.31 (s, 1H), 7.48-7.6.83 (m, 14H), 6.45 (dd, J$_1$=4.0 Hz, J$_2$=10.0 Hz, 1H), 4.40-4.48 (m, 1H), 3.93-3.98 (m, 2H); 3.77-3.81 (m, 1H), 3.75 (s, 3H); ESI-LCMS: m/z=576 [M+H]$^+$.

Step 6. Compound 16-7—To a stirred solution of compound 16-6 (5.8 g, 10.1 mmol) in dry THF (100 mL) were added imidazole (3.4 g, 50.4 mmol) and PPh$_3$ (13.6 g, 50.4 mmol). A solution of I$_2$ (12.8 g, 50.4 mmol) in THF (30 mL) was added dropwise under N$_2$ at 0° C. The mixture was stirred at R.T. for 18 hours and then was quenched with Na$_2$S$_2$O$_3$ solution. The mixture was extracted with EtOAc. The organic layer was dried by Na$_2$SO$_4$ and concentrated. Silica gel column chromatography give compound 16-7 (3.4 g, yield 49.2%) as a colorless solid. $^1$H NMR (CD$_3$OD, 400 MHz) δ 8.06 (s, 1H), 7.13-7.36 (m, 12H), 6.78 (d, J=8.8 Hz, 2H), 6.47 (dd, J$_1$=7.2 Hz, J$_2$=9.2 Hz, 1H), 4.19-4.26 (m, 1H), 3.77-3.83 (m, 1H), 3.71 (s, 3H), 3.47-3.62 (m, 2H); ESI-MS: m/z=686 [M+H]$^+$.

Step 7. Compound 16-8—To a stirred solution of compound 16-7 (3.4 g, 5.0 mmol) in dry THF was added DBU (1.2 g, 7.5 mmol). The mixture was stirred at 60° C. for 8 hours. The solution was quenched with a NaHCO$_3$ solution and extracted with EtOAc. The organic layer was dried by Na$_2$SO$_4$ and concentrated. The residue was purified by a silica gel column to afford compound 16-8 (2.10 g, yield 76.1%) as a colorless solid. $^1$H NMR (CD$_3$OD, 400 MHz) δ 8.08 (s, 1H), 7.19-7.68 (m, 12H), 6.82-6.86 (m, 2H), 6.74 (dd, J$_1$=6.0 Hz, J$_2$=8.8 Hz, 1H), 4.95 (t, J=10 Hz, 1H), 4.74 (s, 1H); 4.55 (t, J=1.6 Hz, 1H), 3.77 (s, 3H); ESI-MS: m/z=558 [M+H]$^+$.

Step 8. Compound 16-9—To a stirred solution of compound 16-8 (2.1 g, 3.8 mmol) in dry THF were added 4-methyl-morpholine (2.1 g, 20.8 mmol) and benzyl triethylammonium azide (BnEt$_3$NN$_3$) (80.0 mL, 80.0 mmol in CH$_3$CN). A solution of I$_2$ (20.1 g 78.7 mmol) in THF was added dropwise at 0° C. The mixture was stirred at R.T. for 18 hours. The solution was quenched with Na$_2$S$_2$O$_3$ solution and extracted with EtOAc. The organic layer was washed with a NaHCO$_3$ solution, dried over Na$_2$SO$_4$ and concentrated to give the crude product. The crude product was dissolved in dry pyridine and BzCl (0.9 g, 6.6 mmol) was added. The mixture was stirred at R.T. for 18 hours. The solution was quenched with NaHCO$_3$ solution, extracted with EtOAc. The organic layer was dried over Na$_2$SO$_4$ and concentrated. After purification by silica gel column, compound 16-9 (2.0 g, yield 63.3%) was obtained as a white foam.

Step 9. Compound 16-10—To a stirred solution of compound 16-9 (2.0 g, 2.4 mmol) in dry DMF was added NaOBz (2.5 g, 17.4 mmol) and 15-crown-5 (3.4 mL, 17.4 mmol). The mixture was stirred at 100-105° C. for 48 hours. The solution was diluted with EA and filtered. The filtrate was washed with brine and dried over Na$_2$SO$_4$. The solvent was removed, and the residue was a purified by a silica gel column to afford compound 16-10 (crude, 540 mg, yield 27.1%).

Step 10. Compound 16-11—Compound 16-10 (540 mg, 0.66 mmol) was dissolved in 80% AcOH solution, and the mixture was stirred at R.T. for 18 hours. The solution was concentrated and purified by a silica gel column to give compound 16-11 (228 mg, crude).

Step 11. Compound (30)—Compound 16-11 (228 mg) was dissolved in MeOH/NH$_3$. The mixture was stirred at R.T. for 18 hours. The solvent was removed to give crude (30), which was purified on RP HPLC with MeOH/water to give 73.8 mg of (30) as an ivory solid; $^1$H NMR (DMSO-d$_6$) δ 10.96 (br, 1H), 8.29 (s, 1H), 6.71 (d, J=6.8 Hz, 1H), 6.62 (t, J=7.6 Hz, 1H), 6.29 (s, 2H), 5.78 (t, J=6.0 Hz, 1H), 4.85 (m, 1H), 3.87 (d, J=6.4 Hz, 2H); MS m/z=343.2 [M−1]$^−$.

Example 31

Preparation of 4'-azido-2'-deoxy-2'-fluoroguanosine 5'-(O-phenyl-N—((S)-cyclohexoxycarbonyleth-1-yl))phosphoramidate (31)

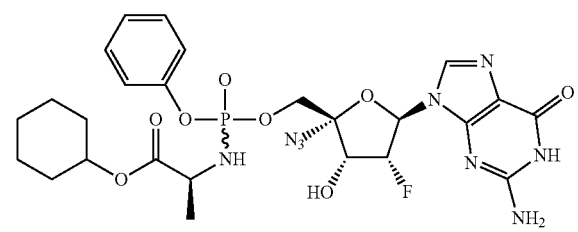

To a solution of 4'-azido-2'-fluoro-N$^2$-(4-methoxytrityl)-2'-deoxyguanosine (50 mg, 0.084 mmol) in THF (1.0 mL) under argon was added dropwise 1.0 M tert-BuMgCl in THF (0.15 mL). The resulting solution was stirred at R.T. for 30 min and O-phenyl-N—(S)-1-(cyclohexoxycarbonyl)ethylphosphoramidic chloride (1.0 M in THF, 0.13 mL) was added. The reaction mixture was stirred at R.T. for overnight. The progress of the reaction was monitored by TLC. Additional 1.0 M tert-BuMgCl in THF (0.17 mL) followed by (O-phenyl-N—((S)-cyclopropoxycarbonyleth-1-yl))phosphoramidic chloride (1.0 M in THF, 0.17 mL) was added to the reaction mixture, and the reaction mixture was stirred for 2 days at R.T. The reaction mixture was then cooled with ice, quenched with aqueous ammonium chloride, diluted with ethyl acetate, washed with aqueous ammonium three times, dried over sodium sulfate, and concentrated. Chromatography on silica gel with 5-7% MeOH in DCM gave a mixture of two isomers as an off-white foam (30.1 mg). The obtained product was dissolved in 80% formic acid (2 mL), and the resulting solution stood at R.T. for 3 hours. The solvent was evaporated at R.T. and co-evaporated with MeOH/toluene three times. Purification on reverse-phase HPLC (C18) using acetonitrile and water, followed by lyophilization, gave (31) (6.3 mg) as a white foam; $^1$H NMR (CD$_3$OD, two isomer) δ 1.24-1.76 (m, 13H), 3.78-3.88 (m, 1H), 4.28-4.38 (m, 1H), 4.39-4.44 (m, 1H), 4.64-4.66 (m, 1H), 5.09, 5.14 (each dd, J=2.8, 5.2 Hz, 1H), 5.09, 5.14 (each dd, J=2.8, 5.2 Hz, 1H), 5.42-5.47 & 5.55-5.6 (2×m, 1H), 6.37, 6.43 (each dd, J=2.0, 6.0 Hz, 1H), 7.09-7.31 (m, 5H), 7.85 (s, 1H); $^{31}$P NMR (CD$_3$OD, two isomers) δ 3.53 (s), 3.46 (s); ESI-LCMS m/z=634.5 [M+H]$^+$.

Example 32

Preparation of 4'-azido-2'-deoxy-2'-fluorouridine 3',5'-cyclic phosphate (32)

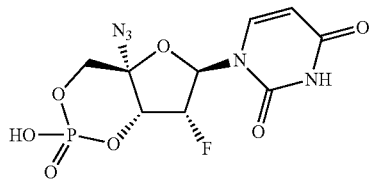

1,2,4-Triazol (21 mg, 0.3 mmol) was suspended in 0.7 mL of dry CH$_3$CN. Triethylamine was added (0.046 mL, 0.33 mmol), and the mixture was vortexed to obtain a clear solution. After addition of POCl$_3$ (0.01 mL, 0.1 mmol), the mixture was vortexed and left for 20 min, and then centrifuged. The supernatant was added to 4'-azido-2'-deoxy-2'-fluorouridine (14 mg, 0.05 mmol), and the mixture was kept at ambient temperature for 1 hour. The reaction was quenched with water, and the phosphate was isolated by IE chromatography on an AKTA Explorer using column HiLoad 16/10 with Q Sepharose High Performance. Separation was done in a linear gradient of NaCl from 0 to 1 N in 50 mM TRIS-buffer (pH 7.5). The fractions eluted at 50-60% NaCl were combined, concentrated and desalted by RP HPLC on Synergy 4 micron Hydro-RP column (Phenominex). A linear gradient of methanol from 0 to 30% in 50 mM triethylammonium buffer was used for elution over 20 min, flow 10 ml/min. Three compounds corresponding to the 5'-monophosphate, 3',5'-diphosphate, and (32) were collected. $^1$H NMR (D$_2$O) δ 7.50-7.49 (d, 1H), 6.05-6.00 (d, 1H), 5.73-5.71 (d, 1H), 5.50-5.35 (dd, 1H), 4.98-4.89 (m, 1H), 4.49-4.34 (m, 2H); $^{31}$P NMR: δ3.45 s; LCMS: m/z 348.2 [M−H]$^-$.

Example 33

Preparation of 4'-azido-2'-deoxy-2'-difluorocytidine 5'-(N,N'-bis((S)-1-(isopropoxycarbonyl)ethyl))phosphordiamidate (33)

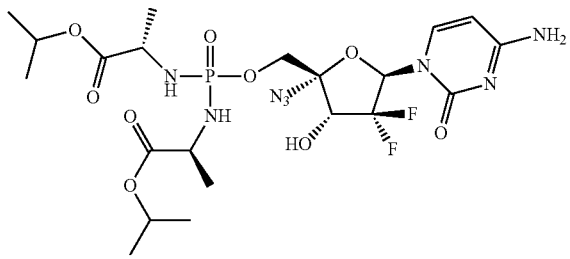

To a stirred of suspension of phosphorous oxychloride (10.0 g, 65.7 mmol) and L-aniline isopropyl ester (21.97 g, 131.5 mmol) in anhydrous DCM (400 mL) was added a solution of TEA (26.57 g, 263 mmol) in DCM (15 mL) dropwise at −78° C. After addition, the mixture was warmed to R.T. and then stirred 6 hours. The solvent was removed, and the residue was dissolved in methyl-butyl ether. The precipitate was removed by filtration, and the filtrate was concentrated to give the crude compound, which was purified on a silica gel column to give (N,N'-bis((S)-1-(isopropoxycarbonyl)ethyl))phosphordiamidic chloride (5.6 g, yield: 27.35%) as colorless oil. To a solution of compound (1) (90 mg, 0.3 mmol) in anhydrous THF (5 mL) was added a solution of t-BuMgCl (0.50 mL, 1M in THF) dropwise at −78° C. The mixture was then stirred at R.T. for 30 min and re-cooled to −78° C. A solution of N,N-bis((S)-1-(isopropoxycarbonyl) ethyl)phosphordiamidic chloride (0.50 mL, 1M in THF) was added dropwise. After addition, the mixture was stirred at R.T. for 14 hours. The reaction was quenched with HCOOH. The solvent was removed, and the residue was purified by prep. HPLC (0.1% HCOOH in MeCN and water) to give (33) (22.6 mg, 12.5%) as a white solid. $^1$H NMR (CD$_3$OD, 400 MHz) δ 7.64 (d, J=7.6 Hz, 1H), 6.45 (br s, 1H), 6.02 (d, J=7.6 Hz, 1H), 4.97-5.06 (m, 2H), 4.61 (t, J=12.0 Hz, 1H), 4.34 (d, J=6.4 Hz, 2H), 3.86-3.97 (m, 2H), 1.35-1.41 (m, 6H), 1.24-1.27 (m, 12H); $^{31}$P NMR (CD$_3$OD, 162 MHz) δ 13.81; ESI-LCMS: m/z 611 [M+H]$^+$.

Example 34

Preparation of 4'-azidoarabinocytidine 5'-(O-phenyl-N—(S)-1-(isopropoxycarbonyl)ethyl)phosphoramidate (34)

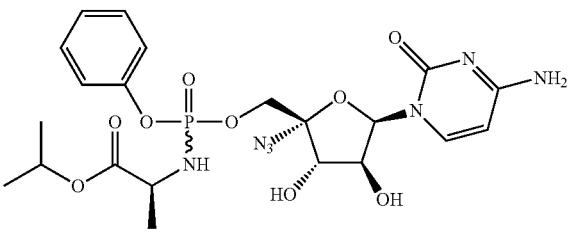 [SMILES: CC(C)OC(=O)[C@H](C)NP(=O)(OC[C@@]1(N=[N+]=[N-])O[C@@H](n2ccc(N)nc2=O)[C@@H](O)[C@@H]1O)Oc1ccccc1]

To a solution of compound (11) (90 mg, 0.32 mmol) in anhydrous THF (3 mL) was added a solution of t-BuMgCl (0.65 mL, 1M in THF) dropwise at −78° C. The mixture was then stirred at R.T. for 30 min and cooled to −78° C. A solution of O-phenyl-N—(S)-1-(isopropoxycarbonyl)ethyl) phosphoramidic chloride (0.65 mL, 1M in THF) was added dropwise. After addition, the mixture was stirred at R.T. for 14 hours. The reaction was quenched with formic acid (3 mL) and concentrated. The residue was purified by HPLC to give compound (34) (4.5 mg, 2.5%). $^1$H NMR (CD$_3$OD, 400 MHz) δ 7.66 (d, J=7.6 Hz, 1H), 7.35-7.39 (m, 2H), 7.17-7.28 (m, 3H), 6.49 (d, J=7.2 Hz, 1H), 5.85 (d, J=7.2 Hz, 1H), 4.94-4.99 (m, 1H), 4.35-4.42 (m, 2H), 4.24-4.28 (m, 1H), 4.13 (d, J=3.6 Hz, 1H), 3.90-3.95 (m, 1H), 1.34 (d, J=7.2 Hz, 3H), 1.21-1.23 (m, 6H); $^{31}$P NMR (CD$_3$OD, 162 MHz) δ 3.59, 3.44; ESI-LCMS: m/z 554 [M+H]$^+$.

Example 35

Preparation of 4'-azidoarabinouridine 5'-(O-phenyl-N—(S)-1-(isopropoxycarbonyl)ethyl)phosphoramidate (35)

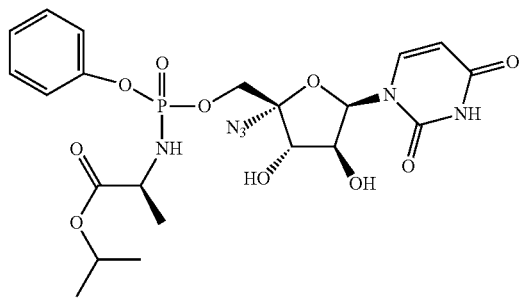 [SMILES: CC(C)OC(=O)[C@H](C)NP(=O)(OC[C@@]1(N=[N+]=[N-])O[C@@H](n2ccc(=O)[nH]c2=O)[C@@H](O)[C@@H]1O)Oc1ccccc1]

Compound 35 (white solid, 18.3 mg, 11%) was prepared using the procedure for preparing compound 34 with (compound (12), 86 mg, 0.30 mmol) in place of compound (11), t-BuMgCl (0.60 mL, 1M in THF), and (S)-phenyl 5-methyl-3-oxohexan-2-ylphosphoramidochloridate (0.60 mL, 1M in THF). $^1$H NMR (CD$_3$OD, 400 MHz) δ 77.61-7.67 (m, 1H), 7.36-7.41 (m, 2H), 7.20-7.29 (m, 3H), 6.43 (d, J=4.8 Hz, 1H), 5.58-5.67 (m, 1H), 4.96-5.02 (m, 1H), 4.28-4.50 (m, 2H), 4.19 (d, J=4.0 Hz, 1H), 3.92-3.97 (m, 1H), 1.36 (d, J=7.2 Hz, 3H), 1.23-1.26 (m, 6H); $^{31}$P NMR (CD$_3$OD, 162 MHz) δ 3.57, 3.45; ESI-LCMS: m/z 555 [M+H]$^+$.

Example 36

Preparation of 4'-azido-2'-deoxy-2'-methylarabinouridine 5'-(O-phenyl-N—(S)-1-(isopropoxycarbonyl)ethyl)phosphoramidate (36)

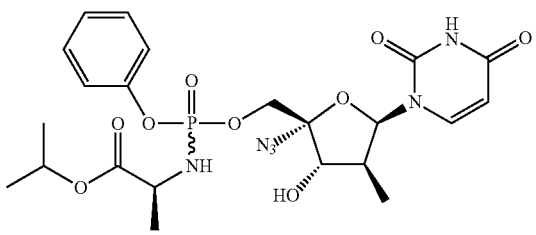 [SMILES: CC(C)OC(=O)[C@H](C)NP(=O)(OC[C@@]1(N=[N+]=[N-])O[C@@H](n2ccc(=O)[nH]c2=O)[C@@H](C)[C@@H]1O)Oc1ccccc1]

To a stirred solution of compound (6) (56 mg, 0.2 mmol) in dry THF (5 mL) was added t-BuMgCl (1M in THF, 0.45 mL) dropwise at –78° C. The solution was warmed to R.T., and the mixture was stirred for 20 min. The mixture was cooled to –78° C. and O-phenyl-N—(S)-1-(isopropoxycarbonyl)ethylphosphoramidic chloride (1M in THF, 0.40 mL) was added. The mixture was then warmed to R.T. gradually and stirred for 3 hours. The reaction was quenched by HCOOH and concentrated. The residue was purified on a silica gel column to give (36) as a white solid (8.3 mg, 7.6%). $^1$H NMR (CD$_3$OD, 400 MHz) δ 7.57-7.59 (m, 1H), 7.37-7.41 (m, 2H), 7.21-7.30 (m, 3H), 6.38 (br s, 1H), 5.65-5.67 (m, 1H), 4.95-4.99 (m, 1H), 4.45-4.49 (m, 2H), 4.07 (br s, 1H), 3.92-3.96 (m, 1H), 2.73-2.79 (m, 1H), 1.33-1.37 (m, 3H), 1.22-1.23 (m, 6H), 0.98-1.02 (m, 3H); $^{31}$P NMR (CD$_3$OD, 162 MHz) δ 3.56, 3.45; ESI-LCMS: m/z=575 [M+Na]$^+$.

Example 37

Preparation of 4'-azido-2'-deoxy-2'-fluoroadenosine 5'-(O-phenyl-N—(S)-1-(isopropoxycarbonyl)ethyl)phosphoramidate (37)

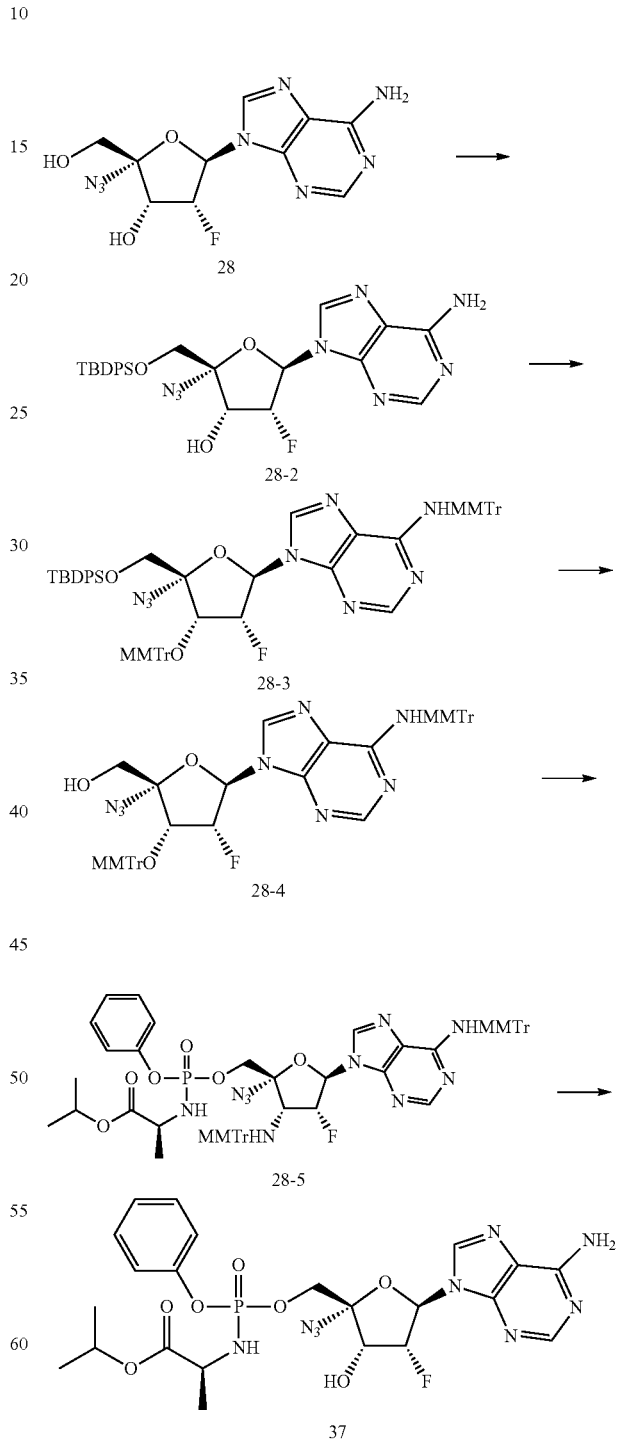

Step 1. Compound 28-2—To an ice-cold solution of (28) (240 mg, 0.77 mmol) in anhydrous pyridine (10 mL) was added TBSCl (318 mg, 1.16 mmol) in small portions under N₂. The reaction mixture was stirred at R.T. overnight. The solvent was removed under vacuum, and the residue was diluted with EA (50 mL), and washed with water and brine. The organic layer was separated, dried over anhydrous Na₂SO₄ and filtered. The filtrate was concentrated in vacuum to give a residue which was purified by silica gel column (DCM/MeOH=100/1 to 50/1) to give compound 28-2 (233 mg, 52%). ESI-LCMS: m/z=549 [M+H]⁺.

Step 2. Compound 28-3—To a mixture of compound 28-2 (233 mg, 0.42 mmol), AgNO₃ (288 mg, 1.70 mmol) and collidine (205 mg, 1.70 mmol) in anhydrous pyridine (10 mL) was added MMTrCl (523 mg, 1.70 mmol) under N₂. The reaction mixture was stirred at R.T. overnight under N₂. The reaction mixture was filtered, and the solvent was removed under vacuum. The residue was diluted with EA, and washed with water and brine. The filtrate was washed with saturated aqueous NaHCO₃ and followed by brine. The organic layer was separated, dried over anhydrous Na₂SO₄ and concentrated to give a residue which was purified on silica gel column to give compound 28-3 (350 mg, 75%). ESI-LCMS: m/z=1093 [M+H]⁺.

Step 3. Compound of 28-4—To the solution of compound 28-3 (350 mg, 0.32 mmol) in anhydrous THF was added TBAF (167 mg, 0.64 mmol) dropwise under N₂. The reaction mixture was stirred at R.T. overnight. The solvent was removed. The residue was dissolved in EA (200 mL), and washed with water and brine. The organic layer was separated, dried over anhydrous Na₂SO₄ and filtered. The filtrate was concentrated in vacuum to give a residue which was purified on silica gel column (DCM/MeOH=100/1 to 80/1) to give compound 28-4 (195 mg, 71%). ESI-LCMS: m/z=855 [M+H]⁺.

Step 4. Compound 28-5—To a stirred compound 28-4 (195 mg, 0.23 mmol) in anhydrous THF (5 mL) was added a solution of t-BuMgCl (0.70 mL, 0.70 in THF) dropwise at 0° C. The mixture was then stirred at R.T. for 40 min and cooled to 0° C. A solution of O-phenyl-N—(S)-1-(isopropoxycarbonyl)ethylphosphoramidic chloride (0.70 mL, 1M in THF) was added dropwise. After addition, the mixture was stirred at R.T. for 12 hours. The reaction was quenched with water and extracted with EA. The organic layer was dried over Na₂SO₄ and concentrated. The residue was purified by column on silica gel (PE:EA=5:1 to 2:1) to give compound 28-5 (103 mg, 40%). ESI-LCMS: m/z=1123 [M+H]⁺.

Step 5. Compound (37)—Compound 28-5 (103 mg, 0.10 mmol) was dissolved in 5 mL AcOH/H₂O (v/v=4:1). The mixture was stirred at 50° C. overnight. The solvent was removed under vacuum, and the residue was purified on silica gel column to give (37) as a white solid (9 mg, 16%). ¹H NMR (CDCl₃, 400 MHz) δ 8.25 (S, 1H), 7.92 (S, 1H), 7.25~7.29 (m, 2H), 7.11~7.15 (m, 3H), 6.34 (d, J=19.6 Hz, 1H), 5.82 (bs, 2H), 5.49~5.64 (m, 1H), 5.29~5.35 (m, 1H), 4.94~4.99 (m, 1H), 4.46~4.51 (m, 1H), 4.33~4.38 (m, 1H), 3.89~3.94 (m, 2H), 1.28~1.32 (m, 3H), 1.21~1.18 (m, 6H). ³¹P NMR (CDCl₃, 162 MHz) δ 2.63, 2.55. ESI-LCMS: m/z=580 [M+H]⁺.

Example 38

Preparation of 4'-azido-2'-deoxy-2'-α-fluoro-2'-β-methylcytidine (38)

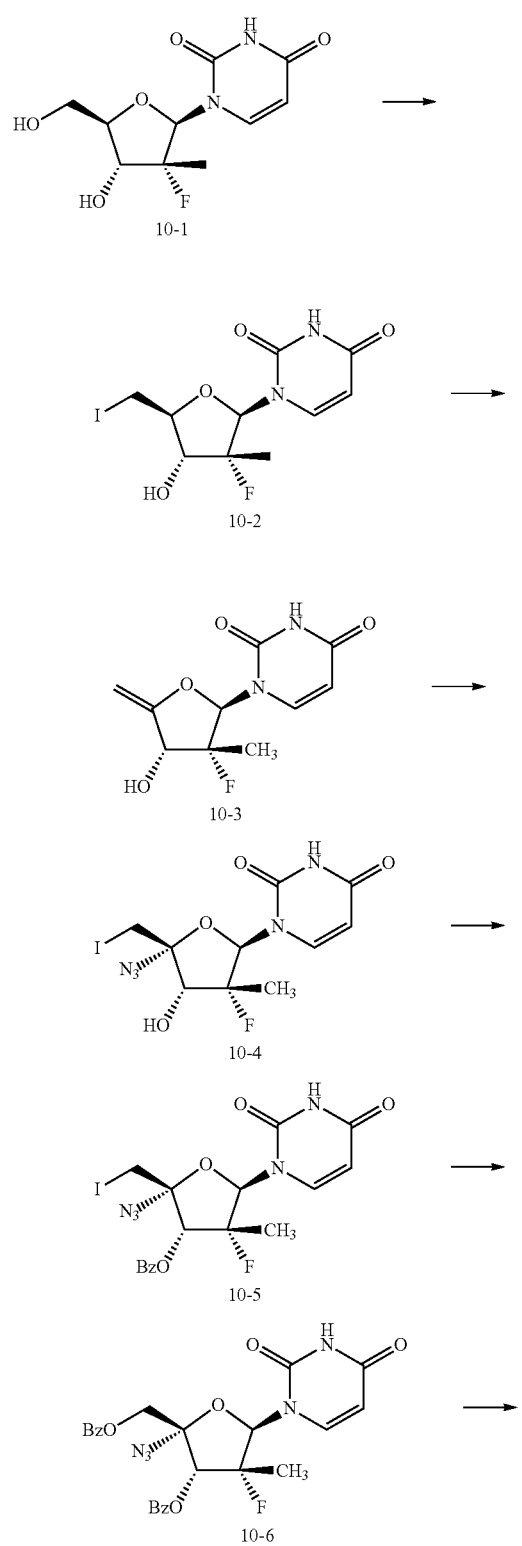

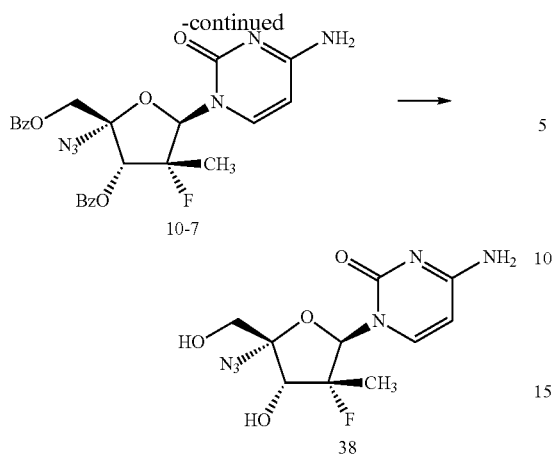

Step 1. Compound 10-2—To a stirred suspension of compound 10-1 (1.46 g, 5.62 mmol), PPh$_3$ (4.413 g, 16.84 mmol) and pyridine (5 mL) in anhydrous THF (40 mL) was added dropwise a solution of I$_2$ (2.852 g, 11.23 mmol) in THF (20 mL) at 0° C. After addition, the mixture was warmed to R.T. and stirred for 14 hours. The solution was quenched with saturated aqueous Na$_2$S$_2$O$_3$ (100 mL) and extracted with EA (100 mL 3 times). The organic layer was dried over Na$_2$SO$_4$ and concentrated. The residue was purified on a silica gel column (DCM/MeOH=100:1 to 50:1) to afford compound 10-2 as a white solid (1.51 g, 72.4%).

Step 2. Compound 10-3—Compound 10-2 (150 mg, 0.41 mmol) and CH$_3$ONa (66 mg, 1.22 mmol) were dissolved in anhydrous methanol (10 mL). The mixture was stirred at 60° C. for 12 hours. The reaction was quenched with CO$_2$. The solvent was removed, and the residue was purification on a silica gel column (MeOH/DCM=1/50 to 1/10) to afford compound 10-3 as a white solid (52 mg, 50.9%).

Step 3. Compound 10-4—To a stirred solution of BnEt$_3$NCl (1.169 g, 5.02 mmol) in MeCN (10 mL) was added NaN$_3$ (0.326 g, 5.02 mmol). The mixture was sonicated for 20 min and then stirred at R.T. for 16 hours. The solution was filtrated into a solution of compound 10-3 (0.15 g, 0.619 mmol) and NMM (0.626 g, 6.19 mmol) in anhydrous THF (10 mL). The mixture was cooled to 0° C. and a solution of I$_2$ (1.574 g, 5.02 mmol) in THF (5 mL) was added dropwise. Stirring was continued at 0-10° C. for 20 hours. N-Acetyl cystein was added until no gas evolved. Saturated aqueous Na$_2$S$_2$O$_3$ was added until a light yellow solution achieved. The solution was concentrated and then diluted with EA. The organic phase was washed with brine and dried over Na$_2$SO$_4$. The solvent was removed, and the residue was purified on a silica gel column (DCM:MeOH=50:1 to 10:1) to give compound 10-4 (0.183 g, 70.8%) as a white solid.

Step 4. Compound 10-5—To a stirred solution of compound 10-4 (0.6 g, 1.46 mmol) in anhydrous pyridine (15 mL) was added BzCl (0.408 mg, 2.92 mmol) dropwise at 0° C. The mixture was stirred at R.T. for 10 hours. The reaction was quenched with H$_2$O and the solution was concentrated. The residue was dissolved in EA and washed with Sat. aqueous NaHCO$_3$. The organic layer was dried over Na$_2$SO$_4$ and concentrated. The residue was purified on a silica gel column (PE/EA=10/1 to 1/1) to give 10-5 (0.22 g, 26.6%) as light yellow foam.

Step 5. Compound 10-6—Compound 5 (100 mg, 0.194 mmol), BzONa (279 mg, 1.94 mmol) and 15-crown-5 (427 mg, 1.94 mmol) were suspended in DMF (20 mL). The mixture was stirred at 95° C. for 1 day. The precipitate was removed by filtration, and the filtrate was diluted with EA. The solution was washed with brine and dried over Na$_2$SO$_4$. The solvent was removed, and the residue was purified on a silica gel column (PE/EA=4/1 to 2/1) to afford compound 10-6 (87 mg, 88.1%).

Step 6. Compound 10-7—A solution of compound 10-6 (200 mg, 0.39 mmol), DMAP (95.87 mg, 0.79 mmol) and TEA (79.36 mg, 0.79 mmol) in MeCN (15 mL) was treated with 2,4,6-triispropylbenzenesulfonyl chloride (TPSCl, 237.3 mg, 0.79 mmol). The mixture was stirred at R.T. for 12 hours. To the mixture was added NH$_3$ in THF (50 mL), and the mixture was stirred for additional 2 hours. The solution was evaporated under reduced pressure, and the residue was purified on a silica gel column (DCM/MeOH=100:1 to 10:1) to give compound 10-7.

Step 7. Compound (38)—Compound 10-7 (0.15 g, 0.295 mmol) was dissolved in methanolic ammonia (30 mL), and the mixture was stirred at R.T. for 14 hours. The solvent was removed, and the residue was purified on a silica gel column (DCM/MeOH=30:1 to 10:1) to give (38) as a white solid (29 mg, 35.5%). $^1$H NMR (CD$_3$OD, 400 MHz) δ 8.01 (s, 1H), 6.56 (d, J=18.0 Hz, 1H), 5.94 (d, J=7.6 Hz, 1H), 4.14 (d, J=7.6 Hz, 1H), 3.87 (d, J=7.6 Hz, 1H), 3.75 (d, J=7.6 Hz, 1H), 1.28 (dd, J$_1$=31.6 Hz, J$_2$=7.2 Hz, 3H); ESI-MS: m/z=301.1 [M+H]$^+$.

Example 39

Preparation of 4'-azido-2'-deoxy-2'-difluorouridine 5'-(N,N-bis((S)-isopropoxycarbonyleth-1-yl))phosphordiamidate (39)

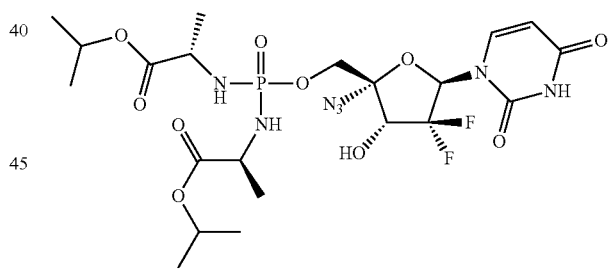

To a solution of compound (5) (90 mg, 0.29 mmol) in anhydrous THF (5 mL) was added a solution of t-BuMgCl (0.5 mL, 1M in THF) dropwise at −78° C. The mixture was then stirred at R.T. for 30 min and cooled to −78° C. A solution of N,N'-bis((S)-1-(isopropoxycarbonyl)ethyl)phosphordiamidic chloride (0.5 mL, 1M in THF) was added dropwise. After addition, the mixture was stirred at R.T. for 14 hours. The reaction was quenched with HCOOH. The organic layer was dried over Na$_2$SO$_4$ and concentrated. The residue was purified by HPLC to give (39) (27.1 mg, 14.3%) as a white solid. $^1$H NMR (CD$_3$OD, 400 MHz) δ7.62 (d, J=8.0 Hz, 1H), 6.32 (t, J=7.6 Hz, 1H), 5.82 (d, J=8.0 Hz, 1H), 4.95-5.01 (m, 2H), 4.64 (t, J=12.8 Hz, 1H), 4.27-4.36 (m, 2H), 3.82-

3.98 (m, 2H), 1.37 (d, J=7.2 Hz, 3H), 1.23-1.26 (m, 6H); $^{31}$P NMR (CD$_3$OD, 162 MHz) δ13.83. ESI-LCMS: m/z=612 [M+H]$^+$.

Example 40

Preparation of 4'-azido-2'-deoxy-2'-fluorouridine 5'-(N,N'-bis((S)-1-isopropoxycarbonyl)ethyl))phosphordiamidate (40)

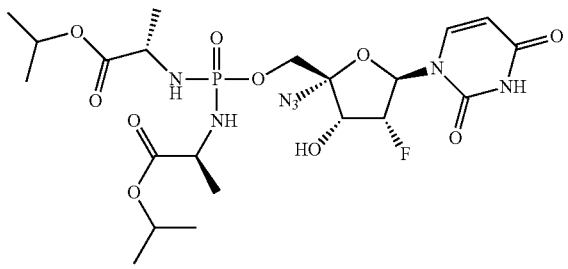 [SMILES: CC(C)OC(=O)[C@H](C)NP(=O)(N[C@@H](C)C(=O)OC(C)C)OC[C@@]1(N=[N+]=[N-])O[C@@H](n2ccc(=O)[nH]c2=O)[C@H](F)[C@@H]1O]

Compound 40 (white solid, 24.8 mg, 13.93%) was prepared using the procedure for preparing compound 39 with (compound (17), 86 mg, 0.3 mmol) in place of compound (5), t-BuMgCl (0.55 mL, 1M in THF), and (N,N-bis((S)-isopropoxycarbonyleth-1-yl))phosphordiamidic chloride (0.55 mL, 1M in THF). $^1$H NMR (CD$_3$OD, 400 MHz) δ7.70 (d, J=8.0 Hz, 1H), 6.09 (dd, J$_1$=2.0 Hz, J$_2$=20.4 Hz, 1H), 5.76 (d, J=8.0 Hz, 1H), 5.30 (ddd, J$_1$=2.0 Hz, J$_2$=5.6 Hz, J$_3$=53.6 Hz, 1H), 4.94-5.01 (m, 2H), 4.70 (dd, J$_1$=5.6 Hz, J$_2$=20.4 Hz, 1H), 4.13-4.27 (m, 2H), 3.81-3.90 (m, 2H), 1.36 (d, J=7.2 Hz, 3H), 1.22-1.25 (m, 6H); $^{31}$P NMR (CD$_3$OD, 162 MHz) δ13.69. ESI-LCMS: m/z=594 [M+H]$^+$.

Example 41

Preparation of 4'-azido-2'-deoxy-2'-fluorouridine 3',5'-cyclic thiophosphoric acid methyl ester (41)

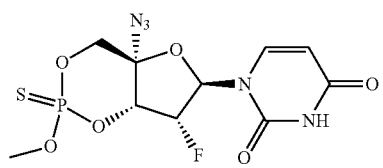

To an ice-cold suspension of compound (17) (150 mg, 0.52 mmol) in dry pyridine (4 mL) was added tetrazole (0.37 M in MeCN, 4 mL, 1.48 mmol), followed by addition of methyl N,N,N',N'-tetraisopropylphosphordiamidite (204 mg, 0.78 mmol) dropwise over 5 min. The resultant mixture was stirred at the ambient temperature for 16 hours before bis(3-triethoxysilyl)propyl-tetrasulfide (TEST) (0.42 mL, 0.8 mmol) was added. The resulting light yellow suspension was stirred for 3 hours at R.T. The reaction mixture was cooled down (ice/water bath), and was diluted with EA (100 mL), washed with saturated NaHCO$_3$ and followed by brine, dried over anhydrous Na$_2$SO$_4$ and concentrated in-vacuo to give crude product residue. The crude product was purified by flash chromatography on silica gel and then further purified on HPLC to give (41) (21.2 mg, 11%) as a white solid. $^1$H NMR (CD$_3$OD, 400 MHz) δ7.69 (d, J=8.0 Hz, 1H), 6.06 (d, J=22.0 Hz, 1H), 5.71 (d, J=8.0 Hz, 1H), 5.67-5.52 (dd, J=55.6 Hz, 5.6 Hz, 1H), 5.35-5.26 (dt, J=25.6 Hz, 4.0 Hz, 1H), 4.66 (m, 2H), 3.85 (d, J=13.6 Hz, 3H). $^{31}$P NMR (CD$_3$OD, 162 MHz) δ62.66. ESI-LCMS: m/z=402 [M+Na]$^+$.

Example 42

Preparation of 4'-azido-2'-deoxy-2'-fluorouridine 3',5'-cyclic thiophosphoric acid isopropyl ester (42)

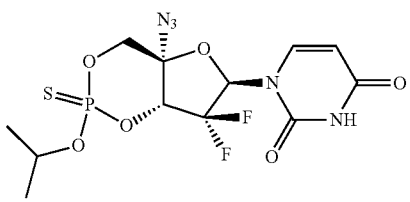

Compound 42 (white solid, 15.5 mg, 7.4%) was prepared using the procedure for preparing compound 41 using (compound (5), 150 mg, 0.49 mmol) in place of compound (17), and isopropyl N,N,N',N'-tetraisopropylphosphordiamidite (213 mg, 0.74 mmol). $^1$H NMR (CD$_3$OD, 400 MHz) δ7.73 (d, J=6.8 Hz, 1H), 6.35 (br, 1H), 5.77 (d, J=8.0 Hz, 1H), 5.35 (br, 1H), 4.92 (m, 1H), 4.78 (m, 2H), 1.40 (t, 6H). $^{31}$P NMR (CD$_3$OD, 162 MHz) δ58.53. ESI-LCMS: m/z 426 [M+H]$^+$.

Example 43

Preparation of 4'-azidoribavirin (43)

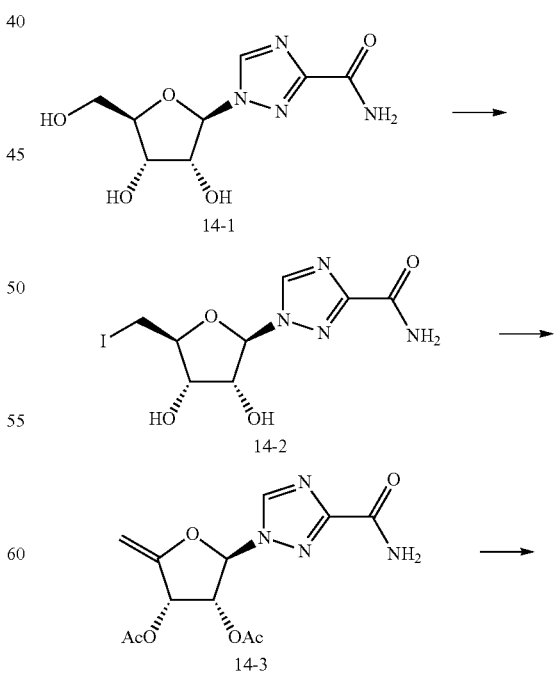

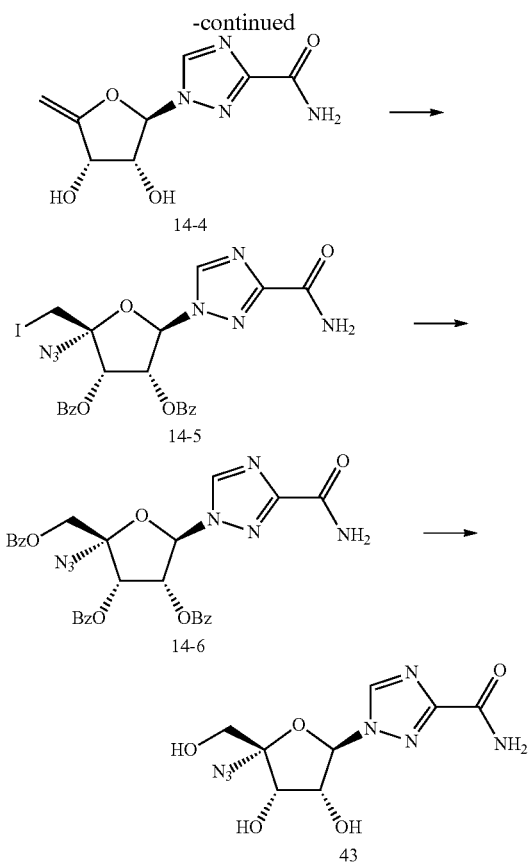

Step 1. Compound 14-2—A solution of PPh$_3$ (17.48 g, 66.6 mmol) and I$_2$ (15.61 g, 61.5 mmol) in pyridine (100 mL) was stirred at R.T. for 20 min and then compound 14-1 (10.0 g, 41.0 mmol) was added. The reaction mixture was stirred at R.T. for 12 hours, concentrated to dryness, and co-evaporated with toluene twice. The crude product was purified on a silica gel column (DCM/MeOH=20:1 to 7.5:1) to afford compound 14-2 (8.21 g, 56.5%).

Step 2. Compound 14-3—Compound 14-2 (200 mg, 0.56 mmol) and CH$_3$ONa (305 mg, 5.65 mmol) were dissolved in anhydrous methanol (10 mL). The mixture was stirred at 60° C. for 12 h. The solvent was removed, and the residue was co-evaporated with MeCN. The residue was re-dissolved in MeCN and Ac$_2$O (1.15 g, 11.298 mmol) was added. The suspension was heated to 60° C. and stirred for 5 hours. After cooling, the solution was adjusted to pH=7.5 by slow addition of a saturated aqueous NaHCO$_3$. The mixture was extracted with EA and brine. The organic phase was concentrated and purified on a silica gel column (MeOH/DCM=1/50 to 1/10) to afford compound 14-3 as a white solid (102 mg, 57.1%).

Step 3. Compound 14-4—Compound 14-3 (0.10 g, 0.32 mmol) was dissolved in methanolic ammonia (30 mL), and the mixture was stirred at R.T. for 14 hours. The solvent was removed, and the residue was purified on a silica gel column (DCM/MeOH=30:1 to 10:1) to give compound 14-4 as a white solid (51 mg, 68.7%).

Step 4. Compound 14-5—To a stirred solution of BnEt$_3$NCl (1.169 g, 5.02 mmol) in MeCN (10 mL) was added NaN$_3$ (0.326 g, 5.02 mmol). The mixture was sonicated for 20 min and then stirred at R.T. for 16 hours. The solution was filtrated into a solution of compound 14-4 (0.20 g, 0.885 mmol) and NMM (0.447 g, 4.424 mmol) in anhydrous THF (10 mL). The mixture was cooled to 0° C., and a solution of I$_2$ (1.123 g, 4.43 mmol) in THF (5 mL) was added dropwise. Stirring was continued at 0-10° C. for 20 hours. The reaction mixture was cooled to 0° C., and DMAP (90 mg, 0.885 mmol) and BzCl (619 mg, 4.42 mmol) were added. The mixture was stirred at R.T. for 4 hours and then diluted with EA. N-Acetyl cystein was added until no gas evolved. Saturated Na$_2$S$_2$O$_3$ in aqueous NaHCO$_3$ was added until a light yellow solution was achieved. The solution was concentrated and then diluted with EA. The organic phase was washed with brine and dried over Na$_2$SO$_4$. The solvent was removed, and the residue was purified on a silica gel column (DCM:MeOH=50:1 to 10:1) to give compound 14-5 (0.351 g, 57.2%) as a white solid.

Step 5. Compound 14-6—Compound 14-5 (300 mg, 0.498 mmol), BzONa (716 mg, 4.98 mmol) and 15-crown-5 (1.094 g, 4.98 mmol) were suspended in DMF (60 mL). The mixture was stirred at 95° C. for 1 day. The precipitate was removed by filtration, and the filtrate was diluted with EA. The solvent was washed with brine and dried over Na$_2$SO$_4$. The solvent was removed, and the residue was purified by column (PE/EA=4/1 to 2/1) to afford compound 14-6 (199 mg, 67.3%).

Step 6. Compound (43)—Compound 14-6 (1.51 g, 2.49 mmol) was dissolved in methanolic ammonia (50 mL), and the solution was stirred at R.T. for 14 hours. The solvent was removed, and the residue was purified on a silica gel column (DCM/MeOH=30:1 to 10:1) to give (43) as a white solid (403 mg, 56.4%). $^1$H NMR (DMSO-d$_6$, 400 MHz) δ8.93 (s, 1H), 7.90 (s, 1H), 7.66 (s, 1H), 6.10 (d, J=4.8 Hz, 1H), 5.81 (d, J=6.4 Hz, 2H), 5.39 (t, J=6.0 Hz, 1H), 4.59 (q, J=5.6 Hz, 1H), 4.37 (dd, J$_1$=6.0 Hz, J$_2$=5.2 Hz, 1H), 3.51-3.57 (m, 1H), 3.35-3.45 (m, 1H); ESI-MS: m/z=308 [M+Na]$^+$.

Example 44

Preparation of 4'-azidouridine 5'-(N,N'-bis((S)-1-(isopropoxycarbonyl)ethyl))phosphorodiamidate (44)

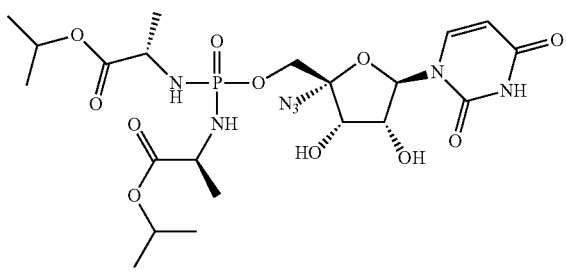 [SMILES: CC(C)OC(=O)[C@H](C)NP(=O)(N[C@@H](C)C(=O)OC(C)C)OC[C@@]1(N=[N+]=[N-])O[C@@H](n2ccc(=O)[nH]c2=O)[C@H](O)[C@@H]1O]

To a stirred solution of 19-2 (100 mg, 0.3 mmol) in anhydrous THF (5 mL) was added a solution of t-BuMgCl (0.6 mL, 1M in THF) dropwise at −78° C. The mixture was then stirred at R.T. for 30 min and cooled to −78° C. A solution of N,N'-bis((S)-1-(isopropoxycarbonyl)ethyl)phosphordiamidic chloride (0.6 mL, 1M in THF) was added dropwise. After addition, the mixture was stirred at R.T. for 16 hours. The reaction was quenched with H$_2$O and extracted with EA. The solvent was concentrated, and the residue was purified on silica gel (PE:EA=2:1) to give an intermediate (80 mg, 41.4%). The intermediate (80 mg, 0.13 mmol) was dissolved in 60% formic acid aqueous solution, and the resulting mixture was stirred at R.T. for 50 hours. The solvent was removed, and the residue was purified on HPLC to give (44) (6.5 mg, 8.3%) as a white solid. $^1$H NMR (DMSO-d6, 400

MHz) δ7.73 (d, J=7.6 Hz, 1H), 6.08 (d, J=6.4 Hz, 1H), 6.03 (br s, 1H), 5.69 (d, J=8.0 Hz, 1H), 5.66 (br s, 1H), 4.95-5.04 (m, 2H), 4.86-4.88 (m, 2H), 4.26 (br s, 2H), 3.72-3.85 (m, 4H), 1.24 (d, J=7.2 Hz, 3H), 1.17-1.20 (m, 6H). $^{31}$P NMR (DMSO-d6, 162 MHz) δ12.82. ESI-LCMS: m/z=592 [M+H]$^+$.

5.54 (m, 1H), 4.81-4.84 (m, 1H), 4.62-4.69 (m, 2H), 1.41 (t, J=6.0 Hz, 6H); $^{31}$P NMR (CD$_3$OD, 162 MHz) δ59.58; ESI-LCMS: m/z 407 [M+H]$^+$.

Example 45

Preparation of 4'-azido-2'-deoxy-2'-fluorouridine 3',5'-cyclic thiophosphoric acid isopropyl ester (45)

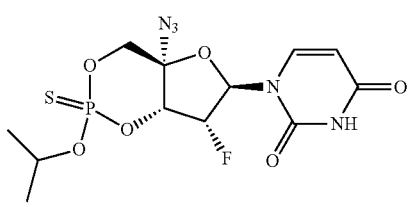

To an ice-cold suspension of compound (17) (100 mg, 0.35 mmol) in dry pyridine (3 mL) was added tetrazole (0.37 M in MeCN, 3 mL, 1.11 mmol), followed by addition of isopropyl N,N,N',N'-tetraisopropylphosphordiamidite (151 mg, 0.52 mmol) dropwise after 5 min. The resultant mixture was stirred at the ambient temperature for 16 hours before TEST (0.42 mL, 0.8 mmol) was added. The resulting light yellow suspension was stirred for 3 hours at R.T. The reaction mixture was cooled down (ice/water bath), diluted with EA (100 mL), washed with saturated NaHCO$_3$ aq. and followed by brine, dried over anhydrous Na$_2$SO$_4$ and concentrated in-vacuo to give a crude product residue. The crude product was purified on silica gel (DCM/MeOH; 95:5) and then further purified on HPLC to give (45) (30.5 mg, 21.6%) as a white solid. $^1$H NMR (CD$_3$OD, 400 MHz) δ7.70 (d, J=8.0 Hz, 1H), 6.15 (d, J=22.4 Hz, 1H), 5.71 (d, J=8.0 Hz, 1H), 5.62 (dd, J$_1$=5.2 Hz, J$_2$=55.6 Hz, 1H), 5.38-5.47 (m, 1H), 4.80-4.85 (m, 1H), 4.59-4.71 (m, 2H), 1.39-1.41 (m, 6H); $^{31}$P NMR (CD$_3$OD, 162 MHz) δ59.36; ESI-LCMS: m/z=430 [M+Na]$^+$.

Example 46

Preparation of 4'-azido-2'-deoxy-2'-fluorocytidine 3',5'-cyclic thiophosphoric acid isopropyl ester (46)

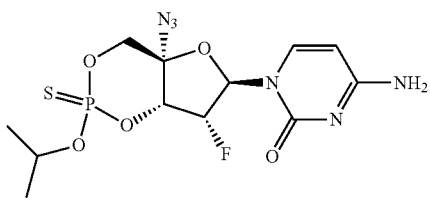

Compound 46 (white solid, 7.2 mg, 8.5%) was prepared using the procedure for preparing compound 45 using (compound (2), 60 mg, 0.21 mmol) in place of compound (17), and isopropyl N,N,N',N'-tetraisopropylphosphordiamidite (92 mg, 0.32 mmol). $^1$H NMR (CD$_3$OD, 400 MHz) δ7.69 (d, J=7.6 Hz, 1H), 5.87-5.93 (m, 2H), 5.58-5.67 (m, 1H), 5.50-

Example 47

Preparation of 4'-azidoarabinoguanosine (47)

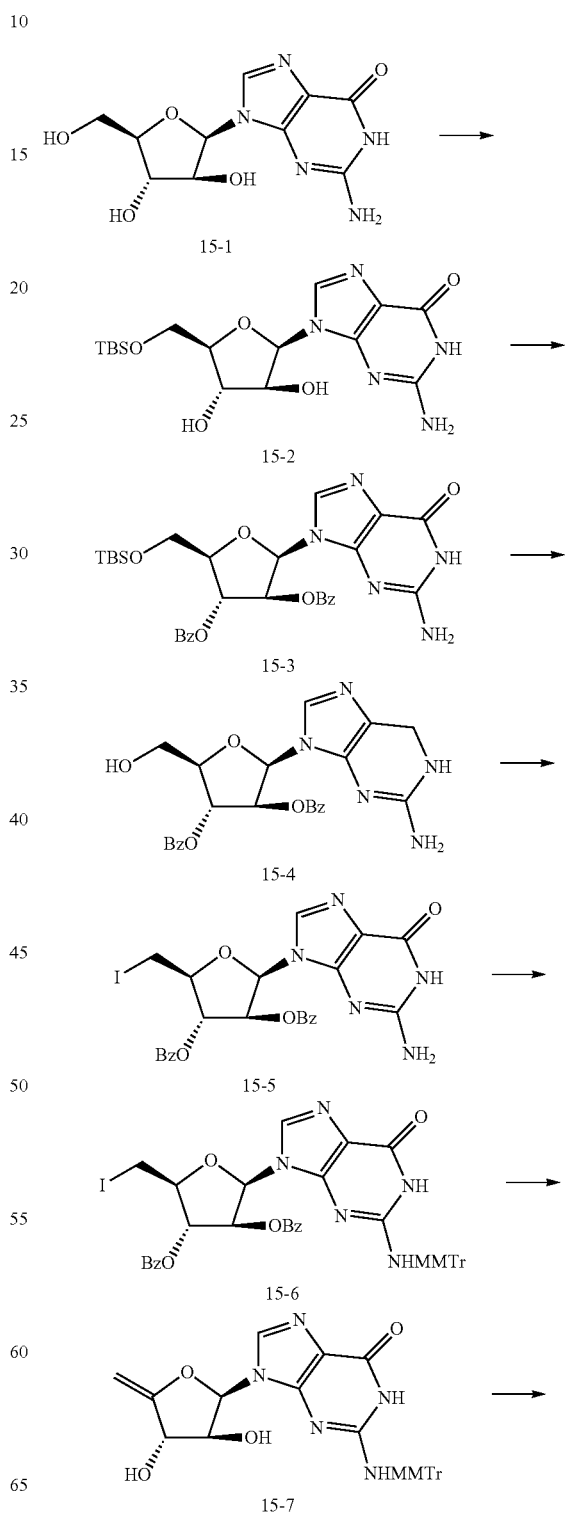

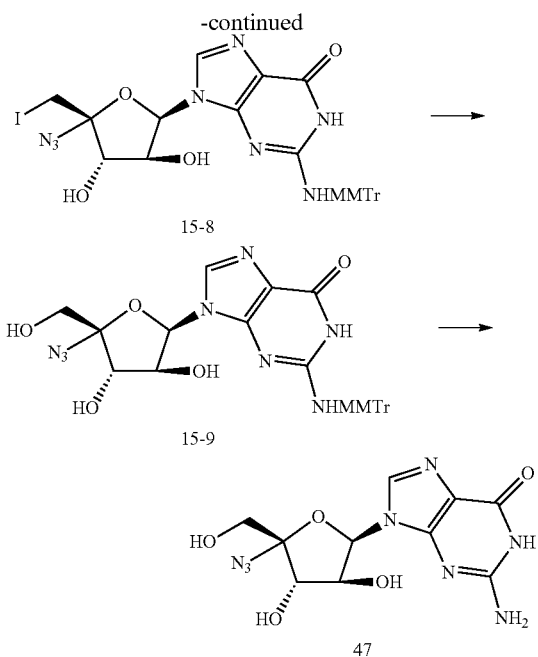

Step 1. Compound 15-2—To a stirred solution of compound 15-1 (5.0 g, 17.7 mmol) in dry DMF (30 mL) were added imidazole (2.4 mL, 35.4 mmol) and TBSCl (5.3 g, 35.4 mmol) at 0° C. The mixture was then stirred at R.T. for 18 hour. The reaction mixture was cooled to 0° C. and quenched with ice water. The resulting precipitate was collected and washed with water and acetone to give compound 15-2 (6.3 g, yield 89.8%) as a white solid. $^1$H NMR (DMSO-d6, 400 MHz) δ 10.58 (s, 1H), 7.69 (s, 1H), 6.46 (s, 2H), 5.99 (d, J=4.4 Hz, 1H), 5.62 (d, J=4.8 Hz, 1H), 5.52 (d, J=4.4 Hz, 1H), 4.04-4.09 (m, 2H), 3.71-3.85 (m, 2H), 0.88 (s, 9H), 0.04 (s, 6H); ESI-MS: m/z=398 [M+H]$^+$.

Step 2. Compound 15-3—To a stirred suspension of compound 15-2 (6.3 g, 182.39 mmol) in dry pyridine (80 mL) was added Bz$_2$O (42.0 g, 185.8 mmol). The mixture was stirred at R.T. for 48 hours. The reaction mixture was diluted with DCM (200 mL). The precipitate was collected and washed with DCM to give compound 15-3 (7.8 g, yield 81.4%) as a white solid. $^1$H NMR (DMSO-d6, 400 MHz) δ 10.60 (s, 1H), 7.44-8.04 (m, 11H), 6.44-6.46 (m, 3H), 5.99 (t, J=5.2 Hz, 1H), 5.89 (t, J=6.4 Hz, 1H), 4.40 (d, J=5.6 Hz, 1H), 3.98-4.05 (m, 2H), 0.86 (s, 9H), 0.05 (s, 6H); ESI-MS: m/z=606 [M+H]$^+$ Step 3. Compound 15-4—To a stirred solution of compound 15-3 (7.8 g, 12.9 mmol) in dry DCM (100 mL) was added TsOH (monohydrate, 3.3 g, 19.3 mmol) at 0° C. The mixture was stirred at 0° C. for 2 hours. The reaction was quenched with NaHCO$_3$ solution, extracted with DCM. The organic layer was dried over Na$_2$SO$_4$ and concentrated. The residue was purified on silica gel column to afford compound 15-4 (5.2 g, yield 82.1%) as a white solid. $^1$H NMR (DMSO-d6, 400 MHz) δ 10.59 (s, 1H), 7.41-8.01 (m, 11H), 6.39-6.44 (m, 3H), 5.86 (dd, J$_1$=4.4 Hz, J$_2$=5.6 Hz, 1H), 5.78 (dd, J$_1$=4.0 Hz, J$_2$=5.6 Hz, 1H), 4.30-4.32 (m, 1H), 3.75-3.81 (m, 2H); ESI-MS: m/z=492 [M+H]$^+$.

Step 4. Compound 15-5—To a stirred solution of compound 15-4 (5.2 g, 10.6 mmol), imidazole (2.9 g, 42.4 mmol) and PPh$_3$ (8.3 g, 31.8 mmol) in dry THF (100 mL) was added dropwise a solution of I$_2$ (8.1 g, 31.8 mmol) in dry THF (50 mL) under N$_2$ at 0° C. The reaction mixture was stirred at R.T. overnight. The reaction was quenched with Na$_2$S$_2$O$_3$ solution and extracted with EtOAc. The organic layer was dried over Na$_2$SO$_4$ and concentrated. Purification on silica gel column gave compound 15-5 (4.6 g, yield 72.3%) as a white solid. $^1$H NMR (DMSO-d6, 400 MHz) δ 10.66 (s, 1H), 7.46-8.06 (m, 11H), 6.49-6.51 (m, 3H), 5.98 (t, J$_1$=4.8 Hz, J$_2$=5.6 Hz, 1H), 5.81 (t, J=5.2 Hz, 1H), 4.43-4.47 (m, 1H), 3.69-3.81 (m, 2H); ESI-MS: m/z=602 [M+H]$^+$.

Step 5. Compound 15-6—A mixture of MMTrCl (3.09 g, 10 mmol) and silver nitrate (2.83 g, 11 mmol) in 20 mL of pyridine was stirred at R.T. for 1 hour. Compound 15-5 (2.67 g, 4.45 mmol) in DMF (15 mL) was added, and the resulting mixture was stirred at R.T. for 6 hours. Additional MMTrCl (3.09 g) and silver nitrate (2.83 g) were added, and the mixture was stirred at R.T. for 3 days. The mixture was diluted with EA, and the precipitate was filtered. The filtrate was washed with brine 5 times, dried over sodium sulfate, and concentrated. Purification on silica gel column with 3-6% i-PrOH in DCM gave compound 15-6 (2.64 g) as a white foam.

Step 6. Compound 15-7—A solution of compound 15-6 (2.64 g, 3.02 mmol) and DBU (3.93 mmol) in THF (30 mL) was heated at 55-57° C. for 6 hours. The mixture was then cooled to R.T., diluted with EA, washed brine (3 times), dried over sodium sulfate, and concentrated. Purification on silica gel column with 3-6% i-PrOH in DCM gave an olefinyl intermediate, which was dissolved in 7 M NH$_3$ in MeOH. The solution stood at R.T. overnight and concentrated. Purification on silica gel column with 5-7% i-PrOH in DCM gave compound 15-7 (1.20 g) as a white foam.

Step 7. Compound 15-8—A mixture of BnEt$_3$NCl (1.03 g, 4.5 mmol) and NaN$_3$ (306 mg, 4.95 mmol) in anhydrous MeCN (50 mL) was sonicated for 10 min and then stirred at R.T. for 6 hours. The solution was taken out by syringe to another flask and concentrated to about 20 mL. The solution was added to a stirred solution of compound 15-7 (730 mg, 1.34 mmol) and NMM (50 uL, 0.45 mmol) in THF (15 mL). The solution was cooled with ice, and a solution of I$_2$ (590 mg, 2.3 mmol) in THF (13 mL) was added. The resulting reaction mixture was stirred at R.T. for 16 hours. After the mixture was cooled with ice, 5% of aqueous Na$_2$S$_2$O$_3$ (95 mL) was added. The mixture was diluted with EA, washed with 5% aqueous Na$_2$S$_2$O$_3$ twice and with brine once, dried over sodium sulfate, and concentrated to give a foam (crude). A solution of the crude and pyridine (1.1 mL, 13.4 mmol) was added to a mixture of BzCl (0.64 mL, 5.36 mmol) and silver nitrate (1.4 g, 5.36 mmol) in DMF (15 mL) previously stirred at R.T. for 1 hour. The resulting reaction mixture was stirred at R.T. overnight, diluted with EA, and filtered to remove the precipitate. The filtrate was washed with brine 5 times, dried over sodium sulfate, and concentrated. Purification on silica gel column with 0-3% i-PrOH in DCM gave compound 15-8 (0.72 g, crude).

Step 8. Compound 15-9—A mixture of compound 15-8 (crude, 0.72 g) and sodium acetate (0.55 g, 6.7 mmol) in HMPA (5 mL) and DMF (5 mL) was heated at 100-105° C. for 24 hours. The mixture was cooled to R.T., diluted with EA, washed with 5 times, dried over sodium sulfate, and concentrated. The resulting crude was dissolved in 7 N NH$_3$ in MeOH and stirred at R.T for 3 days. The solvent was evaporated, and the residue was chromatographed on silica gel with 5-12% MeOH in DCM to give 5'-chloro-5'-deoxy-N$^2$-(4-methoxytrityl)arabinosylguanosine (111 mg) and compound 15-9 (102 mg).

Step 9. Compound (47)—Compound 15-9 (42 mg) was dissolved in 80% aqueous formic acid, and the resulting solution stood at R.T. for 30 min. The solvent was evaporated, and the residue was co-evaporated with MeOH/toluene three times. The residue was the triturated with hot EA five times. The precipitate was filtered and washed with EA to give (47) (18.4 mg) as an ivory solid; NMR (DMSO-d$_6$) δ 10.6 (br, 1H), 7.713 (s, 1H), 6.49 (s, 2H), 6.17 (d, J=4.8 Hz, 1H), 5.95 (d, J=5.2 Hz, 1H), 5.84 (d, J=4.8 Hz, 1H), 5.50 (t, J=5.6 Hz, 1H), 4.32 (m, 2H), 3.68 (m, 2H); MS m/z=323.3 [M−1]⁻.

Example 48

Preparation of 2-amino-9-(4-aido-2-deoxy-2-fluoro-1-ribofuranosyl)-6-methoxypurine (48)

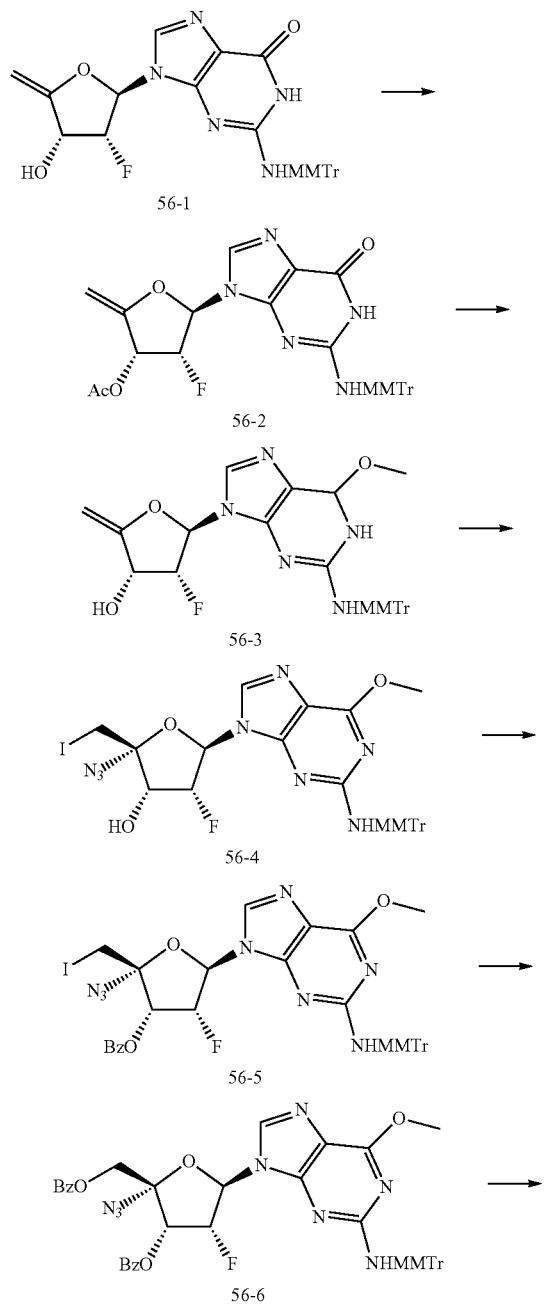

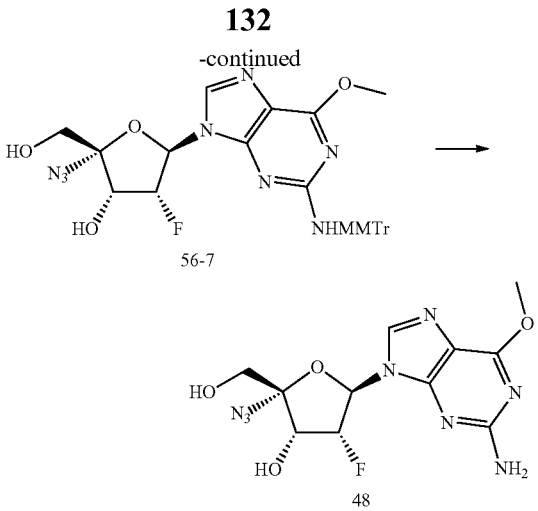

Step 1. Compound 56-2—To a stirred solution of 56-1 (2.7 g. 4.9 mmol) in pyridine (25 mL) was added Ac$_2$O (3.5 mL, 36 mmol) at 0° C. The mixture was stirred at R.T. overnight. The reaction was quenched with saturated NaHCO$_3$, extracted with EA and washed with brine. The organic layer was dried over Na$_2$SO$_4$ and concentrated. The residue was purified by silica gel column chromatography (PE/EA=2:1 to 1:1) to afford 56-2 (2.6 g, yield 92.7%) as a white foam. $^1$H NMR (CD$_3$OD, 400 MHz) δ 8.10 (s, 1H), 7.23-7.37 (m, 13H), 6.85-6.89 (m, 2H), 5.98 (dd, J$_1$=5.2 Hz, J$_2$=13.2 Hz, 1H), 5.28 (dd, J$_1$=J$_2$=5.2 Hz, 1H), 5.11 (ddd, J$_1$=J$_2$=5.2 Hz, J$_3$=40.4 Hz, 1H), 4.52 (dd, J$_1$=J$_2$=1.2 Hz, 1H), 4.26 (d, J=2.4 Hz, 1H), 3.79 (s, 3H), 2.13 (s, 3H).

Step 2. Compound 56-3—Compound 56-2 (2.6 g. 4.7 mmol), BOP (4.1 g, 9.4 mmol) and DBU (1.4 g, 9.4 mmol) were dissolved in dry THF (50 mL). The mixture was stirred at R.T. for 1 hour. The solvent was evaporated under reduced pressure, and anhydrous MeOH (50 mL) and DBU (1.4 g, 9.4 mmol) was added. The mixture was stirred at R.T. for 10 hours. The solvent was removed, and the residue was re-dissolved in EA. The solution was washed with brine and dried over Na$_2$SO$_4$. The solvent was removed, and the residues was purified by column chromatography (PE/EA=3:1 to 2:1) to afford compound 56-3 as a white foam (1.5 g, 54.3%).

Step 3. Compound 56-4—To a stirred solution of compound 56-3 (1.5 g, 2.6 mmol) in dry THF (50 mL), 4-Methylmorpholine (2.7 g, 26 mmol) and BnEt$_3$NN$_3$ (27 mL, 27 mmol in CH$_3$CN) was added a solution of I$_2$ (6.1 g, 24 mmol) in THF (100 mL) dropwise at 0° C. The mixture was stirred at R.T. for 18 hours. The solution was quenched with Na$_2$S$_2$O$_3$ solution and extracted with EA. The organic layer was washed with NaHCO$_3$ solution, dried over Na$_2$SO$_4$ and concentrated under reduced pressure. The crude products were purified by column chromatography (PE/EA=4:1 to 2:1) to afford compound 56-4 as a white foam (1.45 g, yield 76.7%).

Step 4. Compound 56-5—To a stirred solution of compound 56-4 (1.4 g, 1.9 mmol) in dry pyridine (15 mL) was added BzCl (650 mg, 0.46 mmol). The mixture was stirred at R.T. for 2 hours. The solution was quenched with NaHCO$_3$ solution and extracted with EA. The organic layer was dried over Na$_2$SO$_4$ and concentrated. The residue was purified by silica gel chromatography (PE/EA=7:1 to 3:1) to afford compound 55-5 (1.3 g, yield 81.3%) as a white solid.

Step 5. Compound 55-6—To a stirred solution of compound 56-5 (1.2 g, 1.5 mmol) in dry DMF (50 mL) were added NaOBz (1.5 g, 10.6 mmol) and 15-crown-5 (2.64 g, 17.6 mmol). The mixture was stirred at 105° C. for 24 hours.

The solution was diluted with water and extracted with EA. The organic layer was washed with brine and dried over Na$_2$SO$_4$. The solvent was removed, and the residue was purified by silica gel column chromatography (PE/EA=7:1 to 3:1) to afford crude compound 56-6 (960 mg) as a white solid.

Step 6. Compound 56-7—Compound 56-6 (950 mg) was dissolved in methanolic NH$_3$ (saturated). The mixture was stirred at R.T. for 12 hours. The solvent was removed, and the residue was purified by silica gel column chromatography (PE/EA=3:1 to 1:2) to afford to give compound 56-7 (350 mg, yield 48.8%) as white solids.

Step 7. Compound (48)—Compound 56-7 (350 mg, 0.57 mmol) was dissolved in 80% formic acid (5 mL). The mixture was stirred at R.T. for 30 mins. The solution was co-evaporated with toluene for 5 times. The residue was purified by prep. TLC to give (48) (60 mg, 30.9%) as a white solid. $^1$H NMR (MeOD, 400 MHz) δ 8.05 (s, 1H), 6.43 (dd, J$_1$=2.8 Hz, J$_2$=17.2 Hz, 1H), 5.53 (ddd, J$_1$=2.4 Hz, J$_2$=5.2 Hz, J$_3$=53.2 Hz, 1H), 4.94 (dd, J$_1$=5.2 Hz, J$_2$=18.8 Hz, 1H), 4.04 (s, 3H), 3.86 (d, J=12.4 Hz, 1H), 3.71 (d, J=12.4 Hz, 1H); ESI-MS: m/z 341 [M+H]$^+$.

Example 49

Preparation of 2-amino-9-(4-aido-2-deoxy-2-fluoro-1-ribofuranosyl)-6-methoxypurine (49)

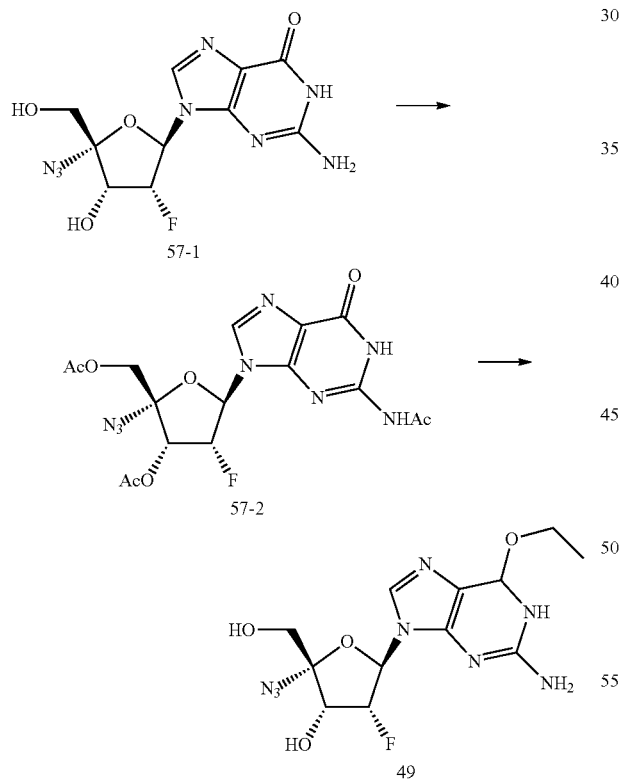

Step 1. Compound 57-2—4'-Azido-2'-deoxy-2'-fluoroguanosine (57-1, 750 mg, 2 mmol) was suspended in 50 ml of dry pyridine, acetic anhydride (1 ml, 10 mmol) and DMAP (122 mg. 1 mmol) were added. The reaction mixture was stirred overnight at 50° C. The solvent was evaporated, and the residue dissolved in the mixture of ethyl acetate and 10% NaHCO$_3$. The organic fraction were separated, washed with water, brine, dried over sodium sulfate and evaporated. Compound 57-2 was isolated by column chromatography in the linear gradient of methanol in DCM from 0 to 10%.

Step 2. Compound (49)—Compound 57-2 (500 mg, 1 mmol) was dissolved in 10 mg of dry CHCl$_3$, TPSCl (1.5 mmol, 450 mg), triethylamine (2 mmol, 0.28 ml) and DMAP (0.1 mmol, 13 mg) were added, and reaction mixture was left at R.T. for 20 h. When no starting material was detected, the solvent was evaporated and sodium ethylate was added (5 mmol, 340 mg). The reaction mixture was left overnight at R.T. LCMS analysis demonstrated a mixture of monoacetylated derivatives and (49). Additional sodium methylate was added (3 mmol, 200 mg), and mixture was heated for 4 h at 37° C. The reaction mixture was neutralized with Dowex 50(H+). The Dowex was filtered, washed with ethanol and the combined liquid was evaporated. Purified was conducted by RP HPLC on Synergy 4 micron Hydro-RP column (Phenominex), and linear gradient of methanol from 15 to 75% in 50 mM triethylammonium buffer was used for elution. The fractions containing (49) were evaporated, lyophilized 4 times with water to remove buffer, and purified again by column chromatography on silica gel in linear gradient of methanol in DCM from 0 to 10% to afford (49) (46 mg) as a solid; $^1$H NMR (CD$_3$OD,): δ 8.03 (s, 1H), 6.42-6.40 (d, 1H), 5.60-5.45 (dd, 1H), 4.96-4.95 (dd, 1H), 4.54-4.51 (m, 2H), 3.80-3.68 (m, 2H), 3.33 (s, 1H), 1.43-1.40 (t, 3H); MS: 355.4 (M+H).

Example 50

Preparation of 4'-azido-1'-methylcytidine (50)

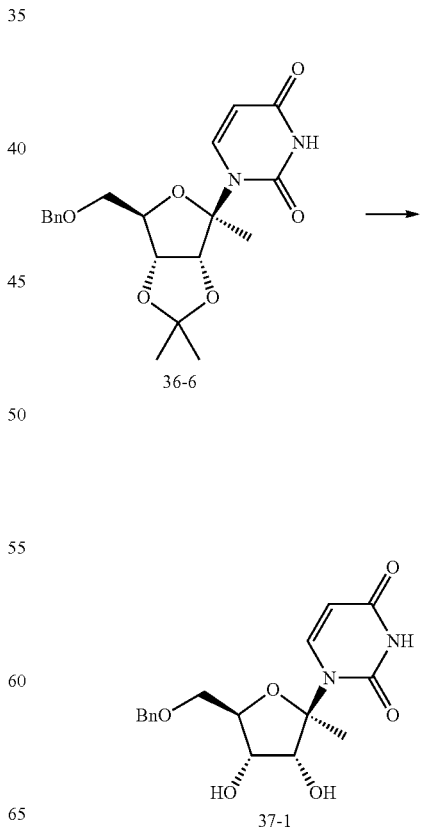

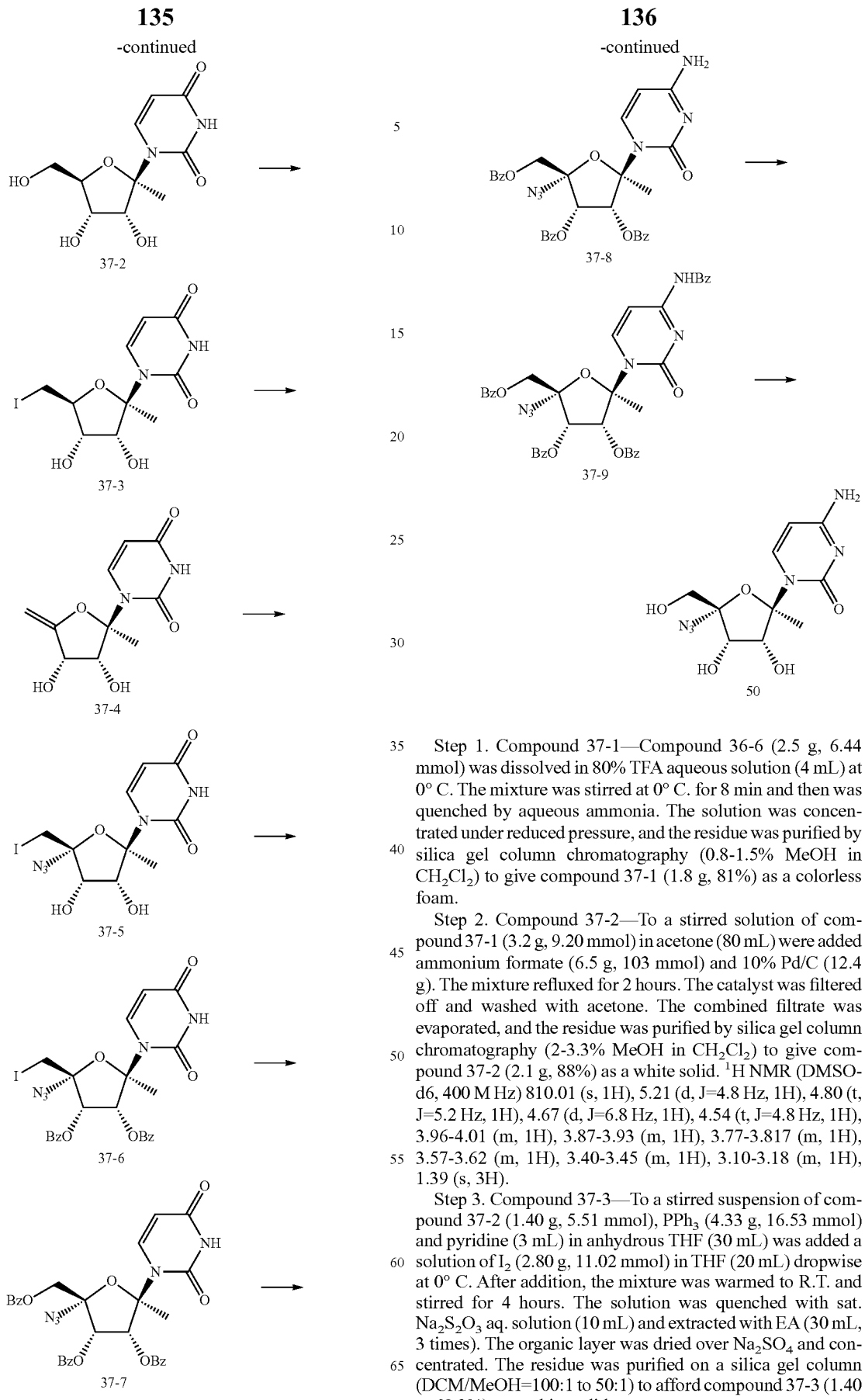

Step 1. Compound 37-1—Compound 36-6 (2.5 g, 6.44 mmol) was dissolved in 80% TFA aqueous solution (4 mL) at 0° C. The mixture was stirred at 0° C. for 8 min and then was quenched by aqueous ammonia. The solution was concentrated under reduced pressure, and the residue was purified by silica gel column chromatography (0.8-1.5% MeOH in $CH_2Cl_2$) to give compound 37-1 (1.8 g, 81%) as a colorless foam.

Step 2. Compound 37-2—To a stirred solution of compound 37-1 (3.2 g, 9.20 mmol) in acetone (80 mL) were added ammonium formate (6.5 g, 103 mmol) and 10% Pd/C (12.4 g). The mixture refluxed for 2 hours. The catalyst was filtered off and washed with acetone. The combined filtrate was evaporated, and the residue was purified by silica gel column chromatography (2-3.3% MeOH in $CH_2Cl_2$) to give compound 37-2 (2.1 g, 88%) as a white solid. $^1$H NMR (DMSO-d6, 400 MHz) 810.01 (s, 1H), 5.21 (d, J=4.8 Hz, 1H), 4.80 (t, J=5.2 Hz, 1H), 4.67 (d, J=6.8 Hz, 1H), 4.54 (t, J=4.8 Hz, 1H), 3.96-4.01 (m, 1H), 3.87-3.93 (m, 1H), 3.77-3.817 (m, 1H), 3.57-3.62 (m, 1H), 3.40-3.45 (m, 1H), 3.10-3.18 (m, 1H), 1.39 (s, 3H).

Step 3. Compound 37-3—To a stirred suspension of compound 37-2 (1.40 g, 5.51 mmol), $PPh_3$ (4.33 g, 16.53 mmol) and pyridine (3 mL) in anhydrous THF (30 mL) was added a solution of $I_2$ (2.80 g, 11.02 mmol) in THF (20 mL) dropwise at 0° C. After addition, the mixture was warmed to R.T. and stirred for 4 hours. The solution was quenched with sat. $Na_2S_2O_3$ aq. solution (10 mL) and extracted with EA (30 mL, 3 times). The organic layer was dried over $Na_2SO_4$ and concentrated. The residue was purified on a silica gel column (DCM/MeOH=100:1 to 50:1) to afford compound 37-3 (1.40 g, 69.3%) as a white solid.

Step 4. Compound 37-4—Compound 37-3 (400 mg, 1.08 mmol) and CH₃ONa (176 mg, 3.26 mmol) were dissolved in anhydrous methanol (10 mL). The mixture was refluxed for 12 hours. The reaction was quenched with dry-ice, and the solvent was removed. The residue was purified on a silica gel column. (MeOH:DCM=1:100 to 1:30) to afford compound 37-4 as a white solid (231 mg, 88.8%). ¹H NMR (CD₃OD, 400 MHz) 7.62 (d, J=8.0 Hz, 1H), 5.67 (d, J=8.4 Hz, 1H), 4.59-4.84 (m, 2H), 4.42-4.45 (m, 1H), 4.33 (t, J=2 Hz, 1H), 1.75 (s, 3H);

Step 5. Compound 37-5—To a stirred solution of compound 37-4 (2.10 g, 8.75 mmol) and NMM (4.42 g, 43.75 mmol) in anhydrous THF (20 mL) was added BnEt₃NN₃ (43.7 mL, 43.8 mmol, 1 M in MeCN). The mixture was cooled to 0° C., and a solution of I₂ (11.12 g, 43.75 mmol) in THF (20 mL) was added dropwise. The mixture was stirred at R.T. for 10 hours. N-acetyl cystein was added until no gas evolved. Saturated Na₂S₂O₃ aq. solution was added until a light yellow solution achieved. The solution was concentrated and then diluted with EA. The organic phase was washed with brine and dried over Na₂SO₄. The solvent was removed, and the residue was purified on a silica gel column (DCM: MeOH=50:1 to 30:1) to give compound 37-5 (2.43 g, 68.1%) as a white solid.

Step 6. Compound 37-6—To a stirred solution of compound 37-5 (0.46 g, 1.11 mmol) in anhydrous pyridine (8 mL) was added BzCl (0.31 mg, 2.78 mmol) dropwise at 0° C. The mixture was stirred at R.T. for 10 hours. The reaction was quenched with H₂O, and the solution was concentrated. The residue was dissolved in EA and washed with saturated NaHCO₃. The organic layer was dried over Na₂SO₄ and concentrated. The residue was purified on a silica gel column (PE:EA=10:1 to 1:1) to give compound 37-6 (0.43 g, 62.9%) as a white solid.

Step 7. Compound 37-7—Compound 37-6 (1.80 g, 2.91 mmol), BzONa (4.20 g, 29.10 mmol) and 15-crown-5 (6.40 g, 29.10 mmol) were suspended in DMF (100 mL). The mixture was stirred at 90° C. for 1 day. The precipitate was removed by filtration, and the filtrate was diluted with EA. The solution was washed with brine and dried over Na₂SO₄. The solvent was removed, and the residue was purified on a silica gel column (PE:EA=10:1 to 2:1) to afford compound 37-7 (1.52 g, 85.3%) as a white solid. ¹H NMR (CD₃OD, 400 MHz) δ7.83-7.95 (m, 5H), 7.82 (d, J=1.2 Hz, 2H), 7.54-7.64 (m, 3H), 7.40-7.47 (m, 5H), 7.31-7.35 (m, 2H), 6.60 (d, J=5.6 Hz, 1H), 6.10 (d, J=6.0 Hz, 1H), 5.53 (d, J=8.4 Hz, 1H), 4.59 (d, J=12 Hz, 1H), 1.98 (s, 3H);

Step 8. Compound 37-8—A solution of compound 37-7 (485 mg, 0.79 mmol), DMAP (193 mg, 1.58 mmol) and TEA (160 mg, 1.58 mmol) in MeCN (5 mL) was treated with 2,4,6-triisopropylbenzenesulfonyl chloride (TPSCl, 479 mg, 1.58 mmol), and the mixture was stirred at room temperature for 12 hours. THF/NH₃ (50 mL, saturated at 0° C.) was added. The mixture was stirred for additional 2 hours. The solvent was evaporated under reduced pressure, and the residue was purified on a silica gel column (DCM/MeOH=100:1 to 70:1) to give compound 37-8 (351 mg, 71.2%) as a white solid.

Step 9. Compound 37-9—To a stirred solution of compound 37-8 (0.41 g, 0.66 mmol) in anhydrous pyridine (8 mL) was added BzCl (0.18 g, 1.32 mmol) dropwise at 0° C. The mixture was stirred at R.T. for 10 hours and then was quenched with H₂O. The solution was concentrated, and the residue was dissolved in EA and washed with saturated NaHCO₃. The organic layer was dried over Na₂SO₄ and concentrated. The residue was purified on a silica gel column (PE/EA=5/1 to 2/1) to give compound 37-9 (0.31 g, 76.7%) as a white solid. ¹H NMR (CDCl₃, 400 MHz) δ8.28 (d, J=8.0 Hz, 1H), 8.08 (d, J=7.6 Hz, 2H), 7.75-7.98 (m, 6H), 7.59-7.63 (m, 2H), 7.41-7.53 (m, 6H), 7.29-7.35 (m, 3H), 7.28 (s, 1H), 7.24 (s, 1H), 6.76-6.81 (m, 1H), 6.01 (d, J=6.4 Hz, 1H), 4.81 (d, J=12.4 Hz, H), 4.59 (d, J=12.4 Hz, H), 2.15 (s, 3H).

Step 10. Compound 50—Compound 37-9 (0.41 g, 0.56 mmol) was dissolved in methanolic ammonia (30 mL, saturated), and the mixture was stirred at R.T. for 14 hours. The solvent was removed, and the residue was purified on a silica gel column (DCM/MeOH=30:1 to 10:1) to give (50) as a white solid (40 mg, 23.5%). ¹H NMR (CD₃OD, 400 MHz) δ8.13 (d, J=8.0 Hz, 1H), 5.84 (d, J=7.6 Hz, 1H), 4.66 (d, J=5.2 Hz, 1H), 4.14 (d, J=5.2 Hz, 1H), 3.54 (dd, J₁=38 Hz, J₂=12 Hz, 2H), 3.21 (s, 3H); ESI-MS: m/z=321.1 [M+Na], 619.1 [2M+Na]⁺.

Example 51

Preparation of 4'-azido-2'-deoxy-2'-α-fluoro-2'-β-methyluridine (51)

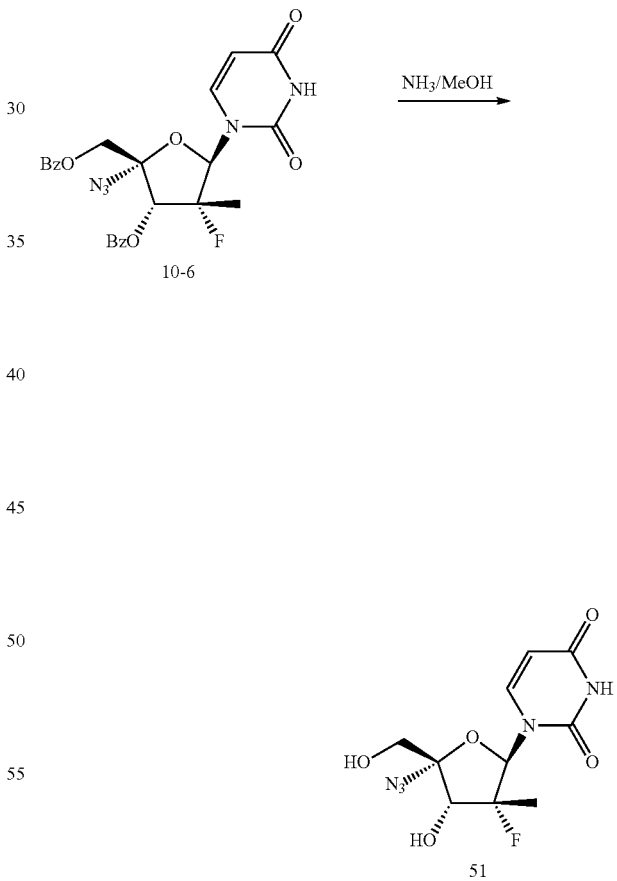

Compound 10-6 (0.22 g, 0.43 mmol) was dissolved in 100 mL methanolic ammonia (saturated at 0° C.), and the mixture was stirred at R.T. for 12 hours. The solvent was removed, and the residue was purified on a silica gel column (2-5% MeOH in DCM) to give (51) as a white solid (47 mg, 36.4%). ¹H NMR (CD₃OD, 400 MHz) δ7.93 (d, J=8.4 Hz, 1H), 6.36 (s, 1H), 5.71 (d, J=8.0 Hz, 1H), 4.17 (d, J=24.4 Hz, 1H), 3.78 (dd, $J_1$=46.4 Hz, $J_2$=12.0 Hz, 2H), 1.36 (d, J=22.4 Hz, 3H); ESI-MS: m/z 324.07 [M+Na]$^+$.

Example 52

Preparation of 4'-azido-2'-deoxy-2'-fluorocytidine 5'-(N,N-bis((S)-isopropoxycarbonyleth-1-yl))phosphorodiamidate (52)

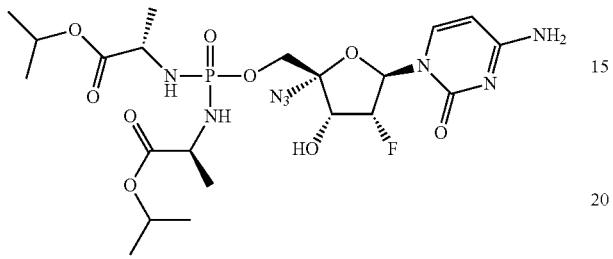

To a stirred of suspension of phosphorous oxychloride (10.0 g, 65.7 mmol) and L-aniline isopropyl ester (21.97 g, 131.5 mmol) in anhydrous DCM (400 mL) was added a solution of TEA (26.57 g, 263 mmol) in DCM (15 mL) dropwise at −78° C. After addition, the mixture was warmed to R.T. and then stirred 6 hours. The solvent was removed, and the residue was dissolved in methyl-butyl ether. The precipitate was removed by filtration, and the filtrate was concentrated to give the crude compound, which was purified on a silica gel column to give (N,N-bis((S)-isopropoxycarbonyleth-1-yl))phosphorodiamidic chloride (5.6 g, yield: 27.35%) as a colorless oil. To a solution of compound (2) (90 mg, 0.3 mmol) in anhydrous THF (5 mL) was added a solution of t-BuMgCl (0.50 mL, 1M in THF) dropwise at −78° C. The mixture was then stirred at R.T. for 30 min and re-cooled to −78° C. A solution of (N,N-bis((S)-isopropoxycarbonyleth-1-yl))phosphordiamidic chloride (0.50 mL, 1M in THF) was added dropwise. After addition, the mixture was stirred at R.T. for 14 hours. The reaction was quenched with HCOOH. The solvent was removed, and the residue was purified by prep. HPLC (0.1% HCOOH in MeCN and water) to give (52) (22.6 mg, 12.53%) as a white solid. $^1$H NMR (CD$_3$OD, 400 MHz) δ 7.64 (d, J=7.6 Hz, 1H), 6.45 (br s, 1H), 6.02 (d, J=7.6 Hz, 1H), 4.97-5.06 (m, 2H), 4.61 (t, J=12.0 Hz, 1H), 4.34 (d, J=6.4 Hz, 2H), 3.86-3.97 (m, 2H), 1.35-1.41 (m, 6H), 1.24-1.27 (m, 12H); $^{31}$P NMR (CD$_3$OD, 162 MHz) δ 13.81; ESI-LCMS: m/z=611 [M+H]$^+$.

Example 53

Preparation of 4'-azido-2'-chloro-2'-deoxycytidine (53)

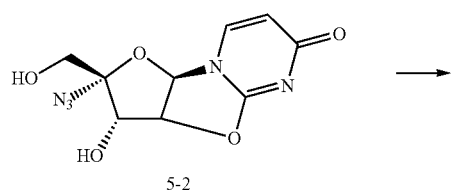

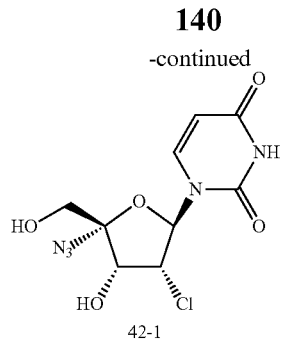

42-1

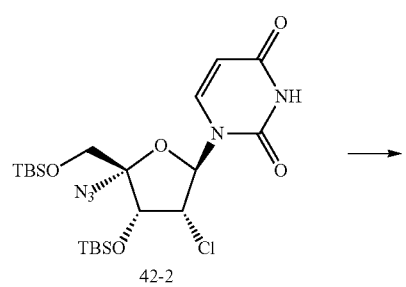

42-2

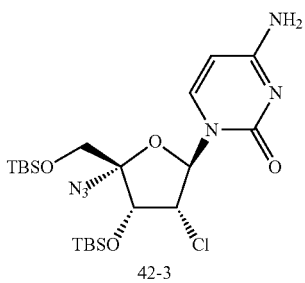

42-3

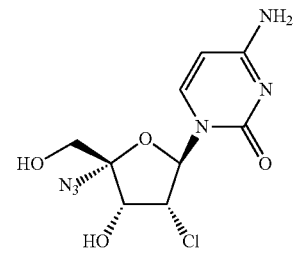

53

Step 1. Compound 42-1—To a stirred suspension of compound 5-2 (1.1 g, 4.2 mmol) in anhydrous DMF (10 mL) was added AlCl$_3$ (1.4 g, 10.5 mmol) under N$_2$. The reaction stirred at 120° C. for 3 hours. The solution was concentrated, and the residue was purified by silica gel column chromatography (1-20% MeOH in DCM) to give compound 42-1 (870 mg, 68.2%) as a white solid. $^1$H NMR (CD$_3$OD, 400 M Hz) δ 7.92 (d, J=8.0 Hz, 1H), 6.39 (d, J=7.2 Hz, 1H), 5.76 (d, J=8.0 Hz, 1H), 4.74 (dd, $J_1$=5.6, $J_2$=7.2 Hz, 1H), 4.44 (d, J=5.2 Hz, 1H), 3.60 (dd, $J_1$=12.0 Hz, $J_2$=30.8 Hz, 2H).

Step 2. Compound 42-2—To a stirred solution of compound 42-1 (870 mg, 2.9 mmol) in anhydrous pyridine (10 mL) was added TBSCl (1.3 g, 8.7 mmol) at R.T. The mixture was stirred at R.T. for 14 hours. The precipitate was removed by filtration, and filtrate was concentrated. The residue was purified on a silica gel column (10%-50% EA in PE) to give compound 42-2 (400 mg, 26%) as a white solid.

Step 3. Compound 42-3—Compound 42-2 (400 mg, 0.7 mmol), DMAP (171 mg, 1.4 mmol), TPSCl (430 mg, 14.4 mol) and $Et_3N$ (141 mg, 1.4 mmol) were dissolved in MeCN (20 mL). The mixture was stirred at R.T. for 14 hours. The reaction was quenched with aqueous ammonia, and the mixture was stirred at R.T. for 2 hours. The solvent was removed, and the residue was purified on a silica gel column (1-20% MeOH in DCM) to give compound 42-3 (175 mg, 47%) as a white foam.

Step 4. Compound (53)—A mixture of compound 42-3 (175 mg, 0.31 mmol) and $NH_4F$ (100 mg, 2.7 mmol) in MeOH (15 mL) was refluxed for 14 hours. The solvent was removed, and the residue was purified on a silica gel column (5%-10% MeOH in DCM) to give (53) (64.8 mg, 35.4%) as a white solid. $^1$H NMR ($CD_3OD$, 400 M Hz): δ 7.91 (d, J=7.2 Hz, 1H), 6.40 (d, J=6.4 Hz, 1H), 5.95 (d, J=7.2 Hz, 1H), 4.72 (dd, $J_1$=5.6 Hz, $J_2$=6.4 Hz, 1H), 4.47-4.48 (m, 1H), 3.64 (dd, $J_1$=12.0 Hz, $J_2$=30.8 Hz, 2H); ESI-MS: m/z=303 [M+H]$^+$.

Example 54

Preparation of 4'-azido-1'-methyluridine (54)

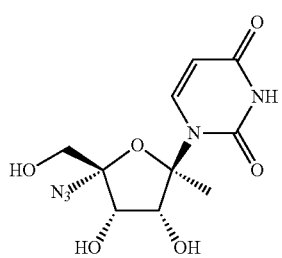 [SMILES: C[C@@]1(n2ccc(=O)[nH]c2=O)O[C@@](CO)(N=[N+]=[N-])[C@@H](O)[C@H]1O]

4'-Azido-1'-methyl-2',3',5'-O-tribenzoyluridine (37-7) (0.20 g, 0.34 mmol) was dissolved in saturated methanolic ammonia (50 mL), and the mixture was stirred at R.T. for 14 hours. The solvent was removed, and the residue was purified on a silica gel column (DCM/MeOH=50:1 to 30:1) to give (54) as a white solid (47 mg, 46.0%). $^1$H NMR ($CD_3OD$, 400 MHz) δ8.15 (d, J=8.4 Hz, 1H), 5.63 (d, J=8.4 Hz, 1H), 4.73 (d, J=5.6 Hz, 1H), 4.17 (d, J=5.2 Hz, 1H), 3.67 (d, J=12.0 Hz, 1H), 3.55 (d, J=12.0 Hz, 1H), 1.76 (s, 3H); ESI-negative-MS: m/z=298.1 [M−H]$^+$, 597.2 [2M+H]$^+$.

Example 55

Preparation of 4'-azidonucleoside 5'-triphosphates (61a-j)

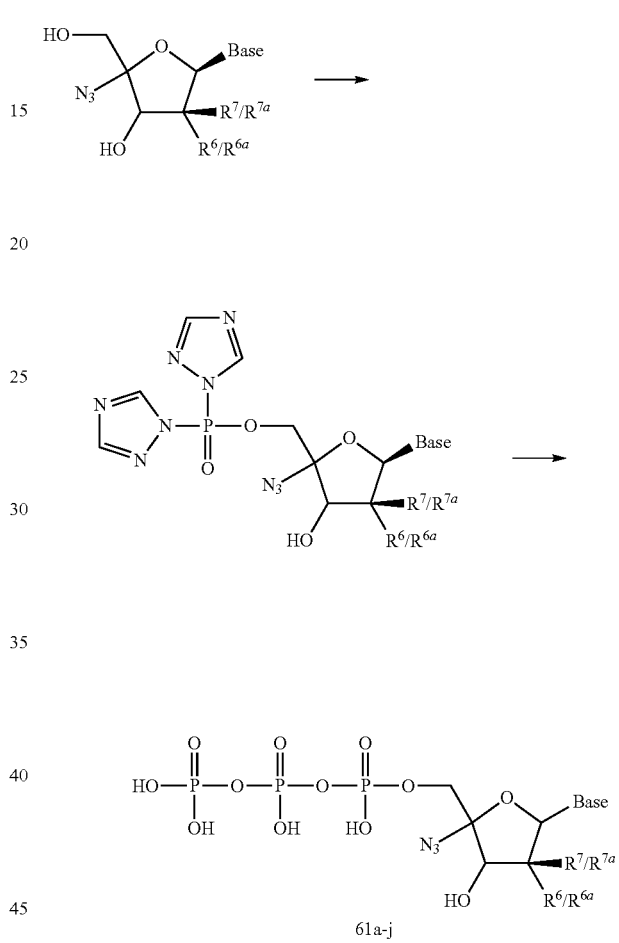

1,2,4-Triazol (42 mg, 0.6 mmol) was suspended 1 ml of dry $CH_3CN$. Triethylamine was added (0.088 ml, 0.63 mmol), and the mixture was vortexed to obtain a clear solution. After addition of $POCl_3$ (0.01 ml, 0.1 mmol), the mixture was vortexed and left for 20 min, and then centrifugated. The supernatant was added to the nucleoside (0.05 mmol), and the mixture was kept at ambient temperature for 1 hour. Tris (tetrabutylammonium) hydrogen pyrophosphate (180 mg, 0.2 mmol) was added, and the mixture was kept for 2 hours more at R.T. The reaction was quenched with water, and the 5'-triphosphate (61a-j) was isolated by IE chromatography on AKTA Explorer using column HiLoad 16/10 with Q Sepharose High Performance. The separation was done in a linear gradient of NaCl from 0 to 1N in 50 mM TRIS-buffer (pH7.5). The fractions containing 5'-triphosphate were combined, concentrated and desalted by RP HPLC on Synergy 4 micron Hydro-RP column (Phenominex). A linear gradient of methanol from 0 to 20% in 50 mM triethylammonium acetate buffer (pH 7.5) was used for elution.

TABLE 1
The following compounds were synthesized according the procedure above:
| Compound | $^{31}$P NMR Pα | $^{31}$P NMR Pβ | $^{31}$P NMR Pδ | MS (M$^-$) |
|---|---|---|---|---|
| 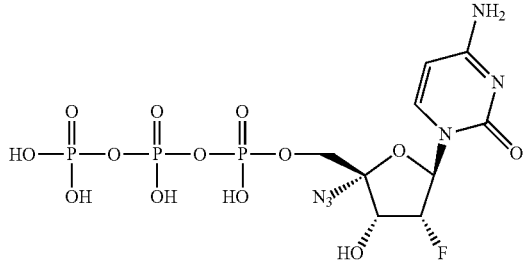 61a | −12.33d | −23.04 | −9.95 | 525.3 |
| 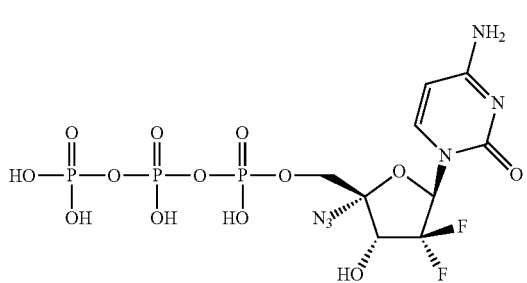 61b | −12.34d | −23.15 | −10.50d | 543.1 |
| 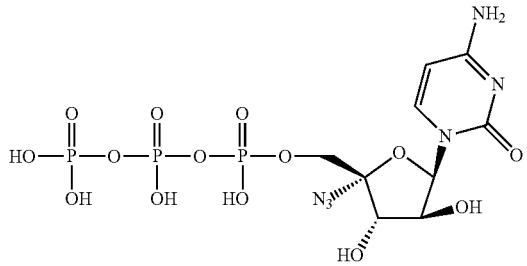 61c | −11.70 | −20.64 | −5.53 | 523.3 |
| 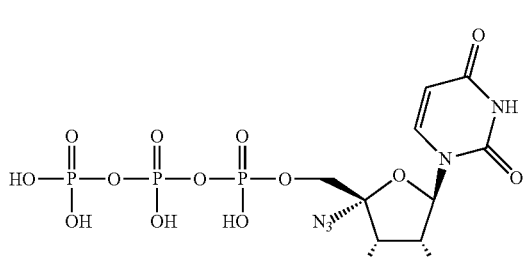 61d | −12.31d | −23.09 | −9.58 | 524.4 |
| 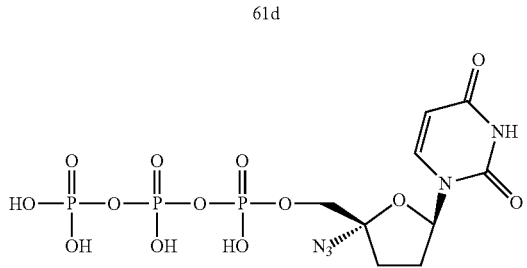 61e | −12.29d | −22.97 | −10.71 | 526.1 |

TABLE 1-continued

The following compounds were synthesized according the procedure above:

| Compound | ³¹P NMR Pα | ³¹P NMR Pβ | ³¹P NMR Pδ | MS (M⁻) |
|---|---|---|---|---|
| 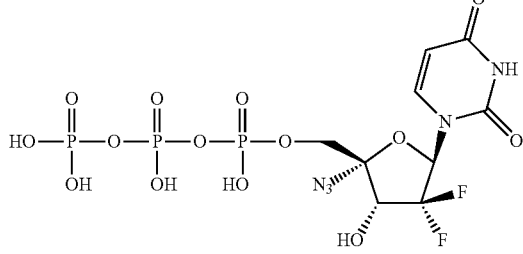 61f | −12.40d | −23.25t | −10.92d | 544.2 |
| 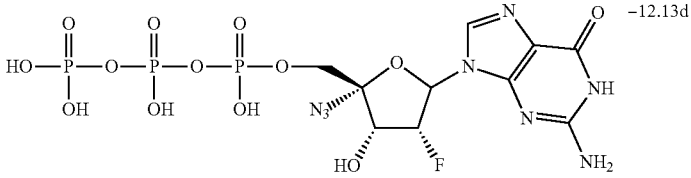 61g | −12.13d | −22.93 | −10.49 | 565.3 |
| 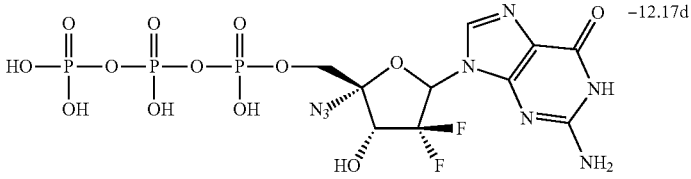 61h | −12.17d | −22.20t | −7.47d | 583.1 |
| 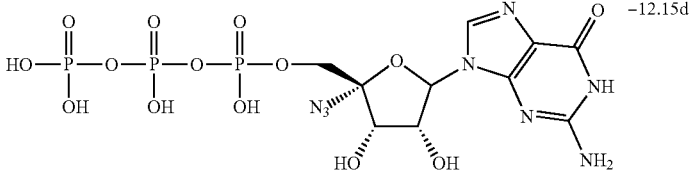 61i | −12.15d | −22.51t | −9.35 | 563.1 |
| 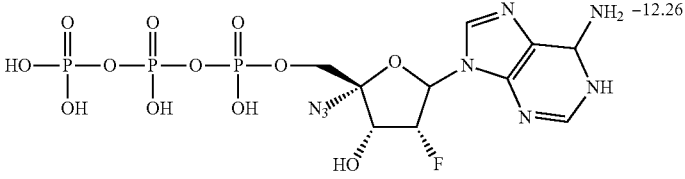 61j | −12.26 | −22.29 | −10.75 | 549.2 |

Example 56

RSV Antiviral Assays

CPE reduction assays were performed as described by Sidwell and Huffman et al., *Appl Microbiol.* (1971) 22(5): 797-801 with slight modifications. HEp-2 cells (ATCC) at a concentration of 6000 cell/well were infected with RSV Long strain (ATCC) at a multiplicity of infection (m.o.i.) of 0.01, and each of the test compounds were provided to duplicate wells at final concentrations starting from 100 μM using ⅓ stepwise dilutions. For each compound, two wells were set aside as uninfected, untreated cell controls (CC), and two wells per test compound received virus only as a control for virus replication (VC). The assay was stopped after 6 days, before all of the cells in the virus-infected untreated control wells exhibited signs of virus cytopathology (giant cell formation, syncytia). At the end of the incubation, 20 μl of cell counting kit-8 reagent (CCK-8, Dojindo Molecular Technologies, Inc.) were added to each well. After 4 hour incubation, the absorbance was measured in each well according to manufacturer's instruction, and the 50% effective concentration ($EC_{50}$) was calculated by using regression analysis, based on the mean O.D. at each concentration of compound.

RT-PCR based assays were performed in HEp-2 cells (ATCC: CCL-23) at a concentration of 20000 cell/well were plated in 96 well plates and incubated overnight. Each of the test compounds were ⅓ serially diluted and dosed to HEp-2 cells in duplicates. The highest final concentration for each compound was 100 uM. After 24 hour compound pre-incubation, RSV A2 (ATCC: VR-1540) at MOI of 0.1 was added. Two wells per compound were set aside as uninfected, untreated cell controls (CC), and four wells per test compound received virus only as a control for virus replication (VC). The assay was stopped 4 days after virus infection and conditioned media was removed for viral RNA isolation. The quantities of the RSV virus were measured by real-time PCR using a set of RSV specific primers and probe. The data was analyzed with Prism software with EC50 defined as drug concentration that reduced the viral load 50% from the viral control (VC).

Compounds of Formula (I) and Formula (II) are active in the assay as noted in Tables 2 and 3, where 'A' indicates an $EC_{50}$<1 μM, 'B' indicates an $EC_{50}$ of >1 μM and <10 μM, 'C' indicates an $EC_{50}$>10 μM and <100 μM, and 'D' indicates an $EC_{50}$>100 μM.

TABLE 2

Activity of compounds as determined by CPE assay

| No. | $EC_{50}$ |
|---|---|
| 1 | A |
| 2 | A |
| 3 | — |
| 4 | — |
| 5 | D |
| 6 | D |
| 7 | C |
| 8 | D |
| 9 | D |
| 10 | A |
| 11 | A |
| 12 | D |
| 13 | — |
| 14 | — |
| 15 | A |
| 16 | — |
| 17 | D |
| 18 | B |
| 19 | D |
| 20 | D |
| 21 | A |
| 22 | A |
| 23 | B |
| 24 | D |
| 25 | D |
| 26 | D |
| 27 | A |
| 28 | D |
| 29 | A |
| 30 | — |
| 31 | A |
| 32 | D |
| 33 | A |
| 34 | D |
| 35 | A |
| 36 | D |
| 37 | B |
| 38 | D |
| 39 | D |
| 40 | D |
| 41 | D |
| 42 | C |
| 43 | C |
| 44 | D |
| 45 | D |
| 46 | D |
| 47 | D |
| 48 | B |
| 49 | D |
| 50 | D |
| 51 | D |
| 52 | — |
| 53 | — |
| 54 | — |

TABLE 3

Activity of compounds as determined by RT-PCR assay

| No. | $EC_{50}$ |
|---|---|
| 1 | A |
| 2 | A |
| 3 | — |
| 4 | — |
| 5 | D |
| 6 | — |
| 7 | B |
| 8 | — |
| 9 | — |
| 10 | A |
| 11 | A |
| 12 | D |
| 13 | — |
| 14 | — |
| 15 | A |
| 16 | — |
| 17 | D |
| 18 | B |
| 19 | D |
| 20 | D |
| 21 | A |
| 22 | A |
| 23 | B |
| 24 | D |
| 25 | D |
| 26 | D |
| 27 | A |
| 28 | D |
| 29 | A |
| 30 | D |
| 31 | A |
| 32 | — |
| 33 | A |
| 34 | D |
| 35 | A |
| 36 | D |
| 37 | B |
| 38 | D |
| 39 | D |
| 40 | D |
| 41 | D |
| 42 | D |
| 43 | C |
| 44 | D |
| 45 | D |
| 46 | D |
| 47 | D |
| 48 | A |
| 49 | D |
| 50 | D |
| 51 | D |
| 52 | — |
| 53 | B |
| 54 | — |

TABLE 3-continued

Activity of compounds as determined by RT-PCR assay

| No. | EC$_{50}$ |
|---|---|
| — | — |
| — | — |
| — | — |
| — | — |

Example 57

Influenza Antiviral Assay

To test representative compounds of the invention for their potencies against Influenza A/WSN/33 virus (ATCC: VR-1520), A549 cells (ATCC: CCL-185, human lung carcinoma) were plated at 5000 cells per well in 100 μls of Ham's F12 medium supplemented with ten percent fetal bovine serum (FBS) and one percent penicillin and streptomycin (Pen/Strep) in a 96 well plate. Twenty-four hours post plating, medium was discarded and the cells were washed one time with phosphate buffered saline (PBS) and replaced with Ham's F12 medium with 0.3 percent FBS and one percent Pen/Strep. Each of the test compounds was three fold serially diluted and dosed to A549 cells in duplicates. The highest final concentration for each compound was 100 μM. After 24 hour compound pre-incubation, Influenza A/WSN/33 virus was added at MOI of 0.01 and incubated for 72 hours. Two wells per compound were set aside as uninfected, untreated cell controls, and four wells per compound received virus only as a control for virus replication (VC). The quantities of the Influenza virus in each well were measured by real-time PCR using a set of Influenza A/WSN/33 strain specific primers and probe. The data was analyzed with Microsoft Excel software with percent inhibition defined as compared to the vehicle control. As shown in Table 4, compounds of Formula (I) and Formula (II) are active in the assay.

TABLE 4

Activity of representative compounds as determined by RT-PCR assay.

| No. | Compound Concentration | Percent Inhibition |
|---|---|---|
| 2 | 30 μM | 99.8% |
| 10 | 30 μM | 83.3% |
| 27 | 30 μM | 91% |
| 28 | 30 μM | 94.6% |
| 30 | 30 μM | 99.9% |
| 50 | 30 μM | 90.9% |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of ameliorating or treating a viral infection selected from a human respiratory syncytial virus (RSV) viral infection and an influenza A virus viral infection comprising administering a therapeutically effective amount of a compound of Formula (II), or a pharmaceutically acceptable salt thereof, to a subject suffering from the viral infection, wherein the compound of Formula (II) has the structure:

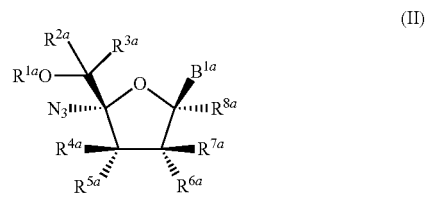

(II)

wherein:
$B^{1a}$ is selected from the group consisting of an optionally substituted heterocyclic base and an optionally substituted heterocyclic base with a protected amino group;
$R^{1a}$ is selected from the group consisting of hydrogen, an optionally substituted acyl,

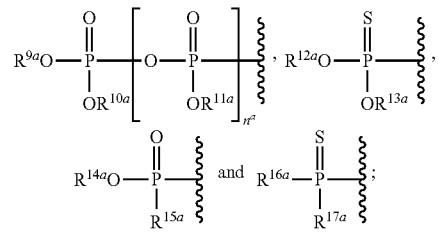

$n^a$ is 0, 1, or 2;
$R^{2a}$ and $R^{3a}$ are independently selected from the group consisting of hydrogen, an optionally substituted $C_{1-6}$ alkyl and an optionally substituted $C_{1-6}$ haloalkyl;
$R^{4a}$ is selected from the group consisting of hydrogen, halogen, an optionally substituted $C_{1-6}$ alkyl, —OR$^{18a}$ and —OC(=O)R$^{19a}$;
$R^{5a}$ is selected from the group consisting of hydrogen, halogen, an optionally substituted $C_{1-6}$ alkyl, —OR$^{20a}$ and —OC(=O)R$^{21a}$;
$R^{6a}$ is selected from the group consisting of hydrogen, halogen, an optionally substituted $C_{1-6}$ alkyl, —OR$^{22a}$ and —OC(=O)R$^{23a}$;
or $R^{5a}$ and $R^{6a}$ are both oxygen atoms and linked together by a carbonyl group;
$R^{7a}$ is selected from the group consisting of hydrogen, halogen, optionally substituted $C_{1-6}$ alkyl, —OR$^{24a}$ and —OC(=O)R$^{25a}$;
$R^{8a}$ is selected from the group consisting of hydrogen, an optionally substituted $C_{1-6}$ alkyl and an optionally substituted $C_{1-6}$ haloalkyl;
$R^{9a}$ and $R^{12a}$ are independently absent or hydrogen;
$R^{10a}$ is absent or hydrogen;
each $R^{11a}$ is independently absent or hydrogen;
$R^{13a}$ is absent or hydrogen;
$R^{14a}$ is selected from the group consisting of an —O-optionally substituted aryl, an —O-optionally substituted heteroaryl and an —O-optionally substituted heterocyclyl, and $R^{15a}$ is an optionally substituted N-linked amino acid or an optionally substituted N-linked amino acid ester derivative; or
$R^{14a}$ is an optionally substituted N-linked amino acid or an optionally substituted N-linked amino acid ester derivative, and $R^{15a}$ is an optionally substituted N-linked amino acid or an optionally substituted N-linked amino acid ester derivative; or $R^{14a}$ is $O^-$, hydroxy or an —O-optionally substituted $C_{1-6}$ alkyl, and $R^{15a}$ and $R^{5a}$ together are O;

$R^{16a}$ is selected from the group consisting of an —O-optionally substituted aryl, an —O-optionally substituted heteroaryl and an —O-optionally substituted heterocyclyl, and $R^{17a}$ is an optionally substituted N-linked amino acid or an optionally substituted N-linked amino acid ester derivative; or $R^{16a}$ is an optionally substituted N-linked amino acid or an optionally substituted N-linked amino acid ester derivative, and $R^{17a}$ is an optionally substituted N-linked amino acid or an optionally substituted N-linked amino acid ester derivative; or $R^{16a}$ is $O^-$, hydroxy or an —O-optionally substituted $C_{1-6}$ alkyl, and $R^{17a}$ and $R^{5a}$ together are O;

$R^{18a}$, $R^{20a}$, $R^{22a}$ and $R^{24}$ are independently hydrogen or an optionally substituted $C_{1-6}$ alkyl; and $R^{19a}$, $R^{21a}$, $R^{23a}$ and $R^{25a}$ are independently selected from the group consisting of an optionally substituted $C_{1-6}$ alkyl and an optionally substituted $C_{3-6}$ cycloalkyl.

2. The method of claim 1, wherein $R^{2a}$ and $R^{3a}$ are hydrogen.

3. The method of claim 1, wherein at least one of $R^{2a}$ and $R^{3a}$ is hydrogen; and the other of $R^{2a}$ and $R^{3a}$ is an optionally substituted $C_{1-6}$ alkyl or an optionally substituted $C_{1-6}$ haloalkyl.

4. The method of claim 1, wherein $R^{1a}$ is hydrogen or an optionally substituted acyl.

5. The method of claim 1, wherein $R^{1a}$ is selected from the group consisting of

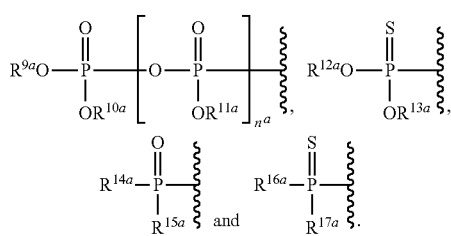

6. The method of claim 5, wherein $R^{1a}$ is

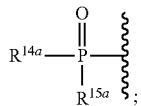

and $R^{14a}$ is an optionally substituted aryl, an optionally substituted N-linked α-amino acid or an optionally substituted N-linked α-amino acid ester derivative.

7. The method of claims 6, wherein $R^{15a}$ is an optionally substituted N-linked α-amino acid or an optionally substituted N-linked α-amino acid ester derivative.

8. The method of claim 5, wherein $R^{1a}$ is

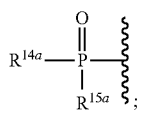

and $R^{14a}$ and $R^{15a}$ each independently have the structure:

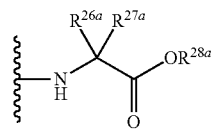

wherein $R^{26a}$ is hydrogen or an optionally substituted $C_{1-4}$-alkyl; $R^{27a}$ is selected from the group consisting of hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl, and an optionally substituted aryl($C_{1-6}$ alkyl); and $R^{28a}$ is selected from the group consisting of hydrogen, an optionally substituted $C_{1-6}$-alkyl, an optionally substituted $C_{3-6}$ cycloalkyl, an optionally substituted aryl, an optionally substituted aryl ($C_{1-6}$ alkyl), and an optionally substituted haloalkyl, or $R^{26a}$ and $R^{27a}$ are taken together to form an optionally substituted $C_{3-6}$ cycloalkyl.

9. The method of claim 8, wherein $R^{26a}$ is hydrogen; $R^{27a}$ is hydrogen or methyl; and $R^{28a}$ is methyl or benzyl.

10. The method of claim 5, wherein $R^{1a}$ is

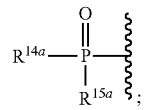

and $R^{14a}$ is $O^-$, hydroxy or an —O-optionally substituted $C_{1-6}$ alkyl, and $R^{15a}$ and $R^{5a}$ together are O.

11. The method of claim 5, wherein $R^{1a}$ is

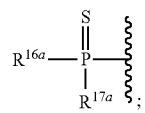

and $R^{16a}$ is an —O-optionally substituted aryl, an optionally substituted N-linked α-amino acid or an optionally substituted N-linked α-amino acid ester derivative.

12. The method of claim 11, wherein $R^{17a}$ is an optionally substituted N-linked α-amino acid or an optionally substituted N-linked α-amino acid ester derivative.

13. The method of claim 5, wherein $R^{1a}$ is

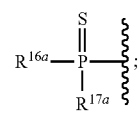

and $R^{16a}$ and $R^{17a}$ each independently have the structure:

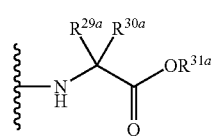

wherein: $R^{29a}$ is selected from the group consisting of hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); $R^{30a}$ is hydrogen or an optionally substituted $C_{1-4}$-alkyl; and $R^{31a}$ is selected from the group consisting of hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted $C_{1-6}$haloalkyl, or $R^{29a}$ and $R^{30a}$ are taken together to form an optionally substituted $C_{3-6}$ cycloalkyl.

14. The method of claim 13, wherein $R^{29a}$ is hydrogen; $R^{30a}$ is hydrogen or methyl; and $R^{31}a$ is methyl or benzyl.

15. The method of claim 1, wherein $R^{1a}$ is

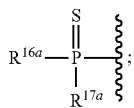

and $R^{16a}$ is O⁻, hydroxy or an —O-optionally substituted $C_{1-6}$ alkyl; and $R^{17a}$ and $R^{5a}$ together are O.

16. The method of claim 1, wherein $B^{1a}$ is selected from the group consisting of:

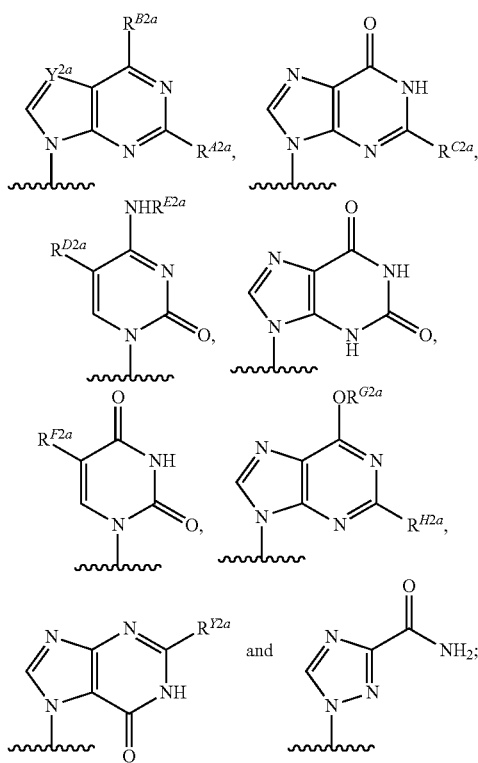

wherein:
$R^{A2a}$ is selected from the group consisting of hydrogen, halogen and NHR$^{J2a}$, wherein R$^{J2a}$ is selected from the group consisting of hydrogen, —C(=O)R$^{K2a}$ and —C(=O)OR$^{L2a}$;
$R^{B2a}$ is halogen or NHR$^{W2a}$, wherein R$^{W2a}$ is selected from the group consisting of hydrogen, an optionally substituted $C_{1-6}$ alkyl, an optionally substituted $C_{2-6}$ alkenyl, an optionally substituted $C_{3-8}$ cycloalkyl, —C(=O)R$^{M2a}$ and —C(=O)OR$^{N2a}$;
$R^{C2a}$ is hydrogen or NHR$^{O2a}$, wherein R$^{O2a}$ is selected from the group consisting of hydrogen, —C(=O)R$^{P2a}$ and —C(=O)OR$^{Q2a}$;
$R^{D2a}$ is selected from the group consisting of hydrogen, halogen, an optionally substituted $C_{1-6}$ alkyl, an optionally substituted $C_{2-6}$ alkenyl and an optionally substituted $C_{2-6}$ alkynyl;
$R^{E2a}$ is selected from the group consisting of hydrogen, an optionally substituted $C_{1-6}$ alkyl, an optionally substituted $C_{3-8}$ cycloalkyl, —C(=O)R$^{R2a}$ and —C(=O)OR$^{S2a}$;
$R^{F2a}$ is selected from the group consisting of hydrogen, halogen, an optionally substituted $C_{1-6}$ alkyl, an optionally substituted $C_{2-6}$ alkenyl and an optionally substituted $C_{2-6}$ alkynyl;
$Y^{2a}$ is N or CR$^{T2a}$, wherein R$^{T2a}$ is selected from the group consisting of hydrogen, halogen, an optionally substituted $C_{1-6}$-alkyl, an optionally substituted $C_{2-6}$-alkenyl and an optionally substituted $C_{2-6}$-alkynyl;
$R^{G2a}$ is an optionally substituted $C_{1-6}$ alkyl;
$R^{H2a}$ is hydrogen or NHR$^{T2a}$, wherein R$^{T2a}$ is independently selected from the group consisting of hydrogen, —C(=O)R$^{u2a}$ and —C(=O)OR$^{V2a}$;
$R^{Y2a}$ is hydrogen or NHR$^{Z2a}$, wherein R$^{Z2a}$ is selected from the group consisting of hydrogen, —C(=O)R$^{AA2a}$ and —C(=O)OR$^{BB2a}$;
$R^{K2a}$, $R^{L2a}$, $R^{M2a}$, $R^{N2a}$, $R^{P2a}$, $R^{Q2a}$, $R^{R2a}$, $R^{S2a}$, $R^{U2a}$, $R^{V2a}$, $R^{AA2a}$ and $R^{BB2a}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloalkynyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl).

17. The method of claim 16, wherein $B^{1a}$ is selected from the group consisting of

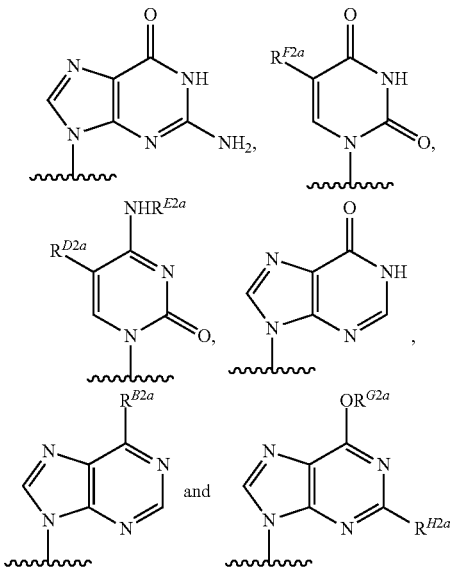

18. The method of claim 1, wherein $R^{7a}$ is —OR$^{24a}$ or an optionally substituted $C_{1-6}$ alkyl; and $R^{8a}$ is hydrogen.

19. The method of claim 1, wherein $R^{7a}$ is hydrogen or a halogen; and $R^{8a}$ is hydrogen.

20. The method of claim 1, wherein $R^{5a}$ is —$OR^{20a}$.
21. The method of claim 1, wherein $R^{6a}$ is —$OR^{22a}$, hydrogen or a halogen.
22. The method of claim 1, wherein $R^{5a}$ and $R^{6a}$ are both oxygen atoms and linked together by a carbonyl group.
23. The method of claim 1, wherein the compound is selected from the group consisting of:
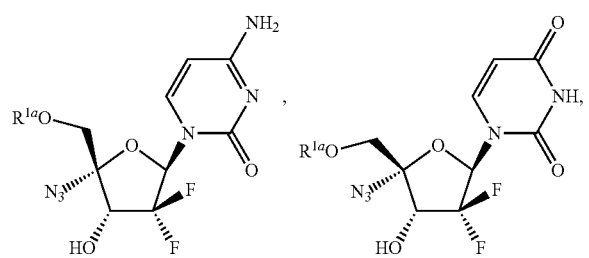
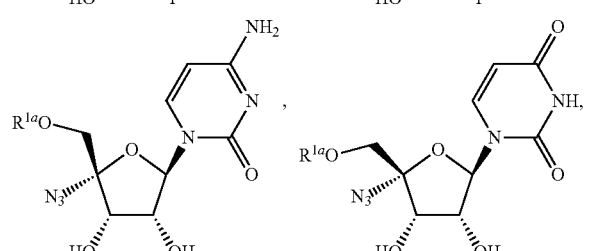
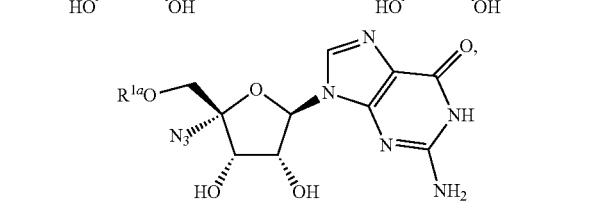
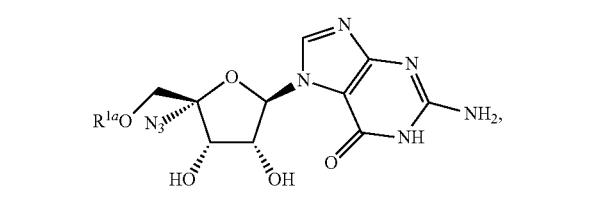
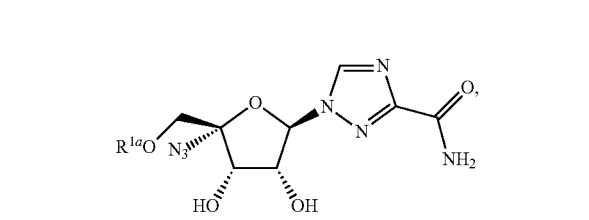
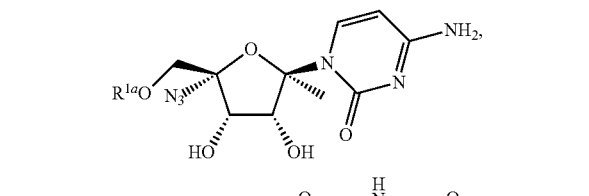
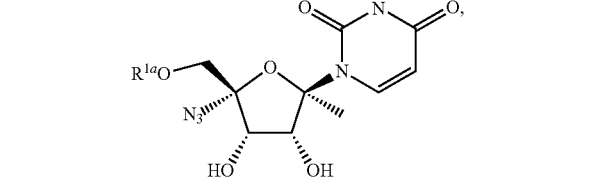
-continued
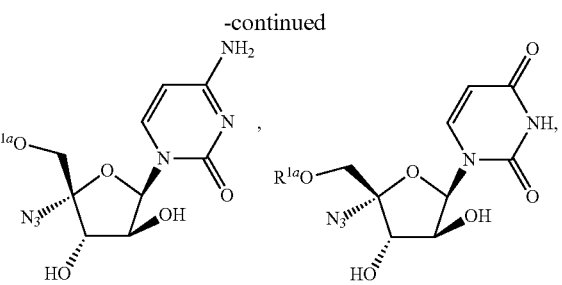
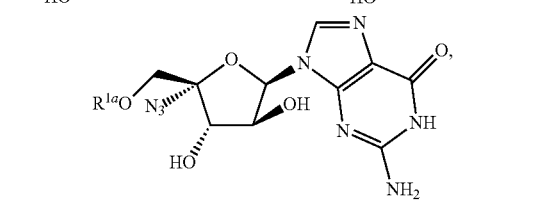
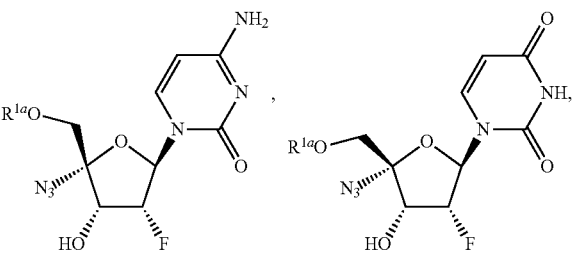
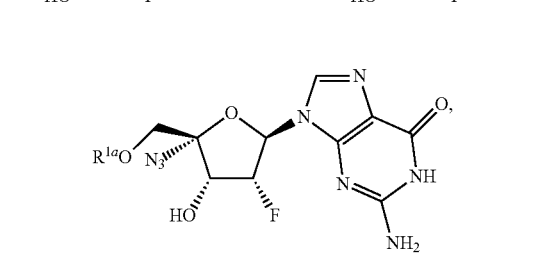
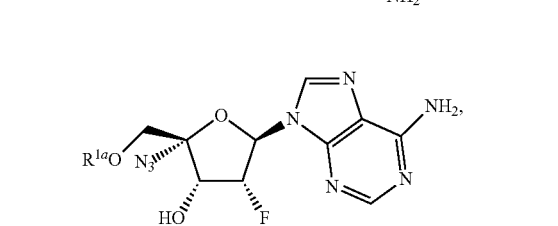
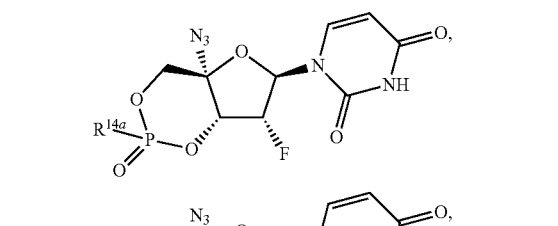
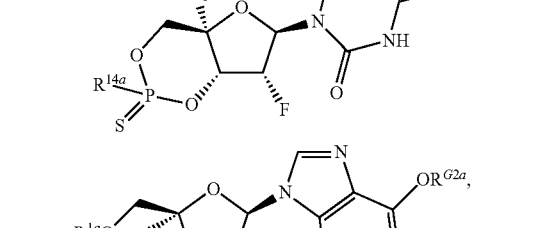
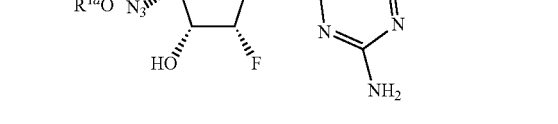

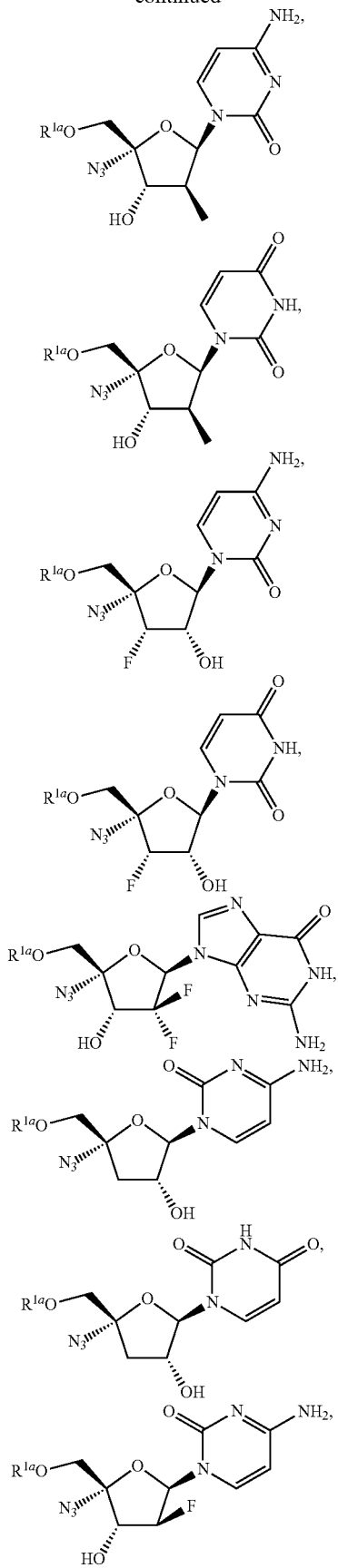
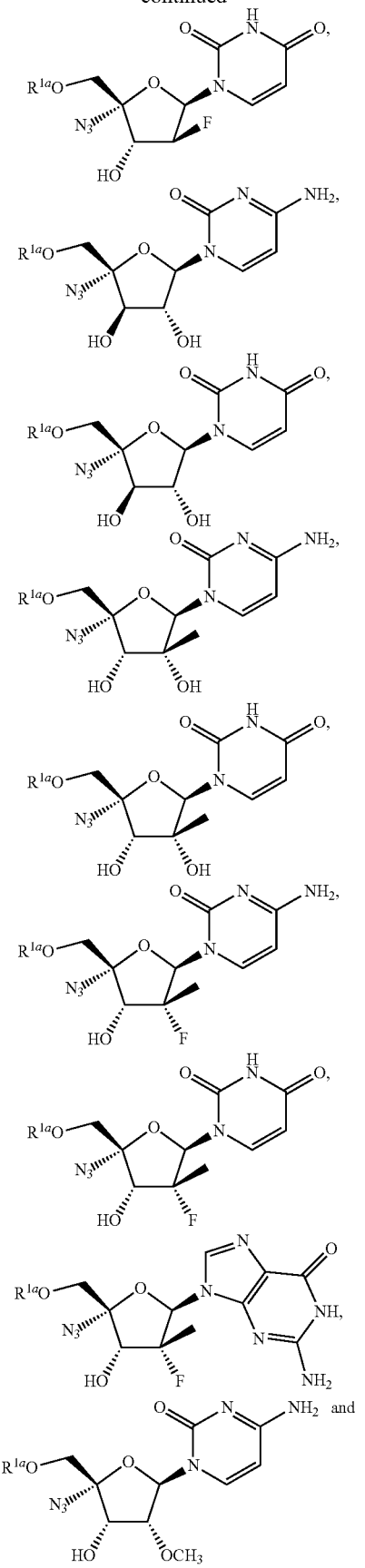

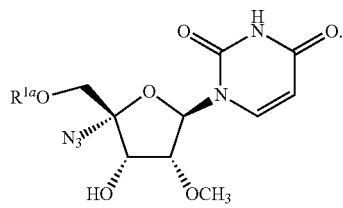
or a pharmaceutically acceptable salt of any of the foregoing.
24. The method of claim 1, wherein the compound is selected from the group consisting of:
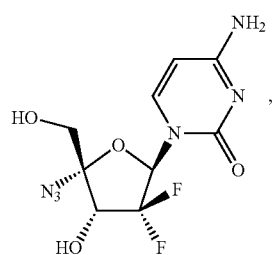 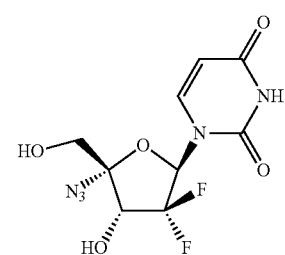
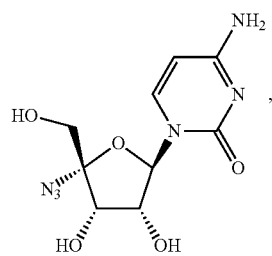 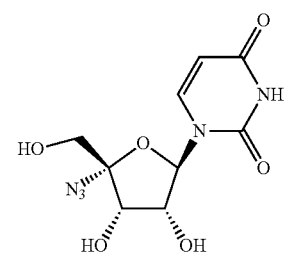
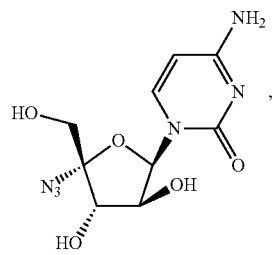 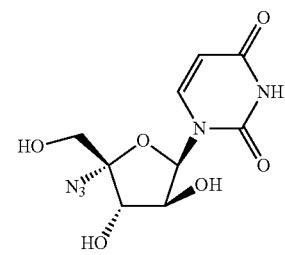
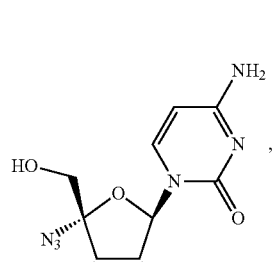 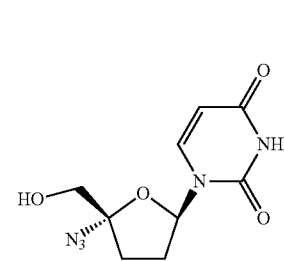
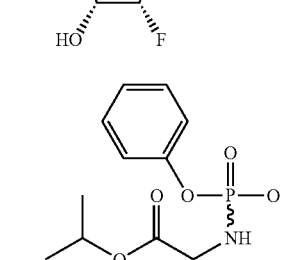 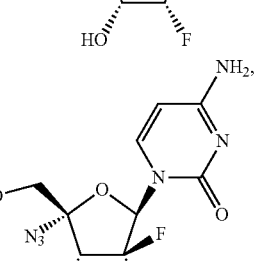
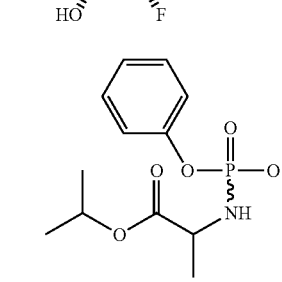
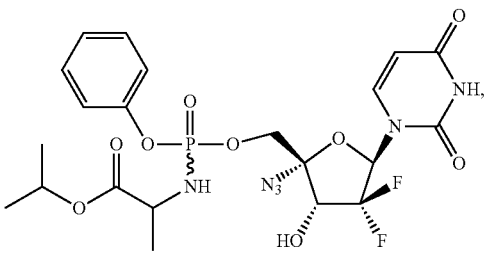
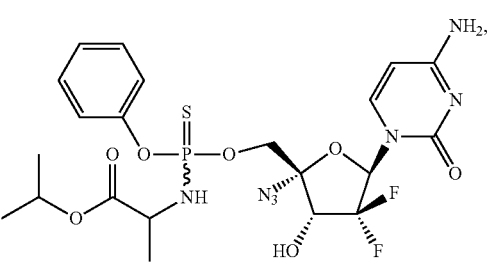
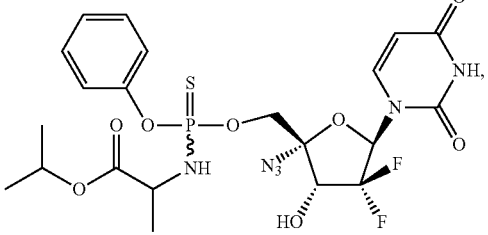
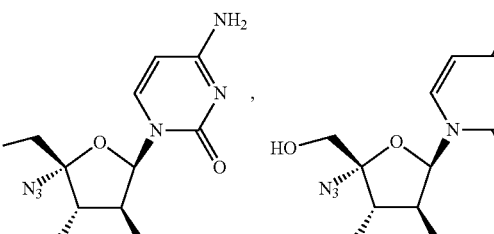
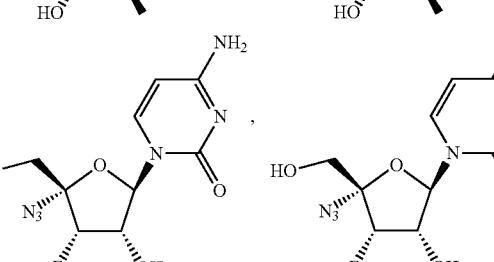
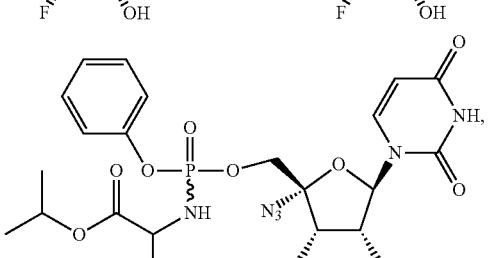
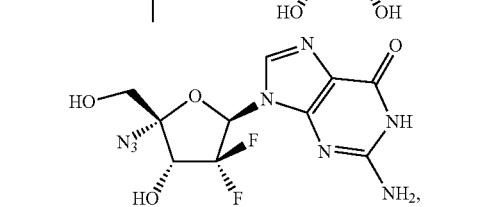

161
-continued
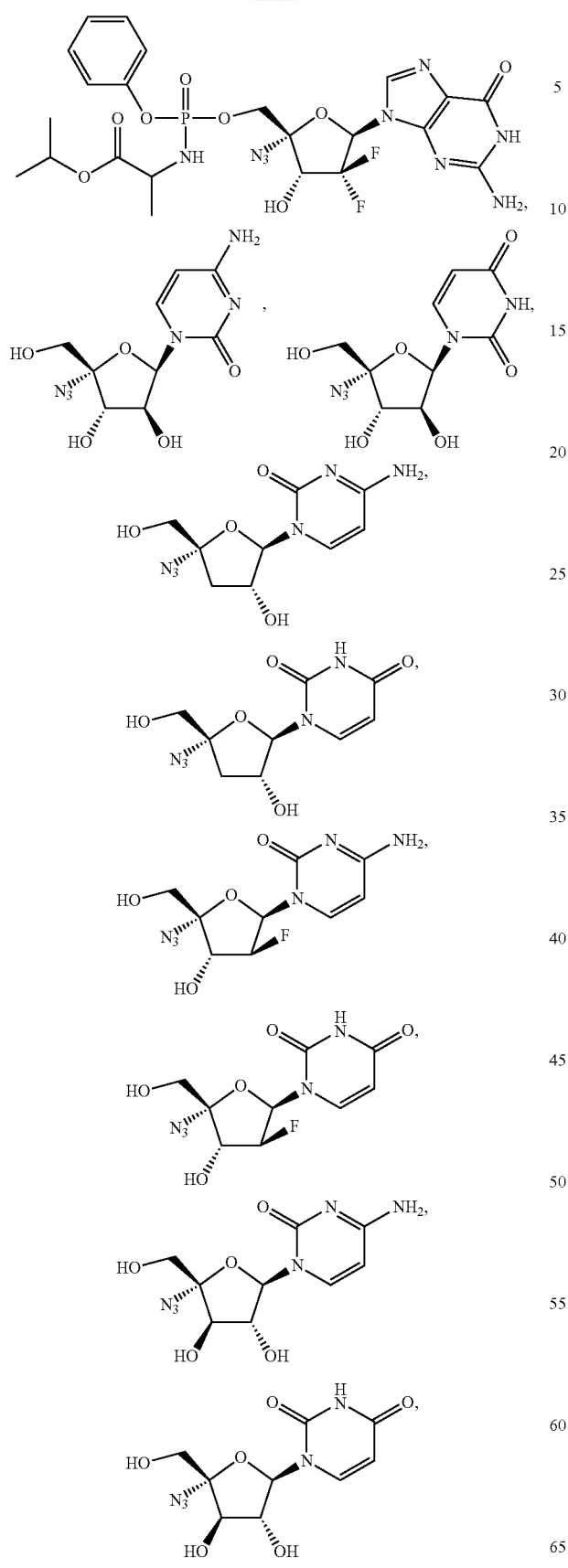
162
-continued
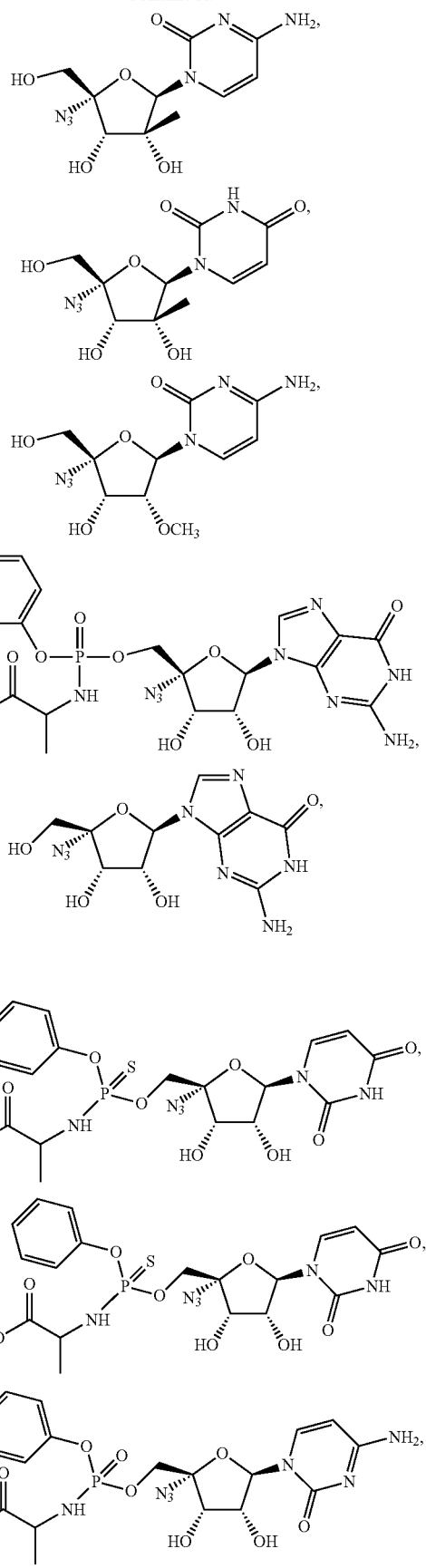

163
-continued
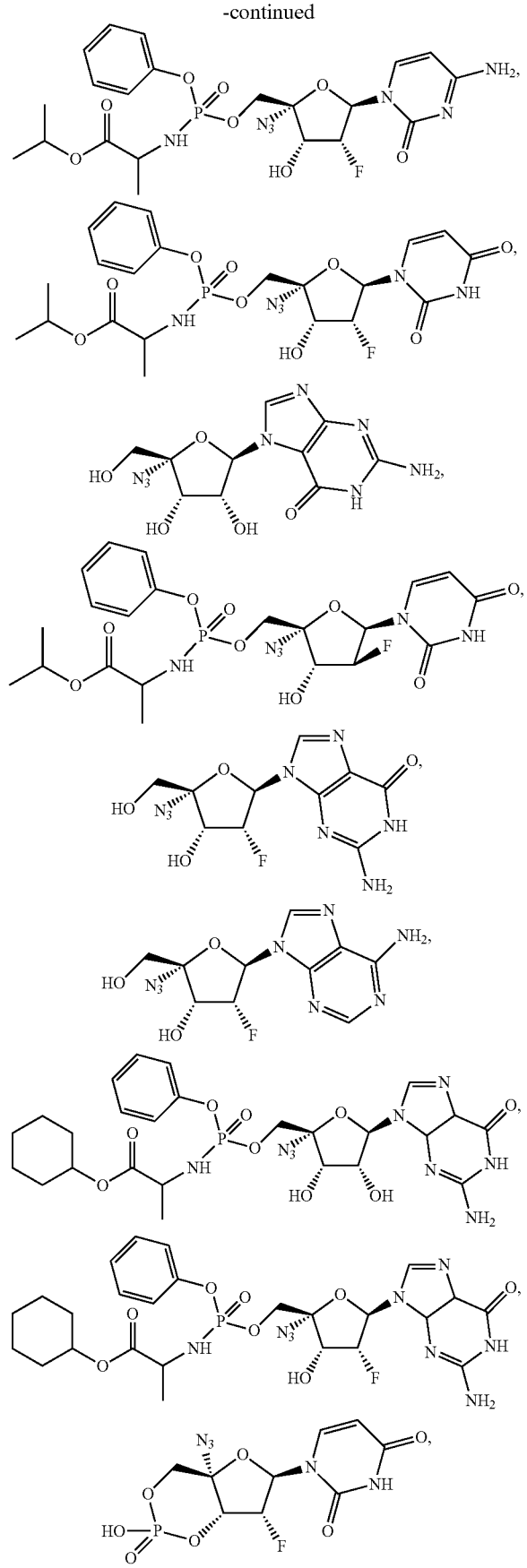
164
-continued
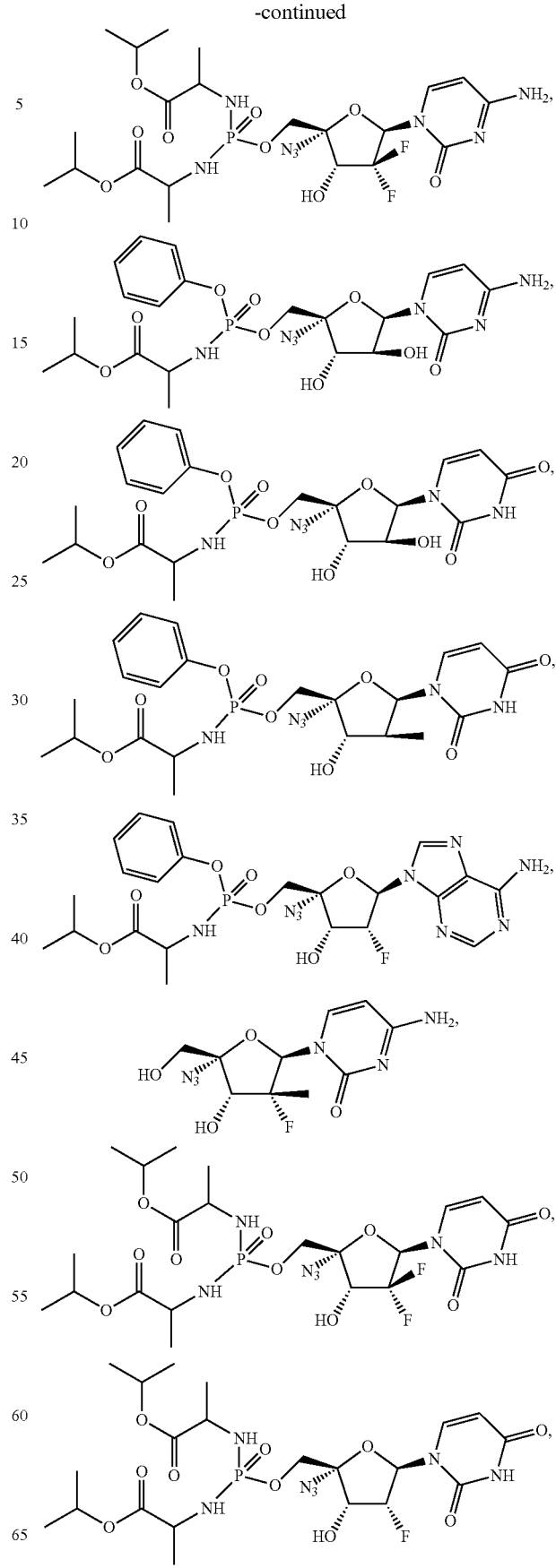

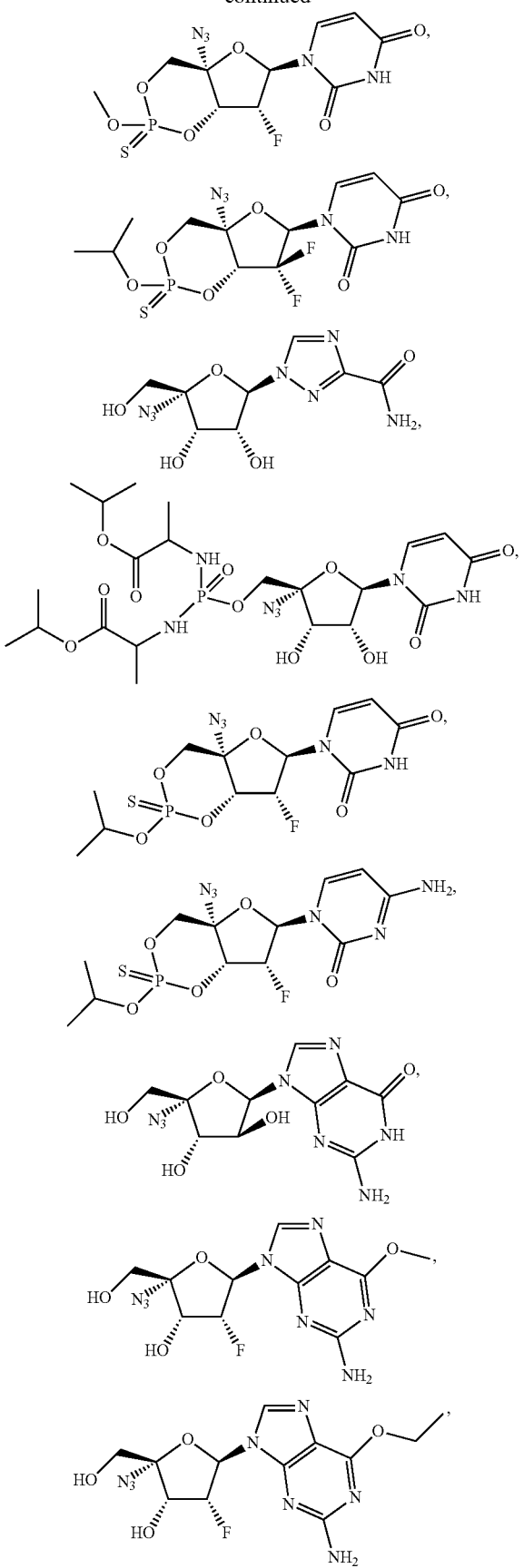

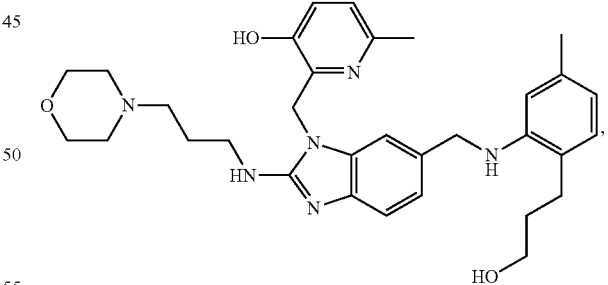

or a pharmaceutically acceptable salt of any of the foregoing.

25. A method of inhibiting replication of a virus selected from human respiratory syncytial virus (RSV) and influenza A virus comprising contacting a cell infected with the virus with an effective amount of the compound recited in claim 1, or a pharmaceutically acceptable salt thereof.

26. A method of ameliorating or treating a viral infection selected from human respiratory syncytial virus viral influenza A virus viral infection comprising contacting a cell infected with the virus with an effective amount of the compound recited in claim 1, or a pharmaceutically acceptable salt thereof.

27. A method of ameliorating or treating a human respiratory syncytial virus viral infection comprising administering a therapeutically effective amount of the compound recited in claim 1, or a pharmaceutically acceptable salt thereof, in combination with a second anti-RSV agent to a subject suffering from the viral infection.

28. The method of claim 27, wherein the second anti-RSV agent is selected from the group consisting of ribavirin, palivizumab, RSV-IGIV, ALN-RSV01, 1-cyclopropyl-3-[[1-(4-hydroxybutyl) benzimidazol-2-yl]methyl]imidazo[4,5-c]pyridin-2-one, (4,4''-bis-{4,6-bis-[3-(bis-carbamoylmethyl-sulfamoyl)-phenylamino]-(1,3,5)triazin-2-ylaminol}-biphenyl-2,2''-disulfonic-acid), -1-(2-fluorophenyl)-3-(2-oxo-5-phenyl-2,3-dihydro-1H-benzo [e][1,4]di-azepin-3-yl)-urea, 5,5'-bis[1-(((5-amino-1H-tetrazolyl)imino)-methyl)]-2,2',4''-methylidynetrisphenol, α-Neuraminic acid, N-acetyl-2-O-[3-(docosyloxy)-2-[(docosyloxy)methyl]-2-methylpropyl]-4,7,8,9-tetrakis(hydrogen sulfate), sodium salt and N-cyclopropyl-6-[4-[(2-phenylbenzoyl)amino]benzoyl]-4,5-dihydrothieno[3,2-d][1]benzazepine-2-carboxamide.

29. A method of treating or ameliorating a human respiratory syncytial virus viral infection comprising contacting a cell infected with the virus with an effective amount of the compound recited in claim 1, or a pharmaceutically acceptable salt thereof, in combination with a second anti-RSV agent.

30. The method of claim 29, wherein the second anti-RSV agent is selected from the group consisting of ribavirin, palivizumab, RSV-IGIV, ALN-RSV01, 1-cyclopropyl -3-[[1-(4-hydroxybutyl)benzimidazol-2-yl]methyl]imidazo[4,5-c] pyridin-2-one, (4,4"-bis-{4,6-bis- [3-(bis-carbamoylmethyl-sulfamoyl)-phenylamino]-(1,3,5)triazin-2-ylamino}-biphenyl-2,2"-disulfonic-acid), (S)-1-(2-fluorophenyl)-3-(2-oxo-5-phenyl-2,3-dihydro-1H-benzo[e][1,4]di-azepin-3-yl)-urea, 5,5'-bis[1-(((5-amino-1H-tetrazolyl)imino)-methyl)]-2,2',4"-methylidynetrisphenol,

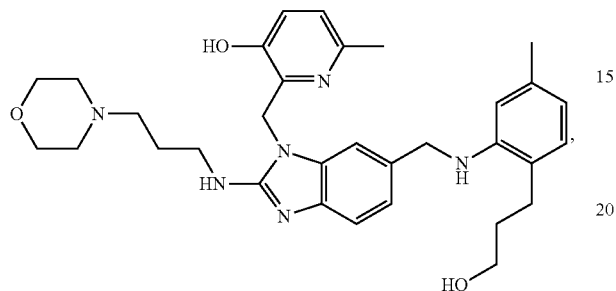

α-Neuraminic acid, N-acetyl-2-O-[3-(docosyloxy)-2-[(docosyloxy)methyl]-2-methylpropyl]-, 4,7,8,9-tetrakis (hydrogen sulfate), sodium salt and N-clopropyl-6-[4-[(2-phenylbenzoyl)amino]benzoyl]-4,5-dihydrothieno[3,2-d][1] benzazepine-2-carboxamide.

* * * * *